United States Patent
Cherney et al.

(10) Patent No.: US 8,835,470 B2
(45) Date of Patent: Sep. 16, 2014

(54) MANDELAMIDE HETEROCYCLIC COMPOUNDS

(75) Inventors: Robert J. Cherney, Princeton, NJ (US); Yanlei Zhang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 91 days.

(21) Appl. No.: 13/642,755

(22) PCT Filed: Apr. 21, 2011

(86) PCT No.: PCT/US2011/033364
§ 371 (c)(1),
(2), (4) Date: Oct. 22, 2012

(87) PCT Pub. No.: WO2011/133734
PCT Pub. Date: Oct. 27, 2011

(65) Prior Publication Data
US 2013/0045964 A1 Feb. 21, 2013

Related U.S. Application Data

(60) Provisional application No. 61/327,315, filed on Apr. 23, 2010.

(51) Int. Cl.
| | | |
|---|---|---|
| A61K 31/506 | (2006.01) | |
| A61K 31/497 | (2006.01) | |
| A61K 31/4439 | (2006.01) | |
| A61K 31/427 | (2006.01) | |
| A61K 31/4245 | (2006.01) | |
| C07D 417/14 | (2006.01) | |
| C07D 413/14 | (2006.01) | |
| C07D 413/04 | (2006.01) | |

(52) U.S. Cl.
CPC ............ *C07D 413/04* (2013.01); *A61K 31/427* (2013.01); *A61K 31/4439* (2013.01); *A61K 31/497* (2013.01); *A61K 31/506* (2013.01); *C07D 413/14* (2013.01); *C07D 417/14* (2013.01); *A61K 31/4245* (2013.01)
USPC ...... 514/364; 514/255.05; 514/256; 514/340; 514/341; 544/333; 544/405; 546/269.1; 548/131

(58) Field of Classification Search
CPC .. C07D 417/14; C07D 413/14; C07D 413/04; A61K 31/506; A61K 31/497; A61K 31/4439; A61K 31/427; A61K 31/4245
USPC .................... 514/255.05, 256, 340, 341, 364; 544/333, 405; 546/269.1; 548/131
See application file for complete search history.

(56) References Cited

U.S. PATENT DOCUMENTS

| | | | |
|---|---|---|---|
| 5,597,825 A | 1/1997 | Himmelsbach et al. | |
| 7,160,883 B2 | 1/2007 | Dyckman et al. | |
| 7,199,142 B2 | 4/2007 | Chen et al. | |
| 7,309,721 B2 | 12/2007 | Budhu et al. | |
| 7,351,725 B2 | 4/2008 | Doherty et al. | |
| 7,479,504 B2 | 1/2009 | Bugianesi et al. | |
| 7,605,171 B2 | 10/2009 | Colandrea et al. | |
| 2005/0033055 A1 | 2/2005 | Bugianesi et al. | |
| 2005/0070506 A1 | 3/2005 | Doherty et al. | |
| 2008/0113961 A1 | 5/2008 | Nishi et al. | |
| 2008/0200535 A1 | 8/2008 | Ohmori et al. | |
| 2009/0076070 A1 | 3/2009 | Harada et al. | |

FOREIGN PATENT DOCUMENTS

| | | |
|---|---|---|
| WO | WO03061567 | 7/2003 |
| WO | WO03062248 | 7/2003 |
| WO | WO03062252 | 7/2003 |
| WO | WO03073986 | 9/2003 |
| WO | WO03105771 | 12/2003 |
| WO | WO2004058149 | 7/2004 |
| WO | WO2004071442 | 8/2004 |
| WO | WO2004103279 | 12/2004 |
| WO | WO2004103306 | 12/2004 |
| WO | WO2004103309 | 12/2004 |

(Continued)

OTHER PUBLICATIONS

Hale, Jeffrey J., "A Rational Utilization of High-Throughput Screening Affords Selective, Orally Bioavailable 1-Benzyl-3-carboxyazetidine Sphingosine-1-phosphate-1 Receptor Agonists," J.Med Chem 47, pp. 6662-6665 (2004).

(Continued)

*Primary Examiner* — Joseph Kosack
*Assistant Examiner* — Matthew Coughlin
(74) *Attorney, Agent, or Firm* — Gary D. Greenblatt

(57) ABSTRACT

Disclosed are compounds of Formula (I) or stereoisomers, salts, or prodrugs thereof, wherein: Q is, or $R_1$ is phenyl substituted with zero to 3 substituents; and $R^1, R^2, R^3, R^4, R^5$, and G are defined herein. Also disclosed are methods of using such compounds as selective agonists for G protein-coupled receptor S1P1, and pharmaceutical compositions comprising such compounds. These compounds are useful in treating, preventing, or slowing the progression of diseases or disorders in a variety of therapeutic areas, such as autoimmune diseases and vascular disease.

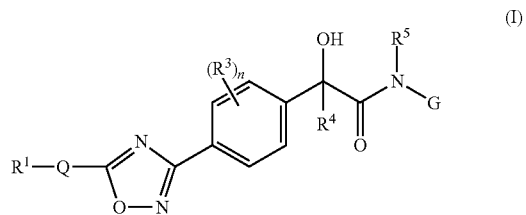

12 Claims, No Drawings

(56) References Cited

FOREIGN PATENT DOCUMENTS

| | | |
|---|---|---|
| WO | WO2004113330 | 12/2004 |
| WO | WO2005000833 | 1/2005 |
| WO | WO2005014525 | 2/2005 |
| WO | WO2005032465 | 4/2005 |
| WO | WO2005058848 | 6/2005 |
| WO | WO2005082089 | 9/2005 |
| WO | WO2006047195 | 5/2006 |
| WO | WO2006100633 | 9/2006 |
| WO | WO2006131336 | 12/2006 |
| WO | WO2006137019 | 12/2006 |
| WO | WO2007024922 | 3/2007 |
| WO | WO2007061458 | 5/2007 |
| WO | WO2007080542 | 7/2007 |
| WO | WO2007085451 | 8/2007 |
| WO | WO2007091396 | 8/2007 |
| WO | WO2007109330 | 9/2007 |
| WO | WO2008016674 | 2/2008 |
| WO | WO2008028937 | 3/2008 |
| WO | WO2008029306 | 3/2008 |
| WO | WO2008029370 | 3/2008 |
| WO | WO2008029371 | 3/2008 |
| WO | WO2008030843 | 3/2008 |
| WO | WO2008035239 | 3/2008 |
| WO | WO2008037476 | 4/2008 |
| WO | WO2008064315 | 5/2008 |
| WO | WO2008074820 | 6/2008 |
| WO | WO2008074821 | 6/2008 |
| WO | WO2008076356 | 6/2008 |
| WO | WO2008079382 | 7/2008 |
| WO | WO2008091967 | 7/2008 |
| WO | WO2008114157 | 9/2008 |
| WO | WO 2008/141731 A2 | 11/2008 |
| WO | WO2009011850 | 1/2009 |
| WO | WO2009043889 | 4/2009 |
| WO | WO2009043890 | 4/2009 |
| WO | WO2009057079 | 5/2009 |
| WO | WO2009074950 | 6/2009 |
| WO | WO 2010085581 A1 * | 7/2010 |
| WO | WO2010142628 | 12/2010 |

OTHER PUBLICATIONS

PCT Search Report issued Oct. 23, 2012.
Chinese Office Action issued on Feb. 24, 2014.
Chinese Search Report issued Mar. 19, 2014.

* cited by examiner

MANDELAMIDE HETEROCYCLIC COMPOUNDS

CROSS-REFERENCE TO RELATED APPLICATIONS

This application claims the benefit of U.S. Provisional Application Ser. No. 61/327,315 filed Apr. 23, 2010.

FIELD OF THE DISCLOSURE

The present invention generally relates to mandelamide heterocyclic compounds useful as $S1P_1$ agonists. Provided herein are mandelamide heterocyclic compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

BACKGROUND OF THE DISCLOSURES

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Downregulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Patent Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Patent Publication No. 2007/0203100), WO 06/047195, WO 06/100633, WO 06/115188, WO 06/131336, WO 2007/024922, WO 07/109330, WO 07/116866, WO 08/023783 (U.S. Patent Publication No. 2008/0200535), WO 08/029370, WO 08/114157, WO 08/074820, WO 09/043889, WO 09/057079, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

SUMMARY OF THE INVENTION

The present invention provides mandelamide heterocyclic compounds, which are useful as modulators of S1P$_1$ activity, including stereoisomers, salts, solvates, and prodrugs thereof.

The present invention also provides processes and intermediates for making the compounds of the present invention or stereoisomers, salts, or prodrugs thereof.

The present invention also provides pharmaceutical compositions comprising a compound of Formula (I), or stereoisomers, pharmaceutically acceptable salts, or prodrugs thereof; and a pharmaceutically acceptable carrier.

The present invention also provides a method of treating a disease or disorder associated with the activity of G protein-coupled receptor S1P$_1$, the method comprising administering to a mammalian patient a compound of Formula (I) or stereoisomers, pharmaceutically acceptable salts, or prodrugs thereof.

The present invention also provides the compounds of the present invention or stereoisomers, pharmaceutically acceptable salts, or prodrugs thereof, for use in therapy.

The present invention also provides the use of the compounds of the present invention or stereoisomers, pharmaceutically acceptable salts, or prodrugs thereof, for the manufacture of a medicament for the treatment or prophylaxis of S1P$_1$ receptor-related conditions, such as autoimmune and vascular diseases.

The compounds of Formula (I) and compositions comprising the compounds are S1P$_1$ agonists, which are selective for S1P$_1$ activity over S1P$_3$ activity. The compounds of Formula (I) and compositions comprising said compounds may be used in treating, preventing or curing various S1P$_1$ receptor-related conditions while reducing or minimizing the side effects due to S1P$_3$ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION

In a first aspect, the present invention provides compounds of Formula (I):

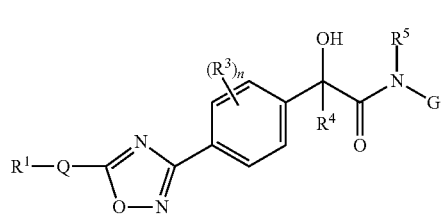

or stereoisomers, salts, or prodrugs thereof, wherein:

Q is

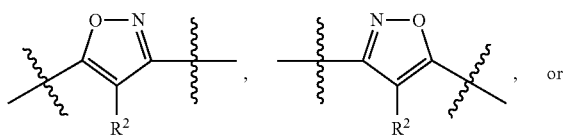

-continued

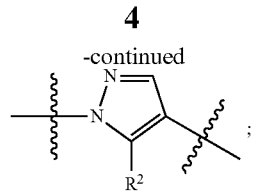

$R^1$ is:
(i) $C_{3-6}$alkyl;
(ii) $C_{3-7}$cycloalkyl substituted with zero to 3 substituents independently selected from halo, —CN, $C_{1-4}$alkyl, $C_{1-4}$alkoxy, $C_{1-3}$fluoroalkyl, $C_{1-3}$chloroalkyl, and/or $C_{1-2}$fluoroalkoxy;
(iii) phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy; or
(iv) pyridinyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

$R^2$ is $C_{1-6}$alkyl, $C_{1-3}$fluoroalkyl, $C_{3-7}$cycloalkyl, or phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

n is zero, 1, or 2;

each $R^3$ is independently $C_{1-3}$alkyl, F, Cl, $C_{1-3}$fluoroalkyl, $C_{1-3}$chloroalkyl, —CN, $C_{1-3}$alkoxy, and/or $C_{1-3}$fluoroalkoxy;

$R^4$ is H or —CH$_3$;

$R^5$ is H or —CH$_3$; and

G is:
(i) H, $C_{1-6}$alkyl, or $C_{3-6}$cycloalkyl;
(ii) $C_{1-6}$alkyl substituted with —NH$_2$, $C_{1-6}$alkoxy, —C(O)OH, —C(O)O($C_{1-6}$alkyl), or —S(O)$_2C_{1-6}$alkyl;
(iii) $C_{1-6}$alkyl substituted with one or more substituents selected from —OH, —CN, and/or cyclopropyl;
(iv) —(CH$_2$)$_{0-3}$—R$^a$, wherein R$^a$ is $C_{3-6}$cycloalkyl substituted with zero to 2 substituents independently selected from —OH, —CN, and/or —CH$_2$OH;
(v) —(CH$_2$)$_{0-3}$—R$^b$, wherein R$^b$ is phenyl substituted with zero to 2 substituents independently selected from —OH, $C_{1-3}$hydroxyalkyl, and/or —S(O)$_2$NH$_2$;
(vi) —(CH$_2$)$_{1-3}$C(O)NR$^c$R$^d$, wherein R$^c$ is H or —CH$_3$; and R$^d$ is H, $C_{1-6}$alkyl, $C_{3-6}$cycloalkyl, $C_{1-6}$hydroxyalkyl, —(CH$_2$)$_{0-2}$(heteroaryl), or —(CH$_2$)$_{0-2}$(heterocyclyl);
(vii) —CH(CN)R$^e$, wherein R$^e$ is phenyl, benzyl, —C(O)NH$_2$, or —C(O)NH($C_{1-3}$alkyl);
(viii) —CHR$^f$C(O)NH(CH$_3$), wherein R$^f$ is $C_{1-6}$alkyl, —CN, phenyl, benzyl, or —CH$_2$CH$_2$-phenyl;
(ix) —(CH$_2$)$_{1-3}$NHC(O)R$^g$, wherein R$^g$ is $C_{1-6}$alkyl or —O($C_{1-6}$alkyl);
(x) —CHR$^h$—(CH$_2$)$_{0-3}$—R$^i$, wherein R$^h$ is H or —CH$_3$, and R$^i$ is heteroaryl;
(xi) —(CH$_2$)$_{0-3}$—R$^j$, wherein R$^j$ is heterocyclyl; or
(xii) —(CH$_2$)$_{1-3}$C(O)—R$^k$, wherein R$^k$ is

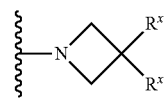

and each $R^x$ is independently selected from H, F, —OH, —CH$_3$, —OCH$_3$, and/or —C(O)OCH$_3$;

wherein each of said heteroaryl groups is substituted with zero to three substituents independently selected from C$_{1-3}$alkyl, —OH, —NH$_2$, phenyl, methylphenyl, benzyl, —CH$_2$CH$_2$-phenyl, pyridinyl, —C(O)OC$_{1-3}$alkyl, and/or —CH$_2$OCH$_3$; and wherein each of said heterocyclyl groups is substituted with zero to three substituents independently selected from C$_{1-3}$alkyl, —OH, —NH$_2$, phenyl, methylphenyl, benzyl, —CH$_2$CH$_2$-phenyl, pyridinyl, —C(O)OC$_{1-3}$alkyl, =O, and/or —CH$_2$OCH$_3$.

One embodiment provides compounds of Formula (II):

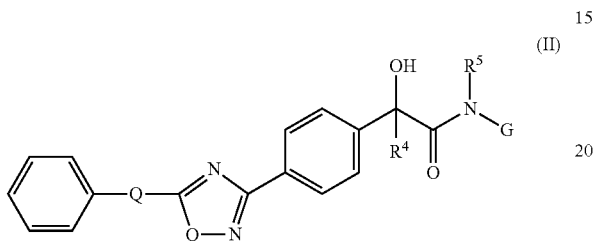

(II)

or stereoisomers, salts, or prodrugs thereof, wherein:

Q is

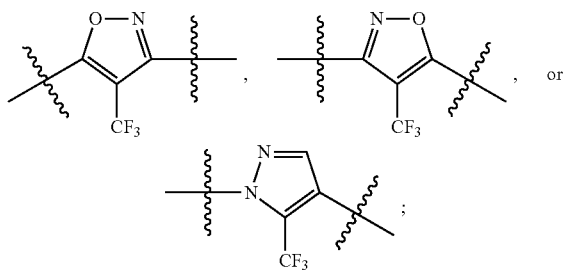

$R^4$ is H or —CH$_3$;
$R^5$ is H or —CH$_3$; and
G is:
(i) H, C$_{1-3}$alkyl, or cyclobutyl;
(ii) C$_{1-2}$alkyl substituted with —NH$_2$, —OCH$_3$, —C(O)OH, —C(O)O(C$_{1-4}$alkyl), or —S(O)$_2$CH$_3$;
(iii) C$_{2-6}$hydroxyalkyl or C$_{1-4}$cyanoalkyl;
(iv) —(CH$_2$)$_{0-2}$—R$^a$, wherein R$^a$ is C$_{3-6}$cycloalkyl substituted with zero or one substituent selected from —OH, —CN, and —CH$_2$OH;
(v) —(CH$_2$)$_{0-2}$—R$^b$, wherein R$^b$ is phenyl substituted with zero or one substituent selected from —OH, C$_{1-2}$hydroxyalkyl, and —S(O)$_2$NH$_2$;
(vi) —(CH$_2$)$_{1-2}$C(O)NR$^c$R$^d$, wherein R$^c$ is H or —CH$_3$; and R$^d$ is H, C$_{1-4}$alkyl, cyclopropyl, —CH$_2$C(CH$_3$)$_2$(OH), —CH$_2$(imidazolyl), N-methylazetidinyl, or

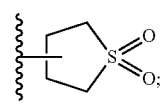

(vii) —CH(CN)R$^e$, wherein R$^e$ is phenyl, benzyl, —C(O)NH$_2$, —C(O)NH(CH$_3$), or —C(O)NH(isopropyl);
(viii) —CHR$^f$C(O)NH(CH$_3$), wherein R$^f$ is —CH$_3$, t-butyl, —CN, or —CH$_2$CH$_2$-phenyl;

(ix) —CH$_2$CH$_2$NHC(O)R$^g$, wherein R$^g$ is —CH$_3$ or —O(t-butyl);
(x) —CHR$^h$—(CH$_2$)$_{0-2}$—R$^i$, wherein R$^h$ is H or —CH$_3$, and R$^i$ is pyrrolyl, thiophenyl, pyrazolyl, imidazolyl, isoxazolyl, oxazolyl, thiazolyl, triazolyl, oxadiazolyl, tetrazolyl, pyridinyl, pyrimidinyl, pyrazinyl, indolyl, or benzimidazolyl, each substituted with zero to three substituents independently selected from C$_{1-3}$alkyl, —NH$_2$, phenyl, methylphenyl, benzyl, —CH$_2$CH$_2$-phenyl, pyridinyl, —C(O)OCH$_2$CH$_3$, and/or —CH$_2$OCH$_3$;
(xi) —(CH$_2$)$_{0-3}$—R$^j$, wherein R$^j$ is azetidinyl, pyrrolidinyl, N-methyl pyrrolidinyl, tetrahydrofuranyl, tetrahydropyranyl, imidazolidinonyl, or

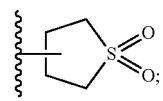

or
(xii) —CH$_2$CH$_2$C(O)—R$^k$, wherein R$^k$ is

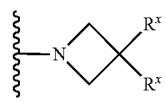

and each $R^x$ is independently selected from H, F, —OH, —CH$_3$, —OCH$_3$, and/or —C(O)OCH$_3$.

One embodiment provides compounds of Formula (III):

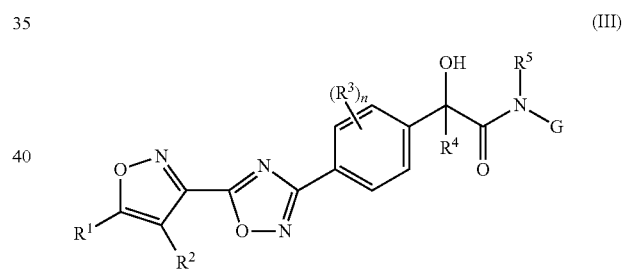

(III)

or stereoisomers, salts, or prodrugs thereof, wherein: $R^1$, $R^2$, $R^3$, $R^4$, $R^5$, and n are defined in the first aspect. Included in this embodiment are compounds in which $R^1$ is phenyl substituted with zero to 3 substituents independently selected from halo, —CN, C$_{1-4}$alkyl, C$_{3-6}$cycloalkyl, C$_{1-4}$alkoxy, C$_{1-3}$fluoroalkyl, C$_{1-3}$chloroalkyl, and/or C$_{1-2}$fluoroalkoxy.

One embodiment provides compounds of Formula (IV):

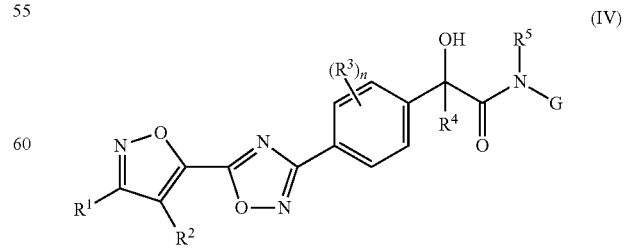

(IV)

or stereoisomers, salts, or prodrugs thereof, wherein: $R^1$, $R^2$, $R^3$, $R^4$, $R^5$, and n are defined in the first aspect. Included in this embodiment are compounds in which R¹ is phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy.

One embodiment provides compounds of Formula (V):

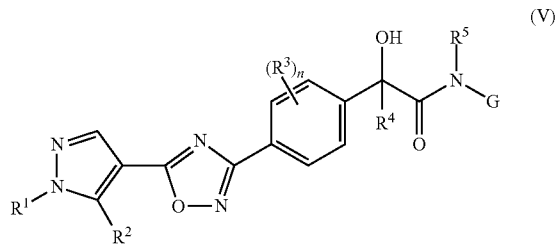

(V)

or stereoisomers, salts, or prodrugs thereof, wherein: R¹, R², R³, R⁴, R⁵, and n are defined in the first aspect. Included in this embodiment are compounds in which R¹ is phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy.

One embodiment provides compounds of Formula (IIIa):

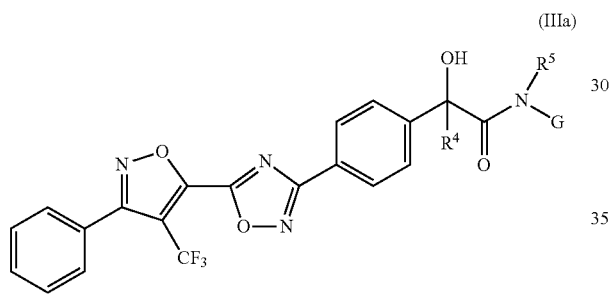

(IIIa)

or stereoisomers, salts, or prodrugs thereof, wherein:
G is:
(i) H, $C_{1-2}$alkyl, or cyclobutyl;
(ii) $C_{1-2}$alkyl substituted with —NH₂, —OCH₃, —C(O)OH, or —S(O)₂CH₃;
(iii) $C_{2-5}$ hydroxyalkyl or $C_{1-4}$cyanoalkyl;
(iv) cyclopropyl substituted with —CN;
(v) —(CH₂)$_{1-2}$C(O)NR$^c$R$^d$, wherein R$^c$ is H or —CH₃, and R$^d$ is H, $C_{1-4}$alkyl, cyclopropyl, —CH₂C(CH₃)₂(OH), —CH₂(imidazolyl), N-methylazetidinyl, or

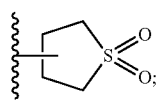

(vi) —CH(CN)R$^e$, wherein R$^e$ is phenyl, benzyl, or —C(O)NH₂;
(vii) —CHR$^f$C(O)NH(CH₃), wherein R$^f$ is —CH₃, t-butyl, —CN, or —CH₂CH₂-phenyl;
(viii) —CH₂CH₂NHC(O)R$^g$, wherein R$^g$ is —CH₃ or —O(t-butyl);
(ix) —CHR$^h$—(CH₂)$_{0-2}$—R$^i$, wherein R$^h$ is H or —CH₃, and R$^i$ is pyrrolyl, thiophenyl, pyrazolyl, imidazolyl, isoxazolyl, oxazolyl, thiazolyl, triazolyl, oxadiazolyl, tetrazolyl, pyridinyl, pyrimidinyl, pyrazinyl, indolyl, or benzimidazolyl, each substituted with zero to three substituents independently selected from $C_{1-3}$alkyl, —NH₂, phenyl, methylphenyl, benzyl, —CH₂CH₂-phenyl, pyridinyl, —C(O)OCH₂CH₃, and/or —CH₂OCH₃;
(x) —(CH₂)$_{0-3}$—R$^j$, wherein R$^j$ is azetidinyl, pyrrolidinyl, tetrahydrofuranyl, tetrahydropyranyl, imidazolidinonyl, or

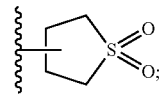

or
(xi) —CH₂CH₂C(O)—R$^k$, wherein R$^k$ is

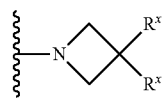

and each R$^x$ is independently H, F, —OH, —CH₃, —OCH₃, and/or —C(O)OCH₃.

One embodiment provides compounds of Formula (IVa):

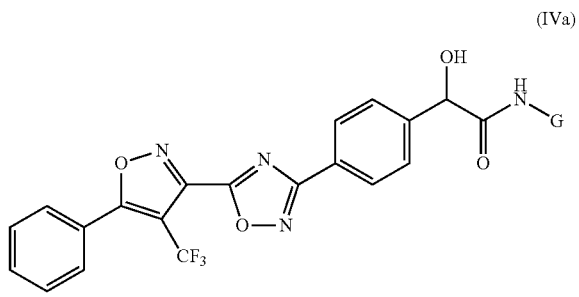

(IVa)

or stereoisomers, salts, or prodrugs thereof, wherein:
G is:
(i) ethyl;
(ii) $C_{2-4}$hydroxyalkyl;
(iii) —CH₂C(O)NHR$^d$, wherein R$^d$ is —CH₃ or —CH₂CH₃; or
(iv) —CH₂(CH₂)$_{0-2}$-R$^i$, wherein R$^i$ is imidazolyl or pyridinyl.

One embodiment provides compounds of Formula (Va):

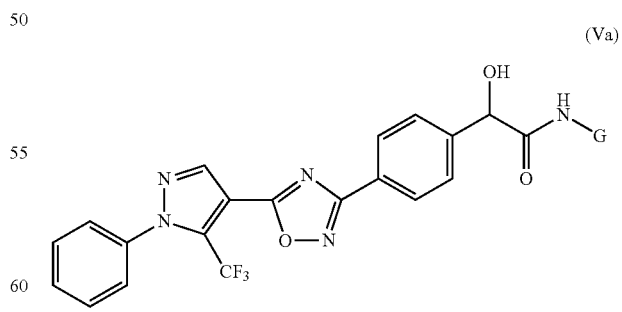

(Va)

or stereoisomers, salts, or prodrugs thereof, wherein:
G is:
(i) $C_{1-3}$alkyl;
(ii) methyl substituted with —C(O)OH or —C(O)O($C_{1-4}$alkyl);

(iii) $C_{2-6}$hydroxyalkyl;
(iv) —$(CH_2)_{0-2}$—$R^a$, wherein $R^a$ is $C_{3-6}$cycloalkyl substituted with zero or one substituent selected from —OH and —$CH_2OH$;
(v) —$(CH_2)_{0-2}$—$R^b$, wherein $R^b$ is phenyl substituted with zero or one substituent selected from —OH, $C_{1-2}$hydroxyalkyl, and —$S(O)_2NH_2$;
(vi) —$CH_2CH_2C(O)NH_2$;
(viii) —$CH_2$-(pyridinyl); or
(vii) —$(CH_2)_2$—$R^j$, wherein $R^j$ is pyrrolidinyl or N-methyl pyrrolidinyl.

One embodiment provides compounds of Formula (I) or stereoisomers, salts, or prodrugs thereof, wherein $R^1$ is $C_{3-6}$alkyl.

One embodiment provides compounds of Formula (I) or stereoisomers, salts, or prodrugs thereof, wherein $R^1$ is $C_{3-7}$cycloalkyl substituted with zero to 3 substituents independently selected from halo, —CN, $C_{1-4}$alkyl, $C_{1-4}$alkoxy, $C_{1-3}$fluoroalkyl, $C_{1-3}$chloroalkyl, and/or $C_{1-2}$fluoroalkoxy.

One embodiment provides compounds of Formula (I) or stereoisomers, salts, or prodrugs thereof, wherein $R^1$ is phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy. Preferably, $R^1$ is phenyl substituted with zero or 1 substituent, wherein said substituent is selected from —CN, —OH, —$CH_3$, —$OCH_3$, —$CF_3$, and —$OCF_3$. The present embodiment includes compounds of Formula (II) in which $R^1$ is unsubstituted phenyl.

One embodiment provides compounds of Formula (I) or stereoisomers, salts, or prodrugs thereof, wherein $R^1$ is pyridinyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy.

One embodiment provides compounds of Formula (I) or stereoisomers, salts, or prodrugs thereof, wherein $R^2$ is $C_{1-2}$alkyl or $C_{1-2}$haloalkyl; preferably $R^2$ is —$CH_3$ or —$CF_3$; and more preferably, $R^2$ is —$CF_3$. The present embodiment includes compounds of Formula (I) in which $R^2$ is —$CF_3$ and $R^1$ is phenyl substituted with zero to 2 substituents independently selected from —CN, —OH, —$CH_3$, —$OCH_3$, —$CF_3$, and/or —$OCF_3$. The present embodiment includes compounds of Formula (II) in which $R^1$ is unsubstituted phenyl and $R^2$ is —$CF_3$.

One embodiment provides compounds of Formula (I) or stereoisomers, salts, or prodrugs thereof, wherein n is zero to 2; and each $R^3$ is independently $C_{1-2}$alkyl, F, Cl, $C_{1-2}$fluoroalkyl, —CN, —OH, $C_{1-2}$alkoxy, and/or $C_{1-2}$fluoroalkoxy. Preferably, n is zero to 2; and each $R^3$ is independently —$CH_3$, F, —$CF_3$, —CN, —OH, —$OCH_3$, and/or —$CF_3$. Preferably, n is zero or 1. Preferably, each $R^3$ is independently —$CH_3$, F, —$CF_3$, —$OCH_3$, and/or —$OCF_3$. The present embodiment includes compounds of Formula (I) in which n is zero. The present embodiment also includes compounds of Formula (II) in which $R^1$ is phenyl, $R^2$ is —$CF_3$, and n is zero.

One embodiment provides compounds of Formula (I) or stereoisomers, salts, or prodrugs thereof, wherein $R^4$ is H. The present embodiment also includes compounds of Formula (II) in which $R^1$ is phenyl, $R^2$ is —$CF_3$, n is zero, and $R^4$ is H.

One embodiment provides compounds of Formula (I) or stereoisomers, salts, or prodrugs thereof, wherein $R^5$ is H. The present embodiment also includes compounds of Formula (II) in which $R^1$ is phenyl, $R^2$ is —$CF_3$, n is zero, and $R^5$ is H.

One embodiment provides compounds of Formula (I) or stereoisomers, salts, or prodrugs thereof, wherein $R^4$ is H and $R^5$ is H. The present embodiment also includes compounds of Formula (II) in which $R^1$ is phenyl, $R^2$ is —$CF_3$, n is zero, $R^4$ is H, and $R^5$ is H.

One embodiment provides compounds of Formula (I) or stereoisomers, salts, or prodrugs thereof, wherein G is H, $C_{1-6}$alkyl, or $C_{3-6}$cycloalkyl; and preferably, G is H, $C_{1-3}$alkyl, or cyclobutyl. The present embodiment also includes compounds of Formula (II) wherein $R^1$ is phenyl, $R^2$ is —$CF_3$, n is zero, and G is H, $C_{1-3}$alkyl, or cyclobutyl. Also, included in this embodiment are compounds of Formula (II) in which $R^4$ is H and $R^5$ is H.

One embodiment provides compounds of Formula (I) or stereoisomers, salts, or prodrugs thereof, wherein G is $C_{1-6}$alkyl substituted with —$NH_2$, $C_{1-6}$alkoxy, —$C(O)OH$, —$C(O)O(C_{1-6}$alkyl), or —$S(O)_2C_{1-6}$alkyl; and preferably G is $C_{1-2}$alkyl substituted with —$NH_2$, —$OCH_3$, —$C(O)OH$, —$C(O)O(C_{1-4}$alkyl), or —$S(O)_2CH_3$. The present embodiment includes compounds of Formula (II) wherein $R^1$ is phenyl, $R^2$ is —$CF_3$, n is zero, and G is $C_{1-2}$alkyl substituted with —$NH_2$, —$OCH_3$, —$C(O)OH$, —$C(O)O(C_{1-4}$alkyl), or —$S(O)_2CH_3$. Also, included in this embodiment are compounds of Formula (II) in which $R^4$ is H and $R^5$ is H.

One embodiment provides compounds of Formula (I) or stereoisomers, salts, or prodrugs thereof, wherein G is $C_{1-6}$alkyl substituted with one or more substituents selected from —OH, —CN, and/or cyclopropyl; preferably G is $C_{1-6}$alkyl substituted with one or more —OH or G is $C_{1-6}$alkyl substituted with one or more —CN; and more preferably G is $C_{2-6}$hydroxyalkyl or $C_{1-4}$cyanoalkyl. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$(CH_2)_{0-3}$—$R^a$, wherein $R^a$ is $C_{3-6}$cycloalkyl substituted with zero to 2 substituents independently selected from —OH, —CN, and/or —$CH_2OH$; and preferably, G is —$(CH_2)_{0-2}$—$R^a$, wherein $R^a$ is $C_{3-6}$cycloalkyl substituted with zero or one substituent selected from —OH, —CN, and —$CH_2OH$. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$(CH_2)_{0-3}$—$R^b$, wherein $R^b$ is phenyl substituted with zero to 2 substituents independently selected from —OH, $C_{1-3}$hydroxyalkyl, and/or —$S(O)_2NH_2$; and preferably, G is —$(CH_2)_{0-2}$—$R^b$, wherein $R^b$ is phenyl substituted with zero or one substituent selected from —OH, $C_{1-2}$hydroxyalkyl, and —$S(O)_2NH_2$. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$(CH_2)_{1-3}C(O)NR^cR^d$, wherein $R^c$ is H or —$CH_3$, and $R^d$ is H, $C_{1-6}$alkyl, $C_{3-6}$cycloalkyl, $C_{1-6}$hydroxyalkyl, —$(CH_2)_{0-2}$(heteroaryl), or —$(CH_2)_{0-2}$(heterocyclyl); and preferably, G is —$(CH_2)_{1-2}C(O)NR^cR^d$, wherein $R^c$ is H or —$CH_3$, and $R^d$ is H, $C_{1-4}$alkyl, cyclopropyl, —$CH_2C(CH_3)_2(OH)$, —$CH_2$(imidazolyl), N-methylazetidinyl, or

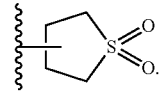

The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —CH(CN)$R^e$, wherein $R^e$ is phenyl, benzyl, —$CH_2CH_2$-phenyl, or —C(O)$NH_2$; and preferably, G is —CH(CN)$R^e$, wherein $R^e$ is phenyl, benzyl, or —C(O)$NH_2$. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$CHR^fC(O)NH(CH_3)$, wherein $R^f$ is $C_{1-6}$alkyl, —CN, phenyl, benzyl, or —$CH_2CH_2$-phenyl; and preferably, $R^f$ is —$CH_3$, t-butyl, —CN, or —$CH_2CH_2$-phenyl. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$(CH_2)_{1-3}NHC(O)R^g$, wherein $R^g$ is $C_{1-6}$alkyl; and G is —$CH_2CH_2NHC(O)R^g$, wherein $R^g$ is —$CH_3$ or —O(t-butyl). The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$CHR^h$—$(CH_2)_{0-3}$—$R^i$, wherein $R^h$ is H or —$CH_3$, and $R^i$ is heteroaryl substituted with zero to three substituents independently selected from $C_{1-3}$alkyl, —OH, —$NH_2$, phenyl, methylphenyl, benzyl, —$CH_2CH_2$-phenyl, pyridinyl, —C(O)O$C_{1-3}$alkyl, and/or —$CH_2OCH_3$. Preferably, G is —$CHR^h$—$(CH_2)_{0-2}$—$R^i$, wherein $R^h$ is H or —$CH_3$, and $R^i$ is pyrrolyl, thiophenyl, pyrazolyl, imidazolyl, isoxazolyl, oxazolyl, thiazolyl, triazolyl, oxadiazolyl, tetrazolyl, pyridinyl, pyrimidinyl, pyrazinyl, indolyl, or benzimidazolyl, each substituted with zero to three substituents independently selected from $C_{1-3}$alkyl, —$NH_2$, phenyl, methylphenyl, benzyl, —$CH_2CH_2$-phenyl, pyridinyl, —C(O)O$CH_2CH_3$, and/or —$CH_2OCH_3$. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$(CH_2)_{0-3}$—$R^j$, wherein $R^j$ is heterocyclyl substituted with zero to three substituents independently selected from $C_{1-3}$alkyl, —OH, —$NH_2$, phenyl, methylphenyl, benzyl, —$CH_2CH_2$-phenyl, pyridinyl, —C(O)O$C_{1-3}$alkyl, =O, and/or —$CH_2OCH_3$. Preferably, G is —$(CH_2)_{0-3}$—$R^j$, wherein $R^j$ is azetidinyl, pyrrolidinyl, N-methyl pyrrolidinyl, tetrahydrofuranyl, tetrahydropyranyl, imidazolidinonyl, or

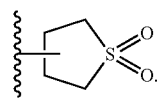

The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$(CH_2)_{1-3}C(O)$—$R^k$, wherein $R^k$ is

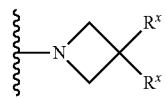

and each $R^x$ is independently H, F, —OH, —$CH_3$, —$OCH_3$, and/or —C(O)$OCH_3$; and preferably, G is —$CH_2CH_2C(O)$—$R^k$, wherein $R^k$ is

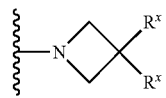

and each $R^x$ is independently H, F, —OH, —$CH_3$, —$OCH_3$, and/or —C(O)$OCH_3$. The present embodiment includes compounds of Formula (II) wherein $R^1$ is phenyl, $R^2$ is —$CF_3$, n is zero, and G is $C_{2-6}$hydroxyalkyl or $C_{1-4}$cyanoalkyl.

One embodiment provides compounds of Formula (I) or stereoisomers, salts, or prodrugs thereof, wherein G is —$CH_2CH_2OH$. The present embodiment includes compounds of Formula (II) wherein $R^1$ is phenyl, $R^2$ is —$CF_3$, n is zero, $R^4$ is H, and $R^5$ is H. Compounds of this embodiment, include, for example, a compound is selected from:

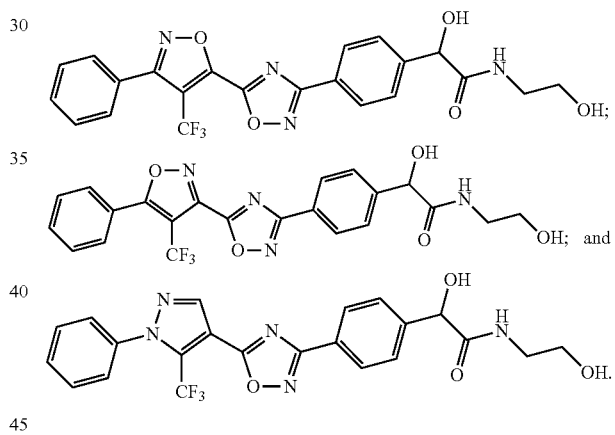

One embodiment provides a compound of Formula (I) or stereoisomers, salts, or prodrugs thereof, wherein G is $C_{3-6}$cycloalkyl substituted with zero or one substituent selected from —CN. The present embodiment includes compounds of Formula (II) wherein $R^1$ is phenyl, $R^2$ is —$CF_3$, n is zero, $R^4$ is H, and $R^5$ is H. One compound of this embodiment is:

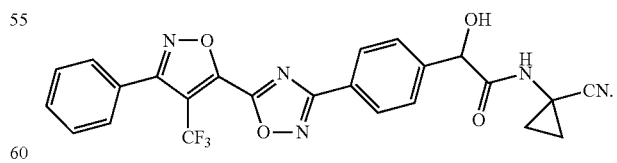

One embodiment provides a compound of Formula (I) or stereoisomers, salts, or prodrugs thereof, wherein G is $C_{1-4}$cyanoalkyl. The present embodiment includes compounds of Formula (II) wherein $R^1$ is phenyl, $R^2$ is —$CF_3$, n is zero, $R^4$ is H, and $R^5$ is H. One compound of this embodiment is:

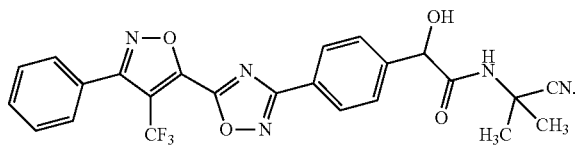 [SMILES: CC(C)(C#N)NC(=O)C(O)c1ccc(-c2noc(-c3onc(-c4ccccc4)c3C(F)(F)F)n2)cc1]

One embodiment provides a compound of Formula (Ia):

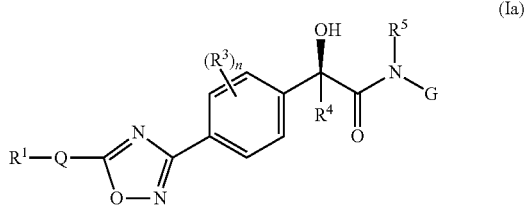

or salts or prodrugs thereof, wherein R¹, R², R³, R⁴, R⁵, n, Q, and G are defined in the first aspect of the invention hereinabove. The present embodiment includes compounds of Formula (Ia) wherein R¹ is phenyl, R² is —CF₃, n is zero, R⁴ is H, and R⁵ is H.

One embodiment provides a compound of Formula (Ib):

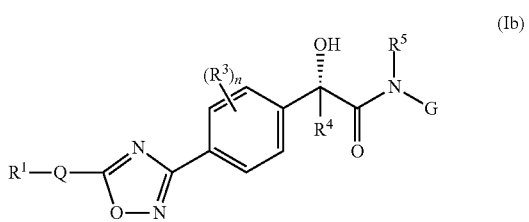

or salts or prodrugs thereof, wherein R¹, R², R³, R⁴, R⁵, n, Q, and G are defined in the first aspect of the invention hereinabove. The present embodiment includes compounds of Formula (Ib) wherein R¹ is phenyl, R² is —CF₃, n is zero, R⁴ is H, and R⁵ is H.

One embodiment provides a compound of Formula (III) or stereoisomers, salts, or prodrugs thereof, wherein said compound is selected from: 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (1); N-(2-amino-2-oxoethyl)-2-hydroxy-2-(4-(5-(3-phenyl-4-(trifluoromethyl)isoxazol-5-yl)-1,2,4-oxadiazol-3-yl)phenyl)acetamide (2); 2-hydroxy-N-(2-hydroxyethyl)-2-(4-(5-(3-phenyl-4-(trifluoromethyl)isoxazol-5-yl)-1,2,4-oxadiazol-3-yl)phenyl)acetamide (3); 3-(2-hydroxy-2-(4-(5-(3-phenyl-4-(trifluoromethyl)isoxazol-5-yl)-1,2,4-oxadiazol-3-yl)phenyl)acetamido)propanoic acid (4); N-(cyanomethyl)-2-hydroxy-2-(4-(5-(3-phenyl-4-(trifluoromethyl)isoxazol-5-yl)-1,2,4-oxadiazol-3-yl)phenyl)acetamide (5); 3-(2-hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (6); 2-hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide (7); 2-hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide (8); N-((4H-1,2,4-triazol-3-yl)methyl)-2-hydroxy-2-(4-(5-(3-phenyl-4-(trifluoromethyl)isoxazol-5-yl)-1,2,4-oxadiazol-3-yl)phenyl)acetamide (9); 2-hydroxy-N-((5-methyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (10); 2-hydroxy-2-(4-(5-(3-phenyl-4-(trifluoromethyl)isoxazol-5-yl)-1,2,4-oxadiazol-3-yl)phenyl)acetamide (11); N-(2-(ethylamino)-2-oxoethyl)-2-hydroxy-2-(4-(5-(3-phenyl-4-(trifluoromethyl)isoxazol-5-yl)-1,2,4-oxadiazol-3-yl)phenyl)acetamide (12); N-ethyl-2-hydroxy-2-(4-(5-(3-phenyl-4-(trifluoromethyl)isoxazol-5-yl)-1,2,4-oxadiazol-3-yl)phenyl)acetamide (13); N-(cyanomethyl)-2-hydroxy-2-(4-(5-(3-phenyl-4-(trifluoromethyl)isoxazol-5-yl)-1,2,4-oxadiazol-3-yl)phenyl)acetamide (14); N-(3-(1H-imidazol-1-yl)propyl)-2-hydroxy-2-(4-(5-(3-phenyl-4-(trifluoromethyl)isoxazol-5-yl)-1,2,4-oxadiazol-3-yl)phenyl)acetamide-TFA (15); 2-hydroxy-N-methyl-2-(4-(5-(3-phenyl-4-(trifluoromethyl)isoxazol-5-yl)-1,2,4-oxadiazol-3-yl)phenyl)acetamide (16); N-((1H-imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide-TFA (17); 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (18); 2-hydroxy-N-((1-methyl-1H-imidazol-4-yl)methyl)-2-(4-(5-(3-phenyl-4-(trifluoromethyl)isoxazol-5-yl)-1,2,4-oxadiazol-3-yl)phenyl)acetamide-TFA (19); 2-hydroxy-N-((1-methyl-1H-imidazol-5-yl)methyl)-2-(4-(5-(3-phenyl-4-(trifluoromethyl)isoxazol-5-yl)-1,2,4-oxadiazol-3-yl)phenyl)acetamide-TFA (20); 2-hydroxy-N-(3-hydroxy-3-methylbutyl)-2-(4-(5-(3-phenyl-4-(trifluoromethyl)isoxazol-5-yl)-1,2,4-oxadiazol-3-yl)phenyl)acetamide (21); 3-(2-hydroxy-2-(4-(5-(3-phenyl-4-(trifluoromethyl)isoxazol-5-yl)-1,2,4-oxadiazol-3-yl)phenyl)acetamido)propanoic acid (22); 2-hydroxy-2-(4-(5-(3-phenyl-4-(trifluoromethyl)isoxazol-5-yl)-1,2,4-oxadiazol-3-yl)phenyl)-N-(3-(pyrrolidin-1-yl)propyl)acetamide (23); N-ethyl-2-hydroxy-N-methyl-2-(4-(5-(3-phenyl-4-(trifluoromethyl)isoxazol-5-yl)-1,2,4-oxadiazol-3-yl)phenyl)acetamide (24); (2S)-2-(2-hydroxy-2-(4-(5-(3-phenyl-4-(trifluoromethyl)isoxazol-5-yl)-1,2,4-oxadiazol-3-yl)phenyl)acetamido)-N,3,3-trimethylbutanamide (25); (2S)-2-(2-hydroxy-2-(4-(5-(3-phenyl-4-(trifluoromethyl)isoxazol-5-yl)-1,2,4-oxadiazol-3-yl)phenyl)acetamido)-N-methyl-4-phenylbutanamide (26); 2-hydroxy-2-(4-(5-(3-phenyl-4-(trifluoromethyl)isoxazol-5-yl)-1,2,4-oxadiazol-3-yl)phenyl)-N—((S)-tetrahydrofuran-3-yl)acetamide (27); 2-hydroxy-2-(4-(5-(3-phenyl-4-(trifluoromethyl)isoxazol-5-yl)-1,2,4-oxadiazol-3-yl)phenyl)-N-(tetrahydro-2H-pyran-4-yl)acetamide (28); 2-hydroxy-2-(4-(5-(3-phenyl-4-(trifluoromethyl)isoxazol-5-yl)-1,2,4-oxadiazol-3-yl)phenyl)-N—((R)-tetrahydrofuran-3-yl)acetamide (29); N-(azetidin-3-yl)-2-hydroxy-2-(4-(5-(3-phenyl-4-(trifluoromethyl)isoxazol-5-yl)-1,2,4-oxadiazol-3-yl)phenyl)acetamide-TFA (30); 2-hydroxy-2-(4-(5-(3-phenyl-4-(trifluoromethyl)isoxazol-5-yl)-1,2,4-oxadiazol-3-yl)phenyl)-N-(3,3-dioxide-tetrahydrothiophen-3-yl)acetamide (31); 2-(2-hydroxy-2-(4-(5-(3-phenyl-4-(trifluoromethyl)isoxazol-5-yl)-1,2,4-oxadiazol-3-yl)phenyl)acetamido)-N-methylpropanamide (32); 2-hydroxy-N-(2-(1-methylazetidin-3-ylamino)-2-oxoethyl)-2-(4-(5-(3-phenyl-4-(trifluoromethyl)isoxazol-5-yl)-1,2,4-oxadiazol-3-yl)phenyl)acetamide (33); 2-hydroxy-2-(4-(5-(3-phenyl-4-(trifluoromethyl)isoxazol-5-yl)-1,2,4-oxadiazol-3-yl)phenyl)-N-(pyridin-2-ylmethyl)acetamide (34); 2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide (35); 2-hydroxy-N-(2-oxo-2-(1,1-dioxide-tetrahydrothiophen-3-ylamino)ethyl)-2-(4-(5-(3-phenyl-4-(trifluoromethyl)isoxazol-5-yl)-1,2,4-oxadiazol-3-yl)phenyl)acetamide (36); 2-hydroxy-2-(4-(5-(3-phenyl-4-

(trifluoromethyl)isoxazol-5-yl)-1,2,4-oxadiazol-3-yl)phenyl)-N-(2-(thiazol-4-yl)ethyl)acetamide (37); 2-hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (38); N—((R)-1-cyanoethyl)-2-hydroxy-2-(4-(5-(3-phenyl-4-(trifluoromethyl)isoxazol-5-yl)-1,2,4-oxadiazol-3-yl)phenyl)acetamide (39); N—((S)-1-cyanoethyl)-2-hydroxy-2-(4-(5-(3-phenyl-4-(trifluoromethyl)isoxazol-5-yl)-1,2,4-oxadiazol-3-yl)phenyl)acetamide (40); N-(1-cyanocyclopropyl)-2-hydroxy-2-(4-(5-(3-phenyl-4-(trifluoromethyl)isoxazol-5-yl)-1,2,4-oxadiazol-3-yl)phenyl)acetamide (41); N-(1,3-dihydroxypropan-2-yl)-2-hydroxy-2-(4-(5-(3-phenyl-4-(trifluoromethyl)isoxazol-5-yl)-1,2,4-oxadiazol-3-yl)phenyl)acetamide (42); N-(2-cyanopropan-2-yl)-2-hydroxy-2-(4-(5-(3-phenyl-4-(trifluoromethyl)isoxazol-5-yl)-1,2,4-oxadiazol-3-yl)phenyl)acetamide (43); N—(S)-1-cyano-2-methylpropyl)-2-hydroxy-2-(4-(5-(3-phenyl-4-(trifluoromethyl)isoxazol-5-yl)-1,2,4-oxadiazol-3-yl)phenyl)acetamide (44); N—((R)-1-cyano-2-methylpropyl)-2-hydroxy-2-(4-(5-(3-phenyl-4-(trifluoromethyl)isoxazol-5-yl)-1,2,4-oxadiazol-3-yl)phenyl)acetamide (45); N—((S)-1-cyanoethyl)-2-hydroxy-2-(4-(5-(3-phenyl-4-(trifluoromethyl)isoxazol-5-yl)-1,2,4-oxadiazol-3-yl)phenyl)acetamide (46); 2-hydroxy-N—((S)-2-hydroxypropyl)-2-(4-(5-(3-phenyl-4-(trifluoromethyl)isoxazol-5-yl)-1,2,4-oxadiazol-3-yl)phenyl)acetamide (47); N-(2,3-dihydroxypropyl)-2-hydroxy-2-(4-(5-(3-phenyl-4-(trifluoromethyl)isoxazol-5-yl)-1,2,4-oxadiazol-3-yl)phenyl)acetamide (48); 2-hydroxy-N-(3-hydroxypropyl)-2-(4-(5-(3-phenyl-4-(trifluoromethyl)isoxazol-5-yl)-1,2,4-oxadiazol-3-yl)phenyl)acetamide (49); 2-hydroxy-N-(2-methoxyethyl)-2-(4-(5-(3-phenyl-4-(trifluoromethyl)isoxazol-5-yl)-1,2,4-oxadiazol-3-yl)phenyl)acetamide (50); tert-butyl 2-(2-hydroxy-2-(4-(5-(3-phenyl-4-(trifluoromethyl)isoxazol-5-yl)-1,2,4-oxadiazol-3-yl)phenyl)acetamido)ethylcarbamate (51); N-(2-aminoethyl)-2-hydroxy-2-(4-(5-(3-phenyl-4-(trifluoromethyl)isoxazol-5-yl)-1,2,4-oxadiazol-3-yl)phenyl)acetamide, TFA (52); N-(2-acetamidoethyl)-2-hydroxy-2-(4-(5-(3-phenyl-4-(trifluoromethyl)isoxazol-5-yl)-1,2,4-oxadiazol-3-yl)phenyl)acetamide (59); 2-hydroxy-N-(2-hydroxyethyl)-2-(4-(5-(3-phenyl-4-(trifluoromethyl)isoxazol-5-yl)-1,2,4-oxadiazol-3-yl)phenyl)acetamide (71); 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (72); N-((2-aminothiazol-4-yl)methyl)-2-hydroxy-2-(4-(5-(3-phenyl-4-(trifluoromethyl)isoxazol-5-yl)-1,2,4-oxadiazol-3-yl)phenyl)acetamide-TFA (73); 3-(2-hydroxy-2-(4-(5-(3-phenyl-4-(trifluoromethyl)isoxazol-5-yl)-1,2,4-oxadiazol-3-yl)phenyl)acetamido)-N,N-dimethylpropanamide (74); 3-(2-hydroxy-2-(4-(5-(3-phenyl-4-(trifluoromethyl)isoxazol-5-yl)-1,2,4-oxadiazol-3-yl)phenyl)acetamido)-N-methylpropanamide (75); N-ethyl-3-(2-hydroxy-2-(4-(5-(3-phenyl-4-(trifluoromethyl)isoxazol-5-yl)-1,2,4-oxadiazol-3-yl)phenyl)acetamido)propanamide (76); 3-(2-hydroxy-2-(4-(5-(3-phenyl-4-(trifluoromethyl)isoxazol-5-yl)-1,2,4-oxadiazol-3-yl)phenyl)acetamido)-N,N-dimethylpropanamide (77); N-tert-butyl-3-(2-hydroxy-2-(4-(5-(3-phenyl-4-(trifluoromethyl)isoxazol-5-yl)-1,2,4-oxadiazol-3-yl)phenyl)acetamido)propanamide (78); N-cyclopropyl-3-(2-hydroxy-2-(4-(5-(3-phenyl-4-(trifluoromethyl)isoxazol-5-yl)-1,2,4-oxadiazol-3-yl)phenyl)acetamido)propanamide (79); 3-(2-hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (80); N-((1H-imidazol-2-yl)methyl)-3-(2-hydroxy-2-(4-(5-(3-phenyl-4-(trifluoromethyl)isoxazol-5-yl)-1,2,4-oxadiazol-3-yl)phenyl)acetamido)propanamide, TFA (81); 2-hydroxy-2-(4-(5-(3-phenyl-4-(trifluoromethyl)isoxazol-5-yl)-1,2,4-oxadiazol-3-yl)phenyl)-N-(thiophen-3-ylmethyl)acetamide (82); N-((4-amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide (83); 2-hydroxy-2-(4-(5-(3-phenyl-4-(trifluoromethyl)isoxazol-5-yl)-1,2,4-oxadiazol-3-yl)phenyl)-N-((1,3,5-trimethyl-1H-pyrazol-4-yl)methyl)acetamide (84); 2-hydroxy-N-(2-(2-oxoimidazolidin-1-yl)ethyl)-2-(4-(5-(3-phenyl-4-(trifluoromethyl)isoxazol-5-yl)-1,2,4-oxadiazol-3-yl)phenyl)acetamide (85); N-((1H-indol-2-yl)methyl)-2-hydroxy-2-(4-(5-(3-phenyl-4-(trifluoromethyl)isoxazol-5-yl)-1,2,4-oxadiazol-3-yl)phenyl)acetamide (86); N-((1H-tetrazol-5-yl)methyl)-2-hydroxy-2-(4-(5-(3-phenyl-4-(trifluoromethyl)isoxazol-5-yl)-1,2,4-oxadiazol-3-yl)phenyl)acetamide (87); 2-hydroxy-2-(4-(5-(3-phenyl-4-(trifluoromethyl)isoxazol-5-yl)-1,2,4-oxadiazol-3-yl)phenyl)-N-(pyrrolidin-2-ylmethyl)acetamide, TFA (88); N-(2-(1H-imidazol-4-yl)ethyl)-2-hydroxy-2-(4-(5-(3-phenyl-4-(trifluoromethyl)isoxazol-5-yl)-1,2,4-oxadiazol-3-yl)phenyl)acetamide, TFA (89); N-((1H-benzo[d]imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide (90); N-(3-(3,3-difluoroazetidin-1-yl)-3-oxopropyl)-2-hydroxy-2-(4-(5-(3-phenyl-4-(trifluoromethyl)isoxazol-5-yl)-1,2,4-oxadiazol-3-yl)phenyl)acetamide (91); 2-hydroxy-N-(3-(3-hydroxy-3-methylazetidin-1-yl)-3-oxopropyl)-2-(4-(5-(3-phenyl-4-(trifluoromethyl)isoxazol-5-yl)-1,2,4-oxadiazol-3-yl)phenyl)acetamide (92); 2-hydroxy-N-(3-(3-hydroxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (93); N-((4-amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide (94); 2-hydroxy-2-(4-(5-(3-phenyl-4-(trifluoromethyl)isoxazol-5-yl)-1,2,4-oxadiazol-3-yl)phenyl)-N-(2-(thiazol-4-yl)ethyl)acetamide (95); 2-hydroxy-N-(3-(3-methoxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (96); methyl 1-(3-(2-hydroxy-2-(4-(5-(3-phenyl-4-(trifluoromethyl)isoxazol-5-yl)-1,2,4-oxadiazol-3-yl)phenyl)acetamido)propanoyl)azetidine-3-carboxylate (97); 2-hydroxy-2-(4-(5-(3-phenyl-4-(trifluoromethyl)isoxazol-5-yl)-1,2,4-oxadiazol-3-yl)phenyl)-N-(thiazol-2-ylmethyl)acetamide (98); 2-hydroxy-N-(oxazol-2-ylmethyl)-2-(4-(5-(3-phenyl-4-(trifluoromethyl)isoxazol-5-yl)-1,2,4-oxadiazol-3-yl)phenyl)acetamide (99); 2-hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (100); 2-hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (101); 2-hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (102); 2-hydroxy-N-((3-(methoxymethyl)-1,2,4-oxadiazol-5-yl)methyl)-2-(4-(5-(3-phenyl-4-(trifluoromethyl)isoxazol-5-yl)-1,2,4-oxadiazol-3-yl)phenyl)acetamide (103); 2-cyano-2-(2-hydroxy-2-(4-(5-(3-phenyl-4-(trifluoromethyl)isoxazol-5-yl)-1,2,4-oxadiazol-3-yl)phenyl)acetamido)-N-methylacetamide (104); N-(1-cyano-2-phenylethyl)-2-hydroxy-2-(4-(5-(3-phenyl-4-(trifluoromethyl)isoxazol-5-yl)-1,2,4-oxadiazol-3- yl)phenyl)acetamide (105); N-(cyano(phenyl)methyl)-2-hydroxy-2-(4-(5-(3-phenyl-4-(trifluoromethyl)isoxazol-5-yl)-1,2,4-oxadiazol-3-yl)phenyl)acetamide (106); N-(2-amino-1-cyano-2-oxoethyl)-2-hydroxy-2-(4-(5-(3-phenyl-4-(trifluoromethyl)isoxazol-5-yl)-1,2,4-oxadiazol-3-yl)phenyl)acetamide (107); 2-hydroxy-N-(1-(4-methyl-4H-1,2,4-triazol-3-yl)ethyl)-2-(4-(5-(3-phenyl-4-(trifluoromethyl)isoxazol-5-yl)-1,2,4-oxadiazol-3-yl)phenyl)acetamide (108); N-((1,3-dimethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide-TFA (109); 2-hydroxy-N-((5-phenyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (110); N—(S)-1-(1H-imidazol-2-yl)ethyl)-2-hydroxy-2-(4-(5-(3-phenyl-4-(trifluoromethyl)isoxazol-5-yl)-1,2,4-oxadiazol-3-yl)phenyl)acetamide, TFA (111); 2-hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (112); 2-hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (113); 2-hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (114); 2-hydroxy-2-(4-(5-(3-phenyl-4-(trifluoromethyl)isoxazol-5-yl)-1,2,4-oxadiazol-3-yl)phenyl)-N-(2-(pyrazin-2-yl)ethyl)acetamide, TFA (115); N-cyclobutyl-2-hydroxy-2-(4-(5-(3-phenyl-4-(trifluoromethyl)isoxazol-5-yl)-1,2,4-oxadiazol-3-yl)phenyl)acetamide (116); 2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide (117); 2-hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (118); ethyl 5-((2-hydroxy-2-(4-(5-(3-phenyl-4-(trifluoromethyl)isoxazol-5-yl)-1,2,4-oxadiazol-3-yl)phenyl)acetamido)methyl)-1H-1,2,4-triazole-3-carboxylate (119); 2-hydroxy-N-((3-isopropylisoxazol-5-yl)methyl)-2-(4-(5-(3-phenyl-4-(trifluoromethyl)isoxazol-5-yl)-1,2,4-oxadiazol-3-yl)phenyl)acetamide (120); N-((1-ethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide (121); 2-hydroxy-2-(4-(5-(3-phenyl-4-(trifluoromethyl)isoxazol-5-yl)-1,2,4-oxadiazol-3-yl)phenyl)-N-((1-p-tolyl-1H-pyrazol-4-yl)methyl)acetamide (122); N-((1-benzyl-1H-imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide (123); 2-hydroxy-N-((1-phenyl-1H-pyrazol-4-yl)methyl)-2-(4-(5-(3-phenyl-4-(trifluoromethyl)isoxazol-5-yl)-1,2,4-oxadiazol-3-yl)phenyl)acetamide (124); 2-hydroxy-N-((4-phenethyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (125); 2-hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide (126); 2-hydroxy-2-(4-(5-(3-phenyl-4-(trifluoromethyl)isoxazol-5-yl)-1,2,4-oxadiazol-3-yl)phenyl)-N-((5-(pyridin-2-yl)thiophen-2-yl)methyl)acetamide (127); 2-hydroxy-N-((5-phenyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (128); N-((1-benzyl-1H-pyrazol-4-yl)methyl)-2-hydroxy-2-(4-(5-(3-phenyl-4-(trifluoromethyl)isoxazol-5-yl)-1,2,4-oxadiazol-3-yl)phenyl)acetamide (129); N-((1,5-dimethyl-1H-pyrrol-2-yl)methyl)-2-hydroxy-2-(4-(5-(3-phenyl-4-(trifluoromethyl)isoxazol-5-yl)-1,2,4-oxadiazol-3-yl)phenyl)acetamide (130); 2-hydroxy-N-((5-methyl-3-phenylisoxazol-4-yl)methyl)-2-(4-(5-(3-phenyl-4-(trifluoromethyl)isoxazol-5-yl)-1,2,4-oxadiazol-3-yl)phenyl)acetamide (131); 2-hydroxy-N-((1-methyl-1H-pyrrol-2-yl)methyl)-2-(4-(5-(3-phenyl-4-(trifluoromethyl)isoxazol-5-yl)-1,2,4-oxadiazol-3-yl)phenyl)acetamide (132); 2-hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide (133); 2-hydroxy-N-((5-methyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (134); 2-hydroxy-N-(2-hydroxyethyl)-2-(4-(5-(3-phenyl-4-(trifluoromethyl)isoxazol-5-yl)-1,2,4-oxadiazol-3-yl)phenyl)propanamide (159); N-(cyanomethyl)-2-hydroxy-2-(4-(5-(3-phenyl-4-(trifluoromethyl)isoxazol-5-yl)-1,2,4-oxadiazol-3-yl)phenyl)propanamide (160); and 2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)propanamide (161).

One embodiment provides a compound of Formula (III) or stereoisomers, salts, or prodrugs thereof, wherein said compound is selected from: 2-hydroxy-N-(2-hydroxyethyl)-2-(4-(5-(1-phenyl-5-(trifluoromethyl)-1H-pyrazol-4-yl)-1,2,4-oxadiazol-3-yl)phenyl)acetamide (53); 2-hydroxy-N-(3-hydroxypropyl)-2-(4-(5-(1-phenyl-5-(trifluoromethyl)-1H-pyrazol-4-yl)-1,2,4-oxadiazol-3-yl)phenyl)acetamide (54); 2-hydroxy-N-(2-hydroxy-2-methylpropyl)-2-(4-(5-(1-phenyl-5-(trifluoromethyl)-1H-pyrazol-4-yl)-1,2,4-oxadiazol-3-yl)phenyl)acetamide (55); tert-butyl 2-(2-hydroxy-2-(4-(5-(1-phenyl-5-(trifluoromethyl)-1H-pyrazol-4-yl)-1,2,4-oxadiazol-3-yl)phenyl)acetamido)acetate (56); 2-hydroxy-N—((S)-2-hydroxypropyl)-2-(4-(5-(1-phenyl-5-(trifluoromethyl)-1H-pyrazol-4-yl)-1,2,4-oxadiazol-3-yl)phenyl)acetamide (57); 2-(2-hydroxy-2-(4-(5-(1-phenyl-5-(trifluoromethyl)-1H-pyrazol-4-yl)-1,2,4-oxadiazol-3-yl)phenyl)acetamido)acetic acid (58); 2-hydroxy-N-methyl-2-(4-(5-(1-phenyl-5-(trifluoromethyl)-1H-pyrazol-4-yl)-1,2,4-oxadiazol-3-yl)phenyl)acetamide (60); N-ethyl-2-hydroxy-2-(4-(5-(1-phenyl-5-(trifluoromethyl)-1H-pyrazol-4-yl)-1,2,4-oxadiazol-3-yl)phenyl)acetamide (61); 2-hydroxy-N-(2-(1-methylpyrrolidin-2-yl)ethyl)-2-(4-(5-(1-phenyl-5-(trifluoromethyl)-1H-pyrazol-4-yl)-1,2,4-oxadiazol-3-yl)phenyl)acetamide (135); 2-hydroxy-2-(4-(5-(1-phenyl-5-(trifluoromethyl)-1H-pyrazol-4-yl)-1,2,4-oxadiazol-3-yl)phenyl)-N-(2-(pyrrolidin-1-yl)ethyl)acetamide (136); 2-hydroxy-2-(4-(5-(1-phenyl-5-(trifluoromethyl)-1H-pyrazol-4-yl)-1,2,4-oxadiazol-3-yl)phenyl)-N-(pyridin-2-ylmethyl)acetamide (137); 2-hydroxy-2-(4-(5-(1-phenyl-5-(trifluoromethyl)-1H-pyrazol-4-yl)-1,2,4-oxadiazol-3-yl)phenyl)-N-(pyridin-3-ylmethyl)acetamide (138); 2-hydroxy-2-(4-(5-(1-phenyl-5-(trifluoromethyl)-1H-pyrazol-4-yl)-1,2,4-oxadiazol-3-yl)phenyl)-N-(pyridin-4-ylmethyl)acetamide (139); 2-hydroxy-N-(4-(2-hydroxyethyl)phenyl)-2-(4-(5-(1-phenyl-5-(trifluoromethyl)-1H-pyrazol-4-yl)-1,2,4-oxadiazol-3-yl)phenyl)acetamide (140); 2-hydroxy-N-(1-hydroxy-2-methylpropan-2-yl)-2-(4-(5-(1-phenyl-5-(trifluoromethyl)-1H-pyrazol-4-yl)-1,2,4-oxadiazol-3-yl)phenyl)acetamide (141); 2-hydroxy-N-(4-hydroxyphenethyl)-2-(4-(5-(1-phenyl-5-(trifluoromethyl)-1H-pyrazol-4-yl)-1,2,4-oxadiazol-3-yl)phenyl)acetamide (142); 2-hydroxy-2-(4-(5-(1-phenyl-5-(trifluoromethyl)-1H-pyrazol-4-yl)-1,2,4-oxadiazol-3-yl)phenyl)-N-(4-sulfamoylphenethyl)acetamide (143); 2-hydroxy-2-(4-(5-(1-phenyl-5-(trifluoromethyl)-1H-pyrazol-4-yl)-1,2,4-oxadiazol-3-yl)phenyl)-N-(4-sulfamoylbenzyl)acetamide (144); N-(1,3-dihydroxypropan-2-yl)-2-hydroxy-2-(4-(5-(1-phenyl-5-(trifluoromethyl)-1H-pyrazol-4-yl)-1,2,4-oxadiazol-3-yl)phenyl)acetamide (145); 2-hydroxy-2-(4-(5-(1-phenyl-5-(trifluoromethyl)-1H-pyrazol-4-yl)-1,2,4-oxadiazol-3-yl)phenyl)-N-propylacetamide (146); 3-(2-hydroxy-2-(4-(5-(1-phenyl-5-(trifluoromethyl)-1H-pyrazol-4-yl)-1,2,4-oxadiazol-3-yl)phenyl)acetamido)propanamide (147);-

2-hydroxy-N-(4-(hydroxymethyl)benzyl)-2-(4-(5-(1-phenyl-5-(trifluoromethyl)-1H-pyrazol-4-yl)-1,2,4-oxadiazol-3-yl)phenyl)acetamide (148); 2-hydroxy-N-(1-hydroxy-4-methylpentan-2-yl)-2-(4-(5-(1-phenyl-5-(trifluoromethyl)-1H-pyrazol-4-yl)-1,2,4-oxadiazol-3-yl)phenyl)acetamide (149); 2-hydroxy-N-(((1R,2R)-2-hydroxycyclohexyl)methyl)-2-(4-(5-(1-phenyl-5-(trifluoromethyl)-1H-pyrazol-4-yl)-1,2,4-oxadiazol-3-yl)phenyl)acetamide (150); 2-hydroxy-N-((1R,2S)-2-(hydroxymethyl)cyclohexyl)-2-(4-(5-(1-phenyl-5-(trifluoromethyl)-1H-pyrazol-4-yl)-1,2,4-oxadiazol-3-yl)phenyl)acetamide (151); 2-hydroxy-N-(((1S,2R)-2-hydroxycyclohexyl)methyl)-2-(4-(5-(1-phenyl-5-(trifluoromethyl)-1H-pyrazol-4-yl)-1,2,4-oxadiazol-3-yl)phenyl)acetamide (152); 2-hydroxy-N-((1R,2R)-2-(hydroxymethyl)cyclohexyl)-2-(4-(5-(1-phenyl-5-(trifluoromethyl)-1H-pyrazol-4-yl)-1,2,4-oxadiazol-3-yl)phenyl)acetamide (153); 2-hydroxy-N-(4-hydroxybutyl)-2-(4-(5-(1-phenyl-5-(trifluoromethyl)-1H-pyrazol-4-yl)-1,2,4-oxadiazol-3-yl)phenyl)acetamide (154); 2-hydroxy-N-(1-(hydroxymethyl)cyclopentyl)-2-(4-(5-(1-phenyl-5-(trifluoromethyl)-1H-pyrazol-4-yl)-1,2,4-oxadiazol-3-yl)phenyl)acetamide (155); 2-hydroxy-N-(3-hydroxybenzyl)-2-(4-(5-(1-phenyl-5-(trifluoromethyl)-1H-pyrazol-4-yl)-1,2,4-oxadiazol-3-yl)phenyl)acetamide (156); 2-hydroxy-N-(4-hydroxybenzyl)-2-(4-(5-(1-phenyl-5-(trifluoromethyl)-1H-pyrazol-4-yl)-1,2,4-oxadiazol-3-yl)phenyl)acetamide (157); and 2-hydroxy-N-((1r,4r)-4-hydroxycyclohexyl)-2-(4-(5-(1-phenyl-5-(trifluoromethyl)-1H-pyrazol-4-yl)-1,2,4-oxadiazol-3-yl)phenyl)acetamide (158);

One embodiment provides a compound of Formula (III) or stereoisomers, salts, or prodrugs thereof, wherein said compound is selected from: 2-hydroxy-N-(2-hydroxyethyl)-2-(4-(5-(5-phenyl-4-(trifluoromethyl)isoxazol-3-yl)-1,2,4-oxadiazol-3-yl)phenyl)acetamide (62); 2-hydroxy-N—((S)-2-hydroxypropyl)-2-(4-(5-(5-phenyl-4-(trifluoromethyl)isoxazol-3-yl)-1,2,4-oxadiazol-3-yl)phenyl)acetamide (63); 2-hydroxy-N-(2-hydroxy-2-methylpropyl)-2-(4-(5-(5-phenyl-4-(trifluoromethyl)isoxazol-3-yl)-1,2,4-oxadiazol-3-yl)phenyl)acetamide (64); N-(3-(1H-imidazol-1-yl)propyl)-2-hydroxy-2-(4-(5-(5-phenyl-4-(trifluoromethyl)isoxazol-3-yl)-1,2,4-oxadiazol-3-yl)phenyl)acetamide, TFA (65); N-(2-amino-2-oxoethyl)-2-hydroxy-2-(4-(5-(5-phenyl-4-(trifluoromethyl)isoxazol-3-yl)-1,2,4-oxadiazol-3-yl)phenyl)acetamide (66); N-ethyl-2-hydroxy-2-(4-(5-(5-phenyl-4-(trifluoromethyl)isoxazol-3-yl)-1,2,4-oxadiazol-3-yl)phenyl)acetamide (67); 2-hydroxy-2-(4-(5-(5-phenyl-4-(trifluoromethyl)isoxazol-3-yl)-1,2,4-oxadiazol-3-yl)phenyl)-N-(pyridin-3-ylmethyl)acetamide-TFA (68); 2-hydroxy-N-(2-(methylamino)-2-oxoethyl)-2-(4-(5-(5-phenyl-4-(trifluoromethyl)isoxazol-3-yl)-1,2,4-oxadiazol-3-yl)phenyl)acetamide (69); and N-(2-(ethylamino)-2-oxoethyl)-2-hydroxy-2-(4-(5-(5-phenyl-4-(trifluoromethyl)isoxazol-3-yl)-1,2,4-oxadiazol-3-yl)phenyl)acetamide)70).

The compounds of Formula (I) have GTPγS S1P$_1$ EC$_{50}$ values of 5 μM or less as measured by the S1P$_1$ Receptor GTPγS Binding Assay described herein below. Preferably, the compounds of Formula (I) have GTPγS S1P$_1$ EC$_{50}$ values in the range of 0.01 nM to 5 μM, and more preferably, in the range of from 0.01 nM to 1 μM. Other preferred compounds of Formula (I) have GTPγS S1P$_1$ EC$_{50}$ values in the range of from 0.01 nM to 100 nM.

The compounds of Formula (I) are selective for S1P$_1$ activity over S1P$_3$ activity as measured by the selectivity ratio of the GTPγS S1P$_3$ EC$_{50}$ value to the GTPγS S1P$_1$ EC$_{50}$ value. The S1P$_1$ Receptor GTPγS Binding Assay and the S1P$_3$ Binding Assay are described herein below. The compounds of Formula (I) have selectivity ratios (GTPγS S1P$_3$/S1P$_1$) of at least 1.4 or greater, preferably at least 50 or greater, and more preferably at least 100 or greater. For example, suitable compounds of Formula (I) can have selectivity ratios in the range of from 50 to 50,000. Other suitable compounds of Formula (I) can have selectivity ratios in the range of from 100 to 50,000.

In one embodiment, the compounds of Formula (I) are provided having GTPγS S1P$_1$ EC$_{50}$ values in the range of from 0.01 nM to 100 nM and selectivity ratios (GTPγS S1P$_3$/S1P$_1$) of at least 50, and more preferably, at least 100.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. For example, "$C_1$-$C_6$alkylene" denotes straight and branched chain alkylene groups with one to six carbon atoms. Further, for example, "$C_{0-4}$alkylene" denotes a bond and straight and branched chain alkylene groups with one to four carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$), and 2,2,2-trfluoroethyl (—$CH_2CF_3$). When numbers appear in a subscript after the symbol "C", the subscript defines with more specificity the number of carbon atoms that a particular haloalkyl group may contain. For example, "$C_{1-4}$haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$hydroxyalkyl.

The term "cyano" refers to the group —CN.

The term "cyanoalkyl" includes both branched and straight-chain saturated alkyl groups substituted with one or more cyano groups. For example, "cyanoalkyl" includes —$CH_2CN$, —$CH_2CH_2CN$, —$C(CH_3)_2CN$, and $C_{1-4}$cyanoalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-4}$alkoxy" is intended to include $C_1$, $C_2$, $C_3$, and $C_4$ alkoxy groups.

"Fluoroalkoxy" and "-O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, and indanyl.

The term "benzyl", as used herein, refers to a methyl group in which one of the hydrogen atoms is replaced by a phenyl group.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, Mack Publishing Company, Easton, Pa., p. 1418 (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, Bundgaard, H. ed., Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, and chronic bacterial infection.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

The methods of treating $S1P_1$-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the $S1P_1$ receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (ENBREL®), adalimumab (HUMIRA®), LT, Il-1 such as anakinra (KINERET®) (an IL-1 receptor antagonist), IL-2, IL-4, IL-5, Il -6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment, and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley & Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, the oxadiazole compounds of the present invention (1.7) may be prepared through the reaction of carboxylic acids (1.1) with N'-hydroxybenzimidamides (1.5) (prepared from the corresponding benzonitriles (1.4)) using a variety of coupling reagents (e.g., EDC, HOBt, BOP, BOP-Cl). Alternatively, the N'-hydroxybenzimidamides may be reacted with acid fluoride (1.2) or acid chloride compounds (1.3). In each case, the initially formed N'-acyloxybenzimidamides (1.6) may spontaneously convert to the oxadiazoles under the reaction conditions. In cases where the N'-acyloxybenzimidamide (1.6) does not cyclize spontaneously, it may be isolated and subjected to reaction conditions to effect the cyclodehydration to (1.7). Such conditions include heating (either conventional or microwave), or treatment with fluoride source (such as tetrabutylammonium fluoride).

Scheme 1

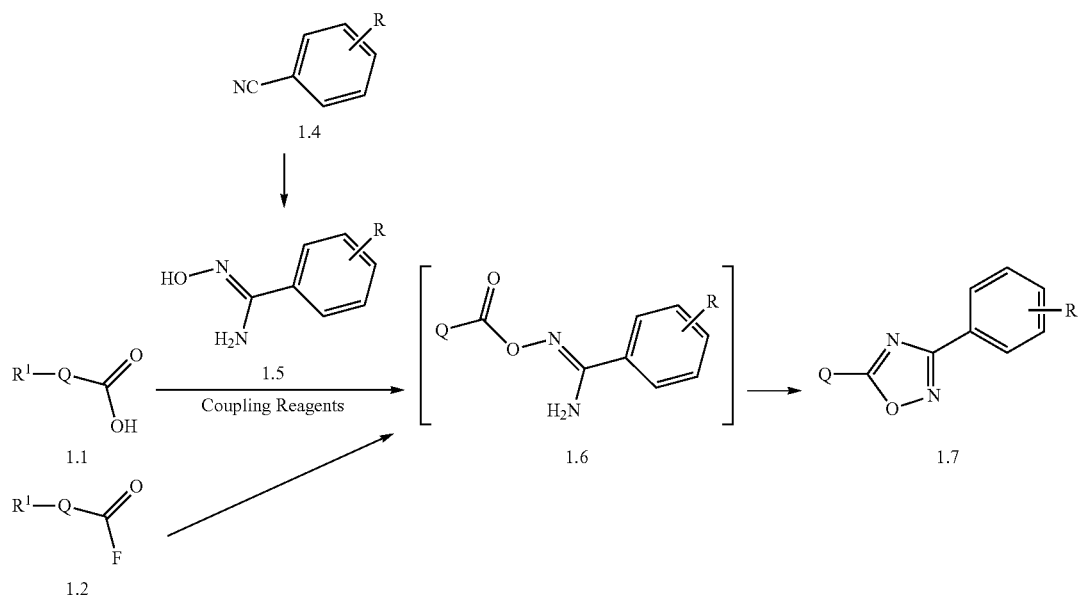

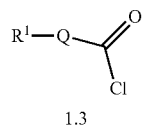
1.3

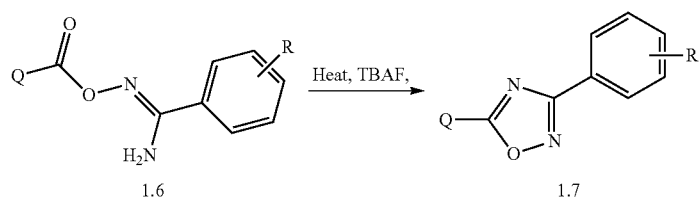
1.6 → 1.7 (Heat, TBAF,)

As shown in Scheme 2, compounds of Formula (I) may be prepared through the reaction of acids (1.1), acid fluorides (1.2), or acid chlorides (1.3) with a fully functionalized N'-acyloxybenzimidamides (2.1) and (2.2) via means described above to produce compounds (2.3) and (2.4), respectively. In many cases, the silyl protection of (2.2) is not needed and the sequence of reactions in Scheme 2 may be performed with (2.1) to provide compounds of Formula (I). Hence, the ester of (2.3) may be hydrolyzed to give (2.5). For example, when $R_1$ is an alkyl ester, treatment with a strong acid in water (e.g., HCl) or hydrolysis with base (e.g., NaOH) will provide the corresponding carboxylic acid (2.5). This carboxylate (2.5) may then be coupled via a variety of coupling reagents (e.g., EDC, HOBt, BOP, and BOP-Cl) with amine (2.7) to directly give compounds of Formula (I). If a silyl protecting group (X=alkyl$_3$Si) was used, compound (2.4) may be hydrolyzed to give (2.6). This carboxylate (2.6) may then be coupled via a variety of coupling reagents (e.g., EDC, HOBt, BOP, BOP-Cl) with amine (2.7) followed by a silyl deprotection step ("step 2") to provide compounds of Formula (I). For example, when X is a trialkylsilyl protecting group, it may be silyl deprotected using strong aqueous acid or tetrabutylammonium fluoride to provide compounds of Formula (I).

Scheme 2

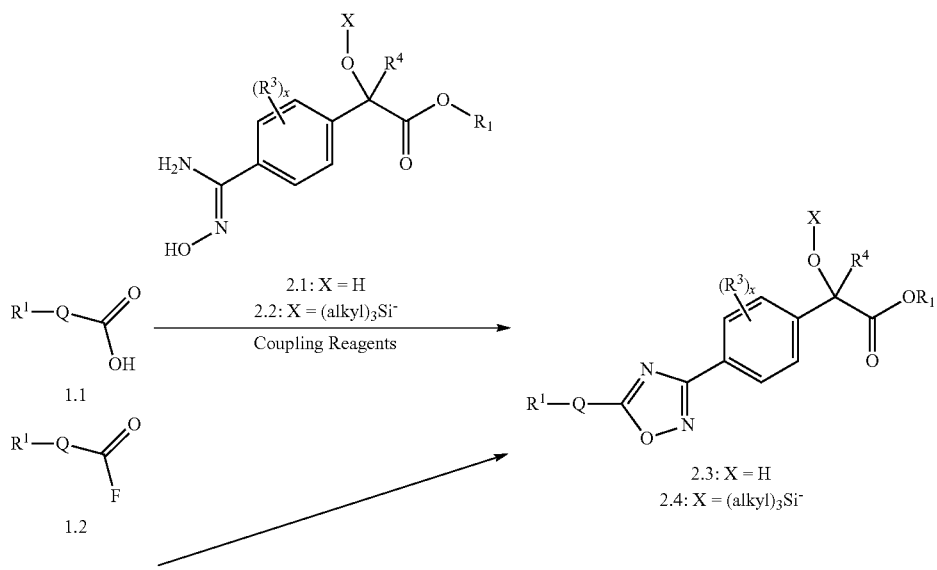

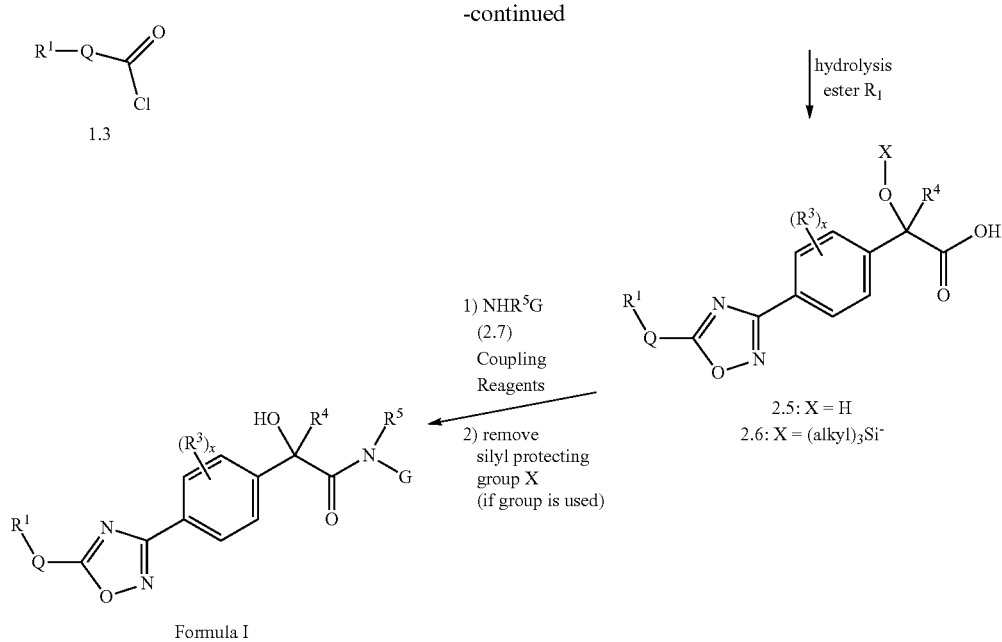

Alternatively, advanced intermediates (2.1) and (2.2) may also be produced as described in Scheme 3. The ketoester (3.1) may be reduced, for example, with $NaBH_4$ (or hydrogenation) to provide the hydroxyester (3.2, $R^4$=H) (for an asymmetric reduction of this type, see: Sun, X. et al., *Chem. Eur. J.*, 15:7302 (2009)). This hydroxyester (3.2, $R^4$=H) may be reacted with hydroxylamine or its salts to provide N'-hydroxybenzimidamide (2.1, $R^4$=H). For the synthesis of another N'-hydroxybenzimidamide (2.2, $R^4$=H), the hydroxyester (3.2, $R^4$=H) may be protected, for example, with a trialkylsilyl chloride to give silyl ether (3.3, $R^4$=H). This silyl ether (3.3, $R^4$50 H) may be reacted with hydroxylamine or its salts to provide N'-hydroxybenzimidamide (2.2, $R^4$=H).

In addition, the tertiary alcohol (2.1, $R^4$=alkyl) may also be produced as shown in Scheme 3. Hence, the ketoester (3.1) may be reacted with an organometallic reagent, for example with $TiMeCl_3$ (see, Reetz, M. T. et al., *Tetrahedron*, 42:2931-2935 (1986)), to provide hydroxyester (3.2, $R^4$=Me) (for an asymmetric addition of this type, see: Yazaki, R. et al., *J. Am. Chem. Soc.*, 131:3195-3197 (2009)). This hydroxyester (3.2, $R^4$=alkyl) may be reacted with hydroxylamine or its salts to provide N'-hydroxybenzimidamide (2.1, $R^4$=alkyl). For the synthesis of the silyl ether analogue, the hydroxyester (3.2, $R^4$=alkyl) may be protected, for example, with a trialkylsilyl chloride to give the silyl ether (3.3, $R^4$=alkyl). This silyl ether (3.3, $R^4$=alkyl) may be reacted with hydroxylamine or its salts to provide N'-hydroxybenzimidamide (2.2, $R^4$=alkyl).

Scheme 3

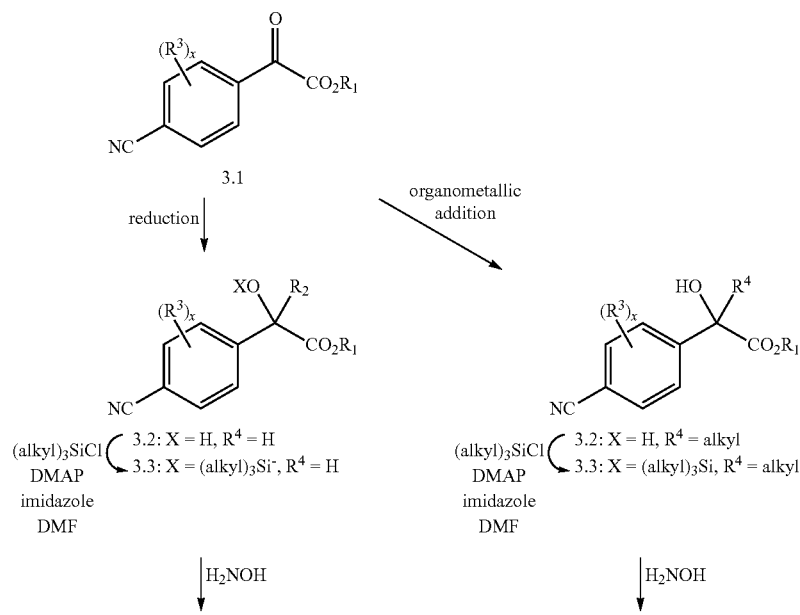

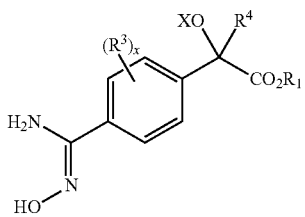 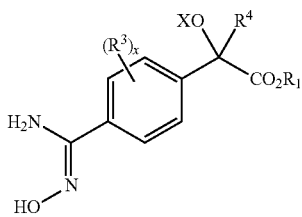

2.1: X = H, R₂ = H
2.2: X = (alkyl)₃Si⁻, R⁴ = H 2.1: X = H, R₂ = alkyl
2.2: X = (alkyl)₃Si⁻, R⁴ = alkyl The carboxylic acid fragments (1.1) of the present invention may be prepared by a variety of methods, including those illustrated in Scheme 4 for the isoxazoles bearing the carboxylic acid group at the 5-position. Reaction of chloro-oxime (4.1) with substituted propiolates (4.2) under basic conditions provides a mixture of isoxazole carboxylates (4.3/4.4) generally in favor of regioisomer (4.3). After separation of the isomers (such as by silica gel chromatography or reverse phase preparative HPLC), (4.4) may be hydrolyzed to give the required isoxazole carboxylic acid (4.5). Reaction of chloro-oxime (4.1) with substituted propargylic alcohols (4.6) under basic conditions provides a mixture of isoxazole carboxylates (4.7/4.8) generally in favor of isomer (4.8). After separation of the isomers (such as by silica gel chromatography or reverse phase preparative HPLC), (4.8) may be oxidized to give acid (4.5). Esters (4.4) may also be obtained regioselectively through the reaction of (4.1) with substituted 2-bromo-acrylates (4.9). When chloro-oximes (4.1) are reacted with unsubstituted propiolates (4.10), isoxazoles (4.11) are produced regioselectively. The unsubstituted isoxazole position may then be converted to a halogenated derivative (4.12) which may then be used for further transformations including but not limited to transition metal cross coupling reactions or insertion reactions.

Scheme 4

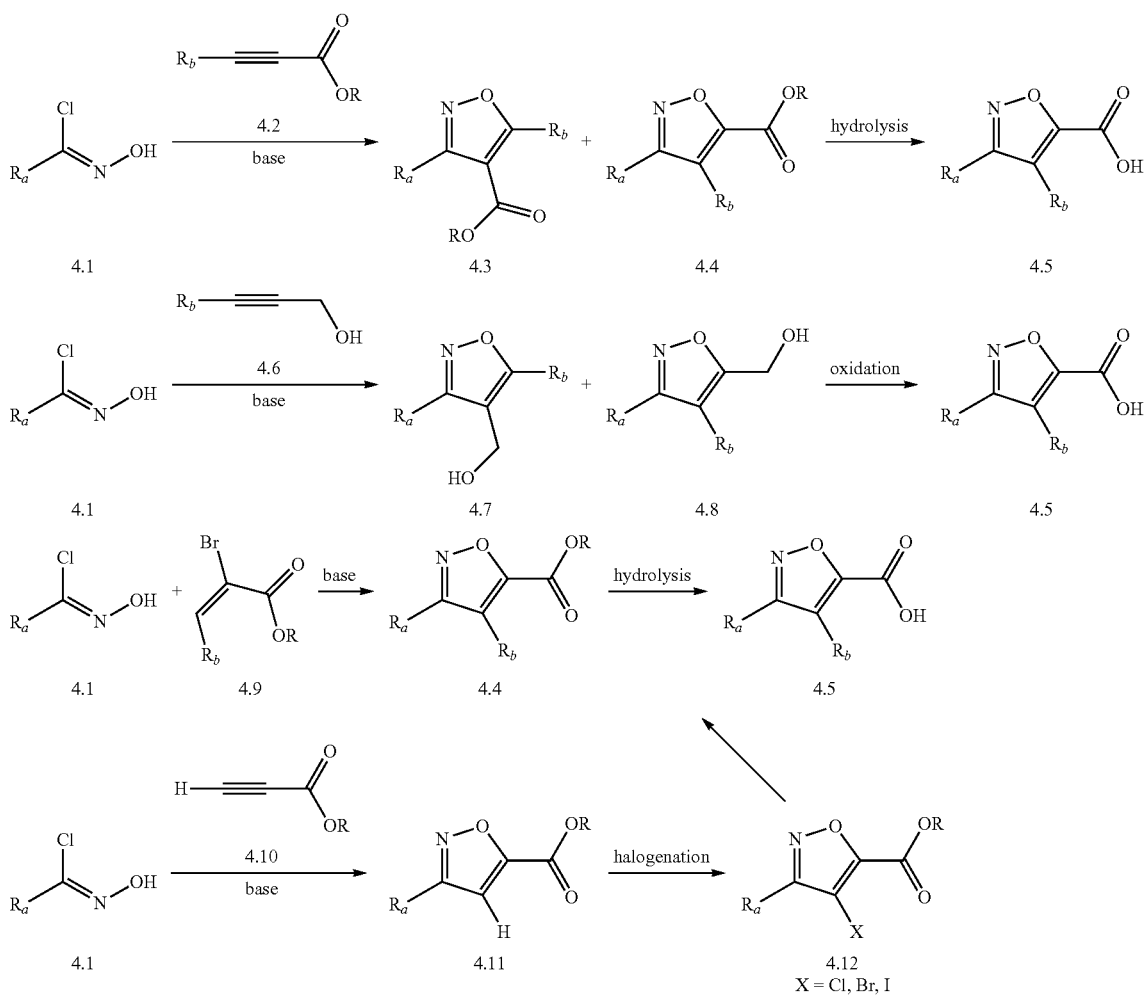

Illustrated in Scheme 5 are approaches for the isoxazoles bearing the carboxylic acid group at the 3-position. Isoxazole-3-carboxylic esters (5.3) may be prepared from the reaction of internal alkynes (5.1) with dimethyl 2-nitromalonate (5.2) under thermal decomposition conditions (heating in an inert solvent or neat) or reaction with chloro-oximes (5.5) under basic conditions. Hydrolysis of the esters (5.3) then provides the acids (5.4). The reaction of terminal alkynes (5.6) with chloro-oximes (5.7) leads to isoxazole esters lacking substitution at the 4-position. The unsubstituted isoxazole position may then be converted to a halogenated derivative (5.9) which may then be used for further transformations including but not limited to transition metal cross coupling reactions or insertion reactions.

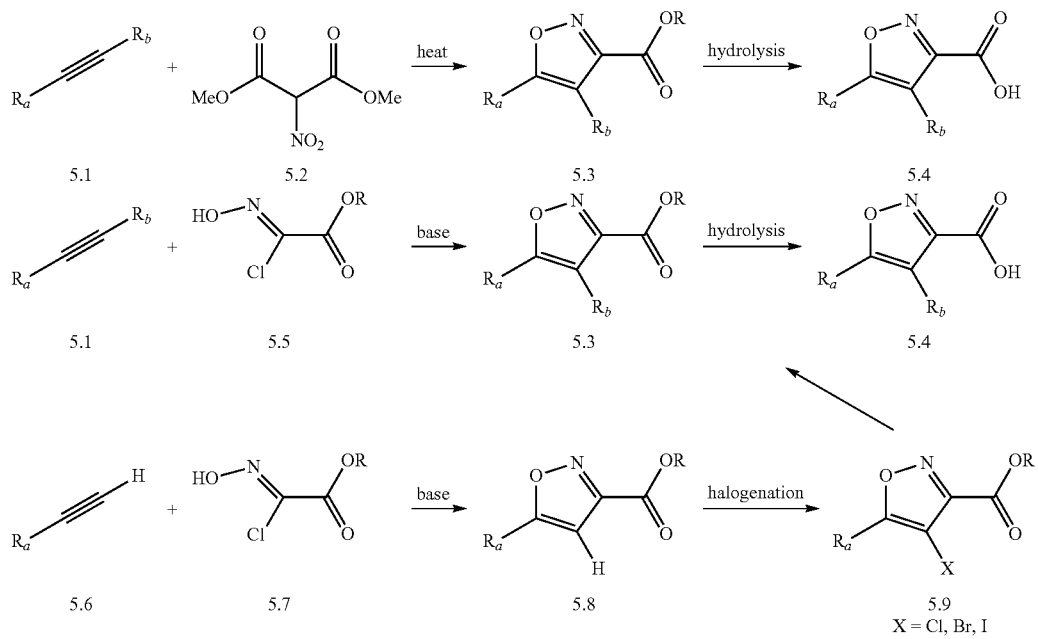

Scheme 5

Abbreviations

AcOH acetic acid
BOC t-butyl carbamate
BOP benzotriazol-1-yloxytris(trimethylamino)phosphonium hexafluorophosphate
BOP-Cl bis-(2-oxo-3-oxazolidinyl)phosphinic chloride
DBU 1,8-diazabicyclo[5.4.0]undec-7-ene
DCE dichloroethane
DCM dichloromethane
DIEA diisopropylethylamine
DMF dimethylformamide
DMAP N,N-Dimethylpyridine-4-amine
DMSO dimethyl sulfoxide
EDC 1-(3-dimethylaminopropyl)-3-ethylcarbodiimide hydrochloride
Et ethyl
EtOAc ethyl acetate
h hour(s)
HATU O-(7-azabenzotriazol-1-yl)-1,1,3,3-tetramethyluronium hexafluorophosphate
HCl hydrochloric acid
HOBt hydroxybenzotriazole
HPLC high pressure liquid chromatography
HMPA hexamethylphosphorus triamide
hr hour(s)
IPA isopropyl alcohol
i-PrOH isopropyl alcohol
LC/MS liquid chromatography/mass spectroscopy
m-CPBA 3-chloroperbenzoic acid
MeCN acetonitrile
MeOH methanol
min minute(s)
MPLC medium pressure liquid chromatography
MS mass spectroscopy
NaOH sodium hydroxide
NMR nuclear magnetic resonance
$Pd_2(dba)_3$ tris-(dibenzylideneacetone)dipalladium
Ph phenyl
rt room temperature
SEM trimethylsilyloxyethoxymethyl
TBAF tetrabutylammonium fluoride
TEA triethylamine
TEMPO 2,2,6,6-tetramethylpiperidine 1-oxyl
TFA trifluoroacetic acid
THF tetrahydrofuran
TMS-Cl chlorotrimethylsilane

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein, but rather is defined by the claims appended hereto.

Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially using Roman numerals (e.g., Intermediate I, Intermediate II, etc.) and are abbreviated as Int-I, Int-II, etc. In some instances the preparation of common intermediates may require multiple steps to be prepared. Each step is identified by the common intermediate and the step, e.g., Int-I-A, Int-I-B, and so forth. Compounds of the Examples are identified by the example and step in which they were prepared (e.g., "1-A" or "Preparation 1A" denotes the Example 1, step A) or by the example only where the compound is the title compound of the example (for example, "1" denotes the title compound of Example 1). In some instances alternate preparations of intermediates or Examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps. The intent of describing alternative preparations is to further enable the preparation of the Examples of this invention.

Those experiments which specify that they were performed in a microwave were conducted in a SmithSynthesizer manufactured by Personal Chemistry or a DISCOVER® microwave manufactured by CEM corporation. The microwave ovens generate a temperature which can be selected to be between 60-250° C. The microwaves automatically monitor the pressure which is between 0-300 PSI. Reaction hold times and temperature set points are reported.

Silica gel purification was performed on an Isco Companion medium pressure liquid chromatography instrument using prepacked silica gel cartridges (Redi-Sep) from Isco (12 g, 24 g, 40 g, 80 g, 120 g, 220, 330 g appropriate to the scale of the purification) using solvent gradients described for each Example but in most cases, 0-100% EtOAc in hexanes (or 25-100%) over 25 minutes.

Retention time data reported for each example uses one of the five following General Analytical HPLC methods:

Method A: Column: Waters Sunfire C18, 3.5-μm particles (3.0×150 mm); 10-100% B gradient over 12 min, then a 3-minute hold at 100% B. Mobile Phase A=0.05% TFA in $CH_3CN$:Water (10:90), Mobile Phase B=0.1% TFA in $CH_3CN$:Water (90:10); Flow Rate=0.5 ml/min; UV detection 220 nM.

Method B: Column: Xbridge Phenyl C18, 3.5-μm particles (3.0×150 mm); 10-100% B gradient over 12 min, then a 3-minute hold at 100% B. Mobile Phase A=0.05% TFA in $CH_3CN$:Water (10:90), Mobile Phase B=0.1% TFA in $CH_3CN$:Water (90:10); Flow Rate=0.5 ml/min; UV detection 220 nM.

Method C: identical to Method A with UV detection 254 nM.

Method D: identical to Method B with UV detection 254 nM.

Method E: Column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 35° C.; Gradient: 0-100% B over 4 minutes, then a 1 min hold at 100% B; flow rate=4 mL/min; UV detection 220 nM.

Preparative HPLC methods use one of the following methods unless otherwise noted in the specific example. Method 1: Column: PHENOMENEX® Luna C18, 5-μm particles (21.2×250 mm) or otherwise stated, Guard Column: none; Mobile Phase A: 90% water with 10% MeOH and 0.1% TFA; Mobile Phase B: 90% MeOH with 10% water and 0.1% TFA; Gradient: 0-100% B over 30 minutes; Flow rate: 15 mL/min, UV detection 220 nM. Method 2: Column: PHENOMENEX® Luna C18, 5-μm particles (21.2×250 mm; Guard Column: none; Mobile Phase A: 5:95 acetonitrile:water with 0.1% TFA; Mobile Phase B: 95:5 acetonitrile:water with 0.1% TFA; Gradient: 0-100% B over 30 minutes; Flow: 20 mL/min, UV detection 220 nM.

Preparation of Intermediate I

3-Phenyl-4-(trifluoromethyl)isoxazole-5-carboxylic acid

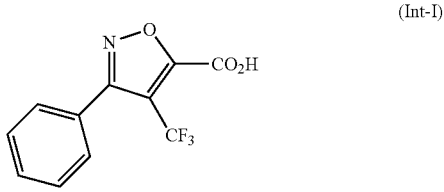 [SMILES: O=C(O)c1onc(-c2ccccc2)c1C(F)(F)F]

Preparation of Int-I-A: 4,4,4-Trifluorobut-2-yn-1-ol

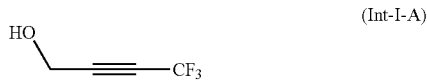

To a solution of diisopropylamine (24.7 mL, 176 mmol) in ether (100 mL) at −78° C. was added a 10M solution of butyllithium in ether (17.6 mL, 176 mmol) over 5 min. After 10 min. at −78° C., 2-bromo-3,3,3-trifluoroprop-1-ene (14.0 g, 80 mmol) was added to the pale yellow solution. After an additional 10 min., paraformaldehyde (2.40 g, 80 mmol) was added, the dry-ice bath was removed, and the reaction mixture was stirred at room temperature overnight. As the reaction mixture approached room temperature, it became dark in color. The reaction was quenched with a 1N aqueous solution of hydrochloric acid (100 mL), diluted with ether (500 mL), washed with a 1N aqueous solution of hydrochloric acid (2×100 mL), washed with brine 100 mL, and dried over anhydrous sodium sulfate. Concentration under reduced pressure afforded a dark liquid which was distilled under Low-Vacuum (~50 Torr, ~50° C.) to give 4,4,4-trifluorobut-2-yn-1-ol (7.1 g, 57.2 mmol, 72% yield) as a pale yellow liquid. $^1$H-NMR (500 MHz, $CDCl_3$) δ ppm 2.31 (br. s., 1H) and 4.38-4.42 (m, 2H).

Alternate Preparation of Int-I-A: 4,4,4-Trifluorobut-2-yn-1-ol

To an ether (pre-dried over magnesium sulfate) solution of phenanthroline (2.16 mg, 0.012 mmol) (indicator) at −78° C. under nitrogen was added a 2M solution of n-butyl lithium in pentane. An orange color immediately appeared. Trifluoromethylacetylene gas was bubbled through the solution at −78° C. After ~4 min. of gas introduction, the orange color almost completely disappeared, the reaction solution became cloudy (due to some precipitation), and a pale light orange color persisted. Paraformaldehyde was added, and the dry ice/isopropanol bath was removed after 5 min. and replaced with a 0° C. ice-bath. Stirring was continued for 45 min., the ice bath was removed, and stirring was continued for an additional 1.25 h. The reaction flask was immersed in a 0° C. ice bath, and a saturated aqueous solution of ammonium chloride (20.0 mL) was added. The layers were separated, and the organic layer was washed with water (2×), washed with brine, and dried over anhydrous sodium sulfate. Concentration under low-vacuum (~50 Torr) without heat afforded a dark brown liquid which was purified by vacuum distillation (~50 Torr, ~50° C.) to give 4,4,4-trifluorobut-2-yn-1-ol (7.1 g, 57.2 mmol, 72% yield) as a colorless liquid.

Preparation of Int-1-B: N-Hydroxybenzimidoyl chloride

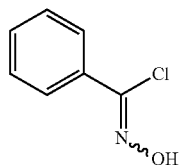

(Int-I-B)

This compound was prepared according to the method of Liu, K. C. et al., *J. Org. Chem.*, 45:3916-1918 (1980).

To a colorless, homogeneous solution of (E)-benzaldehyde oxime (24.4 g, 201 mmol) in N,N-dimethylformamide (60 mL) at room temperature was added N-chlorosuccinimide (26.9 g, 201 mmol) portion-wise over 30 min. During each addition, the reaction mixture became yellow and then gradually returned to near colorlessness. Additionally, an exotherm was noted with each portion added. (It is extremely important to make sure the reaction initiates after the addition of the first ~1/5 of the NCS; an ice-bath was readily available.). After the addition was complete, the homogeneous reaction mixture was stirred overnight at room temperature. The reaction mixture was diluted with 250 mL of water and extracted with ether (3×100 mL). The organic layers were combined, washed with water (2×100 mL), washed with a 10% aqueous solution of lithium chloride (2×100 mL), and washed with brine (100 mL). The aqueous layers were back extracted with ether (100 mL), and the combined organic layers (400 mL) were dried over anhydrous sodium sulfate. Concentration under reduced pressure afforded (Z)—N-hydroxybenzimidoyl chloride (30.84 g, 198 mmol, 98% yield) as a fluffy, pale yellow solid. The product had an HPLC ret. time=1.57 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=155.8. $^1$H-NMR (500 MHz, DMSO-d$_6$) δ ppm 7.30-7.64 (m, 3H), 7.73-7.87 (m, 2H), and 12.42 (s, 1H).

Preparation of Int-I-C: 3-Phenyl-4-(trifluoromethyl)isoxazol-5-yl)methanol

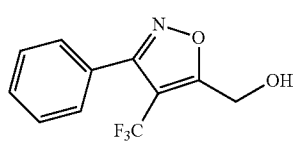

(Int-I-C)

To a pale yellow, homogeneous mixture of N-hydroxybenzimidoyl chloride (5.50 g, 35.4 mmol) and 4,4,4-trifluorobut-2-yn-1-ol (5.46 g, 39.6 mmol) in dichloroethane (85 mL) in a 250 mL round bottom flask at 70° C. was added triethylamine (9.85 mL, 70.7 mmol) in 22 mL of dichloroethane over 2.5 h via an addition funnel (the first ~50% over 2 h and the remaining 50% over 0.5 h). After the addition was complete, the reaction mixture was complete by HPLC (total time at 70° C. was 3 h). The reaction mixture was stirred at room temperature overnight.

The reaction mixture was diluted with dichloromethane (100 mL), washed with water (100 mL), and the organic layer was collected. The aqueous layer was extracted with dichloromethane (2×50 mL), and the combined organic layers were dried over anhydrous sodium sulfate. The solvent was removed under reduced pressure. Analysis indicated that the product mixture was composed of a 86:14 mixture of the desired regioisomer (Int-I-C), (3-phenyl-4-(trifluoromethyl)isoxazol-5-yl)methanol, and the undesired regioisomer, (3-phenyl-5-(trifluoromethyl)isoxazol-4-yl)methanol. The mixture was purified by silica gel chromatography using a mixture of ethyl acetate and hexane (1% to pack and load-5%-9%-12%) to afford (3-phenyl-4-(trifluoromethyl)isoxazol-5-yl)methanol (5.34 g, 21.96 mmol, 62.1% yield) as a pale yellow oil. The compound had an HPLC ret. time=1.91 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=244.2. $^1$H-NMR (500 MHz, CDCl$_3$) δ ppm 2.21 (br. s., 1H), 4.97 (s, 2H), 7.47-7.56 (m, 3H), and 7.65 (d, J=6.60 Hz, 2H).

Alternate Preparation of Int-I: 3-Phenyl-4-(trifluoromethyl)isoxazole-5-carboxylic acid

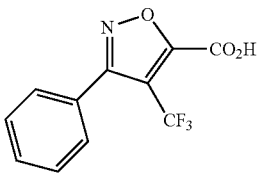

(Int-I)

Preparation of Jones' Reagent

To an orange, homogeneous solution of chromium trioxide (12.4 g, 0.123 mol) in water (88.4 mL) at 0° C. was added sulfuric acid (10.8 mL) dropwise via addition funnel over 30 min. with stirring. The addition funnel was rinsed with water (1 mL) to give 1.23 M solution of Jones' Reagent (0.123 mol of reagent in 100 mL of solvent).

To a solution of (3-phenyl-4-(trifluoromethyl)isoxazol-5-yl)methanol (5.24 g, 21.6 mmol) in acetone (75 mL) at room temperature (immersed in a water bath) was added Jones' Reagent (43.8 mL, 53.9 mmol) via addition funnel slowly over 1.5 h. The dark reaction mixture was stirred at room temperature overnight. By HPLC, the reaction was 93% complete. An additional 0.5 equivalents (9 mL) of the Jones' Reagent was added. After 1 h, the reaction was 95% complete. After an additional 3h, the reaction was 96% complete. An additional 0.5 equivalents (9 mL) of the Jones' Reagent was added. The reaction mixture was stirred for an additional 2.5 h. By HPLC, the reaction was 97% complete. Isopropyl alcohol (6 mL) was added, and the mixture was stirred for 90 min, resulting in a dark green precipitate. The mixture was diluted with ether (600 mL), washed with a 2% aqueous solution of sodium hydrogen sulfite (5×100 mL), and the organic layer was collected. The aqueous layer was back-extracted with ether (2×100 mL). By HPLC, there was no additional product in the aqueous layer. The combined organic layers were washed with water (100 mL), washed with a saturated aqueous solution of brine (100 mL), and dried over anhydrous sodium sulfate. The aqueous layer was back-extracted with ether (100 mL), and the organic layer was added to the previous organic layers. The solution was concentration under reduced pressure to give 3-phenyl-4-(trifluoromethyl)isoxazole-5-carboxylic acid as an off-white solid. The solid was diluted with dichloromethane (200 mL), washed with a 2% aqueous solution of sodium hydrogen sulfite, washed with brine, and dried over anhydrous sodium sulfate. Concentration under reduced pressure afforded 3-phenyl-4-(trifluoromethyl)isoxazole-5-carboxylic acid (3.84 g, 14.93 mmol, 69.3% yield) as a pale yellow solid. The product was 96% pure by HPLC with a ret. time=1.60 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=258.2.

The sodium hydrogen sulfite aqueous layer still contained a significant amount of product. The brine layer contained no additional product and was discarded. The aqueous layer was saturated with sodium chloride, the pH was adjusted to ~3.5, and the solution was extracted with ether (3×100 mL). The organic layer was dried over anhydrous sodium sulfate and concentrated to afford additional 3-phenyl-4-(trifluoromethyl)isoxazole-5-carboxylic acid (1.12 g, 4.36 mmol, 20.21% yield) as a white solid. The product was >99% pure by HPLC with a ret. time=1.60 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=258.1. $^1$H-NMR (500 MHz, DMSO-d$_6$) δ ppm 7.55-7.63 (m, 5H).

The products were combined to give 4.96 g (90% yield) of 3-phenyl-4-(trifluoromethyl)isoxazole-5-carboxylic acid or Int-1.

Alternate Preparation of Int-I: 3-Phenyl-4-(trifluoromethyl)isoxazole-5-carboxylic acid starting with (3-phenyl-4-(trifluoromethyl)isoxazol-5-yl)methanol

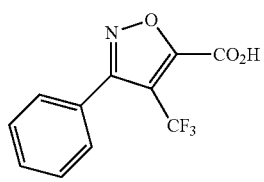
(Int-I)

A mixture of (3-phenyl-4-(trifluoromethyl)isoxazol-5-yl)methanol (2.1 g, 8.64 mmol), TEMPO (0.094 g, 0.604 mmol), and a sodium phosphate buffer (0.67M) (32.2 mL, 21.59 mmol) in acetonitrile (30 mL) was heated to 35° C. A fresh solution of sodium phosphate buffer (40 mL, pH ~6.5) consisting of a 1:1 solution of NaH$_2$PO$_4$ (20 mL, 0.67M) and Na$_2$HPO$_4$ (20 mL, 0.67M) was prepared and used. Solutions of sodium chlorite (3.91 g, 34.5 mmol) in water (4.5 mL) and bleach (4.3 mL, 6% wt.) were added simultaneously over 40 min. The reaction was monitored by HPLC, and after 2 h, ~30% of the starting material remained. After 6 h, 10% remained. Additional bleach (100 μL) was added, and the reaction mixture was left at room temperature overnight. Additional bleach (100 μL) was added. The resulting mixture was allowed to stir at 35° C. for additional 2 h. HPLC indicated complete conversion. The reaction was quenched by the slow addition of a solution of sodium sulfite (2.07 mL, 43.2 mmol) in water (90 mL) at 0° C., resulting in the disappearance of the brown reaction color. The solvent was removed under reduced pressure, and the remaining aqueous residue was extracted with ethyl acetate (3×40 mL). The organic layers were combined, washed with water (8 mL), washed with brine (8 mL), and dried over anhydrous sodium sulfate. Concentration under reduced pressure afforded 3-phenyl-4-(trifluoromethyl)isoxazole-5-carboxylic acid (2.2 g, 8.55 mmol, 99% yield) as a pale yellow solid.

Alternate Preparation of 3-phenyl-4-(trifluoromethyl)isoxazole-5-carboxylic acid starting with 4,4,4-trifluorobut-2-ynoate (Int-I)

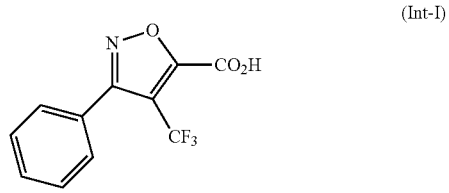 [SMILES: O=C(O)c1onc(-c2ccccc2)c1C(F)(F)F]
(Int-I)

Preparation of Int-I-D: Ethyl 3-phenyl-4-(trifluoromethyl)isoxazole-5-carboxylate

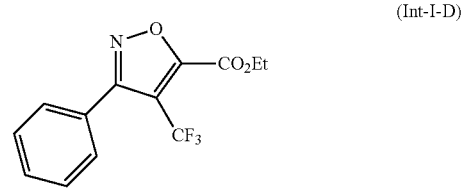 [SMILES: CCOC(=O)c1onc(-c2ccccc2)c1C(F)(F)F]
(Int-I-D)

To a pale yellow mixture of (Z)-N-hydroxybenzimidoyl chloride (1.04 g, 6.68 mmol) and ethyl 4,4,4-trifluorobut-2-ynoate (1.238 g, 7.45 mmol) in diethyl ether (20 mL) at room temperature was added triethylamine (1.86 mL, 13.4 mmol) over 15 min., resulting in a precipitant. After the addition was complete, the pale yellow slurry was stirred at room temperature over the weekend. The heterogeneous reaction mixture was filtered under reduced pressure to remove the triethylamine hydrochloride salt, and the filtrate was concentrated to give the product mixture as a dark yellow, viscous oil (2.03 g). By HPLC, the reaction mixture was composed of a mixture of the desired regioisomer, ethyl 3-phenyl-4-(trifluoromethyl)isoxazole-5-carboxylate, and the undesired regioisomer, ethyl 3-phenyl-5-(trifluoromethyl)isoxazole-4-carboxylate, in an approximately 15:85 ratio. The compound mixture was dissolved in hexane and sonicated for 5 min. The hexane was decanted off, and the dark red, oily residue was found to have only trace product by HPLC. The hexane was removed under reduced pressure, and the residue (1.89 g) was purified by preparative HPLC. The desired fractions containing ethyl 3-phenyl-4-(trifluoromethyl)isoxazole-5-carboxylate were concentrated, and the residue was diluted with dichloromethane, washed with a saturated aqueous solution of sodium bicarbonate, and dried over anhydrous sodium sulfate. Concentration under reduced pressure afforded ethyl 3-phenyl-4-(trifluoromethyl)isoxazole-5-carboxylate (0.087 g, 0.305 mmol, 4.6% yield) as a pale yellow solid. The compound had an HPLC ret. time=2.88 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H-NMR (400 MHz, CDCl$_3$) δ ppm 1.46 (t, J=7.15 Hz, 3H), 4.53 (q, J=7.03 Hz, 2H), 7.48-7.55 (m, 3H), and 7.58 (d, J=7.53 Hz, 2H).

Alternate Preparation of Int-I-D: Ethyl 3-phenyl-4-(trifluoromethyl)isoxazole-5-carboxylic acid starting with ethyl 4,4,4-trifluorobut-2-enoate Preparation of Int-I-E: Ethyl 2,3-dibromo-4,4,4-trifluorobutanoate:

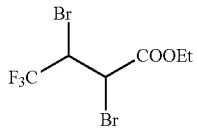

(Int-I-E)

Bromine (18.4 mL, 357 mmol) was added dropwise over 30 minutes to a solution of commercially available (E)-ethyl 4,4,4-trifluorobut-2-enoate (50 g, 297 mmol) in carbon tetrachloride (50 mL) at room temperature under nitrogen. The resulting dark red solution was refluxed for 4 hours. Additional bromine (2 ml) was added and heating was continued until the HPLC analysis showed that the starting material had been consumed. The reaction mixture was concentrated under reduced pressure to give light brown oil which used in the next step without purification. HPLC (XBridge 5µ C18 4.6×50 mm, 4 mL/min, solvent A: 10% MeOH/water with 0.2% H$_3$PO$_4$, solvent B: 90% MeOH/water with 0.2% H$_3$PO$_4$, gradient with 0-100% B over 4 minutes): 2.96 and 3.19 minutes.

Preparation of Int-I-F (Z/E): Ethyl 2-bromo-4,4,4-trifluorobut-2-enoate

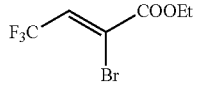

(Int-I-F)

To a solution of ethyl 2,3-dibromo-4,4,4-trifluorobutanoate (Int-1-E) in hexane (200 mL) cooled to 0° C. was added triethylamine (49.7 ml, 357 mmol) dropwise over 35 minutes, during which time a white precipitate formed. The reaction mixture was stirred for an additional 2 hours until LC indicated complete conversion. The solid was filtered and rinsed with hexane (3×50 mL), and the filtrate was concentrated and passed through a short silica gel pad eluting with 10% ethyl acetate/hexane to give (Z/E)-ethyl 2-bromo-4,4,4-trifluorobut-2-enoate (65.5 g, 265 mmol, 89% yield for two steps) as a colorless oil. Alternatively, the crude product can be purified by distillation (85° C./~60 mmHg). $^1$H-NMR (CDCl$_3$, 400 MHz) δ 7.41 (q, 1H, J=7.28 Hz), 4.35 (q, 2H, J=7.11 Hz), 1.38 (t, 3H, J=7.15 Hz); HPLC (XBridge 5µ C18 4.6×50 mm, 4 mL/min, solvent A: 10% MeOH/water with 0.2% H$_3$PO$_4$, solvent B: 90% MeOH/water with 0.2% H$_3$PO$_4$, gradient with 0-100% B over 4 minutes): 3.09 minutes.

Alternate Preparation of Int-I-D: Ethyl 3-phenyl-4-(trifluoromethyl)isoxazole-5-carboxylate

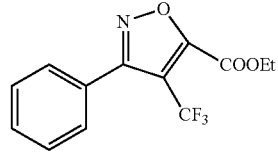

(Int-I-D)

(Z/E)-Ethyl 2-bromo-4,4,4-trifluorobut-2-enoate, Int-I-F, (39.7 g, 161 mmol) and N-hydroxybenzimidoyl chloride (30 g, 193 mmol) were dissolved in ethyl acetate (150 mL). Indium (III) chloride (8.89 g, 40.2 mmol) was added and the resulting mixture stirred for 60 minutes at room temperature under N$_2$. Potassium hydrogen carbonate (32.2 g, 321 mmol) was added to the reaction mixture which was allowed to stir overnight for 14 hours at room temperature. The solvent was removed in vacuo. The residue was re-suspended in 300 mL hexane and stirred for 10 minutes then filtered. The filter cake was washed with hexane (3×30 mL) and the combined filtrate was concentrated in vacuo to give crude product, which was further purified with flash chromatography to generate 33g product (72%) as light yellowish oil as a mixture of the desired isomer Int-I-D and undesired isomer ethyl 3-phenyl-5-(trifluoromethyl)isoxazole-4-carboxylate in a ratio of ~30/1. MS m/e 286.06 (M+H$^+$); $^1$H-NMR (CDCl$_3$, 400 MHz) δ 7.56 (m, 5H), 4.53 (q, 2H, J=7.3 Hz), 1.46 (t, 3H, J=7.2 Hz); HPLC (XBridge 5µ C18 4.6×50 mm, 4 mL/min, Solvent A: 10% MeOH/water with 0.2% H$_3$PO$_4$, Solvent B: 90% MeOH/water with 0.2% H$_3$PO$_4$, gradient with 0-100% B over 4 minutes): 3.57 minutes.

Preparation of Int-I Li salt: 3-Phenyl-4-(trifluoromethyl)isoxazole-5-carboxylic acid, lithium salt

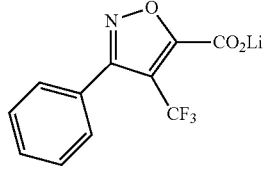

(Int-I Li salt)

A mixture of ethyl 3-phenyl-4-(trifluoromethyl)isoxazole-5-carboxylate (Int-I-D, 0.085 g, 0.298 mmol) and lithium hydroxide hydrate (0.013 g, 0.298 mmol) in methanol (2.0 mL), and water (1.0 mL) was stirred at room temperature overnight. The reaction mixture was concentrated to dryness to give 3-phenyl-4-(trifluoromethyl)isoxazole-5-carboxylic acid, lithium salt (0.079 g, 0.299 mmol, 100% yield) as a pale yellow solid. The compound had an HPLC ret. time=1.72 min.-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=258.0. $^1$H-NMR (400 MHz, CDCl$_3$) δ ppm 7.49-7.57 (m, 3H) and 7.58-7.62 (m, 2H).

Preparation of Int-I-G:
3-Phenyl-4-(trifluoromethyl)isoxazole-5-carbonyl fluoride

(Int-I-G)

To a mixture of 3-phenyl-4-(trifluoromethyl)isoxazole-5-carboxylic acid (3.00 g, 11.7 mmol) and pyridine (1.132 mL, 14.0 mmol) in dichloromethane (100 mL) at room temperature was added 2,4,6-trifluoro-1,3,5-triazine (cyanuric fluoride) (1.18 mL, 14.0 mmol). The reaction mixture was stirred at room temperature overnight, diluted with dichloromethane (300 mL), washed with an ice-cold solution of 0.5N aqueous hydrochloric acid (2×100 mL), and the organic layer was collected. The aqueous layer was back-extracted with dichloromethane (200 mL), and the combined organic layers were dried anhydrous sodium sulfate and concentrated to afford 3-phenyl-4-(trifluoromethyl)isoxazole-5-carbonyl fluoride (2.91 g, 11.2 mmol, 96% yield) as a yellow, viscous oil. The product was found to react readily with methanol and on analysis was characterized as the methyl ester, which had an HPLC ret. time=2.56 min.-Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS M+1=272.3 (methyl ester).

Preparation of Intermediate II

Ethyl 5-phenylisoxazole-3-carboxylate

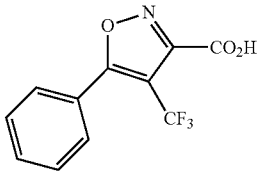
(Int-II)

Preparation of Int-II-A: Ethyl 5-phenylisoxazole-3-carboxylate

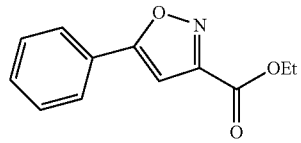
(Int-II-A)

To a mixture of (Z)-ethyl 2-chloro-2-(hydroxyimino)acetate (3.03 g, 20 mmol) and ethynylbenzene (4.39 mL, 40 mmol) in ether (80 mL) at room temperature was added a solution of triethylamine (5.58 mL, 40.0 mmol) in ether (20 mL) dropwise over 60 minutes. The reaction mixture was stirred for 2 h at room temperature. The reaction mixture was filtered, and the filtrate was concentrated to a yellow oil which was purified by flash silica gel chromatography using a mixture of ethyl acetate in hexane (0-12%) to afford ethyl 5-phenylisoxazole-3-carboxylate (3.06 g, 14.09 mmol, 70% yield) as a white solid. The compound had an HPLC retention time=2.99 minutes (YMC-Combi 4.6×50 mm S-5 ODS column) eluting with 10-90% aqueous methanol+0.2% phosphoric acid over a 4 minute gradient. MS:(M+H)=218.12. $^1$H-NMR (400 MHz, CDCl$_3$) δ ppm 1.45 (t, J=7.3Hz, 3H), 4.48 (q, J=7.3, 2H), 6.93 (s, 1H), 7.45-7.53 (m, 3H), and 7.77-7.85 (m, 2H).

Preparation of Int-II-B: Ethyl 4-iodo-5-phenylisoxazole-3-carboxylate

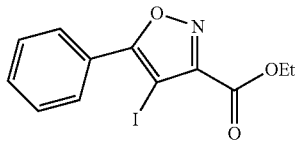
(Int-II-B)

A mixture of ethyl 5-phenylisoxazole-3-carboxylate (406 mg, 1.87 mmol) and N-iodosuccinimide (505 mg, 2.24 mmol) in trifluoroacetic acid (10 mL) was stirred at room temperature for 1.5 h. The volatiles were removed under reduced pressure, and the residue was partitioned between ethyl acetate (50 mL) and water (50 mL). The organic layer was washed with a 1N aqueous solution of sodium hydroxide (50 mL), washed with a 2.5% aqueous solution of sodium bisulfate (50 mL), washed with brine (50 mL), and dried over anhydrous magnesium sulfate. Concentration under reduced pressure afforded ethyl 4-iodo-5-phenylisoxazole-3-carboxylate (641 mg, 1.87 mmol, 100% yield) as a light yellow oil. The compound had an HPLC retention time=3.36 minutes (YMC-Combi 4.6×50 mm S-5 ODS column) eluting with 10-90% aqueous methanol+0.2% phosphoric acid over a 4 minute gradient. MS:(M+H)=343.97. $^1$H-NMR (400 MHz, CDCl$_3$) δ ppm 1.47 (t, J=7.1 Hz, 3H), 4.50 (q, J=7.0Hz, 2H), 7.52-7.56 (m, 3H), and 8.05 (m, 2H).

Large Scale: A mixture of ethyl 5-phenylisoxazole-3-carboxylate (3.05 g, 14.0 mmol) and N-iodosuccinimide (3.79 g, 16.9 mmol) in trifluoroacetic acid (78 mL) was stirred at room temperature for 3.5 h. The volatiles were removed under reduced pressure, and the residue was partitioned between ethyl acetate (150 mL) and water (150 mL). The organic layer was washed with a 1N aqueous solution of sodium hydroxide (150 mL), washed with a 3% aqueous solution of sodium bisulfite (2×150 mL), washed with brine (150 mL), and dried over anhydrous magnesium sulfate. Concentration under reduced pressure afforded ethyl 4-iodo-5-phenylisoxazole-3-carboxylate (4.69 g, 13.7 mmol, 97% yield) as a light yellow oil.

Preparation of Int-II-C: Ethyl 5-phenyl-4-(trifluoromethyl)isoxazole-3-carboxylate

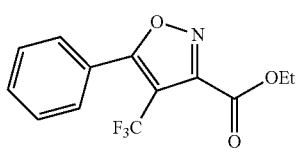
(Int-II-C)

To a solution of ethyl 4-iodo-5-phenylisoxazole-3-carboxylate (638 mg, 1.86 mmol) and copper(I) iodide (70.8 mg, 0.372 mmol) in N,N-dimethylformamide (9 mL) and HMPA (1.2 mL) at room temperature was added methyl 2,2-difluoro-2-(fluorosulfonyl)acetate (0.947 mL, 7.44 mmol) in one portion. The reaction mixture was immediately immersed in an oil bath at 75-80° C. and was stirred for 6 hrs. The reaction mixture was then allowed to cool to room temperature and was stirred overnight. The reaction mixture was partitioned between ethyl ether (125 mL) and a saturated aqueous solution of ammonium chloride (125 mL). The organic layer was washed with a saturated aqueous solution of ammonium chloride (125 mL), washed with water (2×125 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (454 mg, 1.59 mmol, 86% yield) as a colorless oil. The compound had an HPLC retention time=3.44 minutes (YMC-Combi 4.6×50 mm S-5 ODS column) eluting with 10-90% aqueous methanol+0.2% phosphoric acid over a 4 minute gradient. MS:(M+H)=286.01. $^1$H-NMR (400 MHz, CDCl$_3$) δ ppm 1.45 (t, J=7.2 Hz, 3H), 4.51 (q, J=7.3 Hz, 2H), 7.52-7.62 (m, 3H), and 7.69 (d, J=7.5 Hz, 2H).

Large Scale: To a solution of ethyl 4-iodo-5-phenylisoxazole-3-carboxylate (4.62 g, 13.5 mmol) and copper(I) iodide (0.513 g, 2.69 mmol) in N,N-dimethylformamide (59.8 mL) and HMPA (7.48 mL) at room temperature was added methyl 2,2-difluoro-2-(fluorosulfonyl)acetate (6.86 mL, 53.9 mmol) at once. The reaction mixture was immediately immersed in an oil bath at 75-80° C. Stirring was continued at this temperature for 3.5 h. After cooling to room temperature, the reaction mixture was cooled in an ice bath. A saturated aqueous solution of ammonium chloride (~50 mL) was added slowly to quench the reaction. The mixture was partitioned between ethyl ether (400 mL) and a saturated aqueous solution of ammonium chloride (400 mL). The organic layer was washed with a saturated aqueous solution of ammonium chloride (200 mL), washed with water (2×200 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (3.6 g, 12.6 mmol, 94% yield) as a colorless oil.

Preparation of Int-II:
5-Phenyl-4-(trifluoromethyl)isoxazole-3-carboxylic acid

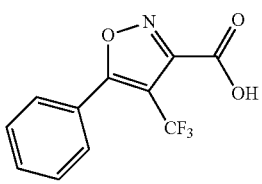

(Int-II)

To a solution of ethyl 5-phenyl-4-(trifluoromethyl)isoxazole-3-carboxylate (3.6 g, 12.6 mmol) in methanol (100 mL) and water (20 mL) at room temperature was added lithium hydroxide, monohydrate (0.583 g, 13.9 mmol). The reaction mixture was stirred at room temperature for 30 minutes. The methanol was removed under reduce pressure, and the residue was diluted with water (~100 mL). Ethyl ether (200 mL) was added, and the pH of the aqueous layer was adjusted to <1 with a 1N aqueous solution of hydrochloric acid. The mixture was transferred to a separatory funnel, and after agitation, the layers were separated. The organic layer was washed with brine (100 mL), dried over anhydrous magnesium sulfate, and concentrated to afford 5-phenyl-4-(trifluoromethyl)isoxazole-3-carboxylic acid (3.12 g, 12.13 mmol, 96% yield) as a white, crystalline solid. The compound had an HPLC retention time=2.58 minutes (YMC-Combi 4.6×50 mm S-5 ODS column) eluting with 10-90% aqueous methanol+0.2% phosphoric acid over a 4 minute gradient. MS:(M+Na)=279.95. $^1$H NMR (400 MHz, CDCl$_3$) δ ppm 7.53-7.64 (m, 3H), and 7.70 (d, J=7.5 Hz, 2H).

Preparation of Int-II-D.
5-Phenyl-4-(trifluoromethyl)isoxazole-3-carbonyl fluoride

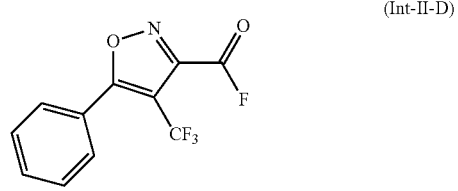 [SMILES: O=C(F)c1noc(-c2ccccc2)c1C(F)(F)F]

(Int-II-D)

To a mixture of 5-phenyl-4-(trifluoromethyl)isoxazole-3-carboxylic acid (197 mg, 0.766 mmol) and pyridine (0.074 mL, 0.919 mmol) in dichloromethane (5 mL) at room temperature was added cyanuric fluoride (0.078 mL, 0.919 mmol). The reaction mixture was stirred at room temperature for 18 h. The mixture was diluted with dichloromethane (40 mL) and washed with an ice-cold 0.5N aqueous solution of hydrochloric acid (20 mL). The aqueous layer was extracted with dichloromethane (20 mL), and the combined organic layers were washed with ice-cold water (20 mL) and dried over anhydrous magnesium sulfate. Concentration under reduced pressure afforded 5-phenyl-4-(trifluoromethyl)isoxazole-3-carbonyl fluoride (199 mg, 0.768 mmol, 100% yield) as a pale yellow oil. The compound had an HPLC retention time=2.53 min. (methyl ester)-Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA.

Preparation of Intermediate III (R/S)-(E/Z)-Ethyl 2-hydroxy-2-(4-(N'-hydroxycarbamimidoyl)phenyl)acetate

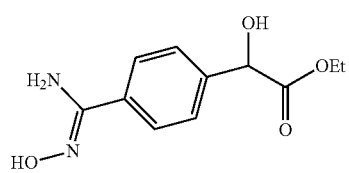

(Int-III)

Preparation of Int-III-A: (R/S)-Ethyl 2-(4-cyanophenyl)-2-hydroxyacetate

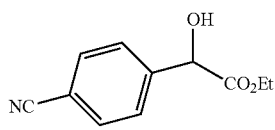
(Int-III-A)

(R/S)-Ethyl 2-(4-cyanophenyl)-2-oxoacetate (1.128 g, 5.55 mmol) was dissolved in MeOH (20 mL) and cooled to 0° C. and NaBH$_4$ (0.105 g, 2.78 mmol) was added. After stirring for 1 h, the solution was concentrated and then EtOAc was added. The EtOAc solution was washed with brine and sat NaHCO$_3$ solution. The organic layer was dried (MgSO$_4$) and concentrated to give ethyl (R/S)-2-(4-cyanophenyl)-2-hydroxyacetate III-A (1.045 g, 5.09 mmol, 92% yield): LCMS=206.1 [M+H]$^+$; $^1$H NMR (400 MHz, methanol-d$_4$) δ ppm 7.58-7.82 (4 H, m), 5.28 (1 H, s), 4.05-4.27 (2 H, m), 1.20 (3 H, t, J=7.15 Hz).

Preparation of Int-III: (R/S)-(E/Z)-Ethyl 2-hydroxy-2-(4-(N'-hydroxycarbamimidoyl)phenyl)acetate

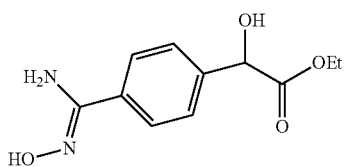
(Int-III)

(R/S)-Ethyl 2-(4-cyanophenyl)-2-hydroxyacetate, (Int-III-A, 1.045 g, 5.09 mmol) was dissolved in i-PrOH (20 mL) and hydroxylamine hydrochloride (0.708 g, 10.18 mmol) and sodium bicarbonate (1.711 g, 20.37 mmol) were added. This was heated at 70° C. for 6 h. After cooling, the solution was concentrated and then EtOAc was added. The EtOAc was washed with brine. The organic layer was dried (MgSO$_4$) and concentrated to give (R/S)-(E/Z)-ethyl 2-hydroxy-2-(4-(N'-hydroxycarbamimidoyl)phenyl)acetate Int-III (0.87 g, 3.65 mmol, 71.7% yield): LCMS=239.1 [M+H]$^+$; $^1$H NMR (400 MHz, methanol-d$_4$) δ ppm 7.64 (2 H, d, J=8.35 Hz), 7.48 (2 H, d, J=7.91 Hz), 5.20 (1 H, s), 4.02-4.29 (2 H, m), 1.09-1.28 (3H, m).

Preparation of Intermediate IV (R/S)-Ethyl 2-hydroxy-2-(4-(5-(3-phenyl-4-(trifluoromethyl)isoxazol-5-yl)-1,2,4-oxadiazol-3-yl)phenyl)acetate

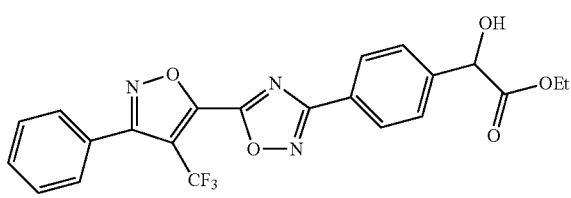
(Int-IV)

(R/S)-(E/Z)-Ethyl 2-hydroxy-2-(4-(N'-hydroxycarbamimidoyl)phenyl)acetate Int-III (375 mg, 1.574 mmol) was dissolved in MeCN (5 mL) and 3-phenyl-4-(trifluoromethyl)isoxazole-5-carbonyl fluoride, (Int-I-G, 408 mg, 1.574 mmol), and N-ethyl-N-isopropylpropan-2-amine (0.357 mL, 2.047 mmol) were added. After stirring overnight, the solution was concentrated and EtOAc was added. The EtOAc was washed with brine and saturated NaHCO$_3$ solution. The organic layer was dried (MgSO$_4$), filtered, and concentrated. The resulting residue was purified by column chromatography (Isco Combiflash Companion, 12 g silica gel, 10% ethyl acetate-hexane for 5 min, then ramped to 50% ethyl acetate-hexane over 7 min, then 50% ethyl acetate-hexane for 3 more min, product came out 8-10 min in fractions 13-17) to give (R/S)-ethyl 2-hydroxy-2-(4-(5-(3-phenyl-4-(trifluoromethyl)isoxazol-5-yl)-1,2,4-oxadiazol-3-yl)phenyl)acetate (Int-IV, 246 mg, 0.500 mmol, 31.8% yield): LCMS=460.0 [M+H]$^+$, $^1$H NMR (400 MHz, chloroform-d) δ ppm 8.22 (2 H, d, J=8.35 Hz), 7.47-7.80 (7H, m), 5.21-5.31 (1 H, m), 4.14-4.38 (2 H, m), 3.59 (1 H, d, J=5.27 Hz), 1.26 (3 H, t, J=7.03 Hz).

Preparation of Intermediate V (R/S)-2-Hydroxy-2-(4-(5-(3-phenyl-4-(trifluoromethyl)isoxazol-5-yl)-1,2,4-oxadiazol-3-yl)phenyl)acetic acid

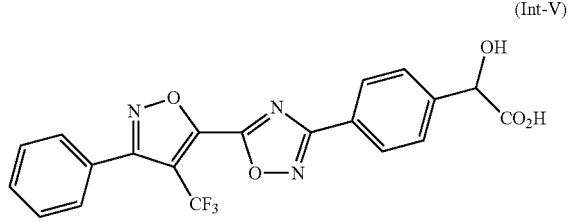 [SMILES: O=C(O)C(O)c1ccc(-c2noc(-c3onc(-c4ccccc4)c3C(F)(F)F)n2)cc1]
(Int-V)

(R/S)-Ethyl 2-hydroxy-2-(4-(5-(3-phenyl-4-(trifluoromethyl)isoxazol-5-yl)-1,2,4-oxadiazol-3-yl)phenyl)acetate (150 mg, 0.327 mmol) was dissolved in THF (2 mL) at 0° C. and MeOH (0.5 mL) and 1N LiOH (0.327 mL, 0.327 mmol) were added. After stirring for 1 h, the solution was concentrated and then EtOAc was added. The EtOAc was washed with 1 N HCl aqueous. The organic layer was dried (MgSO$_4$), filtered and concentrated to give (R/S)-2-hydroxy-2-(4-(5-(3-phenyl-4-(trifluoromethyl)isoxazol-5-yl)-1,2,4-oxadiazol-3-yl)phenyl)acetic acid Int-V (110 mg, 0.240 mmol, 73.4% yield): LCMS=431.9[M+H]$^+$, $^1$H NMR (400 MHz, methanol-d$_4$) δ ppm 8.19 (2 H, d, J=8.79 Hz), 7.51-7.79 (7 H, m), 5.26 (1 H, s).

SFC Chiral Separation of (R/S)-2-hydroxy-2-(4-(5-(3-phenyl-4-(trifluoromethyl)isoxazol-5-yl)-1,2,4-oxadiazol-3-yl)phenyl)acetic acid

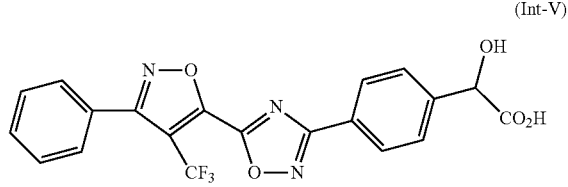 [SMILES: O=C(O)C(O)c1ccc(-c2noc(-c3onc(-c4ccccc4)c3C(F)(F)F)n2)cc1]
(Int-V)

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 2.0 g, 4.6 mmol) was separated into its individual enantiomers by chiral preparative SFC (CHIRALPAK® AD-H 25×3 cm–5 μm, column temperature 45° C., isocratic elution with mobile phase $CO_2$/MeOH=60/40, 130 mL/min, 250 nM, first product peak retention=7.4 min and second product peak retention=9.6 min) to give the separate enantiomers: Int-Va (578 mg) was eluted first at 7.4 min, [α]=48.4° (c.=3.6, DMSO), LCMS=432.1[M+H]$^+$; and Int-Vb (558 mg) was eluted second at 9.6 min, [α]=−68.3° (c.=4.7, $CH_2Cl_2$), LCMS=432.1 [M+H]$^+$.

Preparation of Intermediate VI (R/S)-Ethyl 2-hydroxy-2-(4-(5-(1-phenyl-5-(trifluoromethyl)-1H-pyrazol-4-yl)-1,2,4-oxadiazol-3-yl) phenyl)acetate

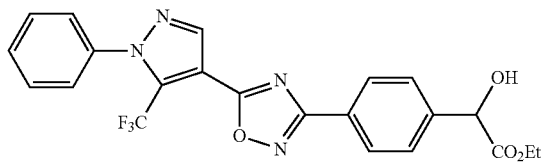

(Int-VI)

1-Phenyl-5-(trifluoromethyl)-1H-pyrazole-4-carboxylic acid (2.28 g, 8.90 mmol), EDC (2.218 g, 11.57 mmol), and HOBT (1.772 g, 11.57 mmol) were added to DMF (1 mL) to make a clear solution. It was stirred for 15 min. (R/S)-(E/Z)-ethyl 2-hydroxy-2-(4-(N'-hydroxycarbamimidoyl)phenyl) acetate (Int-III, 2.54 g, 10.68 mmol) was added to the reaction. It was heated at 140° C. for 2 h, then 0.3 additional equivalents of EDC and HOBT were added. After 30 min, the reaction was cooled and filtered. It was purified by column chromatography (Isco Combiflash Companion, hexane:ethyl acetate (4:1) to provide the product (R/S)-ethyl 2-hydroxy-2-(4-(5-(1-phenyl-5-(trifluoromethyl)-1H-pyrazol-4-yl)-1,2,4-oxadiazol-3-yl)phenyl)acetate (Int-VI, 1.95 g, 4.25 mmol, 47.8% yield): LCMS=459.2 [M+H]$^-$.

Preparation of Intermediate VII (R/S)-2-Hydroxy-2-(4-(5-(1-phenyl-5-(trifluoromethyl)-1H-pyrazol-4-yl)-1,2,4-oxadiazol-3-yl)phenyl)acetic acid

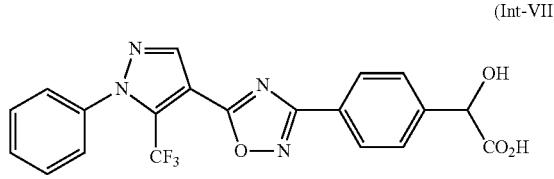

(Int-VII)

(R/S)-Ethyl 2-hydroxy-2-(4-(5-(1-phenyl-5-(trifluoromethyl)-1H-pyrazol-4-yl)-1,2,4-oxadiazol-3-yl)phenyl)acetate (Int-VI, 1.95 g, 4.25 mmol) was dissolved in THF (11 mL) and MeOH (5.50 mL) was added. Then, 1N LiOH (4.25 mL, 4.25 mmol) was added. It was stirred for 10 min and additional 1N LiOH (0.85 mL, 0.85 mmol) was added. After 10 min, more 1N LiOH (0.42 mL, 0.42 mmol) was added. After stirring for 10 min, the solution was concentrated and then EtOAc was added. The EtOAc was washed with 1 N HCl aqueous. The organic layer was dried ($MgSO_4$), filtered and concentrated to give (R/S)-2-hydroxy-2-(4-(5-(1-phenyl-5-(trifluoromethyl)-1H-pyrazol-4-yl)-1,2,4-oxadiazol-3-yl) phenyl)acetic acid (Int-VII, 1.8 g, 4.1 mmol, 97%): LCMS=431.1 [M+H]$^+$.

Preparation of Intermediate VIII (R/S)-Ethyl 2-hydroxy-2-(4-(5-(5-phenyl-4-(trifluoromethyl)isoxazol-3-yl)-1,2,4-oxadiazol-3-yl)phenyl)acetate

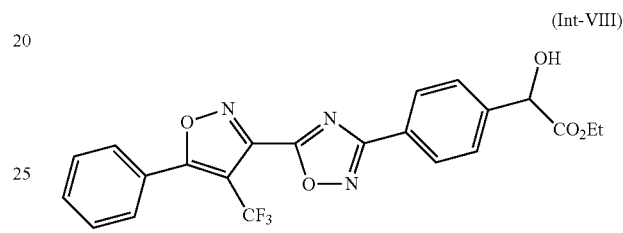

(Int-VIII)

(R/S)-(E/Z)-Ethyl 2-hydroxy-2-(4-(N'-hydroxycarbamimidoyl)phenyl)acetate (Int-III, 427 mg, 1.794 mmol) was dissolved in acetonitrile (5 mL). Next, 5-phenyl-4-(trifluoromethyl)isoxazole-3-carbonyl fluoride (Int-II-D, 465 mg, 1.794 mmol) and N-ethyl-N-isopropylpropan-2-amine (348 mg, 2.69 mmol) were added to the reaction mixture. It was stirred for 3 h. Then, TBAF (235 mg, 0.897 mmol) was added. After 20 min, it was concentrated and ethyl acetate was added. The organic layer was washed with brine, dried ($Na_2SO_4$), and filtered. It was concentrated to provide (R/S)-ethyl 2-hydroxy-2-(4-(5-(5-phenyl-4-(trifluoromethyl)isoxazol-3-yl)-1,2,4-oxadiazol-3-yl)phenyl)acetate (Int-VIII, 385 mg, 0.779 mmol, 43.4% yield): LCMS=460.1 [M+H]$^+$; $^1$H NMR (400 MHz, methanol-$d_4$) δ ppm 8.16 (2 H, d, J=8.36 Hz), 7.54-7.84 (7 H, m), 5.30 (1 H, s), 4.08-4.28 (2 H, m), 1.22 (3 H, t, J=7.04 Hz).

Preparation of Intermediate IX (R/S)-2-Hydroxy-2-(4-(5-(5-phenyl-4-(trifluoromethyl)isoxazol-3-yl)-1,2,4-oxadiazol-3-yl)phenyl) acetic acid

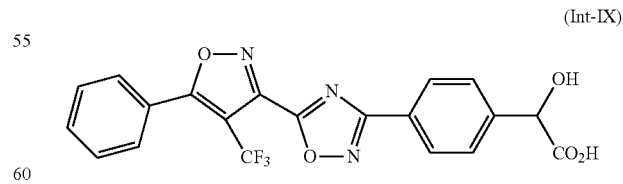

(Int-IX)

(R/S)-Ethyl 2-hydroxy-2-(4-(5-(5-phenyl-4-(trifluoromethyl)isoxazol-3-yl)-1,2,4-oxadiazol-3-yl)phenyl)acetate (Int-VIII, 380 mg, 0.83 mmol) was dissolved in THF (5.00 mL) and MeOH (5 mL). Then, 1N LiOH (0.83 mL, 0.83 mmol) was added. It was stirred for 20 min and additional 1N LiOH (0.83 mL, 0.83 mmol) was added. After stirring for 15 min, the solution was neutralized by 1N HCl to pH=5. The reaction mixture was concentrated and then EtOAc was added. The EtOAc was washed with brine. The organic layer was dried, filtered and concentrated to give (R/S)-2-hydroxy-2-(4-(5-(5-phenyl-4-(trifluoromethyl)isoxazol-3-yl)-1,2,4-oxadiazol-3-yl)phenyl)acetic acid (Int-IX, 376 mg, 0.785 mmol, 95% yield): LCMS=432.1 [M+H]+; 1H NMR (400 MHz, methanol-d4) δ ppm 8.02-8.20 (2 H, m), 7.49-7.79 (7 H, m), 5.27 (1 H, s).

Preparation of Intermediate X (R)-2-Aminopropanenitrile

Preparation of Int-X-A: (R)-tert-Butyl 1-amino-1-oxopropan-2-ylcarbamate

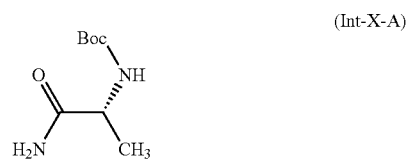

Step A: (R)-2-(tert-Butoxycarbonylamino)propanoic acid (1 g, 5.29 mmol), EDC (1.216 g, 6.34 mmol), and HOBt (0.971 g, 6.34 mmol) were dissolved in CH2Cl2 (5 mL). Ammonia (0.5 M) in dioxane (52.9 mL, 26.4 mmol) and 4-methylmorpholine (3.49 mL, 31.7 mmol) were added to the reaction mixture. After stirring for 1 h, the solvent was removed and ethyl acetate was added. This was washed with brine and saturated NaHCO3 solution. The organic layer was dried and concentrated to provide the product (R)-tert-butyl 1-amino-1-oxopropan-2-ylcarbamate (Int-X-A, 229 mg, 1.217 mmol, 23.02% yield); [M+Na]+=211.2; 1H NMR (400 MHz, methanol-d4) δ ppm 4.06 (1 H, q), 1.44 (9 H, s), 1.31 (3 H, d, J=7.04 Hz).

Preparation of Int-X-B: (R)-tert-Butyl 1-cyanoethylcarbamate

Step B: To a solution of (R)-tert-butyl 1-amino-1-oxopropan-2-ylcarbamate (Int-X-A, 1 g, 5.31 mmol) and 4-methylbenzene-1-sulfonyl chloride (4.05 g, 21.25 mmol) in CH2Cl2 (5 mL) was added pyridine (2.101 g, 26.6 mmol). After 3 h, acetic anhydride (0.651 g, 6.38 mmol) was added. This was stirred overnight before it was concentrated and EtOAc was added. Saturated NaHCO3 was added and the two phase mixture was stirred vigorously for 2 h. The organic layer was washed with 1 N HCl and then saturated NaHCO3. The organic layer was dried and concentrated. The resulting residue was purified by flash chromatography (Isco Combiflash Companion, 40 g silica gel, 15% ethyl acetate-hexane) to provide the product (R)-tert-butyl 1-cyanoethylcarbamate (Int-X-B, 336 mg, 1.974 mmol, 37.2% yield); [M+Na]+=193.2; 1H NMR (400 MHz, methanol-d4) δ ppm 4.51 (1 H, q), 1.34-1.58 (12 H, m).

Preparation of Intermediate X:
(R)-2-Aminopropanenitrile

(R)-tert-Butyl 1-cyanoethylcarbamate (Int-X-B, 20 mg, 0.118 mmol) was dissolved in concentrated formic acid (96%) (5.41 mg, 0.118 mmol). After stirring 2 h, the reaction was concentrated. The resulting residue was dissolved in EtOAc washed with saturated NaHCO3 solution. The organic layer was dried and concentrated to provide the amine (R)-2-aminopropanenitrile (Int-X, 7 mg, 0.100 mmol, 85% yield); 1H NMR (400 MHz, methanol-d4) δ ppm 8.17 (2 H, s), 4.13 (1 H, q, J=7.04 Hz), 1.53 (3 H, d, J=7.04 Hz).

Preparation of Intermediate XI (Int-XI)

(S)-2-Aminopropanenitrile

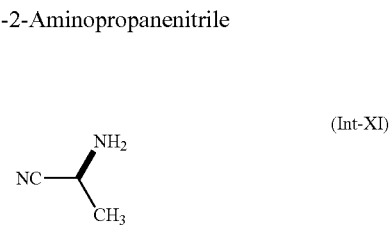

(S)-2-(tert-Butoxycarbonylamino)propanoic acid was incorporated into the above scheme (Int-X, step A) to give (S)-2-aminopropanenitrile (Int-XI); 1H NMR (400 MHz, methanol-d4) δ ppm 8.17 (2 H, s), 4.13 (1 H, q, J=7.04 Hz), 1.53 (3 H, d, J=7.04 Hz).

Preparation of Intermediate XII (R)-2-Amino-3-methylbutanenitrile

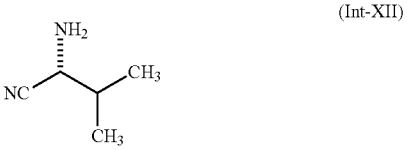

(R)-2-(tert-Butoxycarbonylamino)-3-methylbutanoic acid was incorporated into the above scheme (Int-X, step A) to give (R)-2-amino-3-methylbutanenitrile (Int-XII); 1H NMR (400 MHz, methanol-$d_4$) δ ppm 3.61 (1 H, d, J=5.72 Hz), 1.91 (1 H, dq, J=12.41, 6.72 Hz), 1.06 (6 H, t, J=6.49 Hz).

Preparation of Intermediate XIII (S)-2-Amino-3-methylbutanenitrile

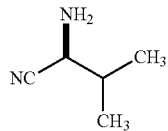

(Int-XIII)

(S)-2-(tert-Butoxycarbonylamino)-3-methylbutanoic acid was incorporated into the above scheme (Int-X, step A) to give (S)-2-amino-3-methylbutanenitrile (Int-XIII); $^1$H NMR (400 MHz, methanol-$d_4$) δ ppm 3.67 (1 H, d, J=5.72 Hz), 1.86-1.99 (1 H, m), 1.06 (6 H, t, J=6.49 Hz).

Preparation of Intermediate XIV

Ethyl 5-(aminomethyl)-1H-1,2,4-triazole-3-carboxylate, TFA

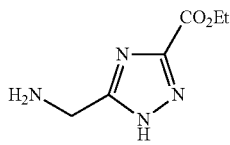

(Int-XIV)

Ethyl 5-((tert-butoxycarbonylamino)methyl)-1H-1,2,4-triazole-3-carboxylate (100 mg, 0.37 mmol) [Borg, S. et al., *J. Org. Chem.*, 60:3112-3120 (1995)] was dissolved in CH$_2$Cl$_2$ (2 mL) and TFA (1 mL). After 1 h, this was concentrated to give ethyl 5-(aminomethyl)-1H-1,2,4-triazole-3-carboxylate, TFA (Int-XIV, 95 mg, 0.33 mmol, 90%); LCMS=171.1 [M+H]$^+$; $^1$H NMR (400 MHz, methanol-$d_4$) δ ppm 4.45 (2 H, q, J=7.12 Hz), 4.35 (2 H, s), 1.40 (3 H, t, J=7.15 Hz).

Example 1

(R/S)-2-Hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide

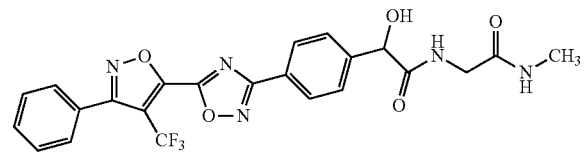

(1)

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 25 mg, 0.058 mmol) was dissolved in DMF (1 mL) and 4-methylmorpholine (0.038 mL, 0.348 mmol), 2-amino-N-methylacetamide, HCl (14.44 mg, 0.116 mmol), and HATU (39.7 mg, 0.104 mmol) were added. This solution was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention=11.4 min) to give (R/S)-2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (6.2 mg, 0.012 mmol, 19.97% yield): LCMS=502.2 [M+H]$^+$; $^1$H NMR (400 MHz, methanol-$d_4$) δ ppm 8.14-8.23 (2 H, m), 7.66-7.79 (4 H, m), 7.52-7.66 (3 H, m), 5.20 (1 H, s), 3.88-4.00 (2 H, m), 3.78-3.88 (2 H, m), 2.75 (3 H, s); HPLC Peak RT=8.1 min (Analytical Method C).

Example 2

(R/S)-N-(2-Amino-2-oxoethyl)-2-hydroxy-2-(4-(5-(3-phenyl-4-(trifluoromethyl)isoxazol-5-yl)-1,2,4-oxadiazol-3-yl)phenyl)acetamide

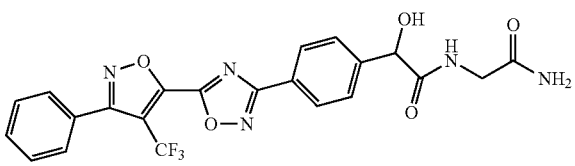

(2)

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 30 mg, 0.07 mmol) was dissolved in DMF (1 mL) prior to the addition of 4-methylmorpholine (0.061 mL, 0.556 mmol), 2-aminoacetamide (6.70 mg, 0.090 mmol), and HATU (39.7 mg, 0.104 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM) to give (R/S)-N-(2-amino-2-oxoethyl)-2-hydroxy-2-(4-(5-(3-phenyl-4-(trifluoromethyl)isoxazol-5-yl)-1,2,4-oxadiazol-3-yl) phenyl)acetamide (17.4 mg, 0.030 mmol, 43.2% yield): LCMS=488.2 [M+H]$^+$; $^1$H NMR (400 MHz, methanol-$d_4$) δ ppm 8.18 (2 H, d, J=8.35 Hz), 7.66-7.80 (4 H, m), 7.51-7.65 (3 H, m), 5.20 (1 H, s), 3.80-4.02 (2 H, m); HPLC Peak RT=8.1 min (Analytical Method D).

Example 3

(R/S)-2-Hydroxy-N-(2-hydroxyethyl)-2-(4-(5-(3-phenyl-4-(trifluoromethyl)isoxazol-5-yl)-1,2,4-oxadiazol-3-yl)phenyl)acetamide

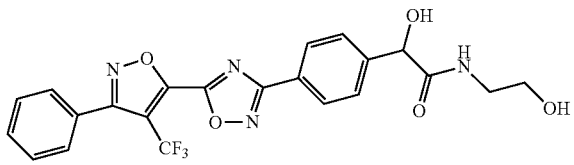

(3)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 130 mg, 0.3 mmol) was dissolved in DMF (2 mL) and cooled to 0° C. prior to the addition of 2-aminoethanol (27.6 mg, 0.452 mmol), 4-methylmorpholine (0.133 mL, 1.206 mmol), and HATU (149 mg, 0.392 mmol). This was stirred overnight and was then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, product retention=33.8 min) to give (R/S)-2-hydroxy-N-(2-hydroxyethyl)-2-(4-(5-(3-phenyl-4-(trifluoromethyl)isoxazol-5-yl)-1,2,4-oxadiazol-3-yl)phenyl)acetamide (34 mg, 0.065 mmol, 21.3% yield): LCMS [M+H]$^+$=475.1; $^1$H NMR (400 MHz, methanol-d$_4$) δ ppm 8.16 (2 H, dd, J=8.35, 4.39 Hz), 7.64-7.77 (4 H, m), 7.47-7.64 (3 H, m), 5.10-5.21 (1 H, m), 4.46 (2 H, t, J=5.49 Hz), 3.55-3.69 (2 H, m), 3.37 (1 H, m). HPLC Peak RT=8.6 min (Analytical Method A).

Example 4

3-(2-Hydroxy-2-(4-(5-(3-phenyl-4-(trifluoromethyl)isoxazol-5-yl)-1,2,4-oxadiazol-3-yl)phenyl)acetamido)propanoic acid (4)

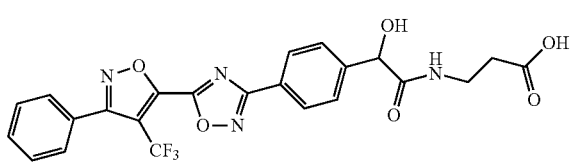

2-Hydroxy-2-(4-(5-(3-phenyl-4-(trifluoromethyl)isoxazol-5-yl)-1,2,4-oxadiazol-3-yl)phenyl)acetic acid (Int-Va, 70 mg, 0.162 mmol) was dissolved in DMF (2 mL) prior to the addition of 4-methylmorpholine (0.107 mL, 0.974 mmol), tert-butyl 3-aminopropanoate-HCl (53.1 mg, 0.292 mmol), and HATU (111 mg, 0.292 mmol). This was stirred overnight before EtOAc and brine were added. The organic layer was washed with brine, 1N HCl, and saturated NaHCO$_3$. The organic layer was then dried (MgSO$_4$), filtered, and concentrated to give tert-butyl 3-(2-hydroxy-2-(4-(5-(3-phenyl-4-(trifluoromethyl)isoxazol-5-yl)-1,2,4-oxadiazol-3-yl)phenyl)acetamido)propanoate (85 mg, 0.152 mmol, 94% yield): LCMS=559.3 [M+H]$^+$, which was taken to the next step. This material, tert-butyl 3-(2-hydroxy-2-(4-(5-(3-phenyl-4-(trifluoromethyl)isoxazol-5-yl)-1,2,4-oxadiazol-3-yl)phenyl)acetamido)propanoate (160 mg, 0.286 mmol), was dissolved in CH$_2$Cl$_2$ (1 mL) and TFA (2.0 mL). This was stirred for 1 h and was then concentrated to give single enantiomer 3-(2-hydroxy-2-(4-(5-(3-phenyl-4-(trifluoromethyl)isoxazol-5-yl)-1,2,4-oxadiazol-3-yl)phenyl)acetamido)propanoic acid (147 mg, 0.293 mmol): LCMS=503.0 [M+H]$^+$; $^1$H NMR (400 MHz, methanol-d$_4$) δ ppm 8.17 (2 H, d, J=8.35 Hz), 7.69 (4 H, d, J=7.91 Hz), 7.52-7.65 (3 H, m), 5.11 (1 H, s), 3.50 (2 H, t, J=6.59 Hz), 2.54 (2 H, t, J=6.81 Hz).

Example 5

(R/S)-N-(Cyanomethyl)-2-hydroxy-2-(4-(5-(3-phenyl-4-(trifluoromethyl)isoxazol-5-yl)-1,2,4-oxadiazol-3-yl)phenyl)acetamide (5)

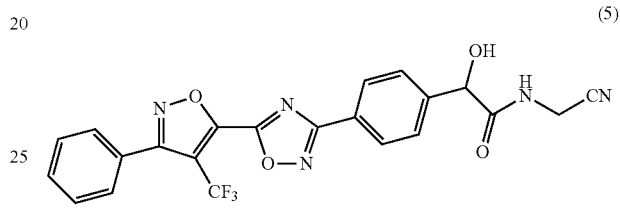

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 50 mg, 0.116 mmol) was dissolved in DMF (1 mL) prior to the addition of 4-methylmorpholine (0.102 mL, 0.927 mmol), 2-aminoacetonitrile, HCl (13.94 mg, 0.151 mmol), and HATU (66.1 mg, 0.174 mmol). This was stirred overnight before EtOAc was added. The EtOAc solution was washed with 1N HCl, sat NaHCO$_3$, and brine. The organic layer was then dried with MgSO$_4$ and concentrated to give N-(cyanomethyl)-2-hydroxy-2-(4-(5-(3-phenyl-4-(trifluoromethyl)isoxazol-5-yl)-1,2,4-oxadiazol-3-yl)phenyl)acetamide (51 mg, 0.088 mmol, 76% yield): LCMS=470.2 [M+H]$^+$; $^1$H NMR (400 MHz, methanol-d$_4$) δ ppm 8.15-8.23 (2 H, m), 7.65-7.76 (4 H, m), 7.53-7.64 (3 H, m), 5.21 (1 H, s), 4.19 (2 H, d, J=2.86 Hz). HPLC Peak RT=9.5 min (Analytical Method A).

Example 6

3-(2-Hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (6)

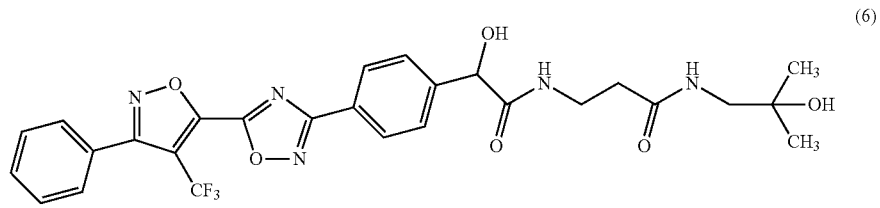 [SMILES: CC(C)(O)CNC(=O)CCNC(=O)C(O)c1ccc(-c2noc(-c3onc(-c4ccccc4)c3C(F)(F)F)n2)cc1]

3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 4, 35 mg, 0.070 mmol) was dissolved in DMF (1 mL) prior to the addition of 1-amino-2-methylpropan-2-ol (12.42 mg, 0.139 mmol), 4-methylmorpholine (0.046 mL, 0.418 mmol), and BOP (61.6 mg, 0.139 mmol). This was stirred for 1 h and was then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, product retention time=33.2 min) to give single enantiomer 3-(2-hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (15.3 mg, 0.026 mmol, 36.8% yield): LC/MS=574.3 [M+H]$^+$; $^1$H NMR (400 MHz, methanol-d$_4$) δ ppm 8.17 (2 H, d, J=8.36 Hz), 7.69 (4 H, d, J=8.14 Hz), 7.52-7.65 (3 H, m), 5.11 (1 H, s), 3.52 (2 H, t, J=6.71 Hz), 3.31 (3 H, dt, J=3.25, 1.57 Hz), 2.48 (2 H, t, J=6.71 Hz), 1.16 (6 H, d, J=1.76 Hz). HPLC Peak RT=9.0 min (Analytical Method D).

Example 7

2-Hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide (7)

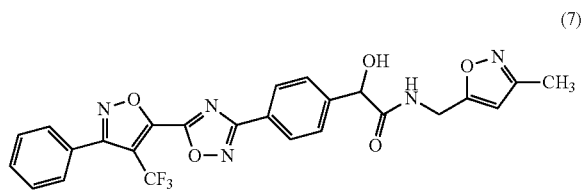 [SMILES: Cc1cc(CNC(=O)C(O)c2ccc(-c3noc(-c4onc(-c5ccccc5)c4C(F)(F)F)n3)cc2)on1]

2-Hydroxy-2-(4-(5-(3-phenyl-4-(trifluoromethyl)isoxazol-5-yl)-1,2,4-oxadiazol-3-yl)phenyl)acetic acid (Int-Va, 35 mg, 0.081 mmol) was dissolved in DMF (1 mL) prior to the addition of 4-methylmorpholine (0.054 mL, 0.487 mmol), (3-methylisoxazol-5-yl)methanamine (16.38 mg, 0.146 mmol), and BOP (64.6 mg, 0.146 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=11.8 min) to give single enantiomer 2-hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide (14.1 mg, 0.025 mmol, 30.8% yield): LCMS=526.3 [M+H]$^+$; $^1$H NMR (400 MHz, methanol-d$_4$) δ ppm 8.13-8.24 (2 H, m), 7.66-7.78 (4 H, m), 7.53-7.66 (3 H, m), 6.04 (1 H, s), 5.19 (1 H, s), 4.51 (2 H, s), 2.22 (3 H, s); HPLC Peak=9.9 min (Analytical Method A).

Example 8

2-Hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide (8)

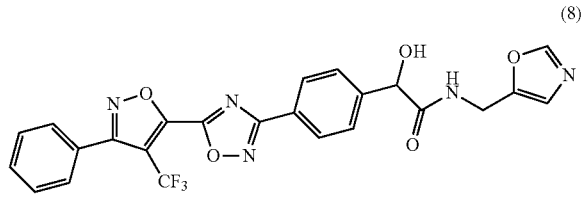 [SMILES: O=C(NCc1cnco1)C(O)c1ccc(-c2noc(-c3onc(-c4ccccc4)c3C(F)(F)F)n2)cc1]

2-Hydroxy-2-(4-(5-(3-phenyl-4-(trifluoromethyl)isoxazol-5-yl)-1,2,4-oxadiazol-3-yl)phenyl)acetic acid (Int-Va, 35 mg, 0.081 mmol) was dissolved in DMF (1 mL) prior to the addition of 4-methylmorpholine (0.054 mL, 0.487 mmol), oxazol-5-ylmethanamine, HCl (19.65 mg, 0.146 mmol), and BOP (64.6 mg, 0.146 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=11.6 min) to give single enantiomer 2-hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide (17.2 mg, 0.032 mmol, 38.8% yield): LCMS=512.3 [M+H]$^+$; $^1$H NMR (400 MHz, methanol-d$_4$) δ ppm 8.13-8.25 (2 H, m), 7.66-7.78 (4 H, m), 7.54-7.66 (4 H, m), 6.04 (1 H, s), 5.19 (1 H, s), 4.51 (2 H, s). HPLC Peak RT=10.1 min (Analytical Method D).

Example 9

N-((4H-1,2,4-Triazol-3-yl)methyl)-2-hydroxy-2-(4-(5-(3-phenyl-4-(trifluoromethyl)isoxazol-5-yl)-1,2,4-oxadiazol-3-yl)phenyl)acetamide (9)

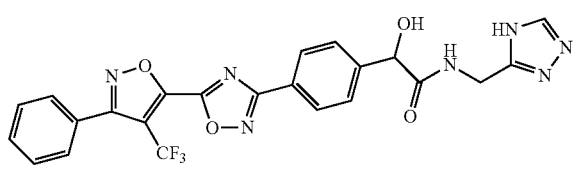

2-Hydroxy-2-(4-(5-(3-phenyl-4-(trifluoromethyl)isoxazol-5-yl)-1,2,4-oxadiazol-3-yl)phenyl)acetic acid (Int-Va, 30 mg, 0.070 mmol) was dissolved in DMF (1 mL) prior to the addition of 4-methylmorpholine (0.046 mL, 0.417 mmol), (1H-1,2,4-triazol-5-yl)methanamine (12.28 mg, 0.125 mmol), and BOP (55.4 mg, 0.125 mmol). This was stirred overnight and then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, retention time=32.9 min) to give single enantiomer N-((1H-1,2,4-triazol-5-yl)methyl)-2-hydroxy-2-(4-(5-(3-phenyl-4-(trifluoromethyl)isoxazol-5-yl)-1,2,4-oxadiazol-3-yl)phenyl)acetamide (22 mg, 0.041 mmol, 58.8% yield): LCMS=512.2 [M+H]; $^1$H NMR (400 MHz, methanol-d$_4$) δ ppm 8.11-8.24 (2 H, m), 7.66-7.78 (4 H, m), 7.54-7.66 (3 H, m), 6.04 (1 H, s), 5.19 (1 H, s), 4.51 (2 H, s). HPLC Peak RT=8.4 min (Analytical Method C).

Example 10

2-Hydroxy-N-((5-methyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (10)

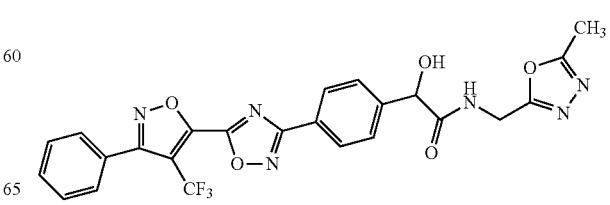

2-Hydroxy-2-(4-(5-(3-phenyl-4-(trifluoromethyl)isoxazol-5-yl)-1,2,4-oxadiazol-3-yl)phenyl)acetic acid (Int-Va, 35 mg, 0.081 mmol) was dissolved in DMF (1 mL) prior to the addition of 4-methylmorpholine (0.054 mL, 0.487 mmol), (5-methyl-1,3,4-oxadiazol-2-yl)methanamine (16.52 mg, 0.146 mmol), and BOP (64.6 mg, 0.146 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=11.5 min) to give single enantiomer 2-hydroxy-N-((5-methyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (15.1 mg, 0.027 mmol, 33.7% yield): LCMS=527.3 [M+H]⁺; ¹H NMR (400 MHz, methanol-d₄) δ ppm 8.13-8.24 (2 H, m), 7.66-7.78 (4 H, m), 7.54-7.66 (3 H, m), 5.21 (1 H, s), 4.63 (2 H, d, J=3.30 Hz), 2.49 (3 H, s). HPLC Peak RT=9.2 min (Analytical Method C).

Example 11

(R/S)-2-Hydroxy-2-(4-(5-(3-phenyl-4-(trifluoromethyl)isoxazol-5-yl)-1,2,4-oxadiazol-3-yl)phenyl)acetamide (11)

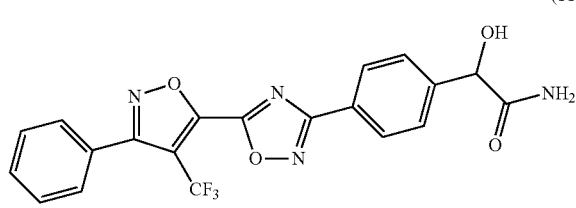

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.076 mL, 0.696 mmol), ammonia (0.5M in dioxane, 0.278 mL, 0.139 mmol), and HATU (39.7 mg, 0.104 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=11.4 min) to give (R/S)-2-hydroxy-2-(4-(5-(3-phenyl-4-(trifluoromethyl)isoxazol-5-yl)-1,2,4-oxadiazol-3-yl)phenyl)acetamide (10 mg, 0.021 mmol, 30.4% yield): LCMS=431.1 [M+H]⁺; ¹H NMR (400 MHz, methanol-d₄) δ ppm 8.18 (2 H, d, J=8.36 Hz), 7.65-7.80 (4 H, m), 7.52-7.65 (3 H, m), 5.11 (1 H, s). HPLC Peak RT=7.9 min (Analytical Method C).

Example 12

(R/S)-N-(2-(Ethylamino)-2-oxoethyl)-2-hydroxy-2-(4-(5-(3-phenyl-4-(trifluoromethyl)isoxazol-5-yl)-1,2,4-oxadiazol-3-yl)phenyl)acetamide (12)

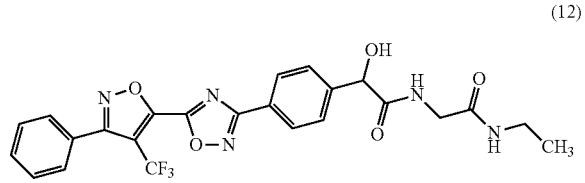 [SMILES: CCNC(=O)CNC(=O)C(O)c1ccc(-c2noc(-c3onc(-c4ccccc4)c3C(F)(F)F)n2)cc1]

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.061 mmol) was dissolved in DMF (1 mL) prior to the addition of 4-methylmorpholine (0.041 mL, 0.369 mmol), ethanamine, HCl (9.02 mg, 0.111 mmol), and HATU (42.0 mg, 0.111 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention=11.6 min) to give (R/S)-N-(2-(ethylamino)-2-oxoethyl)-2-hydroxy-2-(4-(5-(3-phenyl-4-(trifluoromethyl)isoxazol-5-yl)-1,2,4-oxadiazol-3-yl)phenyl)acetamide (8.6 mg, 0.014 mmol, 23.60% yield): LCMS=516.2[M+H]⁺; ¹H NMR (400 MHz, methanol-d₄) δ ppm 8.18 (2 H, d, J=8.36 Hz), 7.65-7.78 (4 H, m), 7.53-7.65 (3 H, m), 5.20 (1 H, s), 3.81-3.96 (2 H, m), 3.23 (2 H, q, J=7.26 Hz), 1.07-1.14 (3 H, m). HPLC Peak RT=9.5 min (Analytical Method D).

Example 13

(R/S)-N-Ethyl-2-hydroxy-2-(4-(5-(3-phenyl-4-(trifluoromethyl)isoxazol-5-yl)-1,2,4-oxadiazol-3-yl)phenyl)acetamide (13)

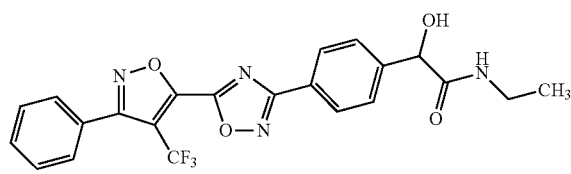

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.041 mL, 0.371 mmol), ethanamine, HCl (4.92 mg, 0.060 mmol), and HATU (31.7 mg, 0.083 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=12.0 min) to give (R/S)-N-ethyl-2-hydroxy-2-(4-(5-(3-phenyl-4-(trifluoromethyl)isoxazol-5-yl)-1,2,4-oxadiazol-3-yl)phenyl)acetamide (14.5 mg, 0.026 mmol, 56.5% yield): LCMS=459.1 [M+H]⁺; ¹H NMR (400 MHz, methanol-d₄) δ ppm 8.17 (2 H, d, J=8.35 Hz), 7.66-7.74 (4 H, m), 7.53-7.64 (3 H, m), 5.10 (1 H, s), 3.21-3.30 (2 H, m), 1.14 (3 H, t, J=7.25 Hz). HPLC Peak RT=10.60 min (Analytical Method C).

Example 14

N-(Cyanomethyl)-2-hydroxy-2-(4-(5-(3-phenyl-4-(trifluoromethyl)isoxazol-5-yl)-1,2,4-oxadiazol-3-yl)phenyl)acetamide (14)

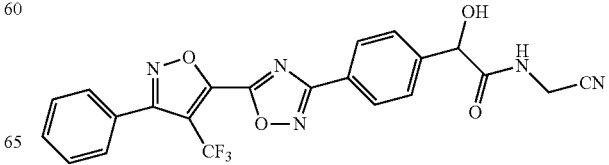

2-Hydroxy-2-(4-(5-(3-phenyl-4-(trifluoromethyl)isoxazol-5-yl)-1,2,4-oxadiazol-3-yl)phenyl)acetic acid (Int-Va, 35 mg, 0.081 mmol) was dissolved in DMF (1 mL) prior to the addition of 4-methylmorpholine (0.054 mL, 0.487 mmol), 2-aminoacetonitrile, HCl (15.02 mg, 0.162 mmol), and HATU (61.7 mg, 0.162 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=33.2 min) to give single enantiomer N-(cyanomethyl)-2-hydroxy-2-(4-(5-(3-phenyl-4-(trifluoromethyl)isoxazol-5-yl)-1,2,4-oxadiazol-3-yl)phenyl)acetamide (18.3 mg, 0.038 mmol, 46.6% yield): LCMS=470.2 [M+H]$^+$; $^1$H NMR (400 MHz, methanol-d$_4$) δ ppm 8.15-8.23 (2 H, m), 7.65-7.76 (4 H, m), 7.53-7.64 (3 H, m), 5.21 (1 H, s), 4.19 (2 H, d, J=2.86 Hz). HPLC Peak RT=9.5 min (Analytical Method A).

Example 15

(R/S)-N-(3-(1H-Imidazol-1-yl)propyl)-2-hydroxy-2-(4-(5-(3-phenyl-4-(trifluoromethyl)isoxazol-5-yl)-1,2,4-oxadiazol-3-yl)phenyl)acetamide-TFA (15)

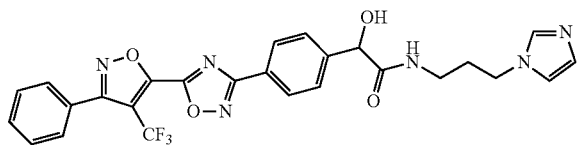

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.061 mL, 0.556 mmol), 1-(3-aminopropyl)imidazole (9.96 µL, 0.083 mmol), and HATU (39.7 mg, 0.104 mmol). The reaction mixture was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=10.6 min) to give (R/S)-N-(3-(1H-imidazol-1-yl)propyl)-2-hydroxy-2-(4-(5-(3-phenyl-4-(trifluoromethyl)isoxazol-5-yl)-1,2,4-oxadiazol-3-yl)phenyl)acetamide-TFA (10 mg, 0.014 mmol, 19.61% yield): LCMS=539.2 [M+H]$^+$; $^1$H NMR (400 MHz, methanol-d$_4$) δ ppm 8.90 (1 H, s), 8.52 (1 H, t, J=6.15 Hz), 8.19 (2 H, d, J=8.35 Hz), 7.47-7.80 (9 H, m), 5.16 (1 H, s), 4.23 (2 H, td, J=6.81, 3.52 Hz), 3.22-3.29 (2 H, m), 2.12 (2 H, dq, J=6.81, 6.66 Hz). HPLC Peak RT=6.3 min (Analytical Method A).

Example 16

(R/S)-2-Hydroxy-N-methyl-2-(4-(5-(3-phenyl-4-(trifluoromethyl)isoxazol-5-yl)-1,2,4-oxadiazol-3-yl)phenyl)acetamide (16)

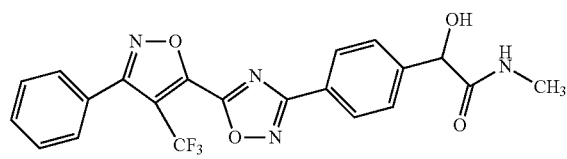

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.061 mL, 0.556 mmol), methanamine-HCl (4.70 mg, 0.070 mmol), and HATU (39.7 mg, 0.104 mmol). The reaction mixture was stirred overnight and then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention time=11.7 min) to give (R/S)-2-hydroxy-N-methyl-2-(4-(5-(3-phenyl-4-(trifluoromethyl)isoxazol-5-yl)-1,2,4-oxadiazol-3-yl)phenyl)acetamide (7 mg, 0.014 mmol, 20.3% yield): LCMS=445.1 [M+H]$^+$); $^1$H NMR (400 MHz, methanol-d$_4$) δ ppm 8.17 (2 H, d, J=7.92 Hz), 7.65-7.78(4 H, m), 7.49-7.66 (3 H, m), 5.12 (1 H, s), 2.79(3 H, s); HPLC Peak RT=8.3 min (Analytical Method A).

Example 17

N-((1H-Imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide-TFA (17)

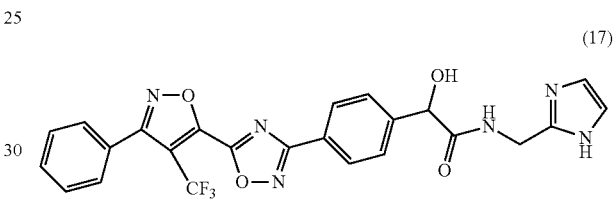

2-Hydroxy-2-(4-(5-(3-phenyl-4-(trifluoromethyl)isoxazol-5-yl)-1,2,4-oxadiazol-3-yl)phenyl)acetic acid (Int-Va, 30 mg, 0.070 mmol) was dissolved in DMF (1 mL) prior to the addition of 4-methylmorpholine (0.046 mL, 0.417 mmol), C-(1H-imidazol-2-yl)-methylamine-2HCl (13.51 mg, 0.139 mmol), and HATU (52.9 mg, 0.139 mmol). This was stirred overnight and was then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, product retention=29.3 min) to give single enantiomer N-((1H-imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide-TFA (8.8 mg, 0.014 mmol, 19.4% yield): LCMS=511.2 [M+H]$^{30}$ ; $^1$H NMR (400 MHz, methanol-d$_4$) δ ppm 8.11-8.24 (2 H, m), 7.43-7.78 (9 H, m), 5.19-5.31 (1 H, m), 4.57-4.77 (2 H, m); HPLC Peak RT=8.1 min (Analytical Method A).

Example 18

2-Hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (18)

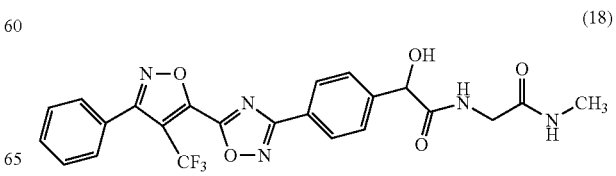

2-Hydroxy-2-(4-(5-(3-phenyl-4-(trifluoromethyl)isoxazol-5-yl)-1,2,4-oxadiazol-3-yl)phenyl)acetic acid (Int-Vb, 60 mg, 0.139 mmol) was dissolved in DMF (1 mL) prior to the addition of 4-methylmorpholine (0.092 mL, 0.835 mmol), 2-amino-N-methylacetamide-HCl (31.2 mg, 0.250 mmol), and HATU (95 mg, 0.250 mmol). This was stirred overnight and was then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, product retention=33.0 min) to give single enantiomer 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (33 mg, 0.064 mmol, 46.4% yield): LCMS=502.2 [M+H]$^+$; $^1$H NMR (400 MHz, methanol-d$_4$) δ ppm 8.14-8.23 (2 H, m), 7.66-7.79 (4 H, m), 7.52-7.66 (3 H, m), 5.20 (1 H, s), 3.88-4.00 (2 H, m), 3.78-3.88 (2 H, m), 2.75 (3 H, s); HPLC Peak RT=9.1 min (Analytical Method B).

Example 19

(R/S)-2-Hydroxy-N-((1-methyl-1H-imidazol-4-yl)methyl)-2-(4-(5-(3-phenyl-4-(trifluoromethyl)isoxazol-5-yl)-1,2,4-oxadiazol-3-yl)phenyl)acetamide-TFA

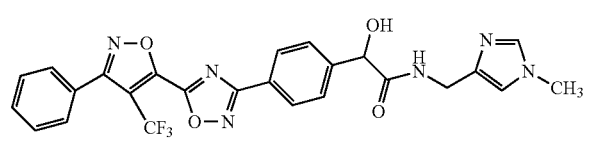

(19)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.046 mL, 0.417 mmol), (1-methyl-1H-imidazol-4-yl)methanamine (15.46 mg, 0.139 mmol), and BOP (55.4 mg, 0.125 mmol). The reaction mixture was stirred overnight and was then purified by preparative HPLC (PHENOMENEX® Luna 5u C18 21×250 mm, gradient elution with Method 1—MeOH/water containing 0.1% trifluoroacetic acid as defined above, 0% B to 100% B over 30 min, 15 mL/min, 220 nM, product retention time=29 min) to give (R/S)-2-hydroxy-N-((1-methyl-1H-imidazol-4-yl)methyl)-2-(4-(5-(3-phenyl-4-(trifluoromethyl)isoxazol-5-yl)-1,2,4-oxadiazol-3-yl)phenyl)acetamide-TFA (18.4 mg, 0.034 mmol, 49.4% yield): LCMS=525.3 [M+H]$^+$; $^1$H NMR (400 MHz, methanol-d$_4$) δ ppm 8.17 (2 H, d, J=8.36 Hz), 7.66-7.77 (4 H, m), 7.53-7.65 (4 H, m), 6.93 (1 H, s), 5.15 (1 H, s), 4.24-4.43 (2 H, m), 3.65-3.76 (3 H, m). HPLC Peak RT=8.2 min (Analytical Method A).

Example 20

(R/S)-2-Hydroxy-N-((1-methyl-1H-imidazol-5-yl)methyl)-2-(4-(5-(3-phenyl-4-(trifluoromethyl)isoxazol-5-yl)-1,2,4-oxadiazol-3-yl)phenyl)acetamide-TFA

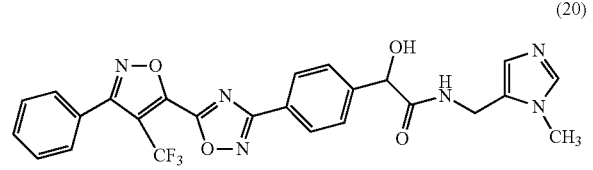 [SMILES: Cn1cncc1CNC(=O)C(O)c1ccc(-c2noc(-c3onc(-c4ccccc4)c3C(F)(F)F)n2)cc1]

(20)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.046 mL, 0.417 mmol), (1-methyl-1H-imidazol-5-yl)methanamine (13.91 mg, 0.125 mmol), and BOP (55.4 mg, 0.125 mmol). This was stirred overnight and was then purified by preparative HPLC (PHENOMENEX® Luna 5u C18 21×250 mm, gradient elution with Method 1—MeOH/water containing 0.1% trifluoroacetic acid as defined above, 0% B to 100% B over 30 min, 15 mL/min, 220 nM, product retention time=29.3 min) to give (R/S)-2-hydroxy-N-((1-methyl-1H-imidazol-5-yl)methyl)-2-(4-(5-(3-phenyl-4-(trifluoromethyl)isoxazol-5-yl)-1,2,4-oxadiazol-3-yl)phenyl)acetamide-TFA (20.0 mg, 0.038 mmol, 54.3% yield): LCMS=525.3 [M+H]$^+$; $^1$H NMR (400 MHz, methanol-d$_4$) δ ppm 8.39 (1 H, s), 8.12-8.24 (2 H, m), 7.66-7.77 (4 H, m), 7.55-7.66 (3 H, m), 7.21 (1 H, s), 5.19 (1 H, s), 4.50 (2 H, d, J=2.20 Hz), 3.75 (3 H, s). HPLC Peak RT=8.2 min (Analytical Method A).

Example 21

(R/S)-2-Hydroxy-N-(3-hydroxy-3-methylbutyl)-2-(4-(5-(3-phenyl-4-(trifluoromethyl)isoxazol-5-yl)-1,2,4-oxadiazol-3-yl)phenyl)acetamide

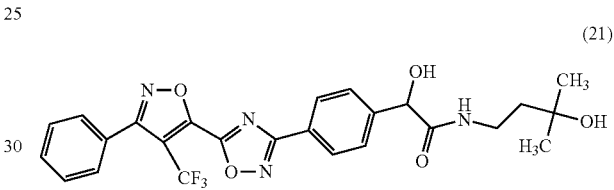

(21)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.046 mL, 0.417 mmol), 4-amino-2-methylbutan-2-ol (12.92 mg, 0.125 mmol), and BOP (55.4 mg, 0.125 mmol). This was stirred overnight and was then purified by preparative HPLC (PHENOMENEX® Luna 5u C18 21×250 mm, gradient elution with Method 1—MeOH/water containing 0.1% trifluoroacetic acid as defined above, 0% B to 100% B over 30 min, 15 mL/min, 220 nM, product retention time=34.1 min) to give (R/S)-2-hydroxy-N-(3-hydroxy-3-methylbutyl)-2-(4-(5-(3-phenyl-4-(trifluoromethyl)isoxazol-5-yl)-1,2,4-oxadiazol-3-yl)phenyl)acetamide (10.5 mg, 0.019 mmol, 26.9% yield): LCMS=517 [M+H]$^+$; $^1$H NMR (400 MHz, methanol-d$_4$) δ ppm 8.12-8.23 (2 H, m), 7.65-7.77 (4 H, m), 7.54-7.66 (3 H, m), 5.10 (1 H, s), 3.32-3.42 (2 H, m), 1.62-1.78 (2 H, m), 1.22 (6 H, s). HPLC Peak RT=9.2 min (Analytical Method A).

Example 22

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid

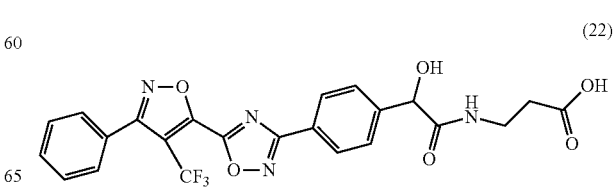

(22)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of N-methylmorpholine (0.031 mL, 0.278 mmol), tert-butyl 3-aminopropanoate-HCl (16.43 mg, 0.090 mmol), and EDC (17.33 mg, 0.090 mmol). This was stirred overnight before EtOAc and brine were added. The organic layer was washed with brine, 1N HCl, and sat NaHCO$_3$. The organic layer was then dried (MgSO$_4$), filtered, and concentrated. The resulting residue was dissolved in CH$_2$Cl$_2$ (1 mL) and TFA (2.0 mL). After 1 h, this was concentrated and then was purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, retention time for product=12.4 min) (R/S)-tert-butyl 3-(2-hydroxy-2-(4-(5-(3-phenyl-4-(trifluoromethyl)isoxazol-5-yl)-1,2,4-oxadiazol-3-yl)phenyl)acetamido)propanoate (10 mg, 0.018 mmol, 25.7% yield): LCMS=559.1 [M+H]$^+$. This material was dissolved in CH$_2$Cl$_2$ (0.5 mL) prior to the addition of TFA (1 mL). After stirring for 1h, the solution was concentrated to give (R/S)-3-(2-hydroxy-2-(4-(5-(3-phenyl-4-(trifluoromethyl)isoxazol-5-yl)-1,2,4-oxadiazol-3-yl)phenyl)acetamido)propanoic acid (10 mg, 0.018 mmol, 98% yield): LCMS=503.0 [M+H]$^+$; $^1$H NMR (400 MHz, methanol-d$_4$) δ ppm 8.17 (2 H, d, J=8.35 Hz), 7.69 (4 H, d, J=7.91 Hz), 7.52-7.65 (3H, m), 5.11 (1 H, s), 3.50 (2 H, t, J=6.59 Hz), 2.54 (2 H, t, J=6.81 Hz); HPLC Peak RT=8.8 min (Analytical Method A).

Example 23

(R/S)-2-Hydroxy-2-(4-(5-(3-phenyl-4-(trifluoromethyl)isoxazol-5-yl)-1,2,4-oxadiazol-3-yl)phenyl)-N-(3-(pyrrolidin-1-yl)propyl)acetamide (23)

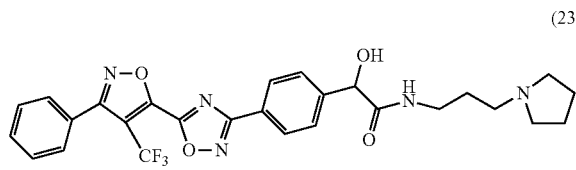

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), 1-(3-aminopropyl)pyrrolidine (11.89 mg, 0.093 mmol), and BOP (41.0 mg, 0.093 mmol). The reaction mixture was stirred overnight and was then concentrated. The resulting residue was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; flow rate=20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(3-(pyrrolidin-1-yl)propyl)acetamide (13.7 mg, 0.025 mmol, 53.5% yield): LCMS=542.2 [M+H]$^+$; $^1$H NMR (400 MHz, methanol-d$_4$) δ ppm 8.18 (2 H, d, J=8.28 Hz), 7.50-7.81 (7 H, m), 5.14 (1 H, s), 3.33-3.41 (2 H, m), 2.90 (4 H, br. s.), 2.78 (2 H, t, J=7.65 Hz), 1.74-2.01 (6 H, m); Analytical LC/MS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.2 min.

Example 24

(R/S)-N-Ethyl-2-hydroxy-N-methyl-2-(4-(5-(3-phenyl-4-(trifluoromethyl)isoxazol-5-yl)-1,2,4-oxadiazol-3-yl)phenyl)acetamide (24)

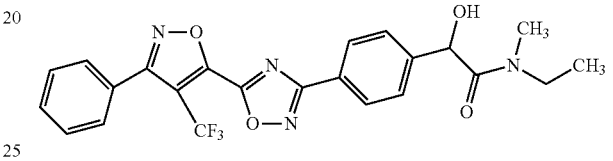

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), N-methylethanamine (4.93 mg, 0.083 mmol), and HATU (31.7 mg, 0.083 mmol). This was stirred overnight and was then purified by preparative HPLC (PHENOMENEX® Luna 5u C18 21.2×100 mm, gradient elution with Method 1—MeOH/water containing 0.1% trifluoroacetic acid as defined above, 0% B to 100% B over 10 min, 20 mL/min, 220 nM, product retention=12.2 min) to give (R/S)-N-ethyl-2-hydroxy-N-methyl-2-(4-(5-(3-phenyl-4-(trifluoromethyl)isoxazol-5-yl)-1,2,4-oxadiazol-3-yl)phenyl)acetamide (11 mg, 0.022 mmol, 47.7% yield): LCMS=473.2 [M+H]$^+$; $^1$H NMR (mixture of rotamers, 400 MHz, methanol-d$_4$) δ ppm 8.16-8.27 (2H, m), 7.48-7.75 (7 H, m), 5.54 (1 H, s), 5.51 (1 H, s), 3.35-3.55 (2 H, m), 2.96 (3 H, s), 2.91 (3 H, s), 1.11 (3 H, t, J=7.15 Hz), 0.92 (3 H, t, J=7.04 Hz).

Example 25

(2S)-2-((R/S)-2-Hydroxy-2-(4-(5-(3-phenyl-4-(trifluoromethyl)isoxazol-5-yl)-1,2,4-oxadiazol-3-yl)phenyl)acetamido)-N,3,3-trimethylbutanamide (25)

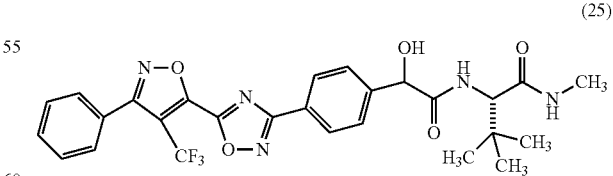

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), (S)-2-amino-N,3,3-trimethylbutanamide (6.69 mg, 0.046 mmol), and HATU (31.7 mg, 0.083 mmol). The reaction mixture was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (S)-2-((R/S)-2-hydroxy-2-(4-(5-(3-phenyl-4-(trifluoromethyl)isoxazol-5-yl)-1,2,4-oxadiazol-3-yl)phenyl)acetamido)-N,3,3-trimethylbutanamide (7.6 mg, 0.013 mmol, 29.1% yield): LCMS=558.0 [M+H]$^+$; $^1$H NMR (Mixture of diastereomers, 400 MHz, methanol-d$_4$) δ ppm 8.17 (4 H, dd, J=8.28, 6.53 Hz), 7.51-7.76 (14 H, m), 5.20 (1 H, s), 5.15 (1 H, s), 4.21 (2 H, d, J=4.02 Hz), 2.74 (3 H, s), 2.71 (3 H, s); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.6 min+2.7 min (mixture of diastereomers).

Example 26

(R/S)-(2S)-2-(2-Hydroxy-2-(4-(5-(3-phenyl-4-(trifluoromethyl)isoxazol-5-yl)-1,2,4-oxadiazol-3-yl)phenyl)acetamido)-N-methyl-4-phenylbutanamide

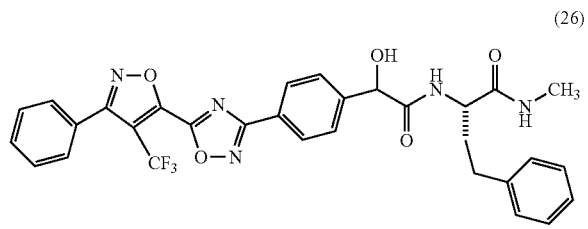 [SMILES: CNC(=O)[C@H](CCc1ccccc1)NC(=O)C(O)c1ccc(-c2noc(-c3onc(-c4ccccc4)c3C(F)(F)F)n2)cc1]

(26)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), (S)-2-amino-N-methyl-4-phenylbutanamide (8.91 mg, 0.046 mmol), and HATU (31.7 mg, 0.083 mmol). The reaction mixture was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (S)-2-((R/S)-2-hydroxy-2-(4-(5-(3-phenyl-4-(trifluoromethyl)isoxazol-5-yl)-1,2,4-oxadiazol-3-yl)phenyl)acetamido)-N-methyl-4-phenylbutanamide (7.3 mg, 0.012 mmol, 25.7% yield): LCMS=606.2 [M+H]$^+$, $^1$H NMR (Mixture of diastereomers, 400 MHz, methanol-d$_4$) δ ppm 8.10-8.25 (4 H, m), 7.48-7.83 (14 H, m), 6.95-7.30 (10 H, m), 5.20 (2 H, d, J=2.01 Hz), 4.24-4.42 (2 H, m), 2.74 (3 H, s), 2.71 (3 H, s), 2.43-2.68 (4 H, m), 1.88-2.16 (4 H, m); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.7 min+2.8 min (mixture of diastereomers).

Example 27

(R/S)-2-Hydroxy-2-(4-(5-(3-phenyl-4-(trifluoromethyl)isoxazol-5-yl)-1,2,4-oxadiazol-3-yl)phenyl)-N—((S)-tetrahydrofuran-3-yl)acetamide

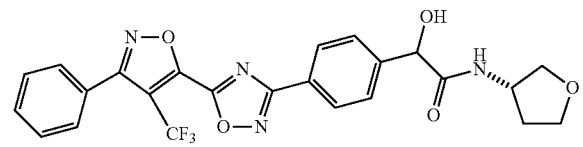

(27)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.07 mmol) was dissolved in DMF (1 mL) prior to the addition of 4-methylmorpholine (38.2 μL, 0.348 mmol), (S)-tetrahydrofuran-3-amine·HCl (15.47 mg, 0.125 mmol), and BOP (55.4 mg, 0.125 mmol). The reaction mixture was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-((S)-tetrahydrofuran-3-yl)acetamide (12.9 mg, 0.026 mmol, 37.1% yield): LCMS=501.1 [M+H]$^+$; $^1$H NMR (400 MHz, methanol-d$_4$) δ ppm 8.05-8.24 (4 H, m), 7.48-7.79 (14 H, m), 5.00-5.21 (2 H, m), 4.35-4.47 (2 H, m), 3.91-3.99 (2 H, m), 3.74-3.91 (4 H, m), 3.57-3.70 (2 H, m), 2.13-2.33 (2 H, m), 1.80-1.98 (2 H, m); Analytical LCMS: column: Mac-mod Halo C18, 4.6×50 mm, 2.7-μm particles; Mobile Phase A: 5:95 acetonitrile:water with 0.05% TFA; Mobile Phase B: 90:10 acetonitrile:water with 0.05% TFA; Temperature: 45° C.; Gradient: 0-100% B over 4 minutes, flow rate=4 mL/min, product retention=2.4 min (mixture of diastereomers).

Example 28

(R/S)-2-Hydroxy-2-(4-(5-(3-phenyl-4-(trifluoromethyl)isoxazol-5-yl)-1,2,4-oxadiazol-3-yl)phenyl)-N-(tetrahydro-2H-pyran-4-yl)acetamide

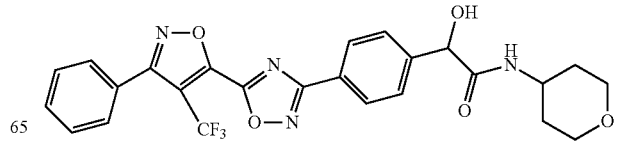

(28)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.07 mmol) was dissolved in DMF (1 mL) prior to the addition of 4-methylmorpholine (38.2 μL, 0.348 mmol), tetrahydro-2H-pyran-4-amine (12.66 mg, 0.125 mmol), and BOP (55.4 mg, 0.125 mmol). The reaction mixture was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(tetrahydro-2H-pyran-4-yl)acetamide (14.3 mg, 0.028 mmol, 40%): LCMS=515.1 [M+H]$^+$; $^1$H NMR (400 MHz, methanol-$d_4$) δ ppm 8.06-8.25 (2 H, m), 7.49-7.78 (7 H, m), 5.04-5.18 (1 H, m), 3.81-4.01 (2 H, m), 3.38-3.58 (2 H, m), 1.73-1.93 (2 H, m), 1.48-1.73 (2 H, m); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.6 min.

Example 29

(R/S)-2-Hydroxy-2-(4-(5-(3-phenyl-4-(trifluoromethyl)isoxazol-5-yl)-1,2,4-oxadiazol-3-yl)phenyl)-N-((R)-tetrahydrofuran-3-yl)acetamide (29)

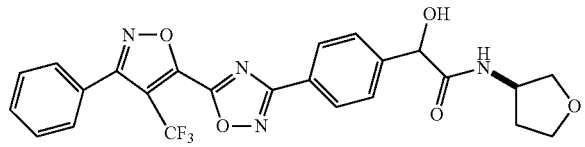

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.046 mL, 0.417 mmol), R(+)-3-aminotetrahydrofuran toluene-4-sulfonate (32.5 mg, 0.125 mmol), and BOP (55.4 mg, 0.125 mmol). This was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(R)-tetrahydrofuran-3-yl)acetamide (14.9 mg, 0.029 mmol, 42.4% yield): LCMS=501.1 [M+H]$^+$; $^1$H NMR (Mixture of diastereomers, 400 MHz, methanol-$d_4$) δ ppm 8.11-8.27 (4H, m), 7.50-7.78 (14 H, m), 5.13 (2 H, s), 4.33-4.48 (2 H, m, J=7.73, 5.91, 3.96, 3.96 Hz), 3.91-4.00 (2 H, m), 3.84-3.90 (2 H, m), 3.75-3.83 (2 H, m), 3.64 (2 H, ddd, J=16.95, 9.02, 3.74 Hz), 2.16-2.31 (2 H, m), 1.83-1.97 (2 H, m); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.6 min (mixture of diastereomers).

Example 30

N-(Azetidin-3-yl)-2-hydroxy-2-(4-(5-(3-phenyl-4-(trifluoromethyl)isoxazol-5-yl)-1,2,4-oxadiazol-3-yl)phenyl)acetamide-TFA (30)

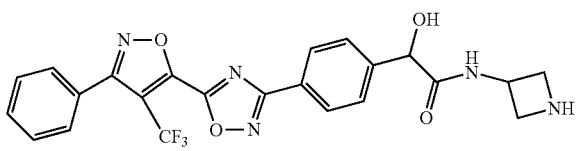

2-Hydroxy-2-(4-(5-(3-phenyl-4-(trifluoromethyl)isoxazol-5-yl)-1,2,4-oxadiazol-3-yl)phenyl)acetic acid (Int-Va, 90 mg, 0.209 mmol) was dissolved in DMF (1 mL) prior to the addition of 4-methylmorpholine (115 μL, 1.043 mmol), 3-amino-azetidine-1-carboxylic acid tert-butyl ester (53.9 mg, 0.313 mmol), and BOP (166 mg, 0.376 mmol). This was stirred overnight before EtOAc was added. The solution was washed with brine, 1N HCl, and sat. NaHCO$_3$ solution. The organic layer was dried and concentrated to give single enantiomer tert-butyl 3-(2-hydroxy-2-(4-(5-(3-phenyl-4-(trifluoromethyl)isoxazol-5-yl)-1,2,4-oxadiazol-3-yl)phenyl)acetamido)azetidine-1-carboxylate (120.6 mg, 0.206 mmol, 99% yield): LCMS=586.4 [M+H]$^+$. A portion of this tert-butyl 3-(2-hydroxy-2-(4-(5-(3-phenyl-4-(trifluoromethyl)isoxazol-5-yl)-1,2,4-oxadiazol-3-yl)phenyl)acetamido)azetidine-1-carboxylate (118 mg, 0.202 mmol) was dissolved in CH$_2$Cl$_2$ (2 mL) and TFA (2 mL). This was stirred for 1 h and then concentrated. The resulting residue was purified by preparative HPLC (PHENOMENEX® Luna 5u C18 21.2×100 mm, gradient elution with Method 1—MeOH/water containing 0.1% trifluoroacetic acid as defined above, 0% B to 100% B% over 10 min, product retention time=10.5 min, 20 mL/min, 220 nM) to give single enantiomer N-(azetidin-3-yl)-2-hydroxy-2-(4-(5-(3-phenyl-4-(trifluoromethyl)isoxazol-5-yl)-1,2,4-oxadiazol-3-yl)phenyl)acetamide-TFA (30 mg, 0.046 mmol, 22.60% yield): LCMS=486.0 [M+H]$^+$; $^1$H NMR (400 MHz, methanol-$d_4$) δ ppm 8.14-8.25 (2 H, m), 7.65-7.78 (4 H, m), 7.54-7.65 (3 H, m), 5.18 (1 H, s), 4.71 (1 H, t, J=7.81 Hz), 4.16-4.32 (4 H, m). HPLC Peak RT=8.3 min (Analytical Method A).

Example 31

2-Hydroxy-2-(4-(5-(3-phenyl-4-(trifluoromethyl)isoxazol-5-yl)-1,2,4-oxadiazol-3-yl)phenyl)-N-(3,3-dioxide-tetrahydrothiophen-3-yl)acetamide (31)

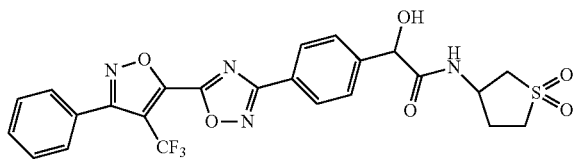

Single enantiomer 2-hydroxy-2-(4-(5-(3-phenyl-4-(trifluoromethyl)isoxazol-5-yl)-1,2,4-oxadiazol-3-yl)phenyl)acetic acid (Int-Va, 30 mg, 0.07 mmol) was dissolved in DMF (1 mL) prior to the addition of 4-methylmorpholine (38.2 µL, 0.348 mmol), tetrahydro-3-thiophenamine 1,1-dioxide (9.40 mg, 0.070 mmol), and BOP (55.4 mg, 0.125 mmol). The reaction mixture was stirred overnight and was then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, product retention time=32.9 min) to give 2-hydroxy-2-(4-(5-(3-phenyl-4-(trifluoromethyl)isoxazol-5-yl)-1,2,4-oxadiazol-3-yl)phenyl)-N-(3,3-dioxide-tetrahydrothiophen-3-yl)acetamide (17.7 mg, 0.031 mmol, 44.5% yield) as a mixture of diastereomers: LCMS=548.9 [M+H]$^+$; $^1$H NMR (Mixture of diastereomers, 400 MHz, methanol-d$_4$) δ ppm 8.56 (2 H, d, J=7.48 Hz), 8.18 (4 H, d, J=8.36 Hz), 7.49-7.77 (14 H, m), 5.15 (2 H, s), 4.56-4.71 (2 H, m), 3.43 (2 H, ddd, J=16.89, 13.37, 7.59 Hz), 3.25-3.29 (2 H, m), 2.99-3.21 (4 H, m), 2.42-2.60 (2 H, m), 2.26 (2 H, ddd, J=16.89, 13.37, 8.69 Hz), HPLC Peak RT=9.4 min (Analytical Method A).

minutes, then a 5-minute hold at 100% B; Flow rate=20 mL/min. Fractions containing the desired product were combined and dried via centrifugal evaporation to give (R/S)-2-(2-hydroxy-2-(4-(5-(3-phenyl-4-(trifluoromethyl)isoxazol-5-yl)-1,2,4-oxadiazol-3-yl)phenyl)acetamido)-N-methyl(S)propanamide (9.6 mg, 0.019 mmol, 40.2% yield): LCMS=516.1 [M+H]$^+$; $^1$H NMR (Mixture of Diastereomers, 400 MHz, methanol-d$_4$) δ ppm 8.11-8.25 (4 H, m), 7.50-7.78 (14 H, m), 5.16 (2 H, d, J=3.08 Hz), 4.37 (2 H, qd, J=7.08, 1.43 Hz), 2.75 (3 H, s), 2.72 (3 H, s), 1.39 (3 H, d, J=7.26 Hz), 1.35 (3 H, d, J=7.04 Hz); Analytical LCMS: column: Macmod Halo C18, 4.6×50 mm, 2.7-µm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.3 min+2.4 min (mixture of diastereomers).

Example 33

(R/S)-2-Hydroxy-N-(2-(1-methylazetidin-3-ylamino)-2-oxoethyl)-2-(4-(5-(3-phenyl-4-(trifluoromethyl)isoxazol-5-yl)-1,2,4-oxadiazol-3-yl)phenyl)acetamide

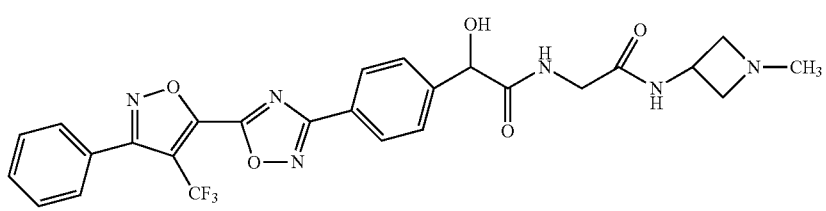

(33)

Example 32

(R/S)-2-(2-Hydroxy-2-(4-(5-(3-phenyl-4-(trifluoromethyl)isoxazol-5-yl)-1,2,4-oxadiazol-3-yl)phenyl)acetamido)-N-methyl(S)propanamide

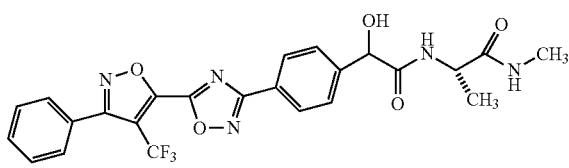

(32)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), (S)-2-amino-N-methylpropanamide-HCl (6.43 mg, 0.046 mmol), and HATU (31.7 mg, 0.083 mmol). The reaction mixture was stirred overnight and was then purified via preparative LCMS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 50-100% B over 25

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 160 mg, 0.371 mmol) was dissolved in DMF (1 mL) prior to the addition of 4-methylmorpholine (0.245 mL, 2.226 mmol), tert-butyl 2-aminoacetate (88 mg, 0.668 mmol), and HATU (254 mg, 0.668 mmol). The reaction mixture was stirred overnight before EtOAc was added. The EtOAc solution was washed with 1N HCl, sat NaHCO$_3$, and brine. The organic layer was then dried (MgSO$_4$) and concentrated to give (R/S)-tert-butyl 2-(2-hydroxy-2-(4-(5-(3-phenyl-4-(trifluoromethyl)isoxazol-5-yl)-1,2,4-oxadiazol-3-yl)phenyl)acetamido)acetate (159.5 mg, 0.293 mmol): LCMS=546.2 [M+H]$^+$. The (R/S)-tert-butyl 2-(2-hydroxy-2-(4-(5-(3-phenyl-4-(trifluoromethyl)isoxazol-5-yl)-1,2,4-oxadiazol-3-yl)phenyl)acetamido)acetate (159 mg, 0.294 mmol) was dissolved in CH$_2$Cl$_2$ (1 mL) and TFA (2.0 mL). This was stirred for 1 h and was then concentrated to give 2-(2-hydroxy-2-(4-(5-(3-phenyl-4-(trifluoromethyl)isoxazol-5-yl)-1,2,4-oxadiazol-3-yl)phenyl)acetamido)acetic acid (148 mg, 0.303 mmol): LCMS=489.1 [M+H]$^+$. A portion of the (R/S)-2-(2-hydroxy-2-(4-(5-(3-phenyl-4-(trifluoromethyl)isoxazol-5-yl)-1,2,4-oxadiazol-3-yl)phenyl)acetamido)acetic acid (30 mg, 0.061 mmol) was dissolved in DMF (1 mL) prior to the addition of 4-methylmorpholine (0.041 mL, 0.369 mmol), 1-methylazetidin-3-amine-2HCl (17.59 mg, 0.111 mmol), and HATU (42.0 mg, 0.111 mmol). This was stirred overnight and was then purified via preparative LCMS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-N-(2-(1-methylazetidin-3-ylamino)-2-oxoethyl)-2-(4-(5-(3-phenyl-4-(trifluoromethyl)isoxazol-5-yl)-1,2,4-oxadiazol-3-yl)phenyl)acetamide (11.3 mg, 0.020 mmol, 32.4% yield): LCMS=557.2 [M+H]⁺; ¹H NMR (400 MHz, methanol-d₄) δ ppm 8.18 (2 H, d, J=8.28 Hz), 7.66-7.80 (4 H, m), 7.55-7.65 (3 H, m), 5.20 (1 H, s), 4.47 (1 H, t, J=7.28 Hz), 3.82-4.02 (4 H, m), 3.49 (2 H, t, J=7.78 Hz), 2.58 (3 H, s); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.1 min.

Example 34

(R/S)-2-Hydroxy-2-(4-(5-(3-phenyl-4-(trifluoromethyl)isoxazol-5-yl)-1,2,4-oxadiazol-3-yl)phenyl)-N-(pyridin-2-ylmethyl)acetamide

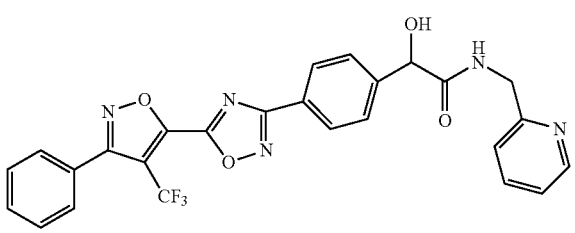

(34)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), pyridin-2-ylmethanamine (9.03 mg, 0.083 mmol), and BOP (36.9 mg, 0.083 mmol). This was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(pyridin-2-ylmethyl)acetamide (9.9 mg, 0.019 mmol, 40.5% yield): LCMS=522.0 [M+H]⁺; ¹H NMR (400 MHz, methanol-d₄) δ ppm 8.47 (1H, dd, J=5.40, 1.88 Hz), 8.11-8.23 (2 H, m), 7.62-7.77 (5 H, m), 7.48-7.61 (3 H, m), 7.21-7.32 (2 H, m), 5.20 (1 H, s), 4.44-4.62 (2 H, m); Analytical LCMS: column: Mac-mod Halo C18, 4.6×50 mm, 2.7-μm particles; Mobile Phase A: 5:95 acetonitrile:water with 0.05% TFA; Mobile Phase B: 90:10 acetonitrile:water with 0.05% TFA; Temperature: 45° C.; Gradient: 0-100% B over 4 minutes, flow rate=4 mL/min, product retention=2.1 min.

Example 35

(R/S)-2-Hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide

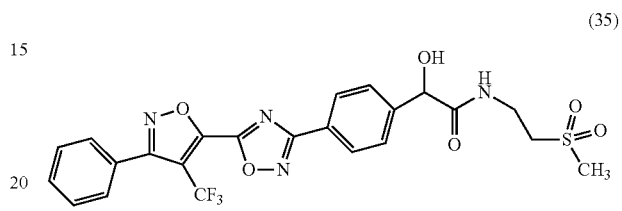

(35)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), 2-(methylsulfonyl)ethanamine (10.28 mg, 0.083 mmol), and BOP (36.9 mg, 0.083 mmol). The reaction mixture was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide (9.2 mg, 0.017 mmol, 36.2% yield): LCMS=537.1 [M+H]⁺; ¹H NMR (400 MHz, methanol-d₄ and CDCl₃) δ ppm 8.15 (2 H, d, J=8.28 Hz), 7.66 (4 H, t, J=7.78 Hz), 7.47-7.60 (3H, m), 5.13 (1 H, s), 3.73 (2 H, t, J=6.40 Hz), 3.23-3.31 (2 H, m), 2.94 (3 H, s); Analytical LCMS: column: Mac-mod Halo C18, 4.6×50 mm, 2.7-μm particles; Mobile Phase A: 5:95 acetonitrile:water with 0.05% TFA; Mobile Phase B: 90:10 acetonitrile:water with 0.05% TFA; Temperature: 45° C.; Gradient: 0-100% B over 4 minutes, flow rate=4 mL/min, product retention=2.4 min.

Example 36

(R/S)-2-Hydroxy-N-(2-oxo-2-(1,1-dioxide-tetrahydrothiophen-3-ylamino)ethyl)-2-(4-(5-(3-phenyl-4-(trifluoromethyl)isoxazol-5-yl)-1,2,4-oxadiazol-3-yl)phenyl)acetamide

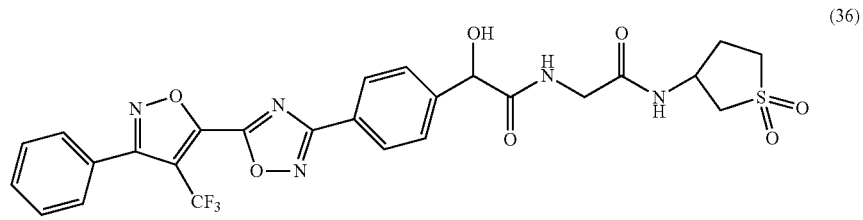 [SMILES: O=C(CNC(=O)C(O)c1ccc(-c2noc(-c3onc(-c4ccccc4)c3C(F)(F)F)n2)cc1)NC1CCS(=O)(=O)C1]

(36)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.061 mmol) was dissolved in DMF (1 mL) prior to the addition of 4-methylmorpholine (0.041 mL, 0.369 mmol), tetrahydro-3-thiophenamine 1,1-dioxide (14.95 mg, 0.111 mmol), and HATU (42.0 mg, 0.111 mmol). The reaction mixture stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-N-(2-oxo-2-(1,1-dioxide-tetrahydrothiophen-3-ylamino)ethyl)-2-(4-(5-(3-phenyl-4-(trifluoromethyl)isoxazol-5-yl)-1,2,4-oxadiazol-3-yl)phenyl)acetamide (8.4 mg, 0.014 mmol, 22.4% yield): LCMS=606.1 [M+H]$^+$; $^1$H NMR (400 MHz, methanol-$d_4$ and CDCl$_3$) δ ppm 8.16 (2 H, d, J=8.53 Hz), 7.61-7.76 (4 H, m), 7.47-7.61 (3 H, m), 5.18 (1 H, s), 4.53-4.63 (1 H, m), 3.77-4.00 (2 H, m), 3.37-3.49 (1 H, m), 3.22-3.29 (1 H, m), 3.10 (1 H, dt, J=13.49, 8.19 Hz), 2.91-3.03 (1 H, m), 2.49 (1 H, dd, J=13.43, 6.90 Hz), 2.16 (1 H, ddd, J=13.24, 8.47, 4.64 Hz); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.3 min.

Example 37

(R/S)-2-Hydroxy-2-(4-(5-(3-phenyl-4-(trifluoromethyl)isoxazol-5-yl)-1,2,4-oxadiazol-3-yl)phenyl)-N-(2-(thiazol-4-yl)ethyl)acetamide (37)

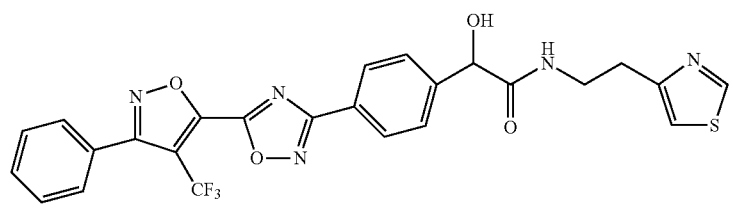

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol) was dissolved in DMF (1 mL) prior to the addition of 4-methylmorpholine (0.031 mL, 0.278 mmol), 2-(thiazole-4-yl)ethylamine (11.89 mg, 0.093 mmol), and BOP (41.0 mg, 0.093 mmol). The reaction mixture was stirred overnight and was then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(2-(thiazol-4-yl)ethyl)acetamide (11.8 mg, 0.022 mmol, 47.0% yield): LCMS=542.2 [M+H]$^+$; $^1$H NMR (400 MHz, methanol-$d_4$) δ ppm 8.82 (1 H, d, J=2.01 Hz), 8.13 (2 H, d, J=8.28 Hz), 7.46-7.69 (7 H, m), 7.08 (1 H, d, J=2.01 Hz), 5.08 (1 H, s), 3.50-3.69 (2 H, m), 3.03 (2 H, t, J=6.90 Hz); Analytical LCMS: column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, flow rate=4 mL/min, product retention=2.6 min.

Example 38

(R/S)-2-Hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (38)

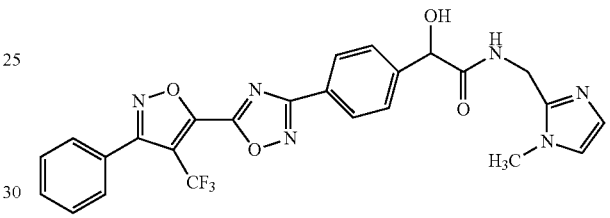

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol) was dissolved in DMF (1 mL) prior to the addition of 4-methylmorpholine (0.046 mL, 0.417 mmol), C-(1-methyl-1H-imidazol-2-yl)-methylamine dihydrochloride (13.91 mg, 0.125 mmol), and BOP (55.4 mg, 0.125 mmol). The reaction mixture was stirred overnight and then purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow rate=20 mL/min. Fractions containing the desired product were combined and dried via centrifugal evaporation to give (R/S)-2-hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (4.9 mg, 0.001 mmol, 13% yield): LCMS=525.1 [M+H]$^+$; $^1$H NMR (400 MHz, methanol-$d_4$) δ ppm 8.10-8.24 (2 H, m), 7.70 (1 H, t, J=8.03 Hz), 7.52-7.64 (3 H, m), 7.00 (1 H, d, J=1.25 Hz), 6.88 (1 H, d, J=1.51 Hz), 5.18 (1 H, s), 4.40-4.58 (2 H, m), 3.60 (3 H, s);

Analytical LCMS: column: Mac-mod Halo C18, 4.6×50 mm, 2.7-μm particles; Mobile Phase A: 5:95 acetonitrile:water with 0.05% TFA; Mobile Phase B: 90:10 acetonitrile:water with 0.05% TFA; Temperature: 45° C.; Gradient: 0-100% B over 4 minutes, flow rate=4 mL/min, product retention=2.0 min.

Example 39

N-((R)-1-Cyanoethyl)-2-hydroxy-2-(4-(5-(3-phenyl-4-(trifluoromethyl)isoxazol-5-yl)-1,2,4-oxadiazol-3-yl)phenyl)acetamide (39)

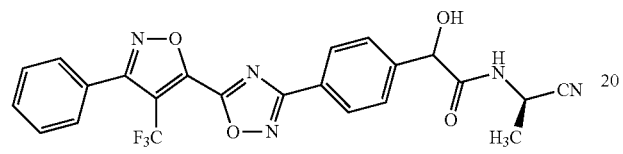

2-Hydroxy-2-(4-(5-(3-phenyl-4-(trifluoromethyl)isoxazol-5-yl)-1,2,4-oxadiazol-3-yl)phenyl)acetic acid (Int-Va, 40 mg, 0.093 mmol) and (R)-2-aminopropanenitrile (Int-X, 13.00 mg, 0.185 mmol) were dissolved in DMF (1 mL). 4-Methylmorpholine (37.5 mg, 0.371 mmol) and HATU (45.8 mg, 0.121 mmol) were added. After stirring 1 h, the mixture was purified by prep HPLC (PHENOMENEX® Luna 5u 21.2×250 mm, gradient elution with Method 2—$CH_3CN$/water containing 0.1% trifluoroacetic acid as defined above, 0% B to 100% B over 35 min, 20 mL/min, 220 nM, product retention=28.5 min) to provide single enantiomer N-((R)-1-cyanoethyl)-2-hydroxy-2-(4-(5-(3-phenyl-4-(trifluoromethyl)isoxazol-5-yl)-1,2,4-oxadiazol-3-yl)phenyl)acetamide (27 mg, 0.055 mmol, 59.6% yield): $[M+H]^+$=484.0; $^1$H NMR (400 MHz, methanol-$d_4$) δ ppm 8.93 (1 H, d, J=7.70 Hz), 8.13-8.24 (2 H, m), 7.50-7.80 (7 H, m), 5.17 (1 H, s), 4.86-4.91 (1 H, m), 1.56 (3 H, d, J=7.04 Hz); HPLC peak RT=9.9 min (Method A).

Example 40

N-((S)-1-Cyanoethyl)-2-hydroxy-2-(4-(5-(3-phenyl-4-(trifluoromethyl)isoxazol-5-yl)-1,2,4-oxadiazol-3-yl)phenyl)acetamide (40)

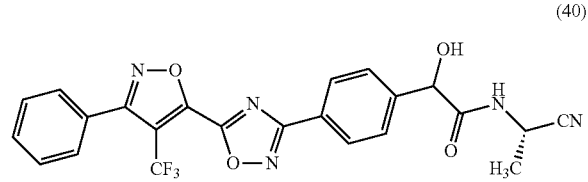 [SMILES: C[C@@H](C#N)NC(=O)C(O)c1ccc(-c2noc(-c3onc(-c4ccccc4)c3C(F)(F)F)n2)cc1]

2-Hydroxy-2-(4-(5-(3-phenyl-4-(trifluoromethyl)isoxazol-5-yl)-1,2,4-oxadiazol-3-yl)phenyl)acetic acid (Int-Va, 37 mg, 0.086 mmol), (S)-2-aminopropanenitrile (Int-XI, 9.0 mg, 0.13 mmol) [see also, McLaughlin, M. et al., *J. Org. Chem.*, 68:50-54 (2003)], 4-methylmorpholine (34.7 mg, 0.343 mmol), and HATU (42.4 mg, 0.112 mmol) were dissolved in DMF (1 mL). After stirring 1 h, the reaction mixture was purified by prep HPLC (PHENOMENEX® 21×250 mm, gradient elution with Method 1—MeOH/water containing 0.1% trifluoroacetic acid as defined above, 0% B to 100% B over 38 min, 25 mL/min, 220 nM, product retention=29.3 min) to provide single enantiomer N—((S)-1-cyanoethyl)-2-hydroxy-2-(4-(5-(3-phenyl-4-(trifluoromethyl)isoxazol-5-yl)-1,2,4-oxadiazol-3-yl)phenyl)acetamide (12 mg, 0.023 mmol, 27.3% yield): $[M+H]^+$=484.2; $^1$H NMR (400 MHz, methanol-$d_4$) δ ppm 8.13-8.25 (2 H, m), 7.54-7.77 (7 H, m), 5.19 (1 H, s), 4.87 (1 H, q), 1.54 (3 H, d, J=7.04 Hz); HPLC peak RT=11.1 min (Method A).

Example 41

N-(1-Cyanocyclopropyl)-2-hydroxy-2-(4-(5-(3-phenyl-4-(trifluoromethyl)isoxazol-5-yl)-1,2,4-oxadiazol-3-yl)phenyl)acetamide (41)

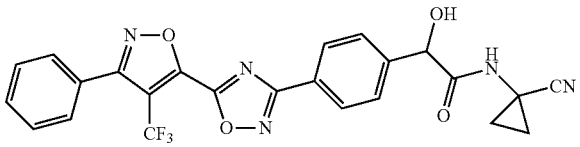

2-Hydroxy-2-(4-(5-(3-phenyl-4-(trifluoromethyl)isoxazol-5-yl)-1,2,4-oxadiazol-3-yl)phenyl)acetic acid (Int-Va, 60 mg, 0.139 mmol), 1-aminocyclopropanecarbonitrile-HCl (24.74 mg, 0.21 mmol), HATU (68.8 mg, 0.181 mmol), and 4-methylmorpholine (56.3 mg, 0.556 mmol) were dissolved in DMF (1 mL). After stirring 1 h, this was purified by prep HPLC (PHENOMENEX® 21.0×250 mm, gradient elution with Method 1—MeOH/water containing 0.1% trifluoroacetic acid as defined above, 0% B to 100% B over 30 min, 25 mL/min, 220 nM, product retention=29.8 min) to provide single enantiomer N-(1-cyanocyclopropyl)-2-hydroxy-2-(4-(5-(3-phenyl-4-(trifluoromethyl)isoxazol-5-yl)-1,2,4-oxadiazol-3-yl)phenyl)acetamide (15 mg, 0.028 mmol, 20.46% yield): LCMS=496.1 $[M+H]^+$; $^1$H NMR (400 MHz, methanol-$d_4$) δ ppm 8.12-8.28 (2 H, m), 7.52-7.79 (7 H, m), 5.16 (1 H, s), 1.42-1.61 (2 H, m), 1.12-1.34 (2 H, m); HPLC peak RT=9.9 min (Method A).

Example 42

N-(1,3-Dihydroxypropan-2-yl)-2-hydroxy-2-(4-(5-(3-phenyl-4-(trifluoromethyl)isoxazol-5-yl)-1,2,4-oxadiazol-3-yl)phenyl)acetamide (42)

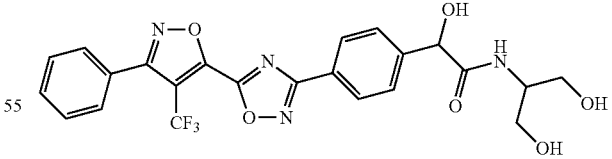

Single enantiomer 2-hydroxy-2-(4-(5-(3-phenyl-4-(trifluoromethyl)isoxazol-5-yl)-1,2,4-oxadiazol-3-yl)phenyl) acetic acid (Int-Va, 30 mg, 0.070 mmol), (R/S)-2-aminopropane-1,3-diol (9.51 mg, 0.104 mmol), 4-methylmorpholine (28.1 mg, 0.278 mmol), and HATU (34.4 mg, 0.090 mmol) were dissolved in DMF (1 mL). After stirring 1 h, the reaction mixture was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.33 min) to provide the product N-(1,3-dihydroxypropan-2-yl)-2-hydroxy-2-(4-(5-(3-phenyl-4-(trifluoromethyl)isoxazol-5-yl)-1,2,4-oxadiazol-3-yl)phenyl)acetamide as a mixture of diastereomers (13 mg, 0.023 mmol, 32.6% yield): LCMS=505.1 [M+H]$^+$; $^1$H NMR (400 MHz, methanol-$d_4$) δ ppm 8.12-8.27 (2 H, m), 7.92-8.01 (1 H, m), 7.50-7.81 (7 H, m), 5.16 (1 H, s), 3.95 (1 H, dt, J=8.53, 5.42 Hz), 3.55-3.79 (4 H, m); HPLC peak RT=8.3 min (Method A).

Example 43

N-(2-Cyanopropan-2-yl)-2-hydroxy-2-(4-(5-(3-phenyl-4-(trifluoromethyl)isoxazol-5-yl)-1,2,4-oxadiazol-3-yl)phenyl)acetamide

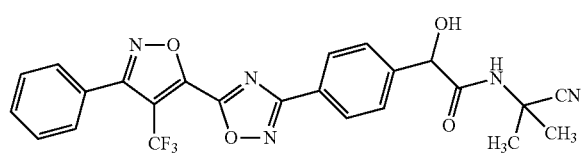

(43)

2-Hydroxy-2-(4-(5-(3-phenyl-4-(trifluoromethyl)isoxazol-5-yl)-1,2,4-oxadiazol-3-yl)phenyl)acetic acid (Int-Va, 30 mg, 0.070 mmol), 2-amino-2-methylpropanenitrile-HCl (12.58 mg, 0.104 mmol) [Ingate, S. T. et al., *Tetrahedron*, 53:17795-17814 (1997)], HATU (34.4 mg, 0.090 mmol), and 4-methylmorpholine (28.1 mg, 0.278 mmol) were dissolved in DMF (1 mL). After stirring 1 h, the mixture was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 40-100% B over 25 minutes, then a 5-minute hold at 100% B; Flow: 20 mL/min. Fractions containing the desired product were combined and dried via centrifugal evaporation to provide single enantiomer N-(2-cyanopropan-2-yl)-2-hydroxy-2-(4-(5-(3-phenyl-4-(trifluoromethyl)isoxazol-5-yl)-1,2,4-oxadiazol-3-yl)phenyl)acetamide (3.7 mg, 0.007 mmol, 10.7% yield): LCMS=498.0 [M+H]$^+$; $^1$H NMR (400 MHz, methanol-$d_4$) δ ppm 8.13-8.19 (2 H, m), 7.49-7.70 (7 H, m), 5.13 (1 H, s), 1.71 (3 H, s), 1.67 (3 H, s); HPLC peak RT=2.9 min (Method E).

Example 44

N-((S)-1-Cyano-2-methylpropyl)-2-hydroxy-2-(4-(5-(3-phenyl-4-(trifluoromethyl)isoxazol-5-yl)-1,2,4-oxadiazol-3-yl)phenyl)acetamide

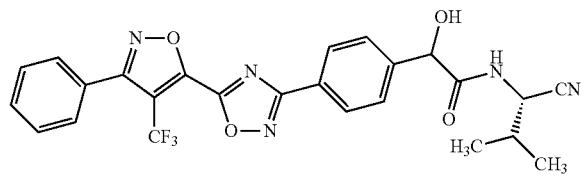

(44)

2-Hydroxy-2-(4-(5-(3-phenyl-4-(trifluoromethyl)isoxazol-5-yl)-1,2,4-oxadiazol-3-yl)phenyl)acetic acid (Int-Va, 45 mg, 0.104 mmol), (S)-2-amino-3-methylbutanenitrile (Int-XIII), formic acid salt (15.04 mg, 0.104 mmol), 4-methylmorpholine (42.2 mg, 0.417 mmol), and HATU (51.6 mg, 0.136 mmol) were dissolved in DMF (1 mL). After stirring 1 h, this was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give single enantiomer N-((S)-1-cyano-2-methylpropyl)-2-hydroxy-2-(4-(5-(3-phenyl-4-(trifluoromethyl)isoxazol-5-yl)-1,2,4-oxadiazol-3-yl)phenyl)acetamide (3.8 mg, 0.007 mmol, 7.1% yield, and its purity was 100%): LCMS=512.1 [M+H]$^+$; $^1$H NMR (500 MHz, methanol-$d_4$) δ ppm 8.16 (2 H, d, J=8.32 Hz), 7.48-7.72 (7 H, m), 5.19 (1 H, s), 4.63 (1 H, d, J=7.49 Hz), 2.01-2.15 (1 H, m, J=13.80, 6.83, 6.83, 6.66 Hz), 1.07 (3 H, d, J=6.66 Hz), 0.95 (3 H, d, J=6.94 Hz); HPLC peak RT=3.0 min (Method E).

Example 45

N-((R)-1-Cyano-2-methylpropyl)-2-hydroxy-2-(4-(5-(3-phenyl-4-(trifluoromethyl)isoxazol-5-yl)-1,2,4-oxadiazol-3-yl)phenyl)acetamide

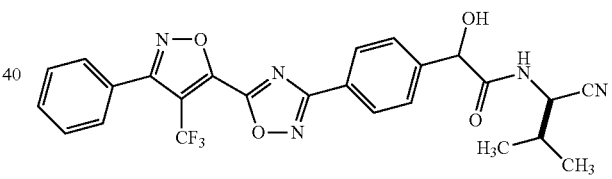

(45)

2-Hydroxy-2-(4-(5-(3-phenyl-4-(trifluoromethyl)isoxazol-5-yl)-1,2,4-oxadiazol-3-yl)phenyl)acetic acid (Int-Va, 40 mg, 0.093 mmol), (R)-2-amino-3-methylbutanenitrile (Int-VII, 9.10 mg, 0.093 mmol), HATU (45.8 mg, 0.121 mmol), and 4-methylmorpholine (37.5 mg, 0.371 mmol) were dissolved in DMF (1 mL). After stirring 1 h, the mixture was purified by prep HPLC (PHENOMENEX® Luna 5u 21.2×250 mm, gradient elution with Method 2—CH$_3$CN/ water containing 0.1% trifluoroacetic acid as defined above, 0% B to 100% B over 35 min, 20 mL/min, 220 nM, product retention=30.3 min) to provide single enantiomer N-((R)-1-cyano-2-methylpropyl)-2-hydroxy-2-(4-(5-(3-phenyl-4-(trifluoromethyl)isoxazol-5-yl)-1,2,4-oxadiazol-3-yl)phenyl)acetamide (20 mg, 0.037 mmol, 40.1% yield): LCMS=512.1 [M+H]$^+$; $^1$H NMR (400 MHz, methanol-$d_4$) δ ppm 8.90 (1 H, d, J=8.58 Hz), 8.13-8.26 (2 H, m), 7.50-7.81 (7 H, m), 5.21 (1 H, s), 4.54-4.69 (1 H, m), 2.05-2.25 (1 H, m), 1.09 (3 H, d, J=6.82 Hz), 0.98 (3 H, d, J=6.60 Hz); HPLC peak RT=10.5 min (Method A).

Example 46

N-((S)-1-Cyanoethyl)-2-hydroxy-2-(4-(5-(3-phenyl-4-(trifluoromethyl)isoxazol-5-yl)-1,2,4-oxadiazol-3-yl)phenyl)acetamide

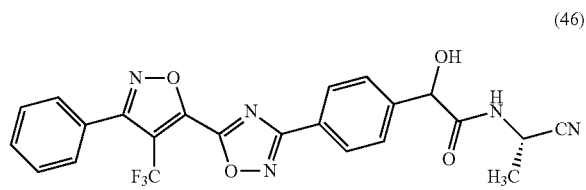 [SMILES: C[C@@H](C#N)NC(=O)C(O)c1ccc(-c2noc(-c3onc(-c4ccccc4)c3C(F)(F)F)n2)cc1]

(46)

2-Hydroxy-2-(4-(5-(3-phenyl-4-(trifluoromethyl)isoxazol-5-yl)-1,2,4-oxadiazol-3-yl)phenyl)acetic acid (Int-Vb, 25 mg, 0.058 mmol), (S)-2-aminopropanenitrile (Int-X, 6.09 mg, 0.087 mmol), HATU (28.7 mg, 0.075 mmol), and 4-methylmorpholine (23.45 mg, 0.232 mmol) were dissolved in DMF (1 mL). The reaction mixture was stirred for 1 h, and then purified by prep HPLC (PHENOMENEX® Luna 5u 21.2×250 mm gradient elution with Method 2—CH$_3$CN/water containing 0.1% trifluoroacetic acid as defined above, 0% B to 100% B over 30 min, 20 mL/min, 220 nM, product retention=25.5 min) to provide single enantiomer N—((S)-1-cyanoethyl)-2-hydroxy-2-(4-(5-(3-phenyl-4-(trifluoromethyl)isoxazol-5-yl)-1,2,4-oxadiazol-3-yl)phenyl)acetamide (10 mg, 0.019 mmol, 32.1% yield): LCMS=484.0 [M+H]$^+$; $^1$H NMR (400 MHz, methanol-d$_4$) δ ppm 8.12-8.26 (2 H, m), 7.50-7.78 (7 H, m), 5.17 (1 H, s), 4.85-4.94 (1 H, m), 1.56 (3 H, d, J=7.26 Hz); HPLC peak RT=9.9 min (Method A).

Example 47

2-Hydroxy-N-((S)-2-hydroxypropyl)-2-(4-(5-(3-phenyl-4-(trifluoromethyl)isoxazol-5-yl)-1,2,4-oxadiazol-3-yl)phenyl)acetamide

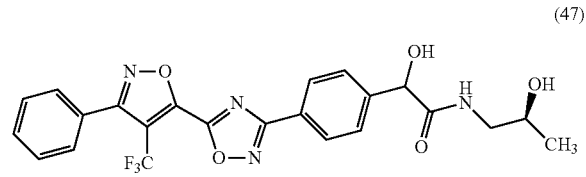 [SMILES: C[C@H](O)CNC(=O)C(O)c1ccc(-c2noc(-c3onc(-c4ccccc4)c3C(F)(F)F)n2)cc1]

(47)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), (S)-(+)-1-amino-2-propanol (7.84 mg, 0.104 mmol), HATU (34.4 mg, 0.090 mmol), and 4-methylmorpholine (28.1 mg, 0.278 mmol) were dissolved in DMF (1 mL). After stirring 1 h, the mixture was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.8 min) to provide 2-hydroxy-N—((S)-2-hydroxypropyl)-2-(4-(5-(3-phenyl-4-(trifluoromethyl)isoxazol-5-yl)-1,2,4-oxadiazol-3-yl)phenyl)acetamide (19 mg, 0.031 mmol, 44.7% yield) as a mixture of diastereomers: LCMS=489.1 [M+H]$^+$; $^1$H NMR (400 MHz, methanol-d$_4$) δ ppm 8.16 (2 H, d, J=8.35 Hz), 7.54-7.74 (7 H, m), 5.15 (1 H, s), 3.80-3.92 (1 H, m), 3.12-3.42 (2 H, m), 1.13 (3 H, d, J=4.83 Hz); HPLC peak RT=8.6 min (Method A).

Example 48

N-((R,S)-2,3-Dihydroxypropyl)-(R/S)-2-hydroxy-2-(4-(5-(3-phenyl-4-(trifluoromethyl)isoxazol-5-yl)-1,2,4-oxadiazol-3-yl)phenyl)acetamide

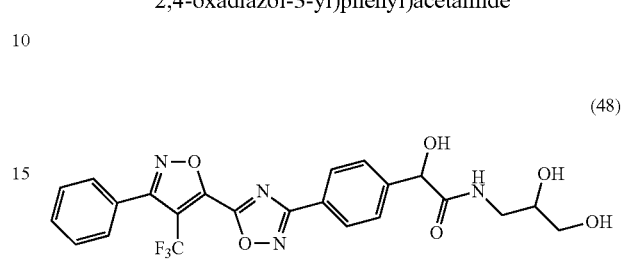

(48)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), (R/S)-3-aminopropane-1,2-diol (9.51 mg, 0.104 mmol), 4-methylmorpholine (28.1 mg, 0.278 mmol), and HATU (34.4 mg, 0.090 mmol) were dissolved in DMF (1 mL). The mixture was stirred for 1 h and then purified by prep HPLC (PHENOMENEX® Luna 5u 21.2×250 mm, gradient elution with Method 1—MeOH/water containing 0.1% trifluoroacetic acid as defined above, 0% B to 100% B over 30 min, 25 mL/min, 220 nM, product retention=28.9 min) to provide (R/S)-N-(2,3-dihydroxypropyl)-2-hydroxy-2-(4-(5-(3-phenyl-4-(trifluoromethyl)isoxazol-5-yl)-1,2,4-oxadiazol-3-yl)phenyl)acetamide (15 mg, 0.022 mmol, 32.1% yield): LCMS=505.1 [M+H]$^+$; $^1$H NMR (400 MHz, methanol-d$_4$) δ ppm 8.17 (2 H, d, J=8.35 Hz), 7.50-7.81 (7 H, m), 5.15 (1 H, s), 3.65-3.79 (1 H, m), 3.41-3.52 (2 H, m), 3.23-3.39 (2 H, m); HPLC peak RT=7.9 min (Method A).

Example 49

(R/S)-2-Hydroxy-N-(3-hydroxypropyl)-2-(4-(5-(3-phenyl-4-(trifluoromethyl)isoxazol-5-yl)-1,2,4-oxadiazol-3-yl)phenyl)acetamide

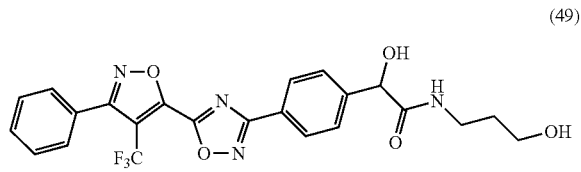 [SMILES: O=C(NCCCO)C(O)c1ccc(-c2noc(-c3onc(-c4ccccc4)c3C(F)(F)F)n2)cc1]

(49)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), 3-aminopropan-1-ol (7.84 mg, 0.104 mmol), 4-methylmorpholine (28.1 mg, 0.278 mmol), and HATU (34.4 mg, 0.090 mmol) were dissolved in DMF (1 mL). The mixture was stirred for 1 h and then purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=29.4 min) to provide (R/S)-2-hydroxy-N-(3-hydroxypropyl)-2-(4-(5-(3-phenyl-4-(trifluoromethyl)isoxazol-5-yl)-1,2,4-oxadiazol-3-yl)phenyl)acetamide (12 mg, 0.018 mmol, 26.5% yield): LCMS=489.1 [M+H]$^+$; $^1$H NMR (400 MHz, chloroform-d) δ ppm 8.12-8.30 (2 H, m), 7.47-7.74 (7 H, m), 7.06 (1 H, br. s.), 5.22 (1 H, d, J=4.83 Hz), 4.38 (1 H, t, J=5.71 Hz), 3.56-3.75 (2 H, m), 3.31-3.52 (2 H, m), 1.91-2.08 (1 H, m), 1.63-1.81 (2 H, m); HPLC peak RT=8.4 min (Method A).

Example 50

(R/S)-2-Hydroxy-N-(2-methoxyethyl)-2-(4-(5-(3-phenyl-4-(trifluoromethyl)isoxazol-5-yl)-1,2,4-oxadiazol-3-yl)phenyl)acetamide

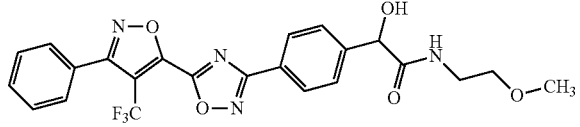

(50)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), 3-aminopropan-1-ol (7.84 mg, 0.104 mmol), 4-methylmorpholine (28.1 mg, 0.278 mmol), and HATU (34.4 mg, 0.090 mmol) were dissolved in DMF (1 mL). The mixture was stirred for 1 h and then purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=29.4 min) to provide (R/S)-2-hydroxy-N-(3-hydroxypropyl)-2-(4-(5-(3-phenyl-4-(trifluoromethyl)isoxazol-5-yl)-1,2,4-oxadiazol-3-yl)phenyl)acetamide (12 mg, 0.018 mmol, 26.5% yield): LCMS=489.1 [M+H]$^+$; $^1$H NMR (400 MHz, chloroform-d) δ ppm 8.20 (2 H, d, J=8.35 Hz), 7.50-7.71 (7 H, m), 6.82-6.90 (1 H, m), 5.20 (1 H, s), 3.41-3.62 (4 H, m), 3.34 (3 H, s) HPLC peak RT=9.1 min (Method A).

Example 51

(R/S)-tert-Butyl 2-(2-hydroxy-2-(4-(5-(3-phenyl-4-(trifluoromethyl)isoxazol-5-yl)-1,2,4-oxadiazol-3-yl)phenyl)acetamido)ethylcarbamate

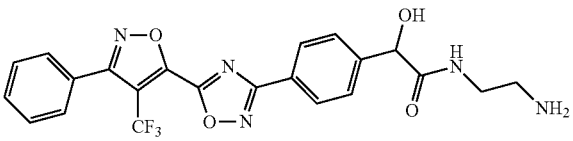

(51)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 170 mg, 0.394 mmol), tert-butyl 2-aminoethylcarbamate (95 mg, 0.591 mmol), 4-methylmorpholine (159 mg, 1.577 mmol), and HATU (195 mg, 0.512 mmol) were dissolved in DMF (1 mL). The reaction mixture was stirred for 1 h and then was purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=31.6 min) to provide (R/S)-tert-butyl 2-(2-hydroxy-2-(4-(5-(3-phenyl-4-(trifluoromethyl)isoxazol-5-yl)-1,2,4-oxadiazol-3-yl)phenyl)acetamido)ethylcarbamate (80 mg, 0.133 mmol, 33.6% yield): LCMS=474.1 [M+H−C$_5$H$_9$O$_2$]$^+$; $^1$H NMR (400 MHz, methanol-d$_4$) δ ppm 8.17 (2 H, d, J=8.35 Hz), 7.51-7.74 (7 H, m), 5.12 (1 H, s), 3.35 (2 H, br. s.), 3.17-3.22 (2 H, m), 1.43 (9 H, s); HPLC peak RT=9.8 min (Method A).

Example 52

(R/S)-N-(2-Aminoethyl)-2-hydroxy-2-(4-(5-(3-phenyl-4-(trifluoromethyl)isoxazol-5-yl)-1,2,4-oxadiazol-3-yl)phenyl)acetamide, TFA (52)

(R/S)-tert-Butyl 2-(2-hydroxy-2-(4-(5-(3-phenyl-4-(trifluoromethyl)isoxazol-5-yl)-1,2,4-oxadiazol-3-yl)phenyl)acetamido)ethylcarbamate (Example 51, 80 mg, 0.139 mmol) was dissolved in dichloromethane (5 mL). TFA (1 mL, 12.98 mmol) was added. The reaction mixture was stirred for 30 min. All solvent was removed to provide (R/S)-N-(2-aminoethyl)-2-hydroxy-2-(4-(5-(3-phenyl-4-(trifluoromethyl)isoxazol-5-yl)-1,2,4-oxadiazol-3-yl)phenyl)acetamide, TFA (70 mg, 0.116 mmol, 83% yield): LCMS=474.1 [M+H]$^+$; $^1$H NMR (400 MHz, methanol-d$_4$) δ ppm 8.62 (1 H, t, J=5.93 Hz), 8.19 (2 H, d, J=8.35 Hz), 7.55-7.76 (7 H, m), 5.20 (1 H, s), 3.39-3.64 (2 H, m), 3.07 (2 H, t, J=6.15 Hz); HPLC peak RT=6.3 min (Method A).

Example 53

(R/S)-2-Hydroxy-N-(2-hydroxyethyl)-2-(4-(5-(1-phenyl-5-(trifluoromethyl)-1H-pyrazol-4-yl)-1,2,4-oxadiazol-3-yl)phenyl)acetamide (53)

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 40 mg, 0.093 mmol), 2-aminoethanol (8.52 mg, 0.139 mmol), HATU (45.9 mg, 0.121 mmol), and 4-methylmorpholine (37.6 mg, 0.372 mmol) were added to a vial. It was stirred for 20 min and then was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.1 min) to provide (R/S)-2-hydroxy-N-(2-hydroxyethyl)-2-(4-(5-(1-phenyl-5-(trifluoromethyl)-1H-pyrazol-4-yl)-1,2,4-oxadiazol-3-yl)phenyl)acetamide (20 mg, 0.040 mmol, 43.2% yield): LCMS=474.1 [M+H]$^+$; $^1$H NMR (400 MHz, methanol-$d_4$) δ ppm 8.46 (1 H, s), 8.12 (2 H, d, J=8.35 Hz), 7.50-7.73 (7 H, m), 5.13 (1 H, s), 3.58-3.69 (2 H, m), 3.35-3.40 (2 H, m); HPLC peak RT=6.8 min (Method A).

Example 54

(R/S)-2-Hydroxy-N-(3-hydroxypropyl)-2-(4-(5-(1-phenyl-5-(trifluoromethyl)-1H-pyrazol-4-yl)-1,2,4-oxadiazol-3-yl)phenyl)acetamide (54)

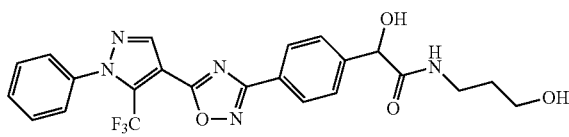

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 40 mg, 0.093 mmol), 3-aminopropan-1-ol (10.47 mg, 0.139 mmol), HATU (45.9 mg, 0.121 mmol), and 4-methylmorpholine (37.6 mg, 0.372 mmol) were dissolved in DMF (1 mL). It was stirred for 20 min and then was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.1 min) to provide (R/S)-2-hydroxy-N-(3-hydroxypropyl)-2-(4-(5-(1-phenyl-5-(trifluoromethyl)-1H-pyrazol-4-yl)-1,2,4-oxadiazol-3-yl)phenyl)acetamide (20 mg, 0.032 mmol, 34.4% yield): LCMS=488.2 [M+H]$^+$; $^1$H NMR (400 MHz, methanol-$d_4$) δ ppm 8.42-8.50 (1 H, m), 8.12 (2 H, dd, J=8.57, 3.30 Hz), 7.51-7.73 (7 H, m), 5.11 (1 H, s), 3.58 (2 H, t, J=6.15 Hz), 3.35 (2 H, t, J=6.81 Hz), 1.74 (2 H, quin, J=6.59 Hz); HPLC peak RT=6.8 min (Method A).

Example 55

(R/S)-2-Hydroxy-N-(2-hydroxy-2-methylpropyl)-2-(4-(5-(1-phenyl-5-(trifluoromethyl)-1H-pyrazol-4-yl)-1,2,4-oxadiazol-3-yl)phenyl)acetamide (55)

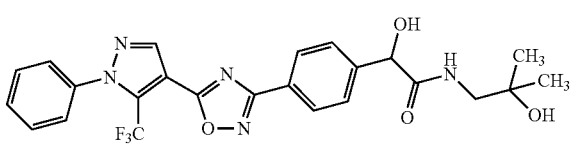

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 40 mg, 0.093 mmol), 1-amino-2-methylpropan-2-ol (12.43 mg, 0.139 mmol), 4-methylmorpholine (37.6 mg, 0.372 mmol), and HATU (45.9 mg, 0.121 mmol) were dissolved in DMF (1 mL). It was stirred for 20 min and was then purified by prep HPLC (PHENOMENEX® Luna 5u 21.2×100 mm, gradient elution with Method 1—MeOH/water containing 0.1% trifluoroacetic acid as defined above, 0% methanol to 100% methanol over 10 min, 20 mL/min, 220 nM, product retention=11.2 min) to provide (R/S)-2-hydroxy-N-(2-hydroxy-2-methylpropyl)-2-(4-(5-(1-phenyl-5-(trifluoromethyl)-1H-pyrazol-4-yl)-1,2,4-oxadiazol-3-yl)phenyl)acetamide (20 mg, 0.036 mmol, 39.2% yield): LCMS=502.2 [M+H]$^+$; $^1$H NMR (400 MHz, methanol-$d_4$) δ ppm 8.48 (1 H, s), 8.13 (2 H, d, J=8.35 Hz), 7.52-7.76 (7 H, m), 5.16 (1 H, s), 3.25 (2 H, s), 1.17 (3 H, s), 1.14 (3 H, s); HPLC peak RT=7.3 min (Method A).

Example 56

(R/S)-tert-Butyl 2-(2-hydroxy-2-(4-(5-(1-phenyl-5-(trifluoromethyl)-1H-pyrazol-4-yl)-1,2,4-oxadiazol-3-yl)phenyl)acetamido)acetate (56)

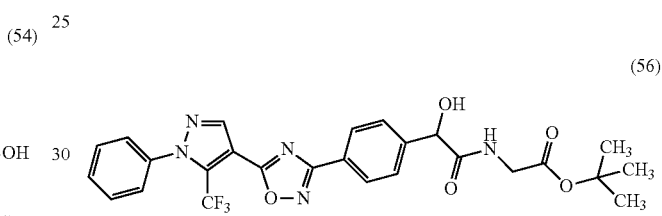

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 40 mg, 0.093 mmol), tert-butyl 2-aminoacetate (18.29 mg, 0.139 mmol), HATU (45.9 mg, 0.121 mmol), and 4-methylmorpholine (37.6 mg, 0.372 mmol) were added to DMF (1 mL). It was stirred for 20 min and then was purified by prep HPLC (PHENOMENEX® Luna 5u 21.2×100 mm, gradient elution with Method 1—MeOH/water containing 0.1% trifluoroacetic acid as defined above, 0% B to 100% B over 15 min, 20 mL/min, 220 nM, product retention=16.4 min) to provide (R/S)-tert-butyl 2-(2-hydroxy-2-(4-(5-(1-phenyl-5-(trifluoromethyl)-1H-pyrazol-4-yl)-1,2,4-oxadiazol-3-yl)phenyl)acetamido)acetate (20 mg, 0.035 mmol, 37.9% yield): LCMS=488.1 [M+H−$C_4H_9$]$^+$; $^1$H NMR (400 MHz, methanol-$d_4$) δ ppm 8.46 (1 H, s), 8.12 (2 H, d, J=8.35 Hz), 7.50-7.75 (7 H, m), 5.17 (1 H, s), 3.90 (2 H, s), 1.44 (9 H, s); HPLC peak RT=9.1 min (Method A).

Example 57

2-Hydroxy-N—((S)-2-hydroxypropyl)-2-(4-(5-(1-phenyl-5-(trifluoromethyl)-1H-pyrazol-4-yl)-1,2,4-oxadiazol-3-yl)phenyl)acetamide (57)

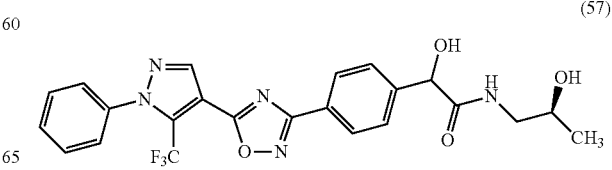

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 40 mg, 0.093 mmol), (S)-1-aminopropan-2-ol (10.47 mg, 0.139 mmol), HATU (45.9 mg, 0.121 mmol), and 4-methylmorpholine (37.6 mg, 0.372 mmol) were added to DMF (1 mL). It was stirred for 20 min before additional HATU (35.3 mg, 0.093 mmol) was added. After stirring for an additional 10 min, it was purified by prep HPLC (PHENOMENEX® Luna 5u 21.2×100 mm, gradient elution with Method 1—MeOH/water containing 0.1% trifluoroacetic acid as defined above, 0% B to 100% B over 15 min, 20 mL/min, 220 nM, product retention 15.1 min) to provide (R/S)-2-hydroxy-N-((S)-2-hydroxypropyl)-2-(4-(5-(1-phenyl-5-(trifluoromethyl)-1H-pyrazol-4-yl)-1,2,4-oxadiazol-3-yl)phenyl)acetamide (20 mg, 0.041 mmol, 43.8% yield) as a mixture of diastereomers: LCMS=488.1 [M+H]$^+$; $^1$H NMR (400 MHz, methanol-$d_4$) δ ppm 8.46 (1 H, s), 8.12 (2 H, d, J=8.35 Hz), 7.52-7.72 (7 H, m), 5.14 (1 H, s), 3.78-3.94 (1 H, m), 3.13-3.34 (2 H, m), 1.13 (3 H, d, J=7.47 Hz); HPLC peak RT=7.0 min (Method A).

Example 58

(R/S)-2-(2-Hydroxy-2-(4-(5-(1-phenyl-5-(trifluoromethyl)-1H-pyrazol-4-yl)-1,2,4-oxadiazol-3-yl)phenyl)acetamido)acetic acid (58)

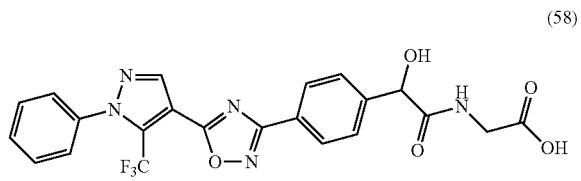 [SMILES: O=C(O)CNC(=O)C(O)c1ccc(-c2noc(-c3cnn(-c4ccccc4)c3C(F)(F)F)n2)cc1]

(R/S)-tert-Butyl 2-(2-hydroxy-2-(4-(5-(1-phenyl-5-(trifluoromethyl)-1H-pyrazol-4-yl)-1,2,4-oxadiazol-3-yl)phenyl)acetamido)acetate (Example 56, 30 mg, 0.055 mmol) was dissolved in THF (3 mL) and MeOH (1.50 mL). Next, LiOH (2.64 mg, 0.110 mmol) was added. After 20 min, additional LiOH (2.64 mg, 0.110 mmol) was added. After another 20 min, 1N HCl was used to adjust the pH to 4-5. The reaction mixture was concentrated. EtOAc was added and the resulting mixture was filtered. The filtrate was concentrated to provide (R/S)-2-(2-hydroxy-2-(4-(5-(1-phenyl-5-(trifluoromethyl)-1H-pyrazol-4-yl)-1,2,4-oxadiazol-3-yl)phenyl)acetamido)acetic acid (15 mg, 0.029 mmol, 52.2% yield): LCMS=488.2 [M+H]$^+$; $^1$H NMR (400 MHz, methanol-$d_4$) δ ppm 8.47 (1 H, s), 8.13 (2 H, d, J=8.35 Hz), 7.53-7.75 (7 H, m), 5.17 (1 H, s), 3.99 (2 H, s); HPLC peak RT=7.1 min (Method A).

Example 59

(R/S)-N-(2-Acetamidoethyl)-2-hydroxy-2-(4-(5-(3-phenyl-4-(trifluoromethyl)isoxazol-5-yl)-1,2,4-oxadiazol-3-yl)phenyl)acetamide (59)

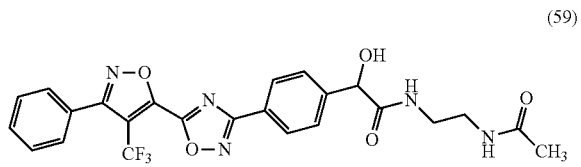 [SMILES: CC(=O)NCCNC(=O)C(O)c1ccc(-c2noc(-c3onc(-c4ccccc4)c3C(F)(F)F)n2)cc1]

(R/S)-N-(2-Aminoethyl)-2-hydroxy-2-(4-(5-(3-phenyl-4-(trifluoromethyl)isoxazol-5-yl)-1,2,4-oxadiazol-3-yl)phenyl)acetamide (Example 52, 30 mg, 0.063 mmol), acetic acid (7.61 mg, 0.127 mmol), HATU (36.1 mg, 0.095 mmol), and 4-methylmorpholine (32.0 mg, 0.317 mmol) were added to DMF (1 mL). This was stirred for 30 min and then was purified by prep HPLC (PHENOMENEX® Luna 5u 21.2×100 mm, 20 mL/min, 220 nM, gradient elution with Method 1—MeOH/water containing 0.1% trifluoroacetic acid as defined above, 0% B to 100% B over 15 min (The product retention time was 18.4 min.) to yield (R/S)-N-(2-acetamidoethyl)-2-hydroxy-2-(4-(5-(3-phenyl-4-(trifluoromethyl)isoxazol-5-yl)-1,2,4-oxadiazol-3-yl)phenyl)acetamide (10 mg, 0.019 mmol, 29.8% yield): LCMS=516.2 [M+H]$^+$; $^1$H NMR (400 MHz, methanol-$d_4$) δ ppm 8.18 (2 H, d, J=8.35 Hz), 7.54-7.73 (7 H, m), 5.12(1 H, s), 3.34-3.39(2 H, m), 3.24-3.29(2 H, m), 1.89(3 H, s); HPLC peak RT=7.4 min (Method A).

Example 60

(R/S)-2-Hydroxy-N-methyl-2-(4-(5-(1-phenyl-5-(trifluoromethyl)-1H-pyrazol-4-yl)-1,2,4-oxadiazol-3-yl)phenyl)acetamide (60)

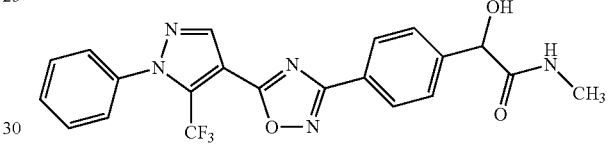

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 35 mg, 0.081 mmol), methanamine-HCl (8.24 mg, 0.122 mmol), HATU (40.2 mg, 0.106 mmol), and 4-methylmorpholine (32.9 mg, 0.325 mmol) were added to DMF (1 mL). The reaction mixture was stirred for 1 h and then purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention 13.0 min) to provide (R/S)-2-hydroxy-N-methyl-2-(4-(5-(1-phenyl-5-(trifluoromethyl)-1H-pyrazol-4-yl)-1,2,4-oxadiazol-3-yl)phenyl)acetamide (30 mg, 0.066 mmol, 82% yield): LCMS=444.2 [M+H]$^+$; $^1$H NMR (400 MHz, methanol-$d_4$) δ ppm 8.46 (1 H, s), 8.07-8.15 (2 H, m), 7.51-7.71(7 H, m), 5.11(1 H, s), 3.35(1 H, s), 2.79 (3 H, s); HPLC peak RT=7.4 min (Method A).

Example 61

(R/S)-N-Ethyl-2-hydroxy-2-(4-(5-(1-phenyl-5-(trifluoromethyl)-1H-pyrazol-4-yl)-1,2,4-oxadiazol-3-yl)phenyl)acetamide (61)

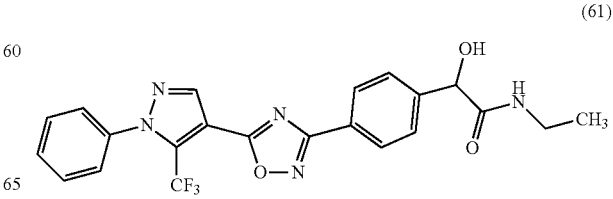

(R/S)-2-Hydroxy-2-(4-(5-(1-phenyl-5-(trifluoromethyl)-1H-pyrazol-4-yl)-1,2,4-oxadiazol-3-yl)phenyl)acetic acid (Int-VII, 35 mg, 0.081 mmol), ethanamine-HCl (9.95 mg, 0.122 mmol), HATU (40.2 mg, 0.106 mmol), and 4-methylmorpholine (32.9 mg, 0.325 mmol) were added to DMF (1 mL). It was stirred for 1 h and then was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.3 min) to provide (R/S)-N-ethyl-2-hydroxy-2-(4-(5-(1-phenyl-5-(trifluoromethyl)-1H-pyrazol-4-yl)-1,2,4-oxadiazol-3-yl)phenyl)acetamide (30 mg, 0.063 mmol, 77% yield): LCMS=458.2 [M+H]$^+$; $^1$H NMR (400 MHz, methanol-d$_4$) δ ppm 8.46 (1 H, s), 8.11 (2 H, d, J=8.58 Hz), 7.51-7.72 (7 H, m), 5.09 (1 H, s), 3.24-3.30 (2 H, m), 1.14 (3 H, t, J=7.15 Hz); HPLC peak RT=7.9 min (Method A).

Example 62

(R/S)-2-Hydroxy-N-(2-hydroxyethyl)-2-(4-(5-(5-phenyl-4-(trifluoromethyl)isoxazol-3-yl)-1,2,4-oxadiazol-3-yl)phenyl)acetamide (62)

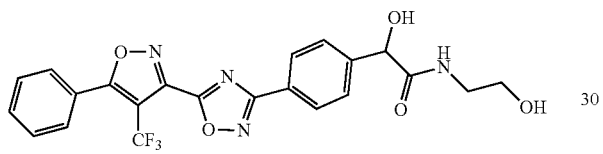

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), 2-aminoethanol (6.37 mg, 0.104 mmol), HATU (34.4 mg, 0.090 mmol), and 4-methylmorpholine (28.1 mg, 0.278 mmol) were added to DMF (1 mL). It was stirred for 1 h and then was purified by prep HPLC (PHENOMENEX® Luna 5u 21.2×100 mm, gradient elution with Method 1—MeOH/water containing 0.1% trifluoroacetic acid as defined above, 0% B to 100% B over 18 min, product retention=17.9 min (20 mL/min, 220 nM) to provide (R/S)-2-hydroxy-N-(2-hydroxyethyl)-2-(4-(5-(5-phenyl-4-(trifluoromethyl)isoxazol-3-yl)-1,2,4-oxadiazol-3-yl)phenyl)acetamide (25 mg, 0.047 mmol, 68.2% yield): LCMS=475.1 [M+H]$^+$; $^1$H NMR (400 MHz, methanol-d$_4$) δ ppm 8.25 (1 H, t, J=5.94 Hz), 8.09-8.19 (2 H, m), 7.58-7.84 (7 H, m), 5.14 (1 H, s), 3.60-3.67 (2 H, m), 3.34-3.44 (2 H, m); HPLC peak RT=8.2 min (Method A).

Example 63

(R/S)-2-Hydroxy-N—((S)-2-hydroxypropyl)-2-(4-(5-(5-phenyl-4-(trifluoromethyl)isoxazol-3-yl)-1,2,4-oxadiazol-3-yl)phenyl)acetamide (63)

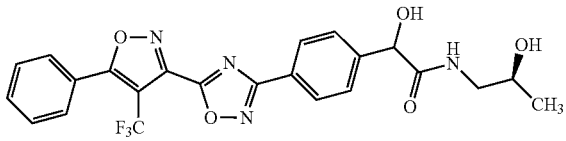

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), (S)-1-aminopropan-2-ol (7.84 mg, 0.104 mmol), HATU (34.4 mg, 0.090 mmol), and 4-methylmorpholine (28.1 mg, 0.278 mmol) were added to DMF (1 mL). The reaction mixture was stirred for 1 h and it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.9 min) to provide (R/S)-2-hydroxy-N—((S)-2-hydroxypropyl)-2-(4-(5-(5-phenyl-4-(trifluoromethyl)isoxazol-3-yl)-1,2,4-oxadiazol-3-yl)phenyl)acetamide (18 mg, 0.033 mmol, 47.1% yield) as a mixture of diastereomers. LCMS=489.2 [M+H]$^+$; $^1$H NMR (400 MHz, methanol-d$_4$) δ ppm 8.09-8.20 (2 H, m), 7.55-7.86 (7 H, m), 5.15 (1 H, s), 3.80-3.94(1 H, m, J=9.11, 6.67, 6.67, 4.62 Hz), 3.09-3.37 (2 H, m), 1.14 (3 H, dd, J=6.27, 1.21 Hz); HPLC peak RT=8.4 min (Method A).

Example 64

(R/S)-2-Hydroxy-N-(2-hydroxy-2-methylpropyl)-2-(4-(5-(5-phenyl-4-(trifluoromethyl)isoxazol-3-yl)-1,2,4-oxadiazol-3-yl)phenyl)acetamide (64)

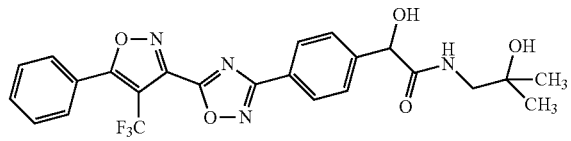

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), 1-amino-2-methylpropan-2-ol (9.30 mg, 0.104 mmol), HATU (34.4 mg, 0.090 mmol), and 4-methylmorpholine (28.1 mg, 0.278 mmol) were added to DMF (1 mL). This was stirred for 1 h and then was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.9 min) to provide (R/S)-2-hydroxy-N-(2-hydroxy-2-methylpropyl)-2-(4-(5-(5-phenyl-4-(trifluoromethyl)isoxazol-3-yl)-1,2,4-oxadiazol-3-yl)phenyl)acetamide (20 mg, 0.037 mmol, 52.6% yield): LCMS=503.2 [M+H]$^+$; $^1$H NMR (400 MHz, methanol-d$_4$) δ ppm 8.11-8.20 (2 H, m), 7.54-7.85 (7 H, m), 5.17 (1 H, s), 3.25 (2 H, s), 1.17 (3 H, s), 1.15 (3 H, s); HPLC peak RT=8.7 min (Method A).

Example 65

(R/S)-N-(3-(1H-Imidazol-1-yl)propyl)-2-hydroxy-2-(4-(5-(5-phenyl-4-(trifluoromethyl)isoxazol-3-yl)-1,2,4-oxadiazol-3-yl)phenyl)acetamide, TFA

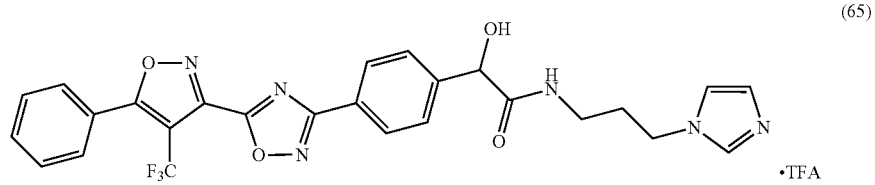 [SMILES: O=C(NCCCn1ccnc1)C(O)c1ccc(-c2noc(-c3noc(-c4ccccc4)c3C(F)(F)F)n2)cc1]

(65)

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), 3-(1H-imidazol-1-yl)propan-1-amine (13.06 mg, 0.104 mmol), HATU (34.4 mg, 0.090 mmol), and 4-methylmorpholine (28.1 mg, 0.278 mmol) were dissolved in DMF (1 mL). This was stirred for 1 h and then was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=10.5 min) to provide (R/S)-N-(3-(1H-imidazol-1-yl)propyl)-2-hydroxy-2-(4-(5-(5-phenyl-4-(trifluoromethyl)isoxazol-3-yl)-1,2,4-oxadiazol-3-yl)phenyl)acetamide-TFA (20 mg, 0.029 mmol, 42.3% yield): LCMS=539.2 [M+H]$^+$; $^1$H NMR (400 MHz, methanol-d$_4$) δ ppm 8.90 (1 H, s), 8.13-8.19 (2 H, m), 7.52-7.83 (9 H, m), 5.16 (1 H, s), 4.23 (2 H, td, J=6.88, 3.41 Hz), 3.26-3.31 (2 H, m), 2.12 (2 H, dq, J=6.82, 6.68 Hz); HPLC peak RT=7.8 min (Method A).

Example 66

(R/S)-N-(2-Amino-2-oxoethyl)-2-hydroxy-2-(4-(5-(5-phenyl-4-(trifluoromethyl)isoxazol-3-yl)-1,2,4-oxadiazol-3-yl)phenyl)acetamide

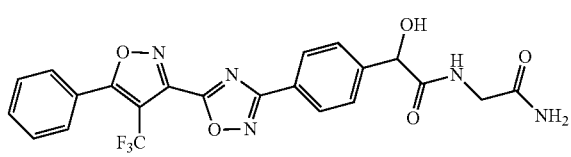

(66)

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), 2-aminoacetamide (7.73 mg, 0.104 mmol), HATU (34.4 mg, 0.090 mmol), and 4-methylmorpholine (28.1 mg, 0.278 mmol) were added to DMF (1 mL). It was stirred for 1 h and then was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.5 min) to provide (R/S)-N-(2-amino-2-oxoethyl)-2-hydroxy-2-(4-(5-(5-phenyl-4-(trifluoromethyl)isoxazol-3-yl)-1,2,4-oxadiazol-3-yl)phenyl)acetamide (18 mg, 0.029 mmol, 42.2% yield): LCMS=488.1 [M+H]$^+$; $^1$H NMR (400 MHz, methanol-d$_4$) δ ppm 8.16 (2 H, d, J=7.48 Hz), 7.58-7.87 (7 H, m), 5.20 (1 H, s), 3.81-4.13 (2 H, m); HPLC peak RT=8.0 min (Method A).

Example 67

(R/S)-N-Ethyl-2-hydroxy-2-(4-(5-(5-phenyl-4-(trifluoromethyl)isoxazol-3-yl)-1,2,4-oxadiazol-3-yl)phenyl)acetamide

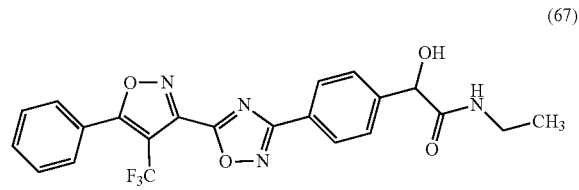 [SMILES: CCNC(=O)C(O)c1ccc(-c2noc(-c3noc(-c4ccccc4)c3C(F)(F)F)n2)cc1]

(67)

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), ethanamine-HCl (8.51 mg, 0.104 mmol), HATU (34.4 mg, 0.090 mmol), and 4-methylmorpholine (28.1 mg, 0.278 mmol) were added to DMF (1 mL). This was stirred for 1 h and then was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention 12.1=min) to provide (R/S)-N-ethyl-2-hydroxy-2-(4-(5-(5-phenyl-4-(trifluoromethyl)isoxazol-3-yl)-1,2,4-oxadiazol-3-yl)phenyl)acetamide (25 mg, 0.049 mmol, 69.8% yield): LCMS=459.1 [M+H]$^+$; $^1$H NMR (400 MHz, methanol-d$_4$) δ ppm 8.14 (2 H, d, J=8.36 Hz), 7.48-7.85 (7 H, m), 5.10 (1 H, s), 3.28 (2 H, dd, J=7.15, 0.99 Hz), 1.14 (3 H, t, J=7.26 Hz); HPLC peak RT=9.2 min (Method A).

Example 68

(R/S)-2-Hydroxy-2-(4-(5-(5-phenyl-4-(trifluoromethyl)isoxazol-3-yl)-1,2,4-oxadiazol-3-yl)phenyl)-N-(pyridin-3-ylmethyl)acetamide-TFA

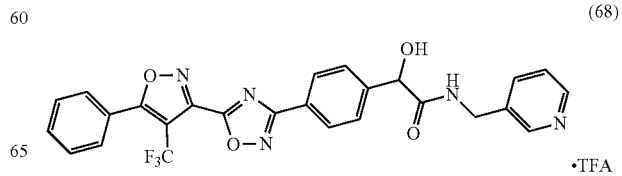

(68)

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), pyridin-3-ylmethanamine (11.28 mg, 0.104 mmol), HATU (34.4 mg, 0.090 mmol), and 4-methylmorpholine (28.1 mg, 0.278 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=10.7 min) to provide (R/S)-2-hydroxy-2-(4-(5-(5-phenyl-4-(trifluoromethyl)isoxazol-3-yl)-1,2,4-oxadiazol-3-yl)phenyl)-N-(pyridin-3-ylmethyl)acetamide-TFA (20 mg, 0.029 mmol, 41.8% yield): LCMS=522.2 [M+H]$^+$; $^1$H NMR (400 MHz, methanol-d$_4$) δ ppm 8.72 (2 H, br. s.), 8.47 (1 H, d, J=8.14 Hz), 8.15 (2 H, d, J=8.58 Hz), 7.99 (1 H, dd, J=7.92, 5.94 Hz), 7.57-7.88 (7 H, m), 5.22 (1 H, s), 4.62 (2 H, s); HPLC peak RT=7.7 min (Method A).

Example 69

(R/S)-2-Hydroxy-N-(2-(methylamino)-2-oxoethyl)-2-(4-(5-(5-phenyl-4-(trifluoromethyl)isoxazol-3-yl)-1,2,4-oxadiazol-3-yl)phenyl)acetamide (69)

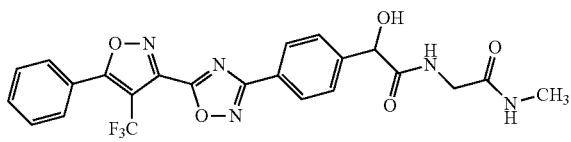

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 30 mg, 0.070 mmol), 2-amino-N-methylacetamide (9.19 mg, 0.104 mmol), HATU (34.4 mg, 0.090 mmol), and 4-methylmorpholine (70.4 mg, 0.696 mmol) were added to DMF (1 mL). This was stirred overnight before it was purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=29.0 min) to provide (R/S)-2-hydroxy-N-(2-(methylamino)-2-oxoethyl)-2-(4-(5-(5-phenyl-4-(trifluoromethyl)isoxazol-3-yl)-1,2,4-oxadiazol-3-yl)phenyl)acetamide (3.5 mg, 6.28 µmol, 9.03% yield): LCMS=502.2 [M+H]$^+$; $^1$H NMR (400 MHz, methanol-d$_4$) δ ppm 8.55 (1 H, br. s.), 8.17 (2 H, d, J=8.14 Hz), 7.59-7.85 (7 H, m), 5.20 (1 H, s), 3.78-4.01 (2 H, m), 2.75 (3 H, s); HPLC peak RT=8.2 min (Method A).

Example 70

(R/S)-N-(2-(Ethylamino)-2-oxoethyl)-2-hydroxy-2-(4-(5-(5-phenyl-4-(trifluoromethyl)isoxazol-3-yl)-1,2,4-oxadiazol-3-yl)phenyl)acetamide (70)

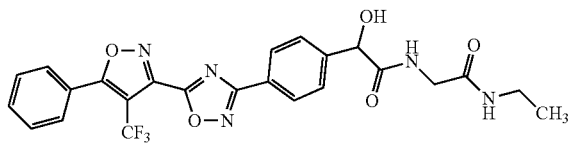

(R/S)-2-Hydroxy-2-(4-(5-(5-phenyl-4-(trifluoromethyl)isoxazol-3-yl)-1,2,4-oxadiazol-3-yl)phenyl)acetic acid (Int-IX, 24 mg, 0.049 mmol), ethanamine-HCl (6.01 mg, 0.074 mmol), 4-methylmorpholine (19.88 mg, 0.197 mmol), and HATU (24.29 mg, 0.064 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 15 min, 20 mL/min, 220 nM, product retention=15.7 min) to provide (R/S)-N-(2-(ethylamino)-2-oxoethyl)-2-hydroxy-2-(4-(5-(5-phenyl-4-(trifluoromethyl)isoxazol-3-yl)-1,2,4-oxadiazol-3-yl)phenyl)acetamide (5 mg, 7.62 µmol, 15.52% yield): LCMS=516.2 [M+H]$^+$; $^1$H NMR (400 MHz, methanol-d$_4$) δ ppm 8.17 (2 H, d, J=8.36 Hz), 7.59-7.84 (7 H, m), 5.20 (1 H, s), 3.79-3.99 (2 H, m), 3.15-3.27 (2 H, m), 1.11 (3 H, t, J=7.26 Hz); HPLC peak RT=8.6 min (Method A).

Example 71

2-Hydroxy-N-(2-hydroxyethyl)-2-(4-(5-(3-phenyl-4-(trifluoromethyl)isoxazol-5-yl)-1,2,4-oxadiazol-3-yl)phenyl)acetamide (71)

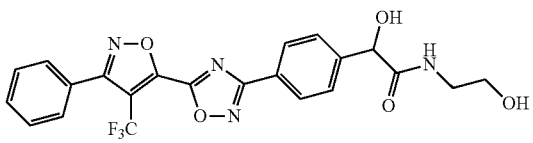

2-Hydroxy-2-(4-(5-(3-phenyl-4-(trifluoromethyl)isoxazol-5-yl)-1,2,4-oxadiazol-3-yl)phenyl)acetic acid (Ex-Va, 60 mg, 0.139 mmol), 2-aminoethanol (12.75 mg, 0.209 mmol), 4-methylmorpholine (56.3 mg, 0.556 mmol), and HATU (68.8 mg, 0.181 mmol) were added to DMF (1 mL). The mixture was stirred for 1 h before it was purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=29.5 min) to provide 2-hydroxy-N-(2-hydroxyethyl)-2-(4-(5-(3-phenyl-4-(trifluoromethyl)isoxazol-5-yl)-1,2,4-oxadiazol-3-yl)phenyl)acetamide (40 mg, 0.078 mmol, 56.4% yield) as a single enantiomer. LCMS=475.2 [M+H]$^+$; $^1$H NMR (400 MHz, methanol-d$_4$) δ ppm 8.15 (2 H, d, J=8.36 Hz), 7.52-7.73 (7 H, m), 5.14 (1 H, s), 3.64 (2 H, t), 3.38 (2 H, td, J=5.67, 3.63 Hz), 2.15 (1 H, s); HPLC peak RT=8.4 min (Method A).

Example 72

2-Hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (72)

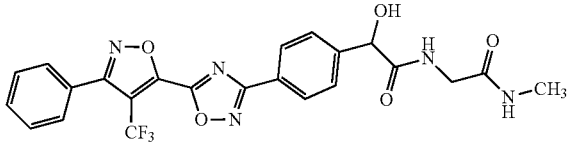

2-Hydroxy-2-(4-(5-(3-phenyl-4-(trifluoromethyl)isoxazol-5-yl)-1,2,4-oxadiazol-3-yl)phenyl)acetic acid (Int-Va, 60 mg, 0.139 mmol), 2-amino-N-methylacetamide (12.26 mg, 0.139 mmol), 4-methylmorpholine (56.3 mg, 0.556 mmol), and HATU (68.8 mg, 0.181 mmol) were added to DMF (1 mL). The mixture was stirred for 1 h before it was purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=29.4 min) to provide 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (13 mg, 0.025 mmol, 18.02% yield) as a single enantiomer. LCMS=502.2 [M+H]$^+$; $^1$H NMR (400 MHz, methanol-d$_4$) δ ppm 8.10-8.25 (2 H, m), 7.53-7.82 (7 H, m), 5.20 (1 H, s), 3.77-4.01 (2 H, m), 2.75 (3 H, s); HPLC peak RT=8.4 min (Method A).

Example 73

(R/S)-N-((2-Aminothiazol-4-yl)methyl)-2-hydroxy-2-(4-(5-(3-phenyl-4-(trifluoromethyl)isoxazol-5-yl)-1,2,4-oxadiazol-3-yl)phenyl)acetamide-TFA 3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 4, 35 mg, 0.070 mmol) was dissolved in DMF (1 mL) prior to the addition of dimethylamine-HCl (11.36 mg, 0.139 mmol), 4-methylmorpholine (0.046 mL, 0.418 mmol), and BOP (61.6 mg, 0.139 mmol). This was stirred for 1 h and was then purified by preparative HPLC (PHENOMENEX® Luna 5u C18 21.2×250 mm, gradient elution with Method 1—MeOH/water containing 0.1% trifluoroacetic acid as defined above, 0% B to 100% B over 30 min, 15 mL/min, 220 nM, product retention time=33.5 min) to give 3-(2-hydroxy-2-(4-(5-(3-phenyl-4-(trifluoromethyl)isoxazol-5-yl)-1,2,4-oxadiazol-3-yl)phenyl)acetamido)-N,N-dimethylpropanamide (16.1 mg, 0.030 mmol, 42.8% yield) as a single enantiomer. LCMS=530.3 [M+H]$^+$; $^1$H NMR (400 MHz, methanol-d$_4$) δ ppm 8.17 (2 H, d, J=8.36 Hz), 7.69 (4 H, d, J=8.14 Hz), 7.49-7.65 (3 H, m), 5.11 (1 H, s), 3.51 (2 H, t, J=6.49 Hz), 2.98 (3 H, s), 2.92 (3 H, s), 2.60 (2 H, t, J=6.60 Hz). HPLC Peak RT=9.6 min (Analytical Method D).

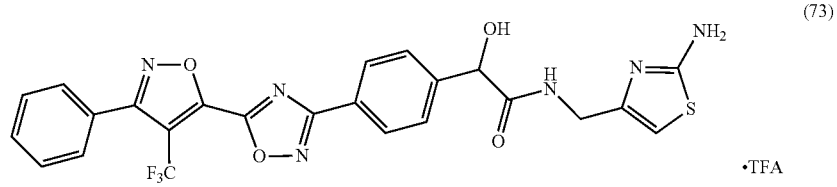 [SMILES: Nc1nc(CNC(=O)C(O)c2ccc(-c3noc(-c4onc(-c5ccccc5)c4C(F)(F)F)n3)cc2)cs1]

(73)

·TFA (R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), 4-(aminomethyl)thiazol-2-amine (13.48 mg, 0.104 mmol), 4-methylmorpholine (28.1 mg, 0.278 mmol), and HATU (34.4 mg, 0.090 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.4 min) to provide (R/S)-N-((2-aminothiazol-4-yl)methyl)-2-hydroxy-2-(4-(5-(3-phenyl-4-(trifluoromethyl)isoxazol-5-yl)-1,2,4-oxadiazol-3-yl)phenyl)acetamide, TFA (10 mg, 0.012 mmol, 17.4% yield): LCMS=543.2 [M+H]$^+$; $^1$H NMR (400 MHz, methanol-d$_4$) δ ppm 8.18 (2 H, d, J=8.36 Hz), 7.53-7.78 (7 H, m), 6.54 (1 H, s), 5.21 (1 H, s), 4.32(2 H, s); HPLC peak RT=8.1 min (Method A).

Example 74

3-(2-Hydroxy-2-(4-(5-(3-phenyl-4-(trifluoromethyl)isoxazol-5-yl)-1,2,4-oxadiazol-3-yl)phenyl)acetamido)-N,N-dimethylpropanamide (74)

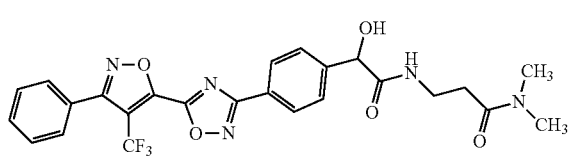

Example 75

(R/S)-3-(2-Hydroxy-2-(4-(5-(3-phenyl-4-(trifluoromethyl)isoxazol-5-yl)-1,2,4-oxadiazol-3-yl)phenyl)acetamido)-N-methylpropanamide (75)

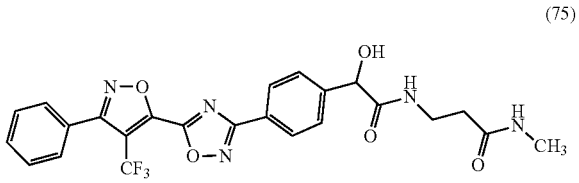 [SMILES: CNC(=O)CCNC(=O)C(O)c1ccc(-c2noc(-c3onc(-c4ccccc4)c3C(F)(F)F)n2)cc1]

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), methanamine-HCl (4.43 mg, 0.066 mmol), 4-methylmorpholine (17.72 mg, 0.175 mmol), and HATU (21.65 mg, 0.057 mmol) were added to DMF (1 mL). This was stirred for 1 h and then purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.6 min) to provide (R/S)-3-(2-hydroxy-2-(4-(5-(3-phenyl-4-(trifluoromethyl)isoxazol-5-yl)-1,2,4-oxadiazol-3-yl)phenyl)acetamido)-N-methylpropanamide (9 mg, 0.015 mmol, 35.2% yield): LCMS=516.3 [M+H]$^+$; $^1$H NMR (400 MHz, methanol-d$_4$) δ ppm 8.17 (2 H, d, J=8.36 Hz), 7.53-7.77 (7 H, m), 5.11 (1 H, s), 3.50 (2 H, td, J=6.71, 2.64 Hz), 2.69 (3 H, s), 2.40 (2 H, t, J=6.71 Hz); HPLC peak RT=8.3 min (Method A).

Example 76

(R/S)-N-Ethyl-3-(2-hydroxy-2-(4-(5-(3-phenyl-4-(trifluoromethyl)isoxazol-5-yl)-1,2,4-oxadiazol-3-yl)phenyl)acetamido)propanamide

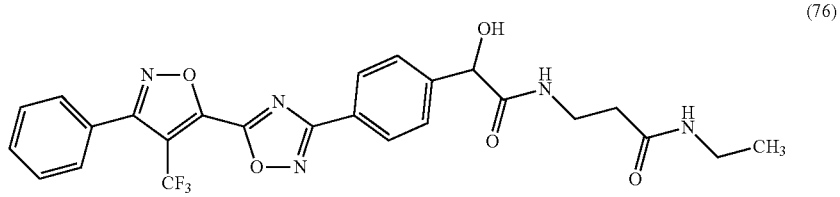 [SMILES: CCNC(=O)CCNC(=O)C(O)c1ccc(-c2noc(-c3onc(-c4ccccc4)c3C(F)(F)F)n2)cc1]

(76)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), ethanamine-HCl (5.36 mg, 0.066 mmol), 4-methylmorpholine (17.72 mg, 0.175 mmol), and HATU (21.65 mg, 0.057 mmol) were added to DMF (1 mL). This was stirred for 1 h and then purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention 13.4) to provide (R/S)-N-ethyl-3-(2-hydroxy-2-(4-(5-(3-phenyl-4-(trifluoromethyl)isoxazol-5-yl)-1,2,4-oxadiazol-3-yl)phenyl)acetamido)propanamide (8 mg, 0.015 mmol, 33.5% yield): LCMS=530.3 [M+H]$^+$; $^1$H NMR (400 MHz, methanol-d$_4$) δ ppm 8.10-8.23 (2 H, m), 7.52-7.74 (7 H, m), 5.11 (1 H, s), 3.43-3.57 (2 H, m), 3.17 (2 H, q, J=7.41 Hz), 2.40 (2 H, t, J=6.71 Hz), 1.09 (3 H, t, J=7.26 Hz); HPLC peak RT=8.6 min (Method A).

Example 77

(R/S)-3-(2-Hydroxy-2-(4-(5-(3-phenyl-4-(trifluoromethyl)isoxazol-5-yl)-1,2,4-oxadiazol-3-yl)phenyl)acetamido)-N,N-dimethylpropanamide

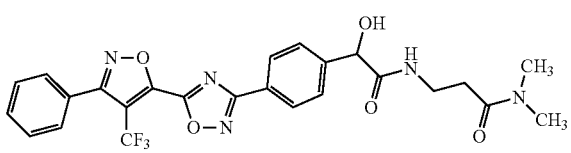

(77)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), dimethylamine-HCl (5.36 mg, 0.066 mmol), 4-methylmorpholine (17.72 mg, 0.175 mmol), and HATU (21.65 mg, 0.057 mmol) were added to DMF (1 mL). This was stirred for 1 h and then purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.4 min) to provide (R/S)-3-(2-hydroxy-2-(4-(5-(3-phenyl-4-(trifluoromethyl)isoxazol-5-yl)-1,2,4-oxadiazol-3-yl)phenyl)acetamido)-N,N-dimethylpropanamide (9 mg, 0.016 mmol, 36.4% yield): LCMS=530.3 [M+H]$^+$; $^1$H NMR (400 MHz, methanol-d$_4$) δ ppm 8.14-8.19 (2 H, m), 7.55-7.71 (7 H, m), 5.11 (1 H, s), 3.51 (2 H, t, J=6.60 Hz), 2.98 (3 H, s), 2.92 (3 H, s), 2.60 (2 H, t, J=6.49 Hz); HPLC peak RT=8.8 min (Method A).

Example 78

(R/S)-N-tert-Butyl-3-(2-hydroxy-2-(4-(5-(3-phenyl-4-(trifluoromethyl)isoxazol-5-yl)-1,2,4-oxadiazol-3-yl)phenyl)acetamido)propanamide

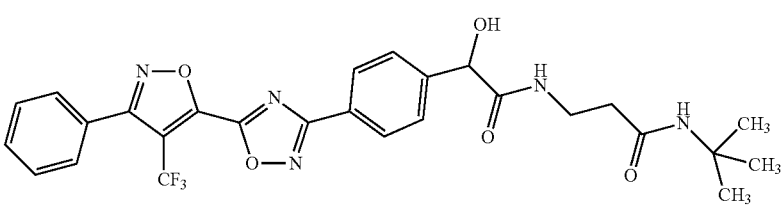

(78)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), 2-methylpropan-2-amine (4.80 mg, 0.066 mmol), 4-methylmorpholine (17.72 mg, 0.175 mmol), and HATU (21.65 mg, 0.057 mmol) were added to DMF (1 mL). This was stirred for 1 h and then purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.9) to provide (R/S)-N-tert-butyl-3-(2-hydroxy-2-(4-(5-(3-phenyl-4-(trifluoromethyl)isoxazol-5-yl)-1,2,4-oxadiazol-3-yl)phenyl)acetamido)propanamide (10 mg, 0.016 mmol, 37.1% yield): LCMS=558.3 [M+H]$^+$; $^1$H NMR (400 MHz, methanol-d$_4$) δ ppm 8.16 (2 H, d, J=8.36 Hz), 7.53-7.74 (7 H, m), 5.11 (1 H, s), 3.41-3.53 (2 H, m), 2.27-2.41 (2 H, m), 1.30 (9 H, s); HPLC peak RT=9.4 min (Method A).

Example 79

(R/S)-N-Cyclopropyl-3-(2-hydroxy-2-(4-(5-(3-phenyl-4-(trifluoromethyl)isoxazol-5-yl)-1,2,4-oxadiazol-3-yl)phenyl)acetamido)propanamide

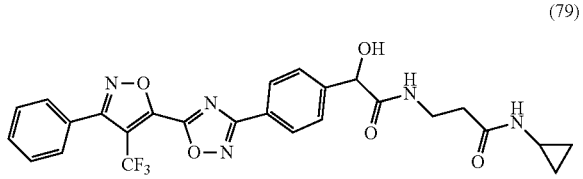 [SMILES: O=C(CCNC(=O)C(O)c1ccc(-c2noc(-c3onc(-c4ccccc4)c3C(F)(F)F)n2)cc1)NC1CC1]

(79)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), cyclopropanamine-HCl (6.15 mg, 0.066 mmol), 4-methylmorpholine (17.72 mg, 0.175 mmol), and HATU (21.65 mg, 0.057 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.3 min) to provide (R/S)-N-cyclopropyl-3-(2-hydroxy-2-(4-(5-(3-phenyl-4-(trifluoromethyl)isoxazol-5-yl)-1,2,4-oxadiazol-3-yl)phenyl)acetamido)propanamide (9 mg, 0.016 mmol, 35.5% yield): LCMS=542.3 [M+H]$^+$; $^1$H NMR (400 MHz, methanol-d$_4$) δ ppm 8.17 (2 H, d, J=8.36 Hz), 7.54-7.75 (7 H, m), 5.10 (1 H, s), 3.45-3.55 (2 H, m), 2.56-2.68 (1 H, m), 2.37 (2 H, t, J=6.49 Hz), 0.63-0.76 (2 H, m), 0.35-0.49 (2 H, m); HPLC peak RT=8.7 min (Method A).

Example 80

(R/S)-3-(2-Hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), 1-amino-2-methylpropan-2-ol (5.85 mg, 0.066 mmol), 4-methylmorpholine (17.72 mg, 0.175 mmol), and HATU (21.65 mg, 0.057 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.2 min) to provide (R/S)-3-(2-hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (2 mg, 2.99 μmol, 6.83% yield): LCMS=574.3 [M+H]$^+$; $^1$H NMR (400 MHz, methanol-d$_4$) δ ppm 8.17 (2 H, d, J=8.36 Hz), 7.50-7.79 (7 H, m), 5.11 (1 H, s), 3.48-3.58 (2 H, m), 3.14-3.22 (2 H, m), 2.48 (2 H, t, J=6.71 Hz), 1.16 (3 H, s), 1.16 (3 H, s); HPLC peak RT=8.2 min (Method A).

Example 81

(R/S)-N-((1H-Imidazol-2-yl)methyl)-3-(2-hydroxy-2-(4-(5-(3-phenyl-4-(trifluoromethyl)isoxazol-5-yl)-1,2,4-oxadiazol-3-yl)phenyl)acetamido)propanamide, TFA

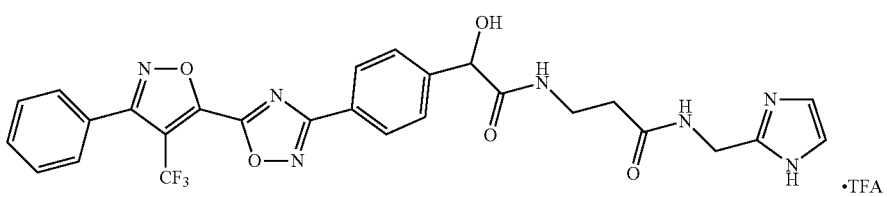

(81)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Example 22, 22 mg, 0.044 mmol), (1H-imidazol-2-yl)methanamine-2HCl (11.17 mg, 0.066 mmol), 4-methylmorpholine (17.72 mg, 0.175 mmol), and HATU (21.65 mg, 0.057 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.1 min) to provide (R/S)—N-((1H-imidazol-2-yl)methyl)-3-(2-hydroxy-2-(4-(5-(3-phenyl-4-(trifluoromethyl)isoxazol-5-yl)-1,2,4-oxadiazol-3-yl)phenyl)acetamido)propanamide-TFA (1 mg, 1.252 μmol, 2.86% yield): LCMS=582.3 [M+H]$^+$; $^1$H NMR (400 MHz, methanol-d$_4$) δ ppm 8.15 (2 H, d, J=8.36 Hz),

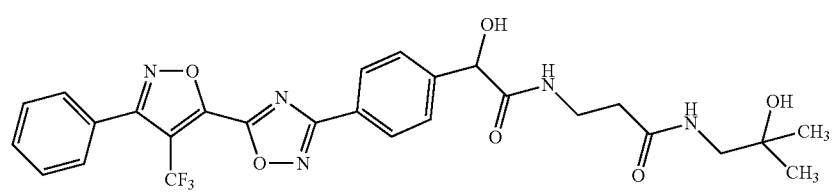

(80)

7.54-7.74 (7 H, m), 7.41 (2 H, s), 5.13 (1 H, s), 4.59 (2 H, s), 3.46-3.69 (2 H, m), 2.44-2.58 (2 H, m); HPLC peak RT=7.7 min (Method A).

Example 82

(R/S)-2-Hydroxy-2-(4-(5-(3-phenyl-4-(trifluoromethyl)isoxazol-5-yl)-1,2,4-oxadiazol-3-yl)phenyl)-N-(thiophen-3-ylmethyl)acetamide

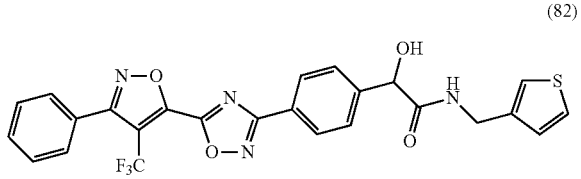 [SMILES: O=C(NCc1ccsc1)C(O)c1ccc(-c2noc(-c3onc(-c4ccccc4)c3C(F)(F)F)n2)cc1]

(82)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), thiophen-3-ylmethanamine (11.8 mg, 0.104 mmol), 4-methylmorpholine (28.1 mg, 0.278 mmol), and HATU (34.4 mg, 0.090 mmol) were added to DMF (1 mL). This was stirred for 1 h before it was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow: 20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(thiophen-3-ylmethyl)acetamide (12.9 mg, 0.025 mmol, 35.2% yield): LCMS=527.1 [M+H]$^+$; $^1$H NMR (400 MHz, methanol-d$_4$) δ ppm 8.16 (2 H, d, J=8.53 Hz), 7.52-7.76 (7 H, m), 7.26 (1 H, dd, J=5.02, 1.25 Hz), 6.85-7.01 (2 H, m), 5.16 (1 H, s), 4.60 (2 H, s); HPLC peak RT=3.0 min (Method E).

Example 83

(R/S)-N-((4-Amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide

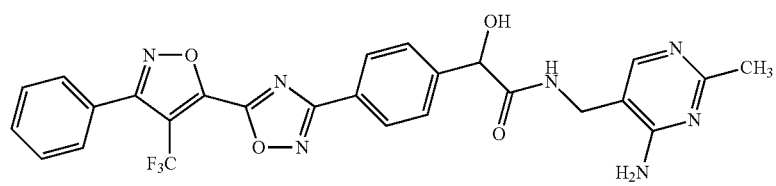

(83)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), 5-(aminomethyl)-2-methylpyrimidin-4-amine-2HCl (22.02 mg, 0.104 mmol), 4-methylmorpholine (28.1 mg, 0.278 mmol), and HATU (34.4 mg, 0.090 mmol) were added to DMF (1 mL). This was stirred for 1 h before it was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to give (R/S)-N-((4-amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide (17.5 mg, 0.032 mmol, 45.6% yield): LCMS=552.1 [M+H]$^+$; $^1$H NMR (400 MHz, methanol-d$_4$) δ ppm 8.14 (2 H, d, J=8.53 Hz), 7.93 (1 H, s), 7.50-7.70 (7 H, m), 5.15 (1 H, s), 4.25 (2 H, d, J=4.02 Hz), 2.40 (3 H, s); HPLC peak RT=2.4 min (Method E).

Example 84

(R/S)-2-Hydroxy-2-(4-(5-(3-phenyl-4-(trifluoromethyl)isoxazol-5-yl)-1,2,4-oxadiazol-3-yl)phenyl)-N-((1,3,5-trimethyl-1H-pyrazol-4-yl)methyl)acetamide

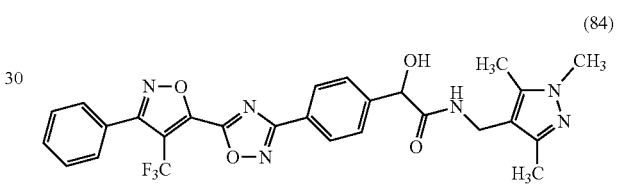

(84)

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 30 mg, 0.070 mmol), (1,3,5-trimethyl-1H-pyrazol-4-yl)methanamine-HCl (18.33 mg, 0.104 mmol), 4-methylmorpholine (28.1 mg, 0.278 mmol), and HATU (34.4 mg, 0.090 mmol) were added to DMF (1 mL). This was stirred for 1 h before it was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 25 minutes, then a 5-minute hold at 100% B; Flow: 20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-((1,3,5-trimethyl-1H-pyrazol-4-yl)methyl)acetamide (17.2 mg, 0.031 mmol, 44.8% yield): LCMS=553.2 [M+H]$^+$; $^1$H NMR (400 MHz, methanol-d$_4$) δ ppm 8.14 (2 H, d, J=8.28 Hz), 7.50-7.69 (8H, m), 5.10 (1 H, s), 4.19 (2 H, d, J=5.27 Hz), 3.65 (3 H, s), 2.17 (3 H, s), 2.12 (3 H, s); HPLC peak RT=2.6 min (Method E).

Example 85

(R/S)-2-Hydroxy-N-(2-(2-oxoimidazolidin-1-yl) ethyl)-2-(4-(5-(3-phenyl-4-(trifluoromethyl)isoxazol-5-yl)-1,2,4-oxadiazol-3-yl)phenyl)acetamide (85)

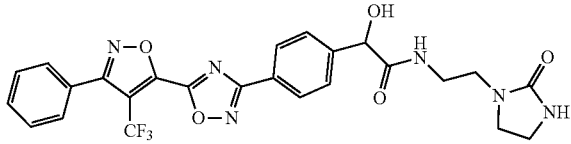

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 25 mg, 0.058 mmol), 1-(2-aminoethyl)imidazolidin-2-one (22.46 mg, 0.087 mmol), 4-methylmorpholine (23.45 mg, 0.232 mmol), and HATU (28.7 mg, 0.075 mmol) were added to DMF (1 mL). This was stirred for 1 h before it was purified via preparative LCMS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to give (R/S)-2-hydroxy-N-(2-(2-oxoimidazolidin-1-yl)ethyl)-2-(4-(5-(3-phenyl-4-(trifluoromethyl)isoxazol-5-yl)-1,2,4-oxadiazol-3-yl)phenyl)acetamide (13.2 mg, 0.024 mmol, 42.0% yield): LCMS=543.1 [M+H]$^+$; $^1$H NMR (400 MHz, methanol-d$_4$) δ ppm 8.11-8.23 (2 H, m), 7.54-7.73 (7 H, m), 5.11 (1 H, s), 3.32-3.49 (6 H, m), 3.21-3.29 (2 H, m); HPLC peak RT=2.4 min (Method E).

Example 86

(R/S)-N-((1H-Indol-2-yl)methyl)-2-hydroxy-2-(4-(5-(3-phenyl-4-(trifluoromethyl)isoxazol-5-yl)-1,2,4-oxadiazol-3-yl)phenyl)acetamide (86)

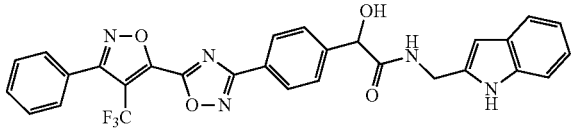

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 20 mg, 0.046 mmol), (1H-indol-2-yl)methanamine (10.17 mg, 0.070 mmol), 4-methylmorpholine (18.76 mg, 0.185 mmol), and HATU (22.92 mg, 0.060 mmol) were added to DMF (1 mL). This was stirred for 1 h before it was purified by prep HPLC (YMC S5 ODS 5u 20×100 mm, gradient elution with Method 1—MeOH/water containing 0.1% trifluoroacetic acid as defined above, 0% B to 100% B over 10 min, 20 mL/min, 220 nM, product retention=12.3 min) to provide (R/S)-N-((1H-indol-2-yl)methyl)-2-hydroxy-2-(4-(5-(3-phenyl-4-(trifluoromethyl)isoxazol-5-yl)-1,2,4-oxadiazol-3-yl)phenyl)acetamide (13 mg, 0.02 mmol, 43.7% yield): LCMS=560.3 [M+H]$^+$; $^1$H NMR (400 MHz, methanol-d$_4$) δ ppm 8.15-8.20 (2 H, m), 7.55-7.75 (9 H, m), 7.27-7.46 (2 H, m), 6.92-7.08 (2 H, m), 6.29 (1 H, s), 5.20 (1 H, s), 4.48-4.64 (2 H, m); HPLC peak RT=10.7 min (Method A).

Example 87

(R/S)-N-((1H-Tetrazol-5-yl)methyl)-2-hydroxy-2-(4-(5-(3-phenyl-4-(trifluoromethyl)isoxazol-5-yl)-1,2,4-oxadiazol-3-yl)phenyl)acetamide (87)

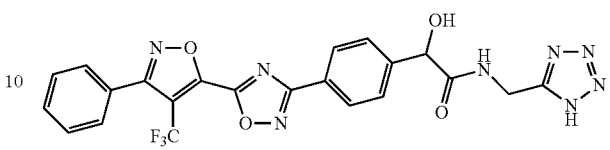

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 20 mg, 0.046 mmol), 5-(aminomethyl)tetrazole (6.89 mg, 0.070 mmol), 4-methylmorpholine (18.76 mg, 0.185 mmol), and HATU (22.92 mg, 0.060 mmol) were added to DMF (1 mL). This was stirred for 1 h and was then purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=29.2 min) to provide (R/S)-N-((1H-tetrazol-5-yl)methyl)-2-hydroxy-2-(4-(5-(3-phenyl-4-(trifluoromethyl)isoxazol-5-yl)-1,2,4-oxadiazol-3-yl)phenyl)acetamide (12 mg, 0.023 mmol, 49.8% yield): LCMS=513.2 [M+H]$^+$; $^1$H NMR (400 MHz, methanol-d$_4$) δ ppm 8.11-8.24 (2 H, m), 7.53-7.75 (7 H, m), 5.22 (1 H, s), 4.67-4.81 (2 H, m); HPLC peak RT=8.8 min (Method A).

Example 88

(R/S)-2-Hydroxy-2-(4-(5-(3-phenyl-4-(trifluoromethyl)isoxazol-5-yl)-1,2,4-oxadiazol-3-yl)phenyl)-N-(pyrrolidin-2-ylmethyl)acetamide, TFA (88)

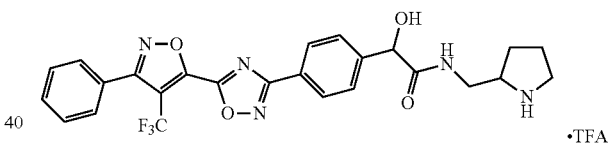

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 30 mg, 0.070 mmol), 2-(aminomethyl)-1N-Boc-pyrrolidine (20.9 mg, 0.104 mmol), 4-methylmorpholine (28.1 mg, 0.278 mmol), and HATU (34.4 mg, 0.090 mmol) were added to DMF (1 mL). This was stirred for 1 h before it was purified by prep HPLC (PHENOMENEX® Luna 5u 21×250 mm, gradient elution with Method 1—MeOH/water containing 0.1% trifluoroacetic acid as defined above, 0% B to 100% B over 10 min, 25 mL/min, 220 nM, product retention=32.9 min) to provide (R/S)-tert-butyl 2-((2-hydroxy-2-(4-(5-(3-phenyl-4-(trifluoromethyl)isoxazol-5-yl)-1,2,4-oxadiazol-3-yl)phenyl)acetamido)methyl)pyrrolidine-1-carboxylate (28 mg, 0.046 mmol, 65.6% yield): LCMS=614.3 [M+H]$^+$. The (R/S)-tert-butyl 2-((2-hydroxy-2-(4-(5-(3-phenyl-4-(trifluoromethyl)isoxazol-5-yl)-1,2,4-oxadiazol-3-yl)phenyl)acetamido)methyl)pyrrolidine-1-carboxylate (28 mg, 0.046 mmol) was added to TFA (1 mL, 12.98 mmol) and stirred for 30 min. The reaction mixture was concentrated to provide (R/S)-2-hydroxy-2-(4-(5-(3-phenyl-4-(trifluoromethyl)isoxazol-5-yl)-1,2,4-oxadiazol-3-yl)phenyl)-N-(pyrrolidin-2-ylmethyl)acetamide, TFA (24 mg, 0.037 mmol, 80% yield): LCMS=514.3 [M+H]$^+$; $^1$H NMR (400 MHz, methanol-d$_4$) δ ppm 8.18 (2 H, d, J=7.92 Hz), 7.54-7.79 (7 H, m), 5.21 (1 H, s), 3.66-3.81 (1 H, m), 3.48-3.62 (2 H, m), 3.16-3.30 (2 H, m), 1.91-2.18 (3 H, m), 1.70-1.82 (1 H, m); HPLC peak RT=8.3 min (Condition A).

Example 89

(R/S)-N-(2-(1H-Imidazol-4-yl)ethyl)-2-hydroxy-2-(4-(5-(3-phenyl-4-(trifluoromethyl)isoxazol-5-yl)-1,2,4-oxadiazol-3-yl)phenyl)acetamide, TFA

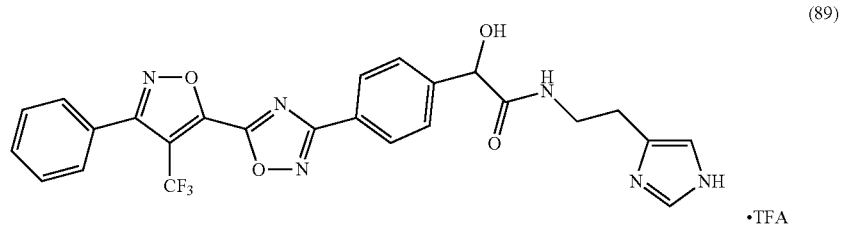 [SMILES: O=C(NCCc1c[nH]cn1)C(O)c1ccc(-c2noc(-c3onc(-c4ccccc4)c3C(F)(F)F)n2)cc1]

(89)

·TFA (R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), histamine-2HCl (7.73 mg, 0.070 mmol), HATU (22.92 mg, 0.060 mmol), and 4-methylmorpholine (18.76 mg, 0.185 mmol) were added to DMF (1 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 0.05% TFA; Mobile Phase B: 95:5 methanol:water with 0.05% TFA; Gradient: 35-100% B over 25 minutes, then a 5-minute hold at 100% B; Flow: 20 mL/min. Fractions containing the desired product were combined and dried via centrifugal evaporation to give (R/S)-N-(2-(1H-imidazol-4-yl)ethyl)-2-hydroxy-2-(4-(5-(3-phenyl-4-(trifluoromethyl)isoxazol-5-yl)-1,2,4-oxadiazol-3-yl)phenyl)acetamide, TFA (9.5 mg, 0.015 mmol, 32.1% yield): LCMS=525.1 [M+H]$^+$; $^1$H NMR (400 MHz, methanol-d$_4$) δ ppm 8.65 (1 H, s), 8.17 (2 H, d, J=8.36 Hz), 7.54-7.75 (7 H, m), 7.16 (1 H, s), 5.09 (1 H, s), 3.57-3.69 (1 H, m), 3.47-3.57 (1 H, m), 2.92 (2 H, t, J=6.71 Hz); HPLC peak RT=2.2 min (Method E).

Example 90

(R/S)-N-((1H-Benzo[d]imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide (R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), (1H-benzo[d]imidazol-2-yl)methanamine (10.24 mg, 0.070 mmol), HATU (22.92 mg, 0.060 mmol), and 4-methylmorpholine (18.76 mg, 0.185 mmol) were added to DMF (1 mL). This was stirred for 1 h before it was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to give (R/S)-N-((1H-benzo[d]imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide (12.8 mg, 0.023 mmol, 49.3% yield): LCMS=561.1 [M+H]$^+$; $^1$H NMR (400 MHz, methanol-d$_4$) δ ppm 8.19 (2 H, d, J=8.58 Hz), 7.51-7.79 (10 H, m), 7.34 (2 H, dd, J=6.05, 3.19 Hz), 5.27 (1 H, s), 4.76-4.94 (2 H, m); HPLC peak RT=2.6 min (Method E).

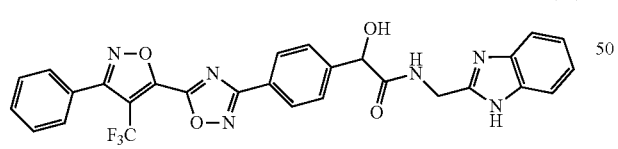

(90)

Example 91

(R/S)-N-(3-(3,3-Difluoroazetidin-1-yl)-3-oxopropyl)-2-hydroxy-2-(4-(5-(3-phenyl-4-(trifluoromethyl)isoxazol-5-yl)-1,2,4-oxadiazol-3-yl)phenyl)acetamide

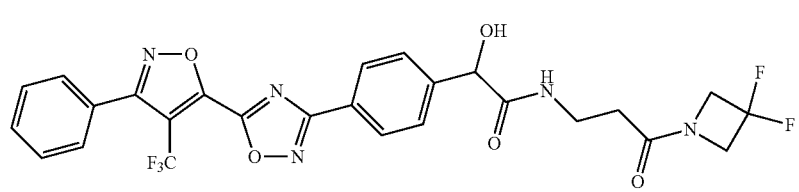

(91)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Int-V, 25 mg, 0.050 mmol), 3,3-difluoroazetidine-HCl (6.45 mg, 0.050 mmol), 4-methylmorpholine (20.13 mg, 0.199 mmol), and HATU (24.60 mg, 0.065 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=10.6 min) to provide (R/S)-N-(3-(3,3-difluoroazetidin-1-yl)- 3-oxopropyl)-2-hydroxy-2-(4-(5-(3-phenyl-4-(trifluoromethyl)isoxazol-5-yl)-1,2,4-oxadiazol-3-yl)phenyl)acetamide (5 mg, 6.53 µmol, 13.12% yield): LCMS=578.3 [M+H]$^+$; $^1$H NMR (400 MHz, methanol-d$_4$) δ ppm 8.14-8.24 (2 H, m), 7.51-7.74 (7 H, m), 5.11 (1 H, s), 4.49 (2 H, td, J=11.77, 7.04 Hz), 4.29 (2 H, t, J=12.21 Hz), 3.45-3.58 (2 H, m), 2.38-2.52 (2 H, m); HPLC peak RT=9.4 min (Method A).

Example 92

(R/S)-2-Hydroxy-N-(3-(3-hydroxy-3-methylazetidin-1-yl)-3-oxopropyl)-2-(4-(5-(3-phenyl-4-(trifluoromethyl)isoxazol-5-yl)-1,2,4-oxadiazol-3-yl)phenyl)acetamide mide (9 mg, 0.014 mmol, 27.8% yield): LCMS=572.3 [M+H]$^+$; $^1$H NMR (400 MHz, methanol-d$_4$) δ ppm 8.16-8.20 (2 H, m), 7.54-7.74 (7 H, m), 5.11 (1 H, s), 3.96-4.04 (2 H, m), 3.81-3.87 (2 H, m), 3.47-3.52 (2 H, m), 2.36-2.43 (2 H, m), 1.44 (3 H, d, J=6.60 Hz); HPLC peak RT=8.3 min (Method A).

Example 93

(R/S)-2-Hydroxy-N-(3-(3-hydroxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide

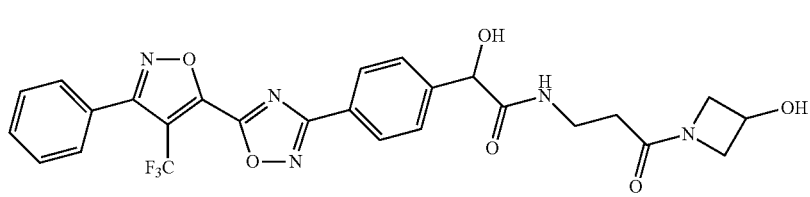

(93)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Int-V, 25 mg, 0.050 mmol), azetidin-3-ol, HCl (5.45 mg, 0.050 mmol), 4-methylmorpholine (20.13 mg, 0.199 mmol), and HATU (24.60 mg, 0.065 mmol) were added to DMF (1 mL). This was stirred for 1 h before it was purified by prep HPLC (Sun Fire C18 5u19×100 mm, gradient elution with Method 1—MeOH/water containing 0.1% trifluoroacetic acid as defined above, 0% B to 100% B over 10 min, product retention=11.15 min (20 mL/min, 220

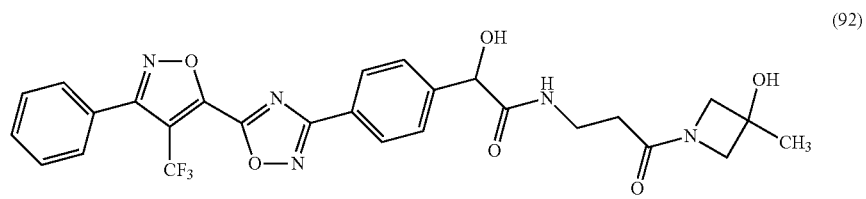 [SMILES: CC1(O)CN(C(=O)CCNC(=O)C(O)c2ccc(-c3noc(-c4onc(-c5ccccc5)c4C(F)(F)F)n3)cc2)C1]

(92)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Int-V, 25 mg, 0.050 mmol), 4-methylmorpholine (20.13 mg, 0.199 mmol), 3-methylazetidin-3-ol, HCl (6.15 mg, 0.050 mmol), and HATU (24.60 mg, 0.065 mmol) were added to DMF (1 mL). This was stirred for 1 h before it was purified by prep HPLC (Sun Fire C18 5u19×100 mm, gradient elution with Method 1—MeOH/water containing 0.1% trifluoroacetic acid as defined above, 0% B to 100% B over 10 min, 20 mL/min, 220 nM, product retention=11.3 min) to provide (R/S)-2-hydroxy-N-(3-(3-hydroxy-3-methylazetidin-1-yl)-3-oxopropyl)-2-(4-(5-(3-phenyl-4-(trifluoromethyl)isoxazol-5-yl)-1,2,4-oxadiazol-3-yl)phenyl)acetanM) to provide (R/S)-2-hydroxy-N-(3-(3-hydroxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (8 mg, 0.013 mmol, 26.2% yield): LCMS=558.3 [M+H]$^+$; $^1$H NMR (400 MHz, methanol-d$_4$) δ ppm 8.19 (2 H, d, J=8.36 Hz), 7.52-7.78 (7 H, m), 5.11 (1 H, s), 4.40-4.57(1 H, m), 4.10-4.38(2 H, m), 3.89(1 H, ddd, J=9.52, 4.24, 1.21 Hz), 3.68-3.80 (1 H, m), 3.49 (2 H, t, J=6.27 Hz), 2.27-2.46 (2 H, m); HPLC peak RT=8.1 min (Method A).

Example 94

N-((4-Amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide (94)

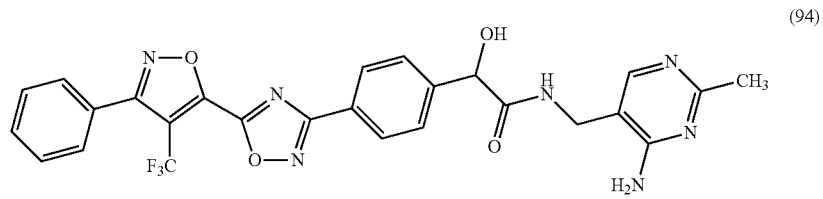 [SMILES: Cc1ncc(CNC(=O)C(O)c2ccc(-c3noc(-c4onc(-c5ccccc5)c4C(F)(F)F)n3)cc2)c(N)n1]

2-Hydroxy-2-(4-(5-(3-phenyl-4-(trifluoromethyl)isoxazol-5-yl)-1,2,4-oxadiazol-3-yl)phenyl)acetic acid (Int-Va, 50 mg, 0.116 mmol), 5-(aminomethyl)-2-methylpyrimidin-4-amine-2 HCl (36.7 mg, 0.174 mmol), 4-methylmorpholine (46.9 mg, 0.464 mmol), and HATU (57.3 mg, 0.151 mmol) were added to DMF (2 mL). The mixture was stirred for 1 h. Methanol was added and the mixture was filtered for prep HPLC. It was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.2 min) to provide single enantiomer N-((4-amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide (45 mg, 0.078 mmol, 67.6% yield): LCMS=552.3 [M+H]$^+$; $^1$H NMR (400 MHz, methanol-d$_4$) δ ppm 8.13-8.25 (2 H, m), 7.91 (1 H, s), 7.53-7.75 (7 H, m), 5.21 (1 H, s), 4.20-4.39 (2 H, m), 2.51 (3 H, s); HPLC peak RT=8.3 min (Method A).

Example 95

(R/S)-2-Hydroxy-2-(4-(5-(3-phenyl-4-(trifluoromethyl)isoxazol-5-yl)-1,2,4-oxadiazol-3-yl)phenyl)-N-(2-(thiazol-4-yl)ethyl)acetamide (95)

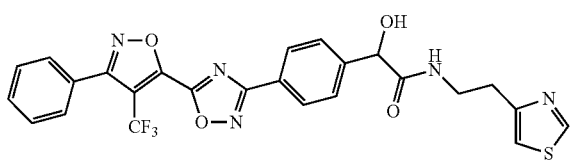

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), 2-(thiazol-4-yl)ethanamine (8.92 mg, 0.070 mmol), 4-methylmorpholine (18.76 mg, 0.185 mmol), and HATU (22.92 mg, 0.060 mmol) were added to DMF (1 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 40-100% B over 25 minutes, then a 5-minute hold at 100% B; Flow: 20 mL/min. Fractions containing the desired product were combined and dried via centrifugal evaporation to give (R/S)-2-hydroxy-2-(4-(5-(3-phenyl-4-(trifluoromethyl)isoxazol-5-yl)-1,2,4-oxadiazol-3-yl)phenyl)-N-(2-(thiazol-4-yl)ethyl)acetamide (10.1 mg, 0.019 mmol, 40.2% yield): LCMS=542.1 [M+H]$^+$; $^1$H NMR (400 MHz, methanol-d$_4$) δ ppm 8.82 (1 H, d, J=2.01 Hz), 8.13 (2 H, d, J=8.28 Hz), 7.49-7.72 (8 H, m), 7.08 (1 H, d, J=2.01 Hz), 5.08 (1 H, s), 3.53-3.69 (2 H, m), 3.03 (2 H, t, J=6.78 Hz); HPLC peak RT=2.6 min (Method E).

Example 96

(R/S)-2-Hydroxy-N-(3-(3-methoxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (96)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Int-V, 25 mg, 0.050 mmol), 3-methoxyazetidine, HCl (6.15 mg, 0.050 mmol), 4-methylmorpholine (20.13 mg, 0.199 mmol), and HATU (24.60 mg, 0.065 mmol) were added to DMF (3 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to give (R/S)-2-hydroxy-N-(3-(3-methoxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (14.1 mg, 0.025 mmol, 49.6% yield): LCMS=572.2 [M+H]$^+$; $^1$H NMR (400 MHz, methanol-d$_4$) δ ppm 8.19 (2 H, dd, J=8.41, 1.88 Hz), 7.54-7.77 (7 H, m), 5.11 (1 H, d, J=2.01 Hz), 4.06-4.31 (3 H, m), 3.84-3.98 (1 H, m), 3.69-3.83 (1 H, m), 3.43-3.56 (2 H, m), 3.26 (3 H, d, J=2.76 Hz), 2.29-2.44 (2 H, m); HPLC peak RT=2.4 min (Method E).

Example 97

(R/S)-Methyl 1-(3-(2-hydroxy-2-(4-(5-(3-phenyl-4-(trifluoromethyl)isoxazol-5-yl)-1,2,4-oxadiazol-3-yl)phenyl)acetamido)propanoyl)azetidine-3-carboxylate (97)

(R/S)-3-(2-Hydroxy-2-(4-(5-(3-phenyl-4-(trifluoromethyl)isoxazol-5-yl)-1,2,4-oxadiazol-3-yl)phenyl)acetamido)propanoic acid (Int-V, 25 mg, 0.050 mmol), methyl azetidine-3-carboxylate-HCl (7.54 mg, 0.050 mmol), 4-methylmorpholine (20.13 mg, 0.199 mmol), and HATU (24.60 mg, 0.065 mmol) were added to DMF (1 mL). This was stirred for 1 h before it was purified via preparative LCMS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give (R/S)-methyl 1-(3-(2-hydroxy-2-(4-(5-(3-phenyl-4-(trifluoromethyl)isoxazol-5-yl)-1,2,4-oxadiazol-3-yl)phenyl)acetamido)propanoyl)azetidine-3-carboxylate (11.9 mg, 0.020 mmol, 39.9% yield): LCMS=600.2 [M+H]$^+$; $^1$H NMR (400 MHz, methanol-d$_4$) δ ppm 8.14-8.26 (2 H, m), 7.54-7.77 (7 H, m), 5.12 (1 H, s), 4.00-4.34 (4 H, m), 3.73 (3 H, d, J=5.27 Hz), 3.39-3.56 (3 H, m), 2.36 (2 H, q, J=6.44 Hz); HPLC peak RT=2.5 min (Method E).

Example 98

(R/S)-2-Hydroxy-2-(4-(5-(3-phenyl-4-(trifluoromethyl)isoxazol-5-yl)-1,2,4-oxadiazol-3-yl)phenyl)-N-(thiazol-2-ylmethyl)acetamide (98)

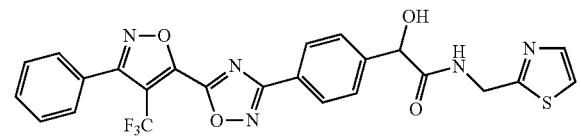

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 23 mg, 0.053 mmol), thiazol-2-ylmethanamine-HCl (12.05 mg, 0.080 mmol), 4-methylmorpholine (21.57 mg, 0.213 mmol), and HATU (26.4 mg, 0.069 mmol) were added to DMF (1 mL). This was stirred for 1 h before it was purified by prep HPLC (YMC S5 20×100 mm, gradient elution with Method 1—MeOH/water containing 0.1% trifluoroacetic acid as defined above 0% B to 100% B over 10 min, 20 mL/min, 220 nM, product retention=11.8 min) to provide (R/S)-2-hydroxy-2-(4-(5-(3-phenyl-4-(trifluoromethyl)isoxazol-5-yl)-1,2,4-oxadiazol-3-yl)phenyl)-N-(thiazol-2-ylmethyl)acetamide (19 mg, 0.033 mmol, 62.3% yield): LCMS=528.2 [M+H]$^+$; $^1$H NMR (400 MHz, methanol-d$_4$) δ ppm 8.13-8.22 (2 H, m), 7.46-7.78 (9 H, m), 5.22 (1 H, s), 4.67-4.82 (2 H, m); HPLC peak RT=9.5 min (Method A).

Example 99

(R/S)-2-Hydroxy-N-(oxazol-2-ylmethyl)-2-(4-(5-(3-phenyl-4-(trifluoromethyl)isoxazol-5-yl)-1,2,4-oxadiazol-3-yl)phenyl)acetamide (99)

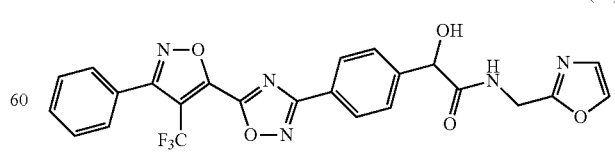

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), oxazol-2-ylmethanamine (6.82 mg, 0.070 mmol), 4-methylmorpholine (18.76 mg, 0.185 mmol), and HATU (22.92 mg, 0.060 mmol) were added to DMF (1 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to give (R/S)-2-hydroxy-N-(oxazol-2-ylmethyl)-2-(4-(5-(3-phenyl-4-(trifluoromethyl)isoxazol-5-yl)-1,2,4-oxadiazol-3-yl)phenyl)acetamide (3.7 mg, 7.23 μmol, 15.60% yield): LCMS=512.1 [M+H]$^+$; $^1$H NMR (400 MHz, methanol-$d_4$) δ ppm 8.16 (2 H, d, J=8.28 Hz), 7.50-7.83 (9 H, m), 7.09 (1 H, s), 5.20 (1 H, s), 4.45-4.67 (2 H, m); HPLC peak RT=2.6 min (Method E).

Example 100

(R/S)-2-Hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (100)

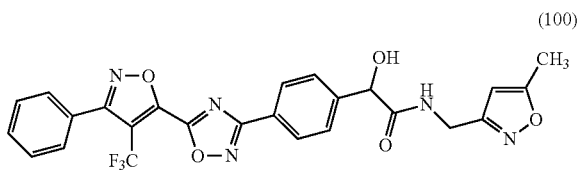 [SMILES: Cc1cc(CNC(=O)C(O)c2ccc(-c3noc(-c4onc(-c5ccccc5)c4C(F)(F)F)n3)cc2)no1]

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), (5-methylisoxazol-3-yl)methanamine (7.80 mg, 0.070 mmol), 4-methylmorpholine (18.76 mg, 0.185 mmol), and HATU (22.92 mg, 0.060 mmol) were added to DMF (1 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 40-100% B over 25 minutes, then a 5-minute hold at 100% B; Flow: 20 mL/min. Fractions containing the desired product were combined and dried via centrifugal evaporation to give (R/S)-2-hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (4.1 mg, 7.41 μmol, 15.99% yield): LCMS=526.1 [M+H]$^+$; $^1$H NMR (400 MHz, methanol-$d_4$) δ ppm 8.11-8.25 (2 H, m), 7.50-7.73 (8 H, m), 5.94 (1 H, s), 5.17 (1 H, s), 4.43(2 H, d, J=2.51 Hz), 2.36 (3 H, s); HPLC peak RT=2.7 min (Method E).

Example 101

(R/S)-2-Hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (101)

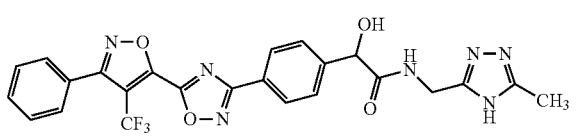

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), methyl-4H-1,2,4 triazole-3-yl-methylamine hydrogen chloride (7.80 mg, 0.070 mmol), 4-methylmorpholine (18.76 mg, 0.185 mmol), and HATU (22.92 mg, 0.060 mmol) were dissolved in DMF (1 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to give (R/S)-2-hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (12.6 mg, 0.024 mmol, 51.2% yield): LCMS=526.1 [M+H]$^+$; $^1$H NMR (400 MHz, methanol-$d_4$) δ ppm 8.15 (2 H, d, J=8.28 Hz), 7.49-7.76 (8 H, m), 5.18 (1 H, s), 4.35-4.61 (2 H, m), 4.26 (1 H, s), 2.41 (3 H, br. s.); HPLC peak RT=2.3 min (Method E).

Example 102

(R/S)-2-Hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (102)

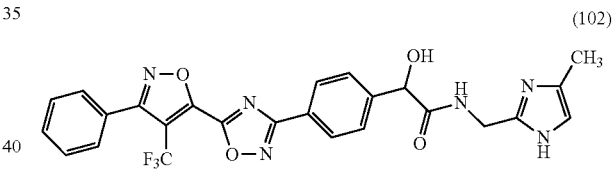

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), C-(4-methyl-1H-imidazol-2-yl)-methylamine hydrochloride (5.15 mg, 0.046 mmol), 4-methylmorpholine (18.76 mg, 0.185 mmol), and HATU (22.92 mg, 0.060 mmol) were dissolved in DMF (1 mL). This was stirred for 1 h before it was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to give (R/S)-2-hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (5.5 mg, 10.07 μmol, 21.71% yield): LCMS=525.2 [M+H]$^+$; $^1$H NMR (400 MHz, methanol-$d_4$) δ ppm 8.15 (2 H, d, J=8.53 Hz), 7.48-7.72 (8 H, m), 6.64 (1 H, d, J=1.00 Hz), 5.17 (1 H, s), 4.28-4.53 (2 H, m), 2.18 (3H, d, J=1.00 Hz); HPLC peak RT=2.5 min (Method E).

Example 103

(R/S)-2-Hydroxy-N-((3-(methoxymethyl)-1,2,4-oxadiazol-5-yl)methyl)-2-(4-(5-(3-phenyl-4-(trifluoromethyl)isoxazol-5-yl)-1,2,4-oxadiazol-3-yl)phenyl)acetamide (103)

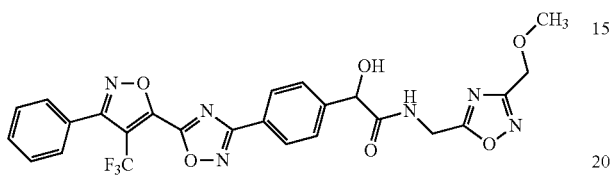

(R/S)-2-Hydroxy-2-(4-(5-(3-phenyl-4-(trifluoromethyl) isoxazol-5-yl)-1,2,4-oxadiazol-3-yl)phenyl)acetic acid (Int-V, 20 mg, 0.046 mmol), (3-(methoxymethyl)-1,2,4-oxadiazol-5-yl)methanamine (9.96 mg, 0.070 mmol), 4-methylmorpholine (18.76 mg, 0.185 mmol), and HATU (22.92 mg, 0.060 mmol) were dissolved in DMF (1 mL). This was stirred for 1 h before it was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to give (R/S)-2-hydroxy-N-((3-(methoxymethyl)-1,2,4-oxadiazol-5-yl)methyl)-2-(4-(5-(3-phenyl-4-(trifluoromethyl)isoxazol-5-yl)-1,2,4-oxadiazol-3-yl)phenyl)acetamide (9.7 mg, 0.017 mmol, 37.6% yield): LCMS=557.2 [M+H]$^+$; $^1$H NMR (400 MHz, methanol-$d_4$) δ ppm 8.16 (2 H, d, J=8.53 Hz), 7.50-7.76 (8 H, m), 5.21 (1 H, s), 4.69 (2 H, d, J=7.53 Hz), 4.54 (2 H, s), 3.43 (3 H, s); HPLC peak RT=2.7 min (Method E).

Example 104

2-Cyano-2-(2-hydroxy-2-(4-(5-(3-phenyl-4-(trifluoromethyl)isoxazol-5-yl)-1,2,4-oxadiazol-3-yl)phenyl)acetamido)-N-methylacetamide (104)

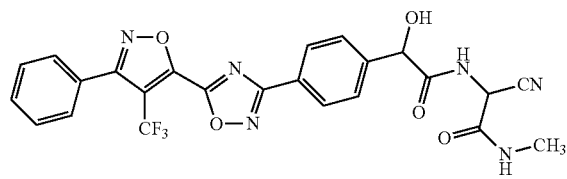

2-Hydroxy-2-(4-(5-(3-phenyl-4-(trifluoromethyl)isoxazol-5-yl)-1,2,4-oxadiazol-3-yl)phenyl)acetic acid (Int-Va, 20 mg, 0.046 mmol), (R/S)-2-amino-2-cyano-N-methylacetamide (7.87 mg, 0.070 mmol), 4-methylmorpholine (18.76 mg, 0.185 mmol), and HATU (22.92 mg, 0.060 mmol) were added to DMF (2 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.5 min) to provide (R/S)-2-cyano-2-(2-hydroxy-2-(4-(5-(3-phenyl-4-(trifluoromethyl)isoxazol-5-yl)-1,2,4-oxadiazol-3-yl)phenyl)acetamido)-N-methylacetamide (8 mg, 0.012 mmol, 26.5% yield) as a mixture of diastereomers. LCMS=527.3 [M+H]$^+$; $^1$H NMR (400 MHz, methanol-$d_4$) δ ppm 8.12-8.28 (2 H, m), 7.48-7.78 (7 H, m), 5.40-5.58 (1 H, m), 5.27 (1 H, s), 2.80 (3 H, s); HPLC peak RT=9.4 min (Method A).

Example 105

N-(1-Cyano-2-phenylethyl)-2-hydroxy-2-(4-(5-(3-phenyl-4-(trifluoromethyl)isoxazol-5-yl)-1,2,4-oxadiazol-3-yl)phenyl)acetamide (105)

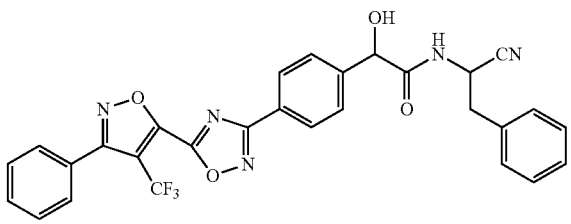

2-Hydroxy-2-(4-(5-(3-phenyl-4-(trifluoromethyl)isoxazol-5-yl)-1,2,4-oxadiazol-3-yl)phenyl)acetic acid (Int-Va, 20 mg, 0.046 mmol), (R/S)-2-amino-3-phenylpropanenitrile hydrochloride (8.47 mg, 0.046 mmol), 4-methylmorpholine (18.76 mg, 0.185 mmol), and HATU (22.92 mg, 0.060 mmol) were added to DMF (2 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=12.2 min) to provide (R/S)-N-(1-cyano-2-phenylethyl)-2-hydroxy-2-(4-(5-(3-phenyl-4-(trifluoromethyl) isoxazol-5-yl)-1,2,4-oxadiazol-3-yl)phenyl)acetamide (8 mg, 0.012 mmol, 26.2% yield) as a mixture of diastereomers: LCMS=546.3 [M+H]$^+$; $^1$H NMR (400 MHz, methanol-$d_4$) δ ppm 8.05-8.17 (2 H, m), 7.18-7.72 (12 H, m), 5.08-5.15 (1 H, m), 5.02 (1 H, t, J=7.70 Hz), 3.11-3.27 (2 H, m); HPLC peak RT=11.0 min (Method A).

Example 106

N-(Cyano(phenyl)methyl)-2-hydroxy-2-(4-(5-(3-phenyl-4-(trifluoromethyl)isoxazol-5-yl)-1,2,4-oxadiazol-3-yl)phenyl)acetamide (106)

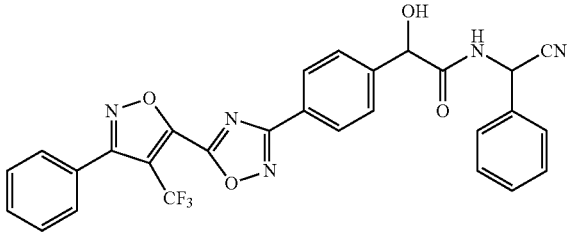

2-Hydroxy-2-(4-(5-(3-phenyl-4-(trifluoromethyl)isoxazol-5-yl)-1,2,4-oxadiazol-3-yl)phenyl)acetic acid (Int-Va, 20 mg, 0.046 mmol), (R/S)-2-phenylglycinonitrile hydrochloride (11.73 mg, 0.070 mmol), 4-methylmorpholine (18.76 mg, 0.185 mmol), and HATU (22.92 mg, 0.060 mmol) were added to DMF (2 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, product retention=12.2 min (20 mL/min, 220 nM) to provide N-(cyano(phenyl)methyl)-2-hydroxy-2-(4-(5-(3-phenyl-4-(trifluoromethyl)isoxazol-5-yl)-1,2,4-oxadiazol-3-yl)phenyl)acetamide (8 mg, 0.013 mmol, 27.2% yield) as a mixture of diastereomers. LCMS=546.3 [M+H]$^+$; $^1$H NMR (400 MHz, methanol-d$_4$) δ ppm 8.17 (2 H, dd, J=8.36, 6.38 Hz), 7.32-7.77 (12 H, m), 6.18 (1 H, d, J=7.04 Hz), 5.24 (1 H, d, J=8.14 Hz); HPLC peak RT=10.9 min (Method A).

Example 107

N-(2-Amino-1-cyano-2-oxoethyl)-2-hydroxy-2-(4-(5-(3-phenyl-4-(trifluoromethyl)isoxazol-5-yl)-1,2,4-oxadiazol-3-yl)phenyl)acetamide (107)

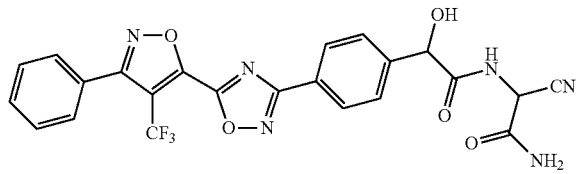

2-Hydroxy-2-(4-(5-(3-phenyl-4-(trifluoromethyl)isoxazol-5-yl)-1,2,4-oxadiazol-3-yl)phenyl)acetic acid (Int-Va, 20 mg, 0.046 mmol), (R/S)-2-amino-2-cyanoacetamide (4.59 mg, 0.046 mmol), 4-methylmorpholine (18.76 mg, 0.185 mmol), and HATU (22.92 mg, 0.060 mmol) were added to DMF (2 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.4 min) to provide N-(2-amino-1-cyano-2-oxoethyl)-2-hydroxy-2-(4-(5-(3-phenyl-4-(trifluoromethyl)isoxazol-5-yl)-1,2,4-oxadiazol-3-yl)phenyl)acetamide (8 mg, 0.013 mmol, 28.6% yield) as a mixture of diastereomers. LCMS=513.2 [M+H]$^+$; $^1$H NMR (400 MHz, methanol-d$_4$) δ ppm 8.12-8.28 (2 H, m), 7.50-7.80 (7 H, m), 5.40-5.63 (1 H, m), 5.27 (1 H, s); HPLC peak RT=9.2 min (Method A).

Example 108

2-Hydroxy-N-(1-(4-methyl-4H-1,2,4-triazol-3-yl)ethyl)-2-(4-(5-(3-phenyl-4-(trifluoromethyl)isoxazol-5-yl)-1,2,4-oxadiazol-3-yl)phenyl)acetamide (108)

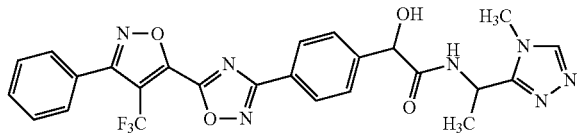

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 17 mg, 0.039 mmol), (R/S)-1-(4-methyl-4H-1,2,4-triazol-3-yl)ethanamine (7.46 mg, 0.059 mmol), 4-methylmorpholine (15.95 mg, 0.158 mmol), and HATU (19.48 mg, 0.051 mmol) were dissolved in DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=12.2 min) to provide 2-hydroxy-N-(1-(4-methyl-4H-1,2,4-triazol-3-yl)ethyl)-2-(4-(5-(3-phenyl-4-(trifluoromethyl)isoxazol-5-yl)-1,2,4-oxadiazol-3-yl)phenyl)acetamide (8 mg, 0.014 mmol, 34.6% yield) as a racemic mixture of diastereomers. LCMS=540.3 [M+H]$^+$; $^1$H NMR (400 MHz, methanol-d$_4$) δ ppm 8.90 (1 H, s), 8.16 (2 H, d, J=8.36 Hz), 7.52-7.77 (7 H, m), 5.36 (1 H, q), 5.21 (1 H, s), 3.62 (3 H, s), 1.69 (3 H, d, J=7.04 Hz); HPLC peak RT=8.4 min (Method A).

Example 109

(R/S)-N-((1,3-Dimethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide-TFA (109)

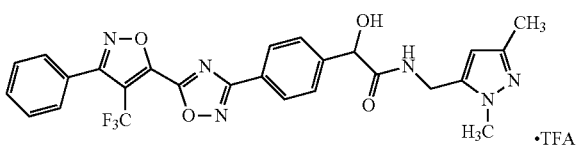

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 17 mg, 0.039 mmol), (1,3-dimethyl-1H-pyrazol-5-yl)methanamine (7.40 mg, 0.059 mmol), 4-methylmorpholine (15.95 mg, 0.158 mmol), and HATU (19.48 mg, 0.051 mmol) were dissolved in DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=13.0 min) to provide (R/S)-N-((1,3-dimethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide, TFA (7 mg, 10.22 μmol, 25.9% yield): LCMS=539.3 [M+H]$^+$; $^1$H NMR (400 MHz, methanol-d$_4$) δ ppm 8.11-8.23 (2 H, m), 7.52-7.76 (7 H, m), 6.06 (1 H, s), 5.18 (1 H, s), 4.44 (2 H, s), 3.77 (3 H, s), 2.21 (3 H, s); HPLC peak RT=9.0 min (Method A).

Example 110

(R/S)-2-Hydroxy-N-((5-phenyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA

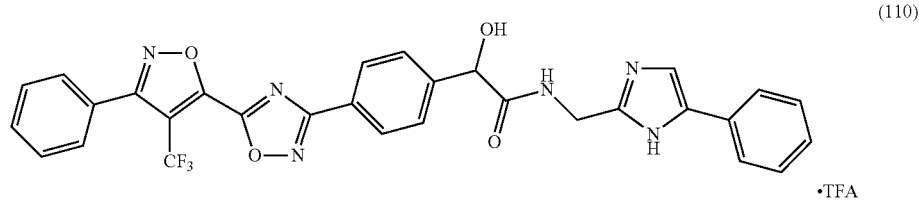 [SMILES: O=C(NCc1ncc(-c2ccccc2)[nH]1)C(O)c1ccc(-c2noc(-c3onc(-c4ccccc4)c3C(F)(F)F)n2)cc1]

(110)

·TFA (R/S)-2-Hydroxy-2-(4-(5-(3-phenyl-4-(trifluoromethyl)isoxazol-5-yl)-1,2,4-oxadiazol-3-yl)phenyl)acetic acid (Int-V, 17 mg, 0.039 mmol), C-(5-phenyl-1H-imidazol-2-yl)-methylamine (6.83 mg, 0.039 mmol), 4-methylmorpholine (15.95 mg, 0.158 mmol), and HATU (19.48 mg, 0.051 mmol) were dissolved in DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=12.0 min) to provide (R/S)-2-hydroxy-N-((5-phenyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (5 mg, 6.85 µmol, 17.38% yield); LCMS=587.3 [M+H]$^+$; $^1$H NMR (400 MHz, methanol-d$_4$) δ ppm 8.12-8.27 (2 H, m), 7.40-7.84 (13 H, m), 5.27 (1 H, s), 4.73 (2 H, q, J=16.29 Hz); HPLC peak RT=9.2 min (Method A).

Example 111

N-((S)-1-(1H-Imidazol-2-yl)ethyl)-2-hydroxy-2-(4-(5-(3-phenyl-4-(trifluoromethyl)isoxazol-5-yl)-1,2,4-oxadiazol-3-yl)phenyl)acetamide, TFA

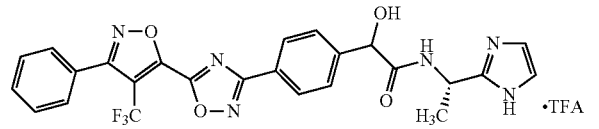

(111)

·TFA

2-Hydroxy-2-(4-(5-(3-phenyl-4-(trifluoromethyl)isoxazol-5-yl)-1,2,4-oxadiazol-3-yl)phenyl)acetic acid (Int-Va, 20 mg, 0.046 mmol), (S)-1-(1H-imidazol-2-yl)ethanamine (5.15 mg, 0.046 mmol), HATU (22.92 mg, 0.060 mmol), and 4-methylmorpholine (18.76 mg, 0.185 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.3 min) to provide N-((S)-1-(1H-imidazol-2-yl)ethyl)-2-hydroxy-2-(4-(5-(3-phenyl-4-(trifluoromethyl)isoxazol-5-yl)-1,2,4-oxadiazol-3-yl)phenyl)acetamide, TFA (17 mg, 0.021 mmol, 44.4% yield) as a single enantiomer. LCMS=525.3 [M+H]$^+$; $^1$H NMR (400 MHz, methanol-d$_4$) δ ppm 8.10-8.27 (2 H, m), 7.42-7.77 (11 H, m), 5.26-5.33 (1 H, m), 5.23 (1 H, s), 1.68 (3 H, d, J=7.26 Hz); HPLC peak RT=8.4 min (Method A).

Example 112

2-Hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide

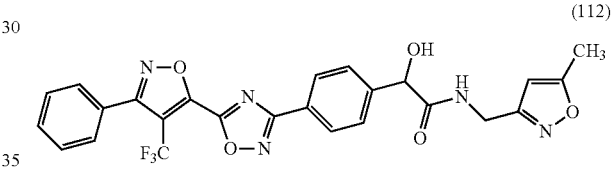

(112)

2-Hydroxy-2-(4-(5-(3-phenyl-4-(trifluoromethyl)isoxazol-5-yl)-1,2,4-oxadiazol-3-yl)phenyl)acetic acid (Int-V, 25 mg, 0.058 mmol), (5-methylisoxazol-3-yl)methanamine (9.75 mg, 0.087 mmol), HATU (28.7 mg, 0.075 mmol), and 4-methylmorpholine (23.45 mg, 0.232 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=14.0 min) to provide 2-hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (15 mg, 0.028 mmol, 48.2% yield) as a single enantiomers. LCMS=526.3 [M+H]$^+$; $^1$H NMR (400 MHz, methanol-d$_4$) δ ppm 8.11-8.23 (2 H, m), 7.50-7.82 (7 H, m), 5.98 (1 H, s), 5.18 (1 H, s), 4.43 (2 H, s), 2.36 (3 H, s); HPLC peak RT=10.0 min (Method A).

Example 113

2-Hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA

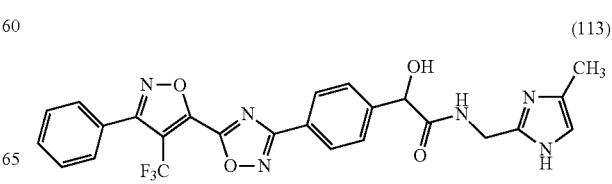

(113)

2-Hydroxy-2-(4-(5-(3-phenyl-4-(trifluoromethyl)isoxazol-5-yl)-1,2,4-oxadiazol-3-yl)phenyl)acetic acid (Int-Va, 25 mg, 0.058 mmol), C-(4-methyl-1H-imidazol-2-yl)-methylamine-HCl (9.66 mg, 0.087 mmol), HATU (28.7 mg, 0.075 mmol), and 4-methylmorpholine (23.45 mg, 0.232 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=12.4 min) to provide 2-hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (10 mg, 0.015 mmol, 25.2% yield) as a single enantiomer. LCMS=525.3 [M+H]$^+$; $^1$H NMR (400 MHz, methanol-d$_4$) δ ppm 8.16 (2 H, d, J=8.36 Hz), 7.43-7.78 (8 H, m), 6.64 (1 H, s), 5.19 (1 H, s), 4.29-4.56 (2 H, m), 2.17 (3 H, s); HPLC peak RT=8.5 min (Method A).

Example 114

2-Hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (114)

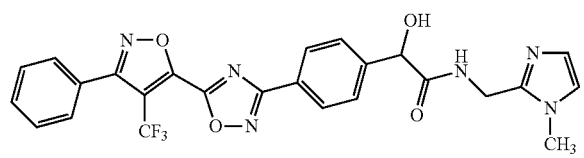

2-Hydroxy-2-(4-(5-(3-phenyl-4-(trifluoromethyl)isoxazol-5-yl)-1,2,4-oxadiazol-3-yl)phenyl)acetic acid (Int-Va, 25 mg, 0.058 mmol), C-(1-Methyl-1H-imidazol-2-yl)-methylamine-HCl (9.66 mg, 0.087 mmol), HATU (28.7 mg, 0.075 mmol), and 4-methylmorpholine (23.45 mg, 0.232 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=12.2 min) to provide 2-hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (9 mg, 0.013 mmol, 22.15% yield) as a single enantiomer. LCMS=525.3 [M+H]$^+$=525.3; 1H NMR (400 MHz, methanol-d$_4$) δ ppm 8.08-8.21 (2 H, m), 7.44-7.75 (8 H, m), 7.00 (1 H, d, J=1.32 Hz), 6.88 (1 H, d, J=1.32 Hz), 5.18 (1 H, s), 4.37-4.60 (2 H, m), 3.60 (3 H, s); HPLC peak RT=8.5 min (Method A).

Example 115

2-Hydroxy-2-(4-(5-(3-phenyl-4-(trifluoromethyl)isoxazol-5-yl)-1,2,4-oxadiazol-3-yl)phenyl)-N-(2-(pyrazin-2-yl)ethyl)acetamide, TFA (115)

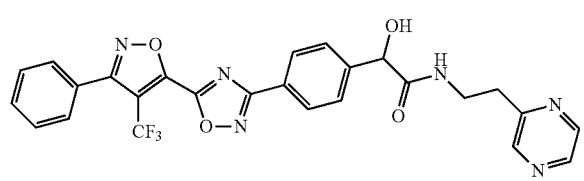

2-Hydroxy-2-(4-(5-(3-phenyl-4-(trifluoromethyl)isoxazol-5-yl)-1,2,4-oxadiazol-3-yl)phenyl)acetic acid (Int-Va, 25 mg, 0.058 mmol), 2-pyrazin-2-yl-ethylamine (10.71 mg, 0.087 mmol), HATU (28.7 mg, 0.075 mmol), and 4-methylmorpholine (23.45 mg, 0.232 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=13.6 min) to provide 2-hydroxy-2-(4-(5-(3-phenyl-4-(trifluoromethyl)isoxazol-5-yl)-1,2,4-oxadiazol-3-yl)phenyl)-N-(2-(pyrazin-2-yl)ethyl)acetamide, TFA (10 mg, 0.018 mmol, 30.6% yield) as a single enantiomer. LCMS=537.4 [M+H]$^+$; $^1$H NMR (400 MHz, methanol-d$_4$) δ ppm 8.05-8.58 (5 H, m), 7.49-7.78 (7 H, m), 5.06 (1 H, s), 3.67 (2 H, dt, J=13.59, 6.74 Hz), 3.05 (2 H, t, J=6.71 Hz); HPLC peak RT=9.1 min (Method A).

Example 116

(R/S)-N-Cyclobutyl-2-hydroxy-2-(4-(5-(3-phenyl-4-(trifluoromethyl)isoxazol-5-yl)-1,2,4-oxadiazol-3-yl)phenyl)acetamide (116)

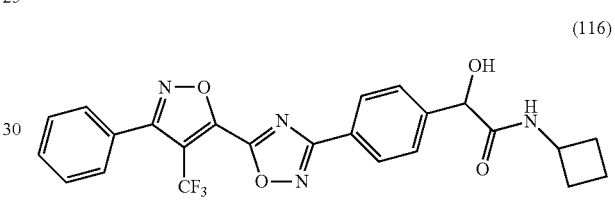

(R/S)-2-Hydroxy-2-(4-(5-(3-phenyl-4-(trifluoromethyl)isoxazol-5-yl)-1,2,4-oxadiazol-3-yl)phenyl)acetic acid (Int-V, 20 mg, 0.046 mmol), cyclobutanamine (4.95 mg, 0.070 mmol), HATU (22.92 mg, 0.060 mmol), and 4-methylmorpholine (18.76 mg, 0.185 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 12 min, 20 mL/min, 220 nM, product retention=14.17 min) to provide (R/S)-N-cyclobutyl-2-hydroxy-2-(4-(5-(3-phenyl-4-(trifluoromethyl)isoxazol-5-yl)-1,2,4-oxadiazol-3-yl)phenyl)acetamide (7 mg, 0.011 mmol, 23.93% yield): LCMS=485.3 [M+H]$^+$; $^1$H NMR (400 MHz, methanol-d$_4$) δ ppm 8.12-8.23 (2 H, m), 7.53-7.73 (7 H, m), 5.09 (1 H, s), 4.15-4.42 (1 H, m), 2.28 (2 H, dddd, J=10.07, 4.90, 4.62, 2.86 Hz), 1.98-2.13 (2 H, m), 1.70-1.79 (2 H, m); HPLC peak RT=10.4 min (Method A).

Example 117

2-Hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide (117)

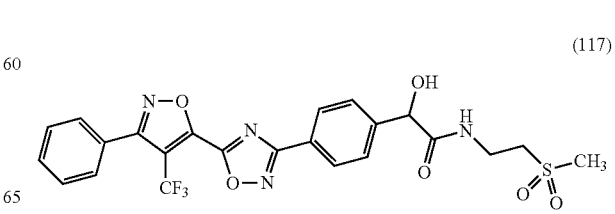

2-Hydroxy-2-(4-(5-(3-phenyl-4-(trifluoromethyl)isoxazol-5-yl)-1,2,4-oxadiazol-3-yl)phenyl)acetic acid (Int-Va, 30 mg, 0.070 mmol), 2-(methylsulfonyl)ethanamine (12.85 mg, 0.104 mmol), HATU (34.4 mg, 0.090 mmol), and 4-methylmorpholine (28.1 mg, 0.278 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.5 min) to provide 2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide (15 mg, 0.027 mmol, 38.2% yield) as a single enantiomer. LCMS=537.3 [M+H]$^+$; $^1$H NMR (400 MHz, methanol-$d_4$) δ ppm 8.17 (2 H, d, J=8.58 Hz), 7.54-7.74 (7 H, m), 5.14 (1 H, s), 3.73 (2 H, t, J=6.60 Hz), 3.35 (2 H, t, J=6.60 Hz), 2.97 (3 H, s); HPLC peak RT=9.3 min (Method A).

Example 118

2-Hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (118)

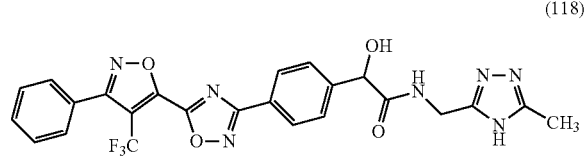 [SMILES: Cc1nnc(CNC(=O)C(O)c2ccc(-c3noc(-c4onc(-c5ccccc5)c4C(F)(F)F)n3)cc2)[nH]1]

2-Hydroxy-2-(4-(5-(3-phenyl-4-(trifluoromethyl)isoxazol-5-yl)-1,2,4-oxadiazol-3-yl)phenyl)acetic acid (Int-Va, 30 mg, 0.070 mmol), (5-methyl-4H-1,2,4-triazol-3-yl)methanamine (11.70 mg, 0.104 mmol), HATU (34.4 mg, 0.090 mmol), and 4-methylmorpholine (28.1 mg, 0.278 mmol) were added to DMF (1 mL). This was stirred for 1 h before it was purified by prep HPLC (PHENOMENEX® Luna 5u 21.2×100 mm, gradient elution with Method 1—MeOH/water containing 0.1% trifluoroacetic acid as defined above, 0% B to 100% B over 10 min, 20 mL/min, 220 nM, product retention=11.3 min) to provide 2-hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (12 mg, 0.022 mmol, 31.7% yield) as a single enantiomer. LCMS=526.4 [M+H]$^+$; $^1$H NMR (400 MHz, methanol-$d_4$) δ ppm 8.17 (2 H, d, J=8.36 Hz), 7.51-7.76 (7 H, m), 5.21 (1 H, s), 4.46-4.66 (2 H, m), 2.52 (3 H, s); HPLC peak RT=8.4 min (Method A).

Example 119

Ethyl 5-((2-hydroxy-2-(4-(5-(3-phenyl-4-(trifluoromethyl)isoxazol-5-yl)-1,2,4-oxadiazol-3-yl)phenyl)acetamido)methyl)-1H-1,2,4-triazole-3-carboxylate (119)

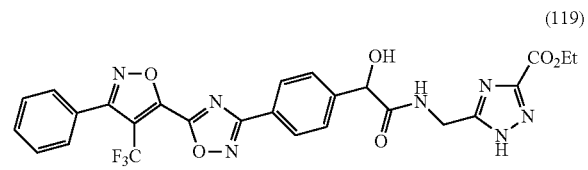 [SMILES: CCOC(=O)c1n[nH]c(CNC(=O)C(O)c2ccc(-c3noc(-c4onc(-c5ccccc5)c4C(F)(F)F)n3)cc2)n1]

2-Hydroxy-2-(4-(5-(3-phenyl-4-(trifluoromethyl)isoxazol-5-yl)-1,2,4-oxadiazol-3-yl)phenyl)acetic acid (Int-Va, 120 mg, 0.278 mmol), ethyl 5-(aminomethyl)-1H-1,2,4-triazole-3-carboxylate, TFA (Int-XIV, 95 mg, 0.334 mmol), 4-methylmorpholine (113 mg, 1.113 mmol), and HATU (138 mg, 0.362 mmol) were added to DMF (1 mL). This was stirred for 1 h before it was purified by prep HPLC (PHENOMENEX® Luna 5u 21×250 mm, gradient elution with Method 1—MeOH/water containing 0.1% trifluoroacetic acid as defined above, 0% B to 100% B over 30 min, 25 mL/min, 220 nM, product retention=30.1 min) to provide ethyl 5-((2-hydroxy-2-(4-(5-(3-phenyl-4-(trifluoromethyl)isoxazol-5-yl)-1,2,4-oxadiazol-3-yl)phenyl)acetamido)methyl)-1H-1,2,4-triazole-3-carboxylate (40 mg, 0.058 mmol, 20.77% yield) as a single enantiomer. LCMS=584.1 [M+H]$^+$; $^1$H NMR (400 MHz, methanol-$d_4$) δ ppm 8.08-8.22 (2 H, m), 7.50-7.78 (7 H, m), 5.22 (1 H, s), 4.48-4.72 (2 H, m), 4.42 (2 H, q, J=7.04 Hz), 1.39 (3 H, t, J=7.04 Hz); HPLC peak RT=10.0 min (Method A).

Examples 120 to 134

Examples 120 to 134 were prepared by the general coupling procedure described below:

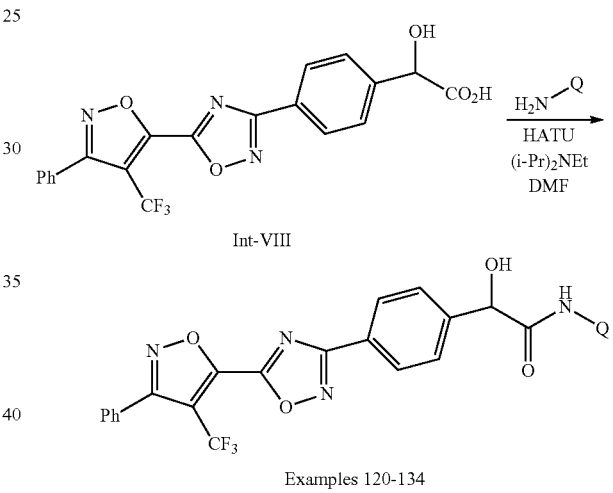

Examples 120-134

General Coupling Procedure

The amines (90 μmol, 2 eq) were weighed into individual 16×100 Wheaton tubes. Next stock solutions were made, containing (R/S)-ethyl 2-hydroxy-2-(4-(5-(5-phenyl-4-(trifluoromethyl)isoxazol-3-yl)-1,2,4-oxadiazol-3-yl)phenyl)acetate (Int-VIII, 361 mg, 45 μmol per reaction, 1 eq) was dissolved in DMF (3 mL), and separately, HATU (730 mg, 90 μmol per reaction, 2 eq) was dissolved in DMF (3.8 mL). To each Wheaton tube containing an amine was added (R/S)-ethyl 2-hydroxy-2-(4-(5-(5-phenyl-4-(trifluoromethyl)isoxazol-3-yl)-1,2,4-oxadiazol-3-yl)phenyl)acetate (Int-VIII) solution (161 μL), followed by HATU solution (180 μL) and N-ethyl-N-isopropylpropan-2-amine (31 μL, 180 μmol, 4 eq). The reactions were agitated at 400 rpm on an INNOVA® platform shaker overnight at rt. After 16 hours, the reactions were transferred to prep LCMS as solutions in DMF. Samples were purified on a Waters Xbridge 19×100 mm C18 column over a 20 min gradient from 0% B to 100% B (solvent A=5:95 MeOH:$H_2O$ with 10 mM $NH_4OAc$, solvent B=95:5 MeOH:$H_2O$ with 10 mM $NH_4OAc$). Fractions containing the desired product were combined and dried for 16 hours in a Genevac at 45° C. to provide Examples 120-134 as racemic mixtures (see Table 1).

TABLE 1

| Ex. | Q | Name | Observed[a] MS Ion (M + H)+ | RT[a] [min] |
|---|---|---|---|---|
| 120 | [H₃C, CH₃ isopropyl-isoxazol-5-yl] | (R/S)-2-hydroxy-N-((3-isopropylisoxazol-5-yl)methyl)-2-(4-(5-(3-phenyl-4-(trifluoromethyl)isoxazol-5-yl)-1,2,4-oxadiazol-3-yl)phenyl)acetamide | 553.9 | 2.9 |
| 121 | [1-ethyl-1H-pyrazol-5-yl, CH₃] | (R/S)-N-((1-ethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide | 538.9 | 2.6 |
| 122 | [1-p-tolyl-1H-pyrazol-4-yl, CH₃] | (R/S)-2-hydroxy-2-(4-(5-(3-phenyl-4-(trifluoromethyl)isoxazol-5-yl)-1,2,4-oxadiazol-3-yl)phenyl)-N-((1-p-tolyl-1H-pyrazol-4-yl)methyl)acetamide | 601.0 | 3.1 |
| 123 | [1-benzyl-1H-imidazol-2-yl, Ph] | (R/S)-N-((1-benzyl-1H-imidazol-2-yl)methyl)-2-hydroxy-2-(4-(5-(3-phenyl-4-(trifluoromethyl)isoxazol-5-yl)-1,2,4-oxadiazol-3-yl)phenyl)acetamide | 601.0 | 2.9 |
| 124 | [1-phenyl-1H-pyrazol-4-yl, Ph] | (R/S)-2-hydroxy-N-((1-phenyl-1H-pyrazol-4-yl)methyl)-2-(4-(5-(3-phenyl-4-(trifluoromethyl)isoxazol-5-yl)-1,2,4-oxadiazol-3-yl)phenyl)acetamide | 587.0 | 2.8 |
| 125 | [4-phenethyl-4H-1,2,4-triazol-3-yl, Ph] | (R/S)-2-hydroxy-N-((4-phenethyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide | 616.0 | 2.7 |
| 126 | [oxazol-5-yl] | (R/S)-2-hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide | 511.9 | 2.5 |
| 127 | [5-(pyridin-2-yl)thiophen-2-yl] | (R/S)-2-hydroxy-2-(4-(5-(3-phenyl-4-(trifluoromethyl)isoxazol-5-yl)-1,2,4-oxadiazol-3-yl)phenyl)-N-((5-(pyridin-2-yl)thiophen-2-yl)methyl)acetamide | 603.9 | 3.0 |

TABLE 1-continued

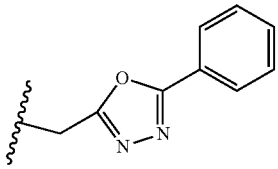 [SMILES: *Cc1nnc(-c2ccccc2)o1]

| Ex. | Q | Name | Observed MS Ion (M + H)+ [a] | RT [a] [min] |
|---|---|---|---|---|
| 128 | 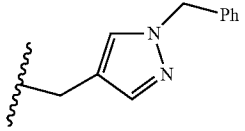 [SMILES: *Cc1cnn(Cc2ccccc2)c1] | (R/S)-2-hydroxy-N-((5-phenyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide | 589.0 | 2.8 |
| 129 | 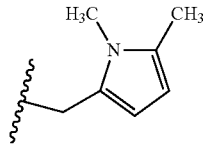 [SMILES: *Cc1ccc(C)n1C] | (R/S)-N-((1-benzyl-1H-pyrazol-4-yl)methyl)-2-hydroxy-2-(4-(5-(3-phenyl-4-(trifluoromethyl)isoxazol-5-yl)-1,2,4-oxadiazol-3-yl)phenyl)acetamide | 601 | 2.9 |
| 130 | 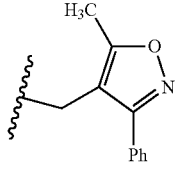 [SMILES: *Cc1c(-c2ccccc2)noc1C] | (R/S)-N-((1,5-dimethyl-1H-pyrrol-2-yl)methyl)-2-hydroxy-2-(4-(5-(3-phenyl-4-(trifluoromethyl)isoxazol-5-yl)-1,2,4-oxadiazol-3-yl)phenyl)acetamide | 538.0 | 3.0 |
| 131 | 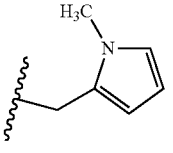 [SMILES: *Cc1cccn1C] | (R/S)-2-hydroxy-N-((5-methyl-3-phenylisoxazol-4-yl)methyl)-2-(4-(5-(3-phenyl-4-(trifluoromethyl)isoxazol-5-yl)-1,2,4-oxadiazol-3-yl)phenyl)acetamide | 602.0 | 3.1 |
| 132 | 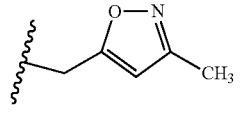 | (R/S)-2-hydroxy-N-((1-methyl-1H-pyrrol-2-yl)methyl)-2-(4-(5-(3-phenyl-4-(trifluoromethyl)isoxazol-5-yl)-1,2,4-oxadiazol-3-yl)phenyl)acetamide | 524.0 | 2.9 |
| 133 | 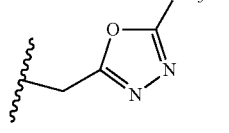 | (R/S)-2-hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide | 525.9 | 2.7 |
| 134 | | (R/S)-2-hydroxy-N-((5-methyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide | 527.2 | 2.4 |

[a] LCMS analyzed on a Waters Masslynx instrument equipped with a 4.6 × 50 mm 2.7 μM MacMod Halo C18 column and using a method of 0-100% B solvent over 4 min at a flow rate of 4 mL/min. Solvent A is 5:95 acetonitrile/water; solvent B is 95:5 acetonitrile/water and both contain 10 mM ammonium acetate.

Examples 135 to 158

Examples 135 to 158 were prepared by the general coupling procedure described below:

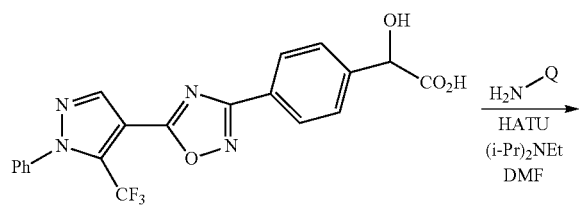

Int-VII

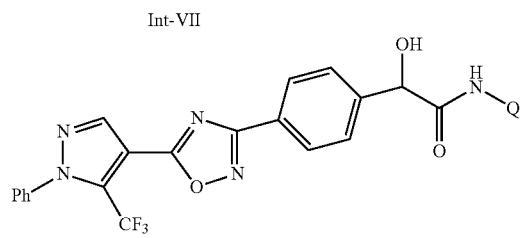

Examples 135-158

General Coupling Procedure

The amines (150 μmol, 3 eq) were weighed into individual 16×100 Wheaton tubes. Next stock solutions were made: (R/S)-2-hydroxy-2-(4-(5-(1-phenyl-5-(trifluoromethyl)-1H-pyrazol-4-yl)-1,2,4-oxadiazol-3-yl)phenyl)acetic acid (Int-VII, 494.5 mg, 50 μmol per reaction, 1 eq) was dissolved in DMF (3 mL), and separately, HATU (541 mg, 100 μmol per reaction, 2 eq) was dissolved in DMF (3.8 mL). To each Wheaton tube containing an amine was added (R/S)-2-hydroxy-2-(4-(5-(1-phenyl-5-(trifluoromethyl)-1H-pyrazol-4-yl)-1,2,4-oxadiazol-3-yl)phenyl)acetic acid (Int-VII) solution (130 μL), followed by HATU solution (165 μL) and N-ethyl-N-isopropylpropan-2-amine (35 μL, 200 μmol, 4 eq). The reactions were agitated at 400 rpm on an INNOVA® platform shaker overnight at rt. After 16 hours, the reactions were transferred to prep LCMS as solutions in DMF. Samples were purified on a Waters Xbridge 19×100 mm C18 column over a 20 min gradient from 0% B to 100% B (solvent A=5:95 MeOH:$H_2O$ with 10 mM $NH_4OAc$, solvent B=95:5 MeOH:$H_2O$ with 10 mM $NH_4OAc$). Fractions containing the desired product were combined and dried for 16 hours in a Genevac at 45° C. to provide Examples 135-158 as racemic mixtures (see Table 2).

TABLE 2

| Ex. | Q | Name | Observed[a] MS Ion (M + H)+ | RT[a] [min] |
|---|---|---|---|---|
| 135 | ![pyrrolidine with CH3] | (R/S)-2-hydroxy-N-(2-(1-methylpyrrolidin-2-yl)ethyl)-2-(4-(5-(1-phenyl-5-(trifluoromethyl)-1H-pyrazol-4-yl)-1,2,4-oxadiazol-3-yl)phenyl)acetamide | 541.2 | 2.0 |
| 136 | ![pyrrolidinyl ethyl] | (R/S)-2-hydroxy-2-(4-(5-(1-phenyl-5-(trifluoromethyl)-1H-pyrazol-4-yl)-1,2,4-oxadiazol-3-yl)phenyl)-N-(2-(pyrrolidin-1-yl)ethyl)acetamide | 527.1 | 2.1 |
| 137 | ![pyridin-2-ylmethyl] | (R/S)-2-hydroxy-2-(4-(5-(1-phenyl-5-(trifluoromethyl)-1H-pyrazol-4-yl)-1,2,4-oxadiazol-3-yl)phenyl)-N-(pyridin-2-ylmethyl)acetamide | 521.1 | 2.4 |
| 138 | ![pyridin-3-ylmethyl] | (R/S)-2-hydroxy-2-(4-(5-(1-phenyl-5-(trifluoromethyl)-1H-pyrazol-4-yl)-1,2,4-oxadiazol-3-yl)phenyl)-N-(pyridin-3-ylmethyl)acetamide | 521.1 | 2.3 |
| 139 | ![pyridin-4-ylmethyl] | (R/S)-2-hydroxy-2-(4-(5-(1-phenyl-5-(trifluoromethyl)-1H-pyrazol-4-yl)-1,2,4-oxadiazol-3-yl)phenyl)-N-(pyridin-4-ylmethyl)acetamide | 521.1 | 2.3 |

TABLE 2-continued

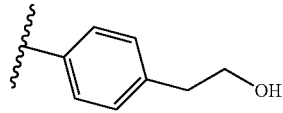 [SMILES: *c1ccc(CCO)cc1]

| Ex. | Q | Name | Observed[a] MS Ion (M + H)+ | RT[a] [min] |
|---|---|---|---|---|
| 140 | 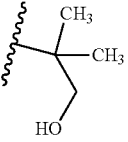 | (R/S)-2-hydroxy-N-(4-(2-hydroxyethyl)phenyl)-2-(4-(5-(1-phenyl-5-(trifluoromethyl)-1H-pyrazol-4-yl)-1,2,4-oxadiazol-3-yl)phenyl)acetamide | 550.1 | 2.5 |
| 141 | 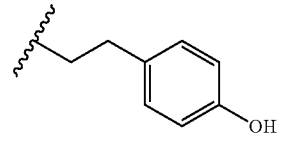 [SMILES: *CCc1ccc(O)cc1] | (R/S)-2-hydroxy-N-(1-hydroxy-2-methylpropan-2-yl)-2-(4-(5-(1-phenyl-5-(trifluoromethyl)-1H-pyrazol-4-yl)-1,2,4-oxadiazol-3-yl)phenyl)acetamide | 502.1 | 2.4 |
| 142 | 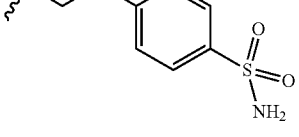 | (R/S)-2-hydroxy-N-(4-hydroxyphenethyl)-2-(4-(5-(1-phenyl-5-(trifluoromethyl)-1H-pyrazol-4-yl)-1,2,4-oxadiazol-3-yl)phenyl)acetamide | 550.1 | 2.5 |
| 143 | 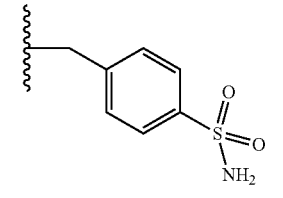 [SMILES: *Cc1ccc(S(N)(=O)=O)cc1] | (R/S)-2-hydroxy-2-(4-(5-(1-phenyl-5-(trifluoromethyl)-1H-pyrazol-4-yl)-1,2,4-oxadiazol-3-yl)phenyl)-N-(4-sulfamoylphenethyl)acetamide | 613.1 | 2.3 |
| 144 | 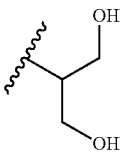 [SMILES: *C(CO)CO] | (R/S)-2-hydroxy-2-(4-(5-(1-phenyl-5-(trifluoromethyl)-1H-pyrazol-4-yl)-1,2,4-oxadiazol-3-yl)phenyl)-N-(4-sulfamoylbenzyl)acetamide | 599.1 | 2.3 |
| 145 | 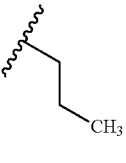 | (R/S)-N-(1,3-dihydroxypropan-2-yl)-2-hydroxy-2-(4-(5-(1-phenyl-5-(trifluoromethyl)-1H-pyrazol-4-yl)-1,2,4-oxadiazol-3-yl)phenyl)acetamide | 504.1 | 2.0 |
| 146 | 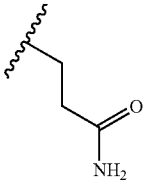 | (R/S)-2-hydroxy-2-(4-(5-(1-phenyl-5-(trifluoromethyl)-1H-pyrazol-4-yl)-1,2,4-oxadiazol-3-yl)phenyl)-N-propylacetamide | 472.1 | 2.6 |
| 147 |  | (R/S)-3-(2-hydroxy-2-(4-(5-(1-phenyl-5-(trifluoromethyl)-1H-pyrazol-4-yl)-1,2,4-oxadiazol-3-yl)phenyl)acetamido)propanamide | 501.1 | 2.0 |

TABLE 2-continued

| Ex. | Q | Name | Observed[a] MS Ion (M + H)+ | RT[a] [min] |
|---|---|---|---|---|
| 148 | 4-(hydroxymethyl)benzyl | (R/S)-2-hydroxy-N-(4-(hydroxymethyl)benzyl)-2-(4-(5-(1-phenyl-5-(trifluoromethyl)-1H-pyrazol-4-yl)-1,2,4-oxadiazol-3-yl)phenyl)acetamide | 550.1 | 2.4 |
| 149 | 1-hydroxy-4-methylpentan-2-yl | (R/S)-2-hydroxy-N-(1-hydroxy-4-methylpentan-2-yl)-2-(4-(5-(1-phenyl-5-(trifluoromethyl)-1H-pyrazol-4-yl)-1,2,4-oxadiazol-3-yl)phenyl)acetamide | 530.2 | 2.6 |
| 150 | ((1R,2R)-2-hydroxycyclohexyl)methyl | (R/S)-2-hydroxy-N-(((1R,2R)-2-hydroxycyclohexyl)methyl)-2-(4-(5-(1-phenyl-5-(trifluoromethyl)-1H-pyrazol-4-yl)-1,2,4-oxadiazol-3-yl)phenyl)acetamide | 542.2 | 2.6 |
| 151 | (1R,2S)-2-(hydroxymethyl)cyclohexyl | (R/S)-2-hydroxy-N-((1R,2S)-2-(hydroxymethyl)cyclohexyl)-2-(4-(5-(1-phenyl-5-(trifluoromethyl)-1H-pyrazol-4-yl)-1,2,4-oxadiazol-3-yl)phenyl)acetamide | 542.2 | 2.6 |
| 152 | ((1S,2R)-2-hydroxycyclohexyl)methyl | (R/S)-2-hydroxy-N-(((1S,2R)-2-hydroxycyclohexyl)methyl)-2-(4-(5-(1-phenyl-5-(trifluoromethyl)-1H-pyrazol-4-yl)-1,2,4-oxadiazol-3-yl)phenyl)acetamide | 542.2 | 2.5 |
| 153 | (1R,2R)-2-(hydroxymethyl)cyclohexyl | (R/S)-2-hydroxy-N-((1R,2R)-2-(hydroxymethyl)cyclohexyl)-2-(4-(5-(1-phenyl-5-(trifluoromethyl)-1H-pyrazol-4-yl)-1,2,4-oxadiazol-3-yl)phenyl)acetamide | 542.1 | 2.5 |
| 154 | 4-hydroxybutyl | (R/S)-2-hydroxy-N-(4-hydroxybutyl)-2-(4-(5-(1-phenyl-5-(trifluoromethyl)-1H-pyrazol-4-yl)-1,2,4-oxadiazol-3-yl)phenyl)acetamide | 502.0 | 2.2 |
| 155 | 1-(hydroxymethyl)cyclopentyl | (R/S)-2-hydroxy-N-(1-(hydroxymethyl)cyclopentyl)-2-(4-(5-(1-phenyl-5-(trifluoromethyl)-1H-pyrazol-4-yl)-1,2,4-oxadiazol-3-yl)phenyl)acetamide | 528.1 | 2.5 |

TABLE 2-continued

[Structure shown with phenyl-pyrazole-CF3, 1,2,4-oxadiazole, phenyl, hydroxy-acetamide-Q framework]

| Ex. | Q | Name | Observed[a] MS Ion (M + H)+ | RT[a] [min] |
|---|---|---|---|---|
| 156 | [3-hydroxybenzyl] | (R/S)-2-hydroxy-N-(3-hydroxybenzyl)-2-(4-(5-(1-phenyl-5-(trifluoromethyl)-1H-pyrazol-4-yl)-1,2,4-oxadiazol-3-yl)phenyl)acetamide | 536.0 | 2.4 |
| 157 | [4-hydroxybenzyl] | (R/S)-2-hydroxy-N-(4-hydroxybenzyl)-2-(4-(5-(1-phenyl-5-(trifluoromethyl)-1H-pyrazol-4-yl)-1,2,4-oxadiazol-3-yl)phenyl)acetamide | 536.0 | 2.4 |
| 158 | [(1r,4r)-4-hydroxycyclohexyl] | (R/S)-2-hydroxy-N-((1r,4r)-4-hydroxycyclohexyl)-2-(4-(5-(1-phenyl-5-(trifluoromethyl)-1H-pyrazol-4-yl)-1,2,4-oxadiazol-3-yl)phenyl)acetamide | 528.1 | 2.2 |

[a]LCMS analyzed on a Waters Masslynx instrument equipped with a 4.6 × 50 mm 2.7 µM MacMod Halo C18 column and using a method of 0-100% B solvent over 4 min at a flow rate of 4 mL/min. Solvent A is 5:95 acetonitrile/water; solvent B is 95:5 acetonitrile/water and both contain 10 mM ammonium acetate.

Example 159

(R/S)-2-Hydroxy-N-(2-hydroxyethyl)-2-(4-(5-(3-phenyl-4-(trifluoromethyl)isoxazol-5-yl)-1,2,4-oxadiazol-3-yl)phenyl)propanamide

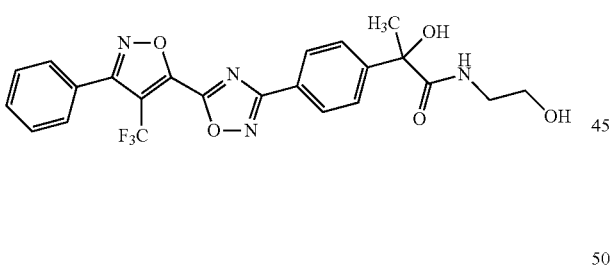

(159)

(R/S)-2-Hydroxy-2-(4-(5-(3-phenyl-4-(trifluoromethyl)isoxazol-5-yl)-1,2,4-oxadiazol-3-yl)phenyl)propanoic acid (Int-XV, 30 mg, 0.067 mmol), BOP (29.8 mg, 0.067 mmol), 4-methylmorpholine (27.3 mg, 0.269 mmol), and 2-aminoethanol (6.17 mg, 0.101 mmol) were added to DMF (1 mL). The reaction mixture was stirred for 1 h and then purified by prep HPLC (PHENOMENEX® 21×250 mm, gradient elution with Method 1—MeOH/water containing 0.1% trifluoroacetic acid as defined above, 0% B to 100% B over 30 min, 25 mL/min, 220 nM, product retention=30.0 min) to provide (R/S)-2-hydroxy-N-(2-hydroxyethyl)-2-(4-(5-(3-phenyl-4-(trifluoromethyl)isoxazol-5-yl)-1,2,4-oxadiazol-3-yl)phenyl)propanamide (6 mg, 9.83 µmol, 14.59% yield): LCMS=489.0 [M+H]+; $^1$H NMR (400 MHz, methanol-$d_4$) δ ppm 8.10-8.21 (2 H, m), 7.53-7.92 (7 H, m), 3.60 (2 H, td, J=5.61, 3.74 Hz), 3.33-3.43 (2 H, m), 1.80 (3 H, s); HPLC peak RT=9.0 min (Method A).

Example 160

(R/S)-N-(Cyanomethyl)-2-hydroxy-2-(4-(5-(3-phenyl-4-(trifluoromethyl)isoxazol-5-yl)-1,2,4-oxadiazol-3-yl)phenyl)propanamide

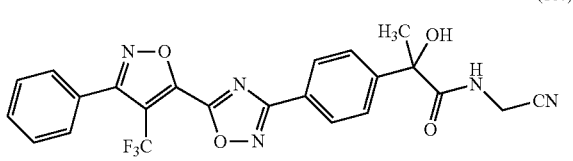

(160)

(R/S)-2-Hydroxy-2-(4-(5-(3-phenyl-4-(trifluoromethyl)isoxazol-5-yl)-1,2,4-oxadiazol-3-yl)phenyl)propanoic acid (Int-XV, (30 mg, 0.067 mmol), 4-methylmorpholine (27.3 mg, 0.269 mmol), and HATU (33.3 mg, 0.088 mmol) were added to DMF (1 mL). This was stirred for 1 h before it was purified by prep HPLC (PHENOMENEX® 21×250 mm, gradient elution with Method 1—MeOH/water containing 0.1% trifluoroacetic acid as defined above, 0% B to 100% B over 30 min, 25 mL/min, 220 nM, product retention=30.21 min) to provide (R/S)-N-(cyanomethyl)-2-hydroxy-2-(4-(5-(3-phenyl-4-(trifluoromethyl)isoxazol-5-yl)-1,2,4-oxadiazol-3-yl)phenyl)propanamide (7 mg, 0.014 mmol, 20.16% yield): LCMS=484.0 [M+H]+; $^1$H NMR (400 MHz, methanol-$d_4$) δ ppm 8.81 (1 H, t, J=5.83 Hz), 8.11-8.23 (2 H, m), 7.51-7.92 (7 H, m), 4.04-4.23 (2 H, m), 1.81 (3 H, s); HPLC peak RT=10.0 min (Method A).

Example 161

(R/S)-2-Hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)propanamide

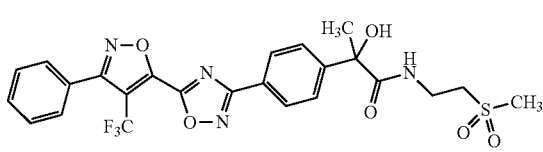

(161)

(R/S)-2-Hydroxy-2-(4-(5-(3-phenyl-4-(trifluoromethyl) isoxazol-5-yl)-1,2,4-oxadiazol-3-yl)phenyl)propanoic acid (Int-XV, 30 mg, 0.067 mmol), 4-methylmorpholine (27.3 mg, 0.269 mmol), and HATU (33.3 mg, 0.088 mmol) were added to DMF (1 mL). This was stirred for 1 h before it was purified by prep HPLC (PHENOMENEX® 21×250 mm, gradient elution with Method 1—MeOH/water containing 0.1% trifluoroacetic acid as defined above, 0% B to 100% B over 30 min, 25 mL/min, 220 nM, product retention=30.07 min) to provide (R/S)-2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)propanamide (6 mg, 7.74 μmol, 11.49% yield): LCMS=551.0 [M+H]$^+$; $^1$H NMR (400 MHz, methanol-d$_4$) δ ppm 8.11-8.27 (2 H, m), 7.49-7.81 (7 H, m), 5.16 (1 H, s), 3.22 (2 H, t, J=6.38 Hz), 3.04 (2 H, t, J=7.26 Hz), 2.82 (3 H, s), 1.46 (3 H, s); HPLC peak RT=9.5 min (Method A).

BIOLOGICAL ASSAYS

S1P$_1$ Binding Assay

Membranes were prepared from CHO cells expressing human S1P$_1$. Cells were dissociated in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 G) and the supernatant was discarded. The membrane pellets were resuspended in buffer containing 50 mM HEPES, pH 7.5, 100 mM NaCl, 1 mM MgCl$_2$, 2 mM EDTA and stored in aliquots at −80° C. after protein concentration determination. Membranes (2 μg/well) and 0.03 nM final concentration of $^{33}$P-S1P ligand (1 mCi/ml, American Radiolabeled Chemicals) were added to the compound plates. Binding was performed for 45 minutes at room temperature, terminated by collecting the membranes onto GF/B filter plates, and radioactivity was measured by TOP-COUNT®. The competition data of the test compounds over a range of concentrations was plotted as percentage inhibition of radioligand specific binding. The IC$_{50}$ is defined as the concentration of competing ligand needed to reduce specific binding by 50%.

Table A below lists S1P$_1$ Binding IC$_{50}$ values from the following examples of this invention measured in the S1P$_1$ binding assay described hereinabove. The results in Table A were rounded to two digits.

TABLE A

| Ex. | S1P$_1$ Binding IC$_{50}$ (nM) |
|---|---|
| 6 | 0.46 |
| 10 | 2.0 |
| 17 | 6.7 |
| 22 | 29 |
| 24 | 350 |
| 26 | 910 |
| 30 | 4.5 |
| 31 | 4.5 |
| 32 | 2.6 |
| 41 | 2.6 |
| 51 | 31 |
| 61 | 8.5 |
| 62 | 3.2 |
| 67 | 17 |
| 71 | 0.85 |
| 74 | 0.30 |
| 86 | 180 |
| 88 | 29 |
| 90 | 13 |
| 93 | 2.9 |
| 116 | 43 |
| 126 | 2.1 |
| 132 | 42 |
| 137 | 4.9 |
| 152 | 260 |

Receptor [35S] GTPγS Binding Assays

Compounds were loaded in a 384 FALCON® v-bottom plate (0.5 μl/well in a 3-fold dilution). Membranes prepared from S1P$_1$/CHO cells or EDG3-Ga15-bla HEK293T cells were added to the compound plate (40 μl/well, final protein 3 μg/well) with MULTIDROP®. [$^{35}$S]GTP (1250 Ci/mmol, Perkin Elmer) was diluted in assay buffer: 20 mM HEPES, pH7.5, 10 mM MgCl$_2$, 150 mM NaCl, 1 mM EGTA, 1 mM DTT, 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to a 384 well FB filter plates via GPCR robot system. The filter plate was washed with water 4 times by using the modified manifold Embla plate washer and dried at 60° C. for 45 min. 30 μl of MicroScint 20 scintillation fluid was added to each well for counting at Packard TOP-COUNT®. EC$_{50}$ is defined as the agonist concentration that corresponds to 50% of the Ymax (maximal response) obtained for each individual compound tested.

TABLE B

| Ex. | GTPγS S1P$_1$ EC$_{50}$ (nM) | GTPγS S1P$_3$ EC$_{50}$ (nM) |
|---|---|---|
| 6 | 0.67 | 3135 |
| 10 | 4.7 | 13140 |
| 17 | 6.7 | 6906 |
| 22 | 103.4 | 62500* |
| 24 | 1049 | 62500* |
| 26 | 4283 | 6202 |
| 30 | 50.9 | 31250** |
| 31 | 11.9 | 9539 |
| 32 | 1.5 | 16060 |
| 41 | 15.7 | 3641 |
| 51 | 89.4 | 13630 |
| 61 | 34.2 | 62500* |
| 62 | 12.6 | 9213 |
| 67 | 17.4 | 17500 |
| 71 | 2 | 10468 |
| 74 | 1.9 | 3430 |
| 86 | 1560 | 31250** |

TABLE B-continued

| Ex. | GTPγS S1P$_1$ EC$_{50}$ (nM) | GTPγS S1P$_3$ EC$_{50}$ (nM) |
|---|---|---|
| 88 | 102.5 | 5943 |
| 90 | 31.5 | 5379 |
| 93 | 5.8 | 11950 |
| 116 | 161.6 | 62500* |
| 126 | 13.6 | 20180 |
| 132 | 635.7 | 17100 |
| 137 | 41.4 | 11040 |
| 152 | 517.4 | 11227 |

*Detection limit was 62,500 nM in the GTPγS S1P$_3$ assay.
**Detection limit was 32,500 nM in the GTPγS S1P$_3$ assay.

A smaller value for GTPγS S1P$_1$ EC$_{50}$ value indicated greater activity for the compound in the GTPγS S1P$_1$ binding assay. A larger value for the GTPγS S1P$_3$ $_{EC50}$ value indicated less activity in the GTPγS S1P$_3$ binding assay.

The compounds of the present invention, as exemplified by examples in Table B showed GTPγS S1P$_1$ EC$_{50}$ values of less than 5 μM.

The ratios of the GTPγS S1P$_3$ EC$_{50}$ values to the GTPγS S1P$_1$ EC$_{50}$ values, calculated from the data in Table B, are shown in Table C.

TABLE C

| Ex. | GTPγS S1P$_3$/S1P$_1$ |
|---|---|
| 6 | 4679 |
| 10 | 2795 |
| 17 | 1031 |
| 22 | 604* |
| 24 | 60* |
| 26 | 1.4 |
| 30 | 614** |
| 31 | 802 |
| 32 | 10707 |
| 41 | 232 |
| 51 | 153 |
| 61 | 1827* |
| 62 | 731 |
| 67 | 1006 |
| 71 | 5234 |
| 74 | 1805 |
| 86 | 20** |
| 88 | 58 |
| 90 | 171 |
| 93 | 2060 |
| 116 | 387* |
| 126 | 1484 |
| 132 | 27 |
| 137 | 267 |
| 152 | 22 |

*Detection limit was 62,500 nM in the GTPγS S1P$_3$.
**Detection limit was 32,500 nM in the GTPγS S1P$_3$.

In Table C, a larger value for the ratio of the GTPγS S1P$_3$ EC$_{50}$ value to the GTPγS S1P$_1$ EC$_{50}$ value indicates greater selectivity of S1P$_1$ activity over S1P$_3$ activity.

The compounds of the present invention, as exemplified by examples in Table C, show the surprising advantage as agonists of S1P$_1$ and are selective over S1P$_3$.

The compounds of the present invention possess activity as agonists of S1P$_1$ and are selective over S1P$_3$, and thus may be used in treating, preventing, or curing various S1P$_1$ receptor-related conditions while reducing or minimizing the side effects due to S1P$_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, or psoriasis, while reducing or minimizing possible cardiovascular side effects such as bradycardia and hypertension. Other potential uses of the compounds of the present invention include minimizing or reducing rejection of transplanted organs, while reducing or minimizing side effects due to S1P$_3$ activity.

Blood Lymphocyte Reduction Assay (BLR) in Rodents

Lewis rats were dosed orally with test article (as a solution or suspension in the vehicle) or vehicle alone (polyethylene glycol 300, "PEG300"). Blood was drawn at 4 hr by retro-orbital bleeding. Blood lymphocyte counts were determined on an ADVIA® 120 Hematology Analyzer (Siemens Healthcare Diagnostics). The results were measured as a reduction in the percentage of circulating lymphocytes as compared to the vehicle treated group at the 4 hr measurement. The results represent the average results of all animals within each treatment group (n=3-4).

The following examples were tested in the Blood Lymphocyte Reduction assay (BLR) described hereinabove and the results are shown in Table D for rats.

TABLE D

| Ex. | Dose (mg/kg) | % Reduction in Lymphocytes at 4 hr. |
|---|---|---|
| 6 | 3 | 73 |
| 17 | 3 | 69 |
| 31 | 1 | 54 |
| 40 | 1 | 80 |
| 41 | 1 | 80 |
| 71 | 1 | 71 |
| 74 | 3 | 84 |
| 93 | 3 | 73 |

What is claimed is:
1. A compound of Formula (I):

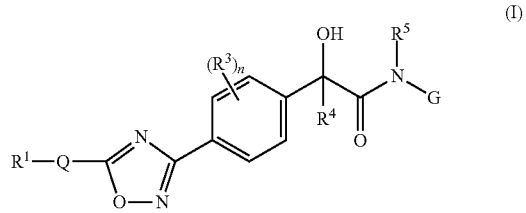

or a pharmaceutically acceptable salt thereof, wherein:
Q is

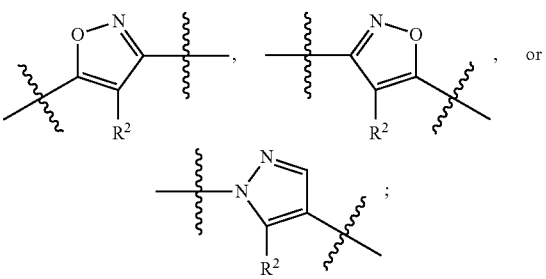

$R^1$ is:
(i) $C_{3-6}$alkyl;
(ii) $C_{3-7}$cycloalkyl substituted with zero to 3 substituents independently selected from halo, —CN, $C_{1-4}$alkyl, $C_{1-4}$alkoxy, $C_{1-3}$fluoroalkyl, $C_{1-3}$chloroalkyl, and/or $C_{1-2}$fluoroalkoxy;

(iii) phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy; or
(iv) pyridinyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

$R^2$ is $C_{1-6}$alkyl, $C_{1-3}$fluoroalkyl, $C_{3-7}$cycloalkyl, or phenyl substituted with zero to 3 substituents independently selected from halo, —CN, $C_{1-4}$alkyl, $C_{3-6}$cycloalkyl, $C_{1-4}$alkoxy, $C_{1-3}$fluoroalkyl, $C_{1-3}$chloroalkyl, and/or $C_{1-2}$fluoroalkoxy;

n is zero, 1, or 2;

each $R^3$ is independently $C_{1-3}$alkyl, F, Cl, $C_{1-3}$fluoroalkyl, $C_{1-3}$chloroalkyl, —CN, $C_{1-3}$alkoxy, and/or $C_{1-3}$fluoroalkoxy;

$R^4$ is H or —$CH_3$;

$R^5$ is H or —$CH_3$; and

G is:
(i) H, $C_{1-6}$alkyl, or $C_{3-6}$cycloalkyl;
(ii) $C_{1-6}$alkyl substituted with —$NH_2$, $C_{1-6}$alkoxy, —C(O)OH, —C(O)O($C_{1-6}$alkyl), or —S(O)$_2$$C_{1-6}$alkyl;
(iii) $C_{1-6}$alkyl substituted with one or more substituents selected from —OH, —CN, and/or cyclopropyl;
(iv) —(CH$_2$)$_{0-3}$—$R^a$, wherein $R^a$ is $C_{3-6}$cycloalkyl substituted with zero to 2 substituents independently selected from —OH, —CN, and/or —$CH_2OH$;
(v) —(CH$_2$)$_{0-3}$—$R^b$, wherein $R^b$ is phenyl substituted with zero to 2 substituents independently selected from —OH, $C_{1-3}$hydroxyalkyl, and/or —S(O)$_2$NH$_2$;
(vi) —(CH$_2$)$_{1-3}$C(O)NR$^c$R$^d$, wherein $R^c$ is H or —$CH_3$; and $R^d$ is H, $C_{1-6}$alkyl, $C_{3-6}$cycloalkyl, $C_{1-6}$hydroxyalkyl, —(CH$_2$)$_{0-2}$(heteroaryl), or —(CH$_2$)$_{0-2}$(heterocyclyl);
(vii) —CH(CN)R$^e$, wherein $R^e$ is phenyl, benzyl, —C(O)NH$_2$, or —C(O)NH($C_{1-3}$alkyl);
(viii) —CHR$^f$C(O)NH(CH$_3$), wherein $R^f$ is $C_{1-6}$alkyl, —CN, phenyl, benzyl, or —CH$_2$CH$_2$-phenyl;
(ix) —(CH$_2$)$_{1-3}$NHC(O)R$^g$, wherein $R^g$ is $C_{1-6}$alkyl or —O($C_{1-6}$alkyl);
(x) —CHR$^h$—(CH$_2$)$_{0-3}$—$R^i$, wherein $R^h$ is H or —$CH_3$, and $R^i$ is heteroaryl;
(xi) —(CH$_2$)$_{0-3}$—$R^j$, wherein $R^j$ is heterocyclyl; or
(xii) —(CH$_2$)$_{1-3}$C(O)—$R^k$, wherein $R^k$ is

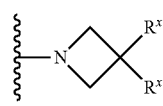

and each $R^x$ is independently selected from H, F, —OH, —$CH_3$, —$OCH_3$, and/or —C(O)OCH$_3$;

wherein each of said heteroaryl groups is substituted with zero to three substituents independently selected from $C_{1-3}$alkyl, —OH, —NH$_2$, phenyl, methylphenyl, benzyl, —CH$_2$CH$_2$-phenyl, pyridinyl, —C(O)OC$_{1-3}$alkyl, and/or —CH$_2$OCH$_3$; and wherein each of said heterocyclyl groups is substituted with zero to three substituents independently selected from $C_{1-3}$alkyl, —OH, —NH$_2$, phenyl, methylphenyl, benzyl, —CH$_2$CH$_2$-phenyl, pyridinyl, —C(O)OC$_{1-3}$alkyl, =O, and/or —CH$_2$OCH$_3$.

2. The compound according to claim 1 of Formula (II):

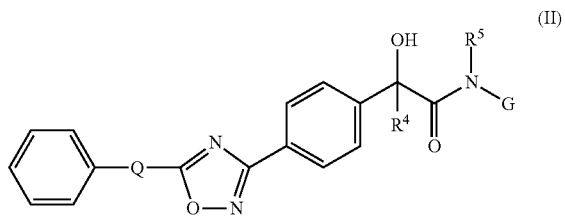

or a pharmaceutically acceptable salt thereof, wherein:

$R^2$ is —$CF_3$;

$R^4$ is H or —$CH_3$;

$R^5$ is H or —$CH_3$; and

G is:
(i) H, $C_{1-3}$alkyl, or cyclobutyl;
(ii) $C_{1-2}$alkyl substituted with —$NH_2$, —$OCH_3$, —C(O)OH, —C(O)O($C_{1-4}$alkyl), or —S(O)$_2$CH$_3$;
(iii) $C_{2-6}$hydroxyalkyl or $C_{1-4}$cyanoalkyl;
(iv) —(CH$_2$)$_{0-2}$—$R^a$, wherein $R^a$ is $C_{3-6}$cycloalkyl substituted with zero or one substituent selected from —OH, —CN, and —$CH_2OH$;
(v) —(CH$_2$)$_{0-2}$—$R^b$, wherein $R^b$ is phenyl substituted with zero or one substituent selected from —OH, $C_{1-2}$hydroxyalkyl, and —S(O)$_2$NH$_2$;
(vi) —(CH$_2$)$_{1-2}$C(O)NR$^c$R$^d$, wherein $R^c$ is H or —$CH_3$; and $R^d$ is H, $C_{1-4}$alkyl, cyclopropyl, —CH$_2$C(CH$_3$)$_2$(OH), —CH$_2$(imidazolyl), N-methylazetidinyl, or

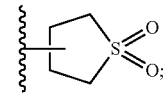

(vii) —CH(CN)R$^e$, wherein $R^e$ is phenyl, benzyl, —C(O)NH$_2$, —C(O)NH(CH$_3$), or —C(O)NH(isopropyl);
(viii) —CHR$^f$C(O)NH(CH$_3$), wherein $R^f$ is —$CH_3$, t-butyl, —CN, or —CH$_2$CH$_2$-phenyl;
(ix) —CH$_2$CH$_2$NHC(O)R$^g$, wherein $R^g$ is —$CH_3$ or —O(t-butyl);
(x) —CHR$^h$—(CH$_2$)$_{0-2}$—$R^i$, wherein $R^h$ is H or —$CH_3$, and $R^i$ is pyrrolyl, thiophenyl, pyrazolyl, imidazolyl, isoxazolyl, oxazolyl, thiazolyl, triazolyl, oxadiazolyl, tetrazolyl, pyridinyl, pyrimidinyl, pyrazinyl, indolyl, or benzimidazolyl, each substituted with zero to three substituents independently selected from $C_{1-3}$alkyl, —NH$_2$, phenyl, methylphenyl, benzyl, —CH$_2$CH$_2$-phenyl, pyridinyl, —C(O)OCH$_2$CH$_3$, and/or —CH$_2$OCH$_3$;
(xi) —(CH$_2$)$_{0-3}$—$R^j$, wherein $R^j$ is azetidinyl, pyrrolidinyl, N-methyl pyrrolidinyl, tetrahydrofuranyl, tetrahydropyranyl, imidazolidinonyl, or

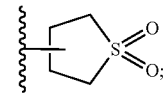

or (xii) —CH₂CH₂C(O)—Rᵏ, wherein Rᵏ is

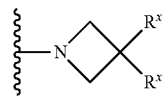

and each Rˣ is independently selected from H, F, —OH, —CH₃, —OCH₃, and/or —C(O)OCH₃.

3. The compound according to claim 2 having Formula (IIIa):

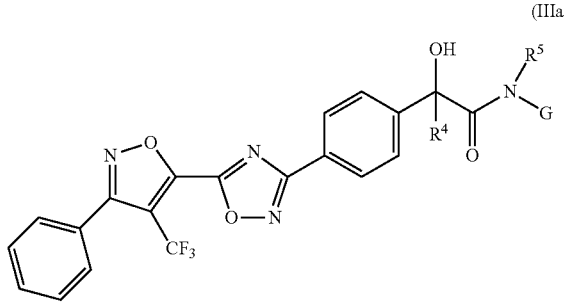

(IIIa)

or a pharmaceutically acceptable salt thereof, wherein:
G is:
(i) H, C₁₋₂alkyl, or cyclobutyl;
(ii) C₁₋₂alkyl substituted with —NH₂, —OCH₃, —C(O)OH, or —S(O)₂CH₃;
(iii) C₂₋₅ hydroxyalkyl or C₁₋₄cyanoalkyl;
(iv) cyclopropyl substituted with —CN;
(v) —(CH₂)₁₋₂C(O)NRᶜRᵈ, wherein Rᶜ is H or —CH₃, and Rᵈ is H, C₁₋₄alkyl, cyclopropyl, —CH₂C(CH₃)₂(OH), —CH₂(imidazolyl), N-methylazetidinyl, or

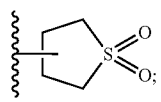

(vi) —CH(CN)Rᵉ, wherein Rᵉ is phenyl, benzyl, or —C(O)NH₂;
(vii) —CHRᶠC(O)NH(CH₃), wherein Rᶠ is —CH₃, t-butyl, —CN, or —CH₂CH₂-phenyl;
(viii) —CH₂CH₂NHC(O)Rᵍ, wherein Rᵍ is —CH₃ or —O(t-butyl);
(ix) —CHRʰ—(CH₂)₀₋₂—Rⁱ, wherein Rʰ is H or —CH₃, and Rⁱ is pyrrolyl, thiophenyl, pyrazolyl, imidazolyl, isoxazolyl, oxazolyl, thiazolyl, triazolyl, oxadiazolyl, tetrazolyl, pyridinyl, pyrimidinyl, pyrazinyl, indolyl, or benzimidazolyl, each substituted with zero to three substituents independently selected from C₁₋₃alkyl, —NH₂, phenyl, methylphenyl, benzyl, —CH₂CH₂-phenyl, pyridinyl, —C(O)OCH₂CH₃, and/or —CH₂OCH₃;
(x) —(CH₂)₀₋₃—Rʲ, wherein Rʲ is azetidinyl, pyrrolidinyl, tetrahydrofuranyl, tetrahydropyranyl, imidazolidinonyl, or

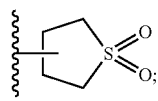

or
(xi) —CH₂CH₂C(O)—Rᵏ, wherein Rᵏ is

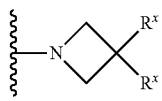

and each Rˣ is independently H, F, —OH, —CH₃, —OCH₃, and/or —C(O)OCH₃.

4. The compound according to claim 2 having Formula (IVa):

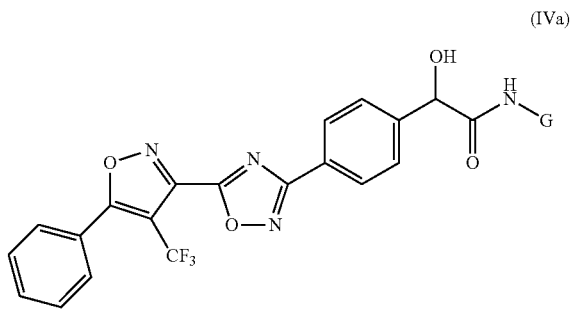

(IVa)

or a pharmaceutically acceptable salt thereof, wherein:
G is:
(i) ethyl;
(ii) C₂₋₄hydroxyalkyl;
(iii) —CH₂C(O)NHRᵈ, wherein Rᵈ is —CH₃ or —CH₂CH₃; or
(iv) —CH₂(CH₂)₀₋₂—Rⁱ, wherein Rⁱ is imidazolyl or pyridinyl.

5. The compound according to claim 2 having Formula (Va):

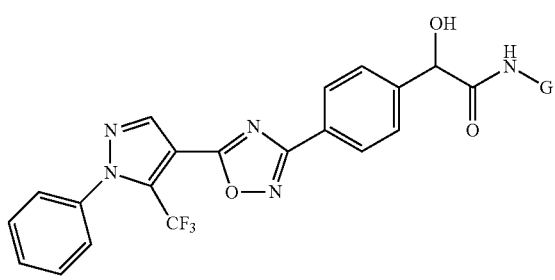

(Va)

or a pharmaceutically acceptable salt thereof, wherein:
G is:
(i) C₁₋₃alkyl;
(ii) methyl substituted with —C(O)OH or —C(O)O(C₁₋₄alkyl);
(iii) C₂₋₆hydroxyalkyl;
(iv) —(CH₂)₀₋₂—Rᵃ, wherein Rᵃ is C₃₋₆cycloalkyl substituted with zero or one substituent selected from —OH and —CH₂OH;

(v) —(CH$_2$)$_{0-2}$—R$^b$, wherein R$^b$ is phenyl substituted with zero or one substituent selected from —OH, C$_{1-2}$hydroxyalkyl, and —S(O)$_2$NH$_2$;
(vi) —CH$_2$CH$_2$C(O)NH$_2$;
(viii) —CH$_2$-(pyridinyl); or
(vii) —(CH$_2$)$_2$—R$^j$, wherein R is pyrrolidinyl or N-methyl pyrrolidinyl.

6. The compound according to claim 1 or a pharmaceutically acceptable salt thereof, wherein said compound is selected from: 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (1); N-(2-amino-2-oxoethyl)-2-hydroxy-2-(4-(5-(3-phenyl-4-(trifluoromethyl)isoxazol-5-yl)-1,2,4-oxadiazol-3-yl)phenyl)acetamide (2); 2-hydroxy-N-(2-hydroxyethyl)-2-(4-(5-(3-phenyl-4-(trifluoromethyl)isoxazol-5-yl)-1,2,4-oxadiazol-3-yl)phenyl)acetamide (3); 3-(2-hydroxy-2-(4-(5-(3-phenyl-4-(trifluoromethyl)isoxazol-5-yl)-1,2,4-oxadiazol-3-yl)phenyl)acetamido)propanoic acid (4); N-(cyanomethyl)-2-hydroxy-2-(4-(5-(3-phenyl-4-(trifluoromethyl)isoxazol-5-yl)-1,2,4-oxadiazol-3-yl)phenyl)acetamide (5); 3-(2-hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (6); 2-hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide (7); 2-hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide (8); N-((4H-1,2,4-triazol-3-yl)methyl)-2-hydroxy-2-(4-(5-(3-phenyl-4-(trifluoromethyl)isoxazol-5-yl)-1,2,4-oxadiazol-3-yl)phenyl)acetamide (9); 2-hydroxy-N-((5-methyl-1,3,4-oxadiazol-2-yl)methyl)-2-4-5-(3-phenyl-4-(trifluoromethyl)isoxazol-5-yl)-1,2,4-oxadiazol-3-yl)phenyl)acetamide (10); 2-hydroxy-2-(4-(5-(3-phenyl-4-(trifluoromethyl)isoxazol-5-yl)-1,2,4-oxadiazol-3-yl)phenyl)acetamide (11); N-(2-(ethylamino)-2-oxoethyl)-2-hydroxy-2-(4-(5-(3-phenyl-4-(trifluoromethyl)isoxazol-5-yl)-1,2,4-oxadiazol-3-yl)phenyl)acetamide (12); N-ethyl-2-hydroxy-2-(4-(5-(3-phenyl-4-(trifluoromethyl)isoxazol-5-yl)-1,2,4-oxadiazol-3-yl)phenyl)acetamide (13); N-(cyanomethyl)-2-hydroxy-2-(4-(5-(3-phenyl-4-(trifluoromethyl)isoxazol-5-yl)-1,2,4-oxadiazol-3-yl)phenyl)acetamide (14); N-(3-(1H-imidazol-1-yl)propyl)-2-hydroxy-2-(4-(5-(3-phenyl-4-(trifluoromethyl)isoxazol-5-yl)-1,2,4-oxadiazol-3-yl)phenyl)acetamide-TFA (15); 2-hydroxy-N-methyl-2-(4-(5-(3-phenyl-4-(trifluoromethyl)isoxazol-5-yl)-1,2,4-oxadiazol-3-yl)phenyl)acetamide (16); N-((1H-imidazol-2-yl)methyl)-2-hydroxy-2-4-5-(3-phenyl-4-(trifluoromethyl)isoxazol-5-yl)-1,2,4-oxadiazol-3-yl)phenyl)acetamide-TFA (17); 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (18); 2-hydroxy-N-((1-methyl-1H-imidazol-4-yl)methyl)-2-(4-5-(3-phenyl-4-(trifluoromethyl)isoxazol-5-yl)-1,2,4-oxadiazol-3-yl)phenyl)acetamide-TFA (19); 2-hydroxy-N-((1-methyl-1H-imidazol-5-yl)methyl)-2-(4-(5-(3-phenyl-4-(trifluoromethyl)isoxazol-5-yl)-1,2,4-oxadiazol-3-yl)phenyl)acetamide-TFA (20); 2-hydroxy-N-(3-hydroxy-3-methylbutyl)-2-(4-(5-(3-phenyl-4-(trifluoromethyl)isoxazol-5-yl)-1,2,4-oxadiazol-3-yl)phenyl)acetamide (21); 3-(2-hydroxy-2-(4-(5-(3-phenyl-4-(trifluoromethyl)isoxazol-5-yl)-1,2,4-oxadiazol-3-yl)phenyl)acetamido)propanoic acid (22); 2-hydroxy-2-(4-(5-(3-phenyl-4-(trifluoromethyl)isoxazol-5-yl)-1,2,4-oxadiazol-3-yl)phenyl)-N-(3-(pyrrolidin-l-yl)propyl)acetamide (23); N-ethyl-2-hydroxy-N-methyl-2-(4-(5-(3-phenyl-4-(trifluoromethyl)isoxazol-5-yl)-1,2,4-oxadiazol-3-yl)phenyl)acetamide (24); (2S)-2-(2-hydroxy-2-(4-(5-(3-phenyl-4-(trifluoromethyl)isoxazol-5-yl)-1,2,4-oxadiazol-3-yl)phenyl)acetamido)-N,3,3-trimethylbutanamide (25); (2S)-2-(2-hydroxy-2-(4-(5-(3-phenyl-4-(trifluoromethyl)isoxazol-5-yl)-1,2,4-oxadiazol-3-yl)phenyl)acetamido)-N-methyl-4-phenylbutanamide (26); 2-hydroxy-2-(4-(5-(3-phenyl-4-(trifluoromethyl)isoxazol-5-yl)-1,2,4-oxadiazol-3-yl)phenyl)-N-((S)-tetrahydrofuran-3-yl)acetamide (27); 2-hydroxy-2-(4-(5-(3-phenyl-4-(trifluoromethyl)isoxazol-5-yl)-1,2,4-oxadiazol-3-yl)phenyl)-N-(tetrahydro-2H-pyran-4-yl)acetamide (28); 2-hydroxy-2-(4-(5-(3-phenyl-4-(trifluoromethyl)isoxazol-5-yl)-1,2,4-oxadiazol-3-yl)phenyl)-N-((R)-tetrahydrofuran-3-yl)acetamide (29); N-(azetidin-3-yl)-2-hydroxy-2-(4-(5-(3-phenyl-4-(trifluoromethyl)isoxazol-5-yl)-1,2,4-oxadiazol-3-yl)phenyl)acetamide-TFA (30); 2-hydroxy-2-(4-(5-(3-phenyl-4-(trifluoromethypisoxazol-5-yl)-1,2,4-oxadiazol-3-yl)phenyl)-N-(3,3-dioxide-tetrahydrothiophen-3-yl)acetamide (31); 2-(2-hydroxy-2-(4-(5-(3-phenyl-4-(trifluoromethyl)isoxazol-5-yl)-1,2,4-oxadiazol-3-yl)phenyl)acetamido)-N-methylpropanamide (32); 2-hydroxy-N-(2-(1-methylazetidin-3-ylamino)-2-oxoethyl)-2-(4-(5-(3-phenyl-4-(trifluoromethyl)isoxazol-5-yl)-1,2,4-oxadiazol-3-yl)phenypacetamide (33); 2-hydroxy-2-(4-(5-(3-phenyl-4-(trifluoromethypisoxazol-5-yl)-1,2,4-oxadiazol-3-yl)phenyl)-N-(pyridin-2-ylmethyl)acetamide (34); 2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)acetamide (35); 2-hydroxy-N-(2-oxo-2-(1,1-dioxide-tetrahydrothiophen-3-ylamino)ethyl)-2-(4-(5-(3-phenyl-4-(trifluoromethyl)isoxazol-5-yl)-1,2,4-oxadiazol-3-yl)phenypacetamide (36); 2-hydroxyl-2-(4-(5-(3-phenyl-4-(trifluoromethyl)isoxazol-5-yl)-1,2,4-oxadiazol-3-yl)phenyl)-N-(2-(thiazol-4-yl)ethyl)acetamide (37); 2-hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (38); N-((R)-1-cyanoethyl)-2-hydroxy-2-(4-(5-(3-phenyl-4-(trifluoromethyl)isoxazol-5-yl)-1,2,4-oxadiazol-3-yl)phenyl)acetamide (39); N-((S)-1-cyanoethyl)-2-hydroxy-2-(4-(5-(3-phenyl-4-(trifluoromethyl)isoxazol-5-yl)-1,2,4-oxadiazol-3-yl)phenyl)acetamide (40); N-(1-cyanocyclopropyl)-2-hydroxy-2-(4-(5-(3-phenyl-4-(trifluoromethyl)isoxazol-5-yl)-1,2,4-oxadiazol-3-yl)phenyl)acetamide (41); N-(1,3-dihydroxypropan-2-yl)-2-hydroxy-2-(4-(5-(3-phenyl-4-(trifluoromethyl)isoxazol-5-yl)-1,2,4-oxadiazol-3-yl)phenyl)acetamide (42); N-(2-cyanopropan-2-yl)-2-hydroxy-2-(4-(5-(3-phenyl-4-(trifluoromethyl)isoxazol-5-yl)-1,2,4-oxadiazol-3-yl)phenyl)acetamide (43); N-((S)-1-cyano-2-methylpropyl)-2-hydroxy-2-(4-(5-(3-phenyl-4-(trifluoromethyl)isoxazol-5-yl)-1,2,4-oxadiazol-3-yl)phenyl)acetamide (44); N-((R)-1-cyano-2-methylpropyl)-2-hydroxy-2-(4-(5-(3-phenyl-4-(trifluoromethyl)isoxazol-5-yl)-1,2,4-oxadiazol-3-yl)phenyl)acetamide (45); N-((S)-1-cyanoethyl)-2-hydroxy-2-(4-(5-(3-phenyl-4-(trifluoromethyl)isoxazol-5-yl)-1,2,4-oxadiazol-3-yl)phenyl)acetamide (46); 2-hydroxy-N-((S)-2-hydroxypropyl)-2-(4-(5-(3-phenyl-4-(trifluoromethyl)isoxazol-5-yl)-1,2,4-oxadiazol-3-yl)phenyl)acetamide (47); N-(2,3-dihydroxypropyl)-2-hydroxy-2-(4-(5-(3-phenyl-4-(trifluoromethyl)isoxazol-5-yl)-1,2,4-oxadiazol-3-yl)phenyl)acetamide (48); 2-hydroxy-N-(3-hydroxypropyl)-2-(4-(5-(3-phenyl-4-(trifluoromethyl)isoxazol-5-yl)-1,2,4-oxadiazol-3-yl)phenyl)acetamide (49); 2-hydroxy-N-(2-methoxyethyl)-2-(4-(5-(3-phenyl-4-(trifluoromethyl)isoxazol-5-yl)-1,2,4-oxadiazol-3-yl)phenyl)acetamide (50); tert-butyl 2-(2-hydroxy-2-(4-(5-(3-phenyl-4-(trifluoromethyl)isoxazol-5-yl)-1,2,4-oxadiazol-3-yl)phenyl)acetamido)ethylcarbamate (51); N-(2-aminoethyl)-2-hydroxy-2-(4-(5-(3-phenyl-4-(trifluoromethyl)isoxazol-5-yl)-1,2,4-oxadiazol-3-yl)phenyl)acetamide, TFA (52); N-(2-acetamidoethyl)-2-hydroxy-2-(4-(5-(3-phenyl-4-(trifluoromethyl)isoxazol-5-yl)-1,2,4-oxadiazol-3-yl)phenyl)acetamide (59); 2-hydroxy-N-(2-hydroxyethyl)-2-(4-(5-(3-phenyl-4-(trifluoromethyl)isoxazol-5-yl)-1,2,4-oxadiazol-3-yl)phenyl)acetamide (71); 2-hydroxy-N-(2-(methylamino)-2-oxoethyl)-2-(4-(5-(3-phenyl-4-(trifluoromethyl)isoxazol-5-yl)-1,2,4-oxadiazol-3-yl)phenyl)acetamide (72); N-((2-aminothiazol-4-yl)methyl)-2-hydroxy-2-(4-(5-(3-phenyl-4-(trifluoromethyl)isoxazol-5-yl)-1,2,4-oxadiazol-3-yl)phenypacetamide-TFA (73); 3-(2-hydroxy-2-(4-(5-(3-phenyl-4-(trifluoromethyl)isoxazol-5-yl)-1,2,4-oxadiazol-3-yl)phenyl)acetamido)-N,N-dimethylpropanamide (74); 3-(2-hydroxy-2-4-5-(3-phenyl-4-(trifluoromethyl)isoxazol-5-yl)-1,2,4-oxadiazol-3-yl)phenyl)acetamido)-N-methylpropanamide (75); N-ethyl-3-(2-hydroxy-2-(4-(5-(3-phenyl-4-(trifluoromethyl)isoxazol-5-yl)-1,2,4-oxadiazol-3-yl)phenyl)acetamido)propanamide (76); 3-(2-hydroxy-2-(4-(5-(3-phenyl-4-(trifluoromethyl)isoxazol-5-yl)-1,2,4-oxadiazol-3-yl)phenyl)acetamido)-N,N-dimethylpropanamide (77); N-tert-butyl-3-(2-hydroxy-2-(4-(5-(3-phenyl-4-(trifluoromethyl)isoxazol-5-yl)-1,2,4-oxadiazol-3-yl)phenyl)acetamido)propanamide (78); N-cyclopropyl-3-(2-hydroxy-2-(4-(5-(3-phenyl-4-(trifluoromethyl)isoxazol-5-yl)-1,2,4-oxadiazol-3-yl)phenyl)acetamido)propanamide (79); 3-(2-hydroxy-2-(4-(5-(3-phenyl-4-(trifluoromethyl)isoxazol-5-yl)-1,2,4-oxadiazol-3-yl)phenyl)acetamido)-N-(2-hydroxy-2-methylpropyl)propanamide (80); N-((1H-imidazol-2-yl)methyl)-3-(2-hydroxy-2-(4-(5-(3-phenyl-4-(trifluoromethyl)isoxazol-5-yl)-1,2,4-oxadiazol-3-yl)phenyl)acetamido)propanamide, TFA (81); 2-hydroxy-2-(4-(5-(3-phenyl-4-(trifluoromethyl)isoxazol-5-yl)-1,2,4-oxadiazol-3-yl)phenyl)-N-(thiophen-3-ylmethyl)acetamide (82); N-((4-amino-2-methylpyrimidin-5-yl)methyl)-2-hydroxyl-2-(4-(5-(3-phenyl-4-(trifluoromethyl)isoxazol-5-yl)-1,2,4-oxadiazol-3-yl)phenyl)acetamide (83); 2-hydroxy-2-(4-(5-(3-phenyl-4-(trifluoromethyl)isoxazol-5-yl)-1,2,4-oxadiazol-3-yl)phenyl)-N-((1,3,5-trimethyl-1H-pyrazol-4-yl)methyl)acetamide (84); 2-hydroxy-N-(2-(2-oxoimidazolidin-1-yl)ethyl)-2-(4-(5-(3-phenyl-4-(trifluoromethyl)isoxazol-5-yl)-1,2,4-oxadiazol-3-yl)phenyl)acetamide (85); N-((1H-indol-2-yl)methyl)-2-hydroxy-2-(4-(5-(3-phenyl-4-(trifluoromethyl)isoxazol-5-yl)-1,2,4-oxadiazol-3-yl)phenyl)acetamide (86); N-((1H-tetrazol-5-yl)methyl)-2-hydroxy-2-(4-(5-(3-phenyl-4-(trifluoromethyl)isoxazol-5-yl)-1,2,4-oxadiazol-3-yl)phenypacetamide (87); 2-hydroxy-2-(4-(5-(3-phenyl-4-(trifluoromethypisoxazol-5-yl)-1,2,4-oxadiazol-3-yl)phenyl)-N-(pyrrolidin-2-ylmethyl)acetamide, TFA (88); N-(2-(1H-imidazol-4-yl)ethyl)-2-hydroxy-2-(4-(5-(3-phenyl-4-(trifluoromethyl)isoxazol-5-yl)-1,2,4-oxadiazol-3-yl)phenyl)acetamide, TFA (89); N-((1H-benzo[d]imidazol-2-yl)methyl)-2-hydroxy-2-(4-(5-(3-phenyl-4-(trifluoromethypisoxazol-5-yl)-1,2,4-oxadiazol-3-yl)phenyl)acetamide (90); N-(3-(3,3-difluoroazetidin-1-yl)-3-oxopropyl)-2-hydroxy-2-(4-(5-(3-phenyl-4-(trifluoromethyl)isoxazol-5-yl)-1,2,4-oxadiazol-3-yl)phenyl)acetamide (91); 2-hydroxy-N-(3-(3-hydroxy-3-methylazetidin-1-yl)-3-oxopropyl)-2-(4-(5-(3-phenyl-4-(trifluoromethyl)isoxazol-5-yl)-1,2,4-oxadiazol-3-yl)phenyl)acetamide (92); 2-hydroxy-N-(3-(3-hydroxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (93); N-((4-amino-2-methylpyrimidin-5-yl)methyl)-2-hydroxy-2-(4-(5-(3-phenyl-4-(trifluoromethyl)isoxazol-5-yl)-1,2,4-oxadiazol-3-yl)phenyl)acetamide (94); 2-hydroxy-2-(4-(5-(3-phenyl-4-(trifluoromethypisoxazol-5-yl)-1,2,4-oxadiazol-3-yl)phenyl)-N-(2-(thiazol-4-yl)ethyl)acetamide (95); 2-hydroxy-N-(3-(3-methoxyazetidin-1-yl)-3-oxopropyl)-2-(4-(5-(3-phenyl-4-(trifluoromethyl)isoxazol-5-yl)-1,2,4-oxadiazol-3-yl)phenyl)acetamide (96); methyl 1-(3-(2-hydroxy-2-(4-(5-(3-phenyl-4-(trifluoromethyl)isoxazol-5-yl)-1,2,4-oxadiazol-3-yl)phenyl)acetamido)propanoyl)azetidine-3-carboxylate (97); 2-hydroxy-2-(4-(5-(3-phenyl-4-(trifluoromethyl)isoxazol-5-yl)-1,2,4-oxadiazol-3-yl)phenyl)-N-(thiazol-2-ylmethyl)acetamide (98); 2-hydroxy-N-(oxazol-2-ylmethyl)-2-(4-(5-(3-phenyl-4-(trifluoromethyl)isoxazol-5-yl)-1,2,4-oxadiazol-3-yl)phenyl)acetamide (99); 2-hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (100); 2-hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (101); 2-hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide (102); 2-hydroxy-N-((3(methoxymethyl)-1,2,4-oxadiazol-5-yl)methyl)-2-(4-(5-(3-phenyl-4-(trifluoromethyl)isoxazol-5-yl)-1,2,4-oxadiazol-3-yl)phenyl)acetamide (103); 2-cyano-2-(2-hydroxy-2-(4-(5-(3-phenyl-4-(trifluoromethyl)isoxazol-5-yl)-1,2,4-oxadiazol-3-yl)phenyl)acetamido)-N-methylacetamide (104); N-(1-cyano-2-phenylethyl)-2-hydroxy-2-(4-(5-(3-phenyl-4-(trifluoromethyl)isoxazol-5-yl)-1,2,4-oxadiazol-3-yl)phenyl)acetamide (105); N-(cyano(phenyl)methyl)-2-hydroxy-2-(4-(5-(3-phenyl-4-(trifluoromethyl)isoxazol-5-yl)-1,2,4-oxadiazol-3-yl)phenyl)acetamide (106); N-(2-amino-1-cyano-2-oxoethyl)-2-hydroxy-2-(4-(5-(3-phenyl-4-(trifluoromethyl)isoxazol-5-yl)-1,2,4-oxadiazol-3-yl)phenyl)acetamide (107); 2-hydroxy-N-(1-(4-methyl-4H-1,2,4-triazol-3-yl)ethyl)-2-(4-(5-(3-phenyl-4-(trifluoromethyl)isoxazol-5-yl)-1,2,4-oxadiazol-3-yl)phenyl)acetamide (108); N-((1,3-dimethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide-TFA (109); 2-hydroxy-N-((5-phenyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (110); N-((S)-1-(1H-imidazol-2-yl)ethyl)-2-hydroxy-2-(4-(5-(3-phenyl-4-(trifluoromethyl)isoxazol-5-yl)-1,2,4-oxadiazol-3-yl)phenyl)acetamide, TFA (111); 2-hydroxy-N-((5-methylisoxazol-3-yl)methyl)-2-(4-(5-(3-phenyl-4-(trifluoromethyl)isoxazol-5-yl)-1,2,4-oxadiazol-3-yl)phenyl)acetamide (112); 2-hydroxy-N-((4-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (113); 2-hydroxy-N-((1-methyl-1H-imidazol-2-yl)methyl)-2-(4-(5-(3-phenyl-4-(trifluoromethyl)isoxazol-5-yl)-1,2,4-oxadiazol-3-yl)phenyl)acetamide, TFA (114); 2-hydroxy-2-(4-(5-(3-phenyl-4-(trifluoromethyl)isoxazol-5-yl)-1,2,4-oxadiazol-3-yl)phenyl)-N-(2-(pyrazin-2-yl)ethyl)acetamide, TFA (115); N-cyclobutyl-2-hydroxy-2-(4-(5-(3-phenyl-4-(trifluoromethyl)isoxazol-5-yl)-1,2,4-oxadiazol-3-yl)phenyl)acetamide (116); 2-hydroxy-N-(2-(methylsulfonypethyl)-2-4-5-(3-phenyl-4-(trifluoromethyl)isoxazol-5-yl)-1,2,4-oxadiazol-3-yl)phenyl)acetamide (117); 2-hydroxy-N-((5-methyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (118); ethyl 5-((2-hydroxy-2-(4-(5-(3-phenyl-4-(trifluoromethyl)isoxazol-5-yl)-1,2,4-oxadiazol-3-yl)phenyl)acetamido)methyl)-1H-1,2,4-triazole-3-carboxylate (119); 2-hydroxy-N-((3-isopropylisoxazol-5-yl)methyl)-2-(4-(5-(3-phenyl-4-(trifluoromethyl)isoxazol-5-yl)-1,2,4-oxadiazol-3-yl)phenyl)acetamide (120); N-((1-ethyl-1H-pyrazol-5-yl)methyl)-2-hydroxy-2-(4-(5-(3-phenyl-4-(trifluoromethyl)isoxazol-5-yl)-1,2,4-oxadiazol-3-yl)phenyl)acetamide (121); 2-hydroxy-2-(4-(5-(3-phenyl-4-(trifluoromethyl)isoxazol-5-yl)-1,2,4-oxadiazol-3-yl)phenyl)-N-((1-p-tolyl-1H-pyrazol-4-yl)methyl)acetamide (122); N-((1-benzyl-1H-imidazol-2-yl)methyl)-2-hydroxyl-2-(4-(5-(3-phenyl-4-(trifluoromethyl)isoxazol-5-yl)-1,2,4-oxadiazol-3-yl)phenyl)acetamide (123); 2-hydroxy-N-((1-phenyl-1H-pyrazol-4-yl)methyl)-2-(4-(5-(3-phenyl-4-(trifluoromethyl)isoxazol-5-yl)-1,2,4-oxadiazol-3-yl)phenyl)acetamide (124); 2-hydroxy-N-((4-phenethyl-4H-1,2,4-triazol-3-yl)methyl)-2-(4-(5-(3-phenyl-4-(trifluoromethyl)isoxazol-5-yl)-1,2,4-oxadiazol-3-yl)phenyl)acetamide (125); 2-hydroxy-N-(oxazol-5-ylmethyl)-2-(4-(5-(3-phenyl-4-(trifluoromethyl)isoxazol-5-yl)-1,2,4-oxadiazol-3-yl)phenyl)acetamide (126); 2-hydroxyl-2-(4-(5-(3-phenyl-4-(trifluoromethyl)isoxazol-5-yl)-1,2,4-oxadiazol-3-yl)phenyl)-N-((5-(pyridin-2-yl)thiophen-2-yl)methyl)acetamide (127); 2-hydroxy-N-((5-phenyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (128); N-((1-benzyl-1H-pyrazol-4-yl)methyl)-2-hydroxy-2-(4-(5-(3-phenyl-4-(trifluoromethyl)isoxazol-5-yl)-1,2,4-oxadiazol-3-yl)phenyl)acetamide (129); N-((1,5-dimethyl-1H-pyrrol-2-yl)methyl)-2-hydroxy-2-(4-(5-(3-phenyl-4-(trifluoromethyl)isoxazol-5-yl)-1,2,4-oxadiazol-3-yl)phenyl)acetamide (130); 2-hydroxy-N-((5-methyl-3-phenylisoxazol-4-yl)methyl)-2-(4-(5-(3-phenyl-4-(trifluoromethyl)isoxazol-5-yl)-1,2,4-oxadiazol-3-yl)phenyl)acetamide (131); 2-hydroxy-N-((1-methyl-1H-pyrrol-2-yl)methyl)-2-(4-(5-(3-phenyl-4-(trifluoromethyl)isoxazol-5-yl)-1,2,4-oxadiazol-3-yl)phenyl)acetamide (132); 2-hydroxy-N-((3-methylisoxazol-5-yl)methyl)-2-(4-(5-(3-phenyl-4-(trifluoromethyl)isoxazol-5-yl)-1,2,4-oxadiazol-3-yl)phenyl)acetamide (133); 2-hydroxy-N-((5-methyl-1,3,4-oxadiazol-2-yl)methyl)-2-(4-(5-(3-phenyl-4-(trifluoromethyl)isoxazol-5-yl)-1,2,4-oxadiazol-3-yl)phenyl)acetamide (134); 2-hydroxy-N-(2-hydroxyethyl)-2-(4-(5-(3-phenyl-4-(trifluoromethyl)isoxazol-5-yl)-1,2,4-oxadiazol-3-yl)phenyl)propanamide (159); N-(cyanomethyl)-2-hydroxy-2-(4-5-(3-phenyl-4-(trifluoromethyl)isoxazol-5-yl)-1,2,4-oxadiazol-3-yl)phenyl)propanamide (160); and 2-hydroxy-N-(2-(methylsulfonyl)ethyl)-2-(4-(5-(3-phenyl-4-(trifluoromethyl)isoxazol-5-yl)-1,2,4-oxadiazol-3-yl)phenyl)propanamide (161).

7. The compound according to claim 1 or a pharmaceutically acceptable salt thereof, wherein said compound is selected from: 2-hydroxy-N-(2-hydroxyethyl)-2-(4-(5-(1-phenyl-5-(trifluoromethyl)-1H-pyrazol-4-yl)-1,2,4-oxadiazol-3-yl)phenyl)acetamide (53); 2-hydroxy-N-(3-hydroxypropyl)-2-(4-(5-(1-phenyl-5-(trifluoromethyl)-1H-pyrazol-4-yl)-1,2,4-oxadiazol-3-yl)phenyl)acetamide (54); 2-hydroxy-N-(2-hydroxy-2-methylpropyl)-2-(4-(5-(1-phenyl-5-(trifluoromethyl)-1H-pyrazol-4-yl)-1,2,4-oxadiazol-3-yl)phenyl)acetamide (55); tert-butyl 2-(2-hydroxy-2-(4-(5-(1-phenyl-5-(trifluoromethyl)-1H-pyrazol-4-yl)-1,2,4-oxadiazol-3-yl)phenyl)acetamido)acetate (56); 2-hydroxy-N-((S)-2-hydroxypropyl)-2-(4-(5-(1-phenyl-5-(trifluoromethyl)-1H-pyrazol-4-yl)-1,2,4-oxadiazol-3-yl)phenyl)acetamide (57); 2-(2-hydroxy-2-(4-(5-(1-phenyl-5-(trifluoromethyl)-1H-pyrazol-4-yl)-1,2,4-oxadiazol-3-yl)phenyl)acetamido)acetic acid (58); 2-hydroxyl-N-methyl-2-(4-(5-(1-phenyl-5-(trifluoromethyl)-1H-pyrazol-4-yl)-1,2,4-oxadiazol -3-yl)phenyl)acetamide (60); N-ethyl-2-hydroxy-2-(4-(5-(1-phenyl-5-(trifluoromethyl)-1H-pyrazol-4-yl)-1,2,4-oxadiazol-3-yl)phenyl)acetamide (61); 2-hydroxy-N-(2-(1-methylpyrrolidin-2-yl)ethyl)-2-(4-(5-(1-phenyl-5-(trifluoromethyl)-1H-pyrazol-4-yl)-1,2,4-oxadiazol-3-yl)phenyl)acetamide (135); 2-hydroxy-2-(4-(5-(1-phenyl-5-(trifluoromethyl)-1H-pyrazol-4-yl)-1,2,4-oxadiazol-3-yl)phenyl)-N-(2-(pyrrolidin-1-yl)ethyl)acetamide (136); 2-hydroxy-2-(4-(5-(1-phenyl-5-(trifluoromethyl)-1H-pyrazol-4-yl)-1,2,4-oxadiazol-3-yl)phenyl)-N-(pyridin-2-ylmethyl)acetamide (137); 2-hydroxy-2-(4-(5-(1-phenyl-5-(trifluoromethyl)-1H-pyrazol-4-yl)-1,2,4-oxadiazol-3-yl)phenyl)-N-(pyridin-3-ylmethyl)acetamide (138); 2-hydroxy-2-(4-(5-(1-phenyl-5-(trifluoromethyl)-1H-pyrazol-4-yl)-1,2,4-oxadiazol-3-yl)phenyl)-N-(pyridin-4-ylmethyl)acetamide (139); 2-hydroxy-N-(4-(2-hydroxyethyl)phenyl)-2-(4-(5-(1-phenyl-5-(trifluoromethyl)-1H-pyrazol-4-yl)-1,2,4-oxadiazol-3-yl)phenyl)acetamide (140); 2-hydroxy-N-(1-hydroxy-2-methylpropan-2-yl)-2-(4-(5-(1-phenyl-5-(trifluoromethyl)-1H-pyrazol-4-yl)-1,2,4-oxadiazol-3-yl)phenyl)acetamide (141); 2-hydroxy-N-(4-hydroxyphenethyl)-2-(4-(5-(1-phenyl-5-(trifluoromethyl)-1H-pyrazol-4-yl)-1,2,4-oxadiazol-3-yl)phenyl)acetamide (142); 2-hydroxy-2-(4-(5-(1-phenyl-5-(trifluoromethyl)-1H-pyrazol-4-yl)-1,2,4-oxadiazol-3-yl)phenyl)-N-(4-sulfamoylphenethyl)acetamide (143); 2-hydroxy-2-(4-(5-(1-phenyl-5-(trifluoromethyl)-1H-pyrazol-4-yl)-1,2,4-oxadiazol-3-yl)phenyl)-N-(4-sulfamoylbenzyl)acetamide (144); N-(1,3-dihydroxypropan-2-yl)-2-hydroxy-2-(4-(5-(1-phenyl-5-(trifluoromethyl)-1H-pyrazol-4-yl)-1,2,4-oxadiazol-3-yl)phenyl)acetamide (145); 2-hydroxy-2-(4-(5-(1-phenyl-5-(trifluoromethyl)-1H-pyrazol-4-yl)-1,2,4-oxadiazol-3-yl)phenyl)-N-propylacetamide (146); 3-(2-hydroxy-2-(4-(5-(1-phenyl-5-(trifluoromethyl)-1H-pyrazol-4-yl)-1,2,4-oxadiazol-3-yl)phenyl)acetamido)propanamide (147); 2-hydroxy-N-(4-(hydroxymethyl)benzyl)-2-(4-(5-(1-phenyl-5-(trifluoromethyl)-1H-pyrazol-4-yl)-1,2,4-oxadiazol-3-yl)phenyl)acetamide (148); 2-hydroxy-N-(1-hydroxy-4-methylpentan-2-yl)-2-(4-(5-(1-phenyl-5-(trifluoromethyl)-1H-pyrazol-4-yl)-1,2,4-oxadiazol-3-yl)phenyl)acetamide (149); 2-hydroxy-N-(((1R,2R)-2-hydroxycyclohexyl)methyl)-2-(4-(5-(1-phenyl-5-(trifluoromethyl)-1H-pyrazol-4-yl)-1,2,4-oxadiazol-3-yl)phenyl)acetamide (150); 2-hydroxy-N-((1R,2S)-2-(hydroxymethyl)cyclohexyl)-2-(4-(5-(1-phenyl-5-(trifluoromethyl)-1H-pyrazol-4-yl)-1,2,4-oxadiazol-3-yl)phenyl)acetamide (151); 2-hydroxy-N-(((1S,2R)-2-hydroxycyclohexyl)methyl)-2-(4-(5-(1-phenyl-5-(trifluoromethyl)-1H-pyrazol-4-yl)-1,2,4-oxadiazol-3-yl)phenyl)acetamide (152); 2-hydroxy-N-((1R,2R)-2-(hydroxymethyl)cyclohexyl)-2-(4-(5-(1-phenyl-5-(trifluoromethyl)-1H-pyrazol-4-yl)-1,2,4-oxadiazol-3-yl)phenyl)acetamide (153); 2-hydroxy-N-(4-hydroxybutyl)-2-(4-5-(1-phenyl-5-(trifluoromethyl)-1H-pyrazol-4-yl)-1,2,4-oxadiazol-3-yl)phenyl)acetamide (154); 2-hydroxy-N-(1-(hydroxymethyl)cyclopentyl)-2-(4-(5-(1-phenyl-5-(trifluoromethyl)-1H-pyrazol-4-yl)-1,2,4-oxadiazol-3-yl)phenyl)acetamide (155); 2-hydroxy-N-(3-hydroxybenzyl)-2-(4-(5-(1-phenyl-5-(trifluoromethyl)-1H-pyrazol-4-yl)-1,2,4-oxadiazol-3-yl)phenyl)acetamide (156); 2-hydroxy-N-(4-hydroxybenzyl)-2-(4-(5-(1-phenyl-5-(trifluoromethyl)-1H-pyrazol-4-yl)-1,2,4-oxadiazol-3-yl)phenyl)acetamide (157); and 2-hydroxy-N-((1r,4r)-4-hydroxycyclohexyl)-2-(4-(5-(1-phenyl-5-(trifluoromethyl)-1H-pyrazol-4-yl)-1,2,4-oxadiazol-3-yl)phenyl)acetamide (158).

8. The compound according to claim 1 or a pharmaceutically acceptable salt thereof, wherein said compound is selected from: 2-hydroxy-N-(2-hydroxyethyl)-2-(4-(5-(5- phenyl-4-(trifluoromethyl)isoxazol-3-yl)-1,2,4-oxadiazol-3-yl)phenyl)acetamide (62); 2-hydroxy-N-((S)-2-hydroxypropyl)-2-(4-(5-(5-phenyl-4-(trifluoromethyl)isoxazol-3-yl)-1,2,4-oxadiazol-3-yl)phenyl)acetamide (63); 2-hydroxy-N-(2-hydroxy-2-methylpropyl)-2-(4-(5-(5-phenyl-4-(trifluoromethyl)isoxazol-3-yl)-1,2,4-oxadiazol-3-yl)phenyl)acetamide (64); N-(3-(1H-imidazol-1-yl)propyl)-2-hydroxy-2-(4-(5-(5-phenyl-4-(trifluoromethyl)isoxazol-3-yl)-1,2,4-oxadiazol-3-yl)phenyl)acetamide, TFA (65); N-(2-amino-2-oxoethyl)-2-hydroxy-2-(4-(5-(5-phenyl-4-(trifluoromethyl)isoxazol-3-yl)-1,2,4-oxadiazol-3-yl)phenyl)acetamide (66); N-ethyl-2-hydroxy-2-(4-(5-(5-phenyl-4-(trifluoromethyl)isoxazol-3-yl)-1,2,4-oxadiazol-3-yl)phenyl)acetamide (67); 2-hydroxy-2-(4-(5-(5-phenyl-4-(trifluoromethyl)isoxazol-3-yl)-1,2,4-oxadiazol-3-yl)phenyl)-N-(pyridin-3-ylmethyl)acetamide-TFA (68); 2-hydroxy-N-(2-(methylamino)-2-oxoethyl)-2-(4-(5-(5-phenyl-4-(trifluoromethyl)isoxazol-3-yl)-1,2,4-oxadiazol-3-yl)phenyl)acetamide (69); and N-(2-(ethylamino)-2-oxoethyl)-2-hydroxy-2-(4-(5-(5-phenyl-4-(trifluoromethyl)isoxazol-3-yl)-1,2,4-oxadiazol-3-yl)phenyl)acetamide (70).

9. A pharmaceutical composition comprising a compound according to claim 1 or stereoisomers or pharmaceutically acceptable salts thereof, and a pharmaceutically acceptable carrier.

10. A method of treating a disease or disorder associated with the activity of G protein-coupled receptor $S1P_1$, the method comprising administering to a mammalian patient having said disease or disorder a compound according to claim 1 or stereoisomers or pharmaceutically acceptable salts thereof, wherein said disease or disorder is bone marrow, organ or transplant rejection, systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, or asthma.

11. The method according to claim 10, wherein said disease or disorder is bone marrow, organ or transplant rejection.

12. The method according to claim 10, wherein said disease or disorder is systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, or asthma.

* * * * *

UNITED STATES PATENT AND TRADEMARK OFFICE
CERTIFICATE OF CORRECTION

PATENT NO. : 8,835,470 B2  
APPLICATION NO. : 13/642755  
DATED : September 16, 2014  
INVENTOR(S) : Robert Cherney et al.

Page 1 of 1

It is certified that error appears in the above-identified patent and that said Letters Patent is hereby corrected as shown below:

In the Claims:

Claim 6, col. 151, line 34, delete "2-4-5-(3" and insert -- 2-(4-(5-(3 --;

Claim 6, col. 151, line 50, delete "2-4-5-(3" and insert -- 2-(4-(5-(3 --;

Claim 6, col. 152, line 32, delete "hydroxyl" and insert -- hydroxy --;

Claim 6, col. 153, line 17, delete "2-4-5-(3" and insert -- 2-(4-(5-(3 --;

Claim 6, col. 153, line 38, delete "hydroxyl" and insert -- hydroxy --;

Claim 6, col. 154, line 62, delete "2-4-5-(3" and insert -- 2-(4-(5-(3 --;

Claim 6, col. 155, line 5, delete "y1)" and insert -- yl) --;

Claim 6, col. 155, line 11, delete "hydroxyl" and insert -- hydroxy --;

Claim 6, col. 155, line 20, delete "hydroxyl" and insert -- hydroxy --;

Claim 6, col. 155, line 45, delete "2-(4-5-(3" and insert -- 2-(4-(5-(3 --;

Claim 7, col. 155, line 66, delete "hydroxyl" and insert -- hydroxy --;

Claim 7, col. 156, lines 52-53, delete "2-(4-5-(1" and insert -- 2-(4-(5-(1 --;

Claim 10, col. 158, line 7, delete "erythematosis," and insert -- erythematosus, --; and Claim 12, col. 158, line 18, delete "erythematosis," and insert -- erythematosus, --, therefor.

Signed and Sealed this  
Nineteenth Day of May, 2015

Michelle K. Lee  
*Director of the United States Patent and Trademark Office*